(12) United States Patent
Jonczyk et al.

(10) Patent No.: US 8,912,216 B2
(45) Date of Patent: Dec. 16, 2014

(54) HETARYL-[1,8]NAPHTHYRIDINE DERIVATIVES

(71) Applicant: Merck Patent GmbH, Darmstadt (DE)

(72) Inventors: Alfred Jonczyk, Darmstadt (DE); Dieter Dorsch, Ober-Ramstadt (DE); Guenter Hoelzemann, Seeheim-Jugenheim (DE); Christiane Amendt, Muehltal/Trautheim (DE); Frank Zenke, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 14/046,703

(22) Filed: Oct. 4, 2013

(65) Prior Publication Data

US 2014/0038960 A1 Feb. 6, 2014

Related U.S. Application Data

(63) Continuation of application No. 13/574,282, filed as application No. PCT/EP2010/007743 on Dec. 17, 2010, now Pat. No. 8,614,226.

(30) Foreign Application Priority Data

Feb. 5, 2010 (EP) ..................... 10001251

(51) Int. Cl.
  *C07D 471/04* (2006.01)
  *A61K 31/4375* (2006.01)
(52) U.S. Cl.
  CPC .......... *C07D 471/04* (2013.01); *A61K 31/4375* (2013.01)
  USPC .......................................... 514/300; 546/122
(58) Field of Classification Search
  CPC ........................ C07D 471/04; A61K 31/4375
  USPC .......................................... 546/122; 514/300
  See application file for complete search history.

(56) References Cited

U.S. PATENT DOCUMENTS

| | | |
|---|---|---|
| 3,948,917 A | 4/1976 | Jeanmart et al. |
| 5,453,423 A | 9/1995 | Long et al. |
| 6,960,598 B2 * | 11/2005 | Carling et al. ............... 514/300 |
| 2004/0072823 A1 | 4/2004 | Peters et al. |
| 2009/0181941 A1 | 7/2009 | Leblanc et al. |

FOREIGN PATENT DOCUMENTS

| | | |
|---|---|---|
| EP | 1724268 A1 | 11/2006 |
| EP | 1849773 A1 | 10/2007 |
| WO | 98/39332 A1 | 9/1998 |
| WO | 2004/081009 A1 | 9/2004 |
| WO | 2009/087225 A2 | 1/2009 |
| WO | 2009/049743 A1 | 4/2009 |
| WO | 2009/124653 A2 | 10/2009 |
| WO | 2009/133070 A1 | 11/2009 |

OTHER PUBLICATIONS

Wagh et al., Adv. Cancer Res. (2008), 100: 1-33.
Delany & Mlodzik, Cell Cycle (2006), 5(24): 2852-2855.
Janetka & Ashwell, Expert Opin Ther Pal. (2009), 19(2): 165-197.
Yoshida, M. el. al., Inl. J. Pharm. (1995), 115,61-67.
Wermuth CG et al., The Practice of Medicinal Chemistry, Academic Press (1996), Chapter 31: 671-696.
Bundgaard H., A Textbook of Drug Design and Development, Harwood Academic Publishers (1991), Chapter 5: 131-191.
Takeshi Kuroda T et al:, J. Med. Chem. (1992), 35(6) 1130-1136.
Makoto Ando et al., Organic Letters (2006),8_17_3805_3808.

* cited by examiner

*Primary Examiner* — Niloofar Rahmani

(57) ABSTRACT

Novel hetaryl-[1,8]naphthyridine derivatives of formula (I)

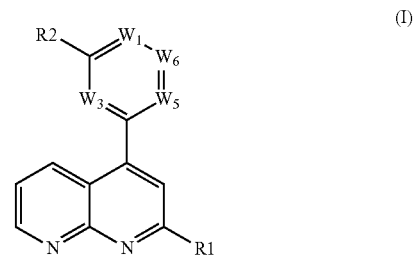

wherein R1, R2, $W_1$, $W_3$, $W_5$ and $W_6$ have the meaning according to claim 1, are inhibitors of ATP consuming proteins, and can be employed, inter alia, for the treatment of tumors.

15 Claims, No Drawings

HETARYL-[1,8]NAPHTHYRIDINE DERIVATIVES

CROSS REFERENCE TO RELATED APPLICATIONS

This is a request for filing a new continuation application under 37 CFR 1.53(b). This application claims priority to, and is a continuation application of U.S. Non-Provisional patent application Ser. No. 13/574,282, filed Aug. 8, 2012, which in turn claims priority to PCT No. PCT/EP2010/007743, filed on Dec. 17, 2010, which in turn claims priority to EP Application No. 10001251.7 each of which is, herein, incorporated by reference in its entirety.

FIELD OF THE INVENTION

The present invention relates to compounds and to the use of compounds in which the inhibition, regulation and/or modulation of signal transduction by ATP consuming proteins like kinases plays a role, particularly to inhibitors of TGF-beta receptor kinases. Objects of the invention are also pharmaceutical compositions that comprise these compounds, and to the use of the compounds for the treatment of kinase-induced diseases.

Proteins which bind ATP and utilize its energy to change conformation, to phosphorylate substrates, and to initiate signaling cascades are known from many classes, like kinases, phosphatases, chaperones or isomerases. With specific tools and techniques ATP-binding proteins can be enriched.

From the large family of protein kinases, split into subfamilies of tyrosine kinases and serine threonine kinases, a partial list includes cAbl, Akt, ALK, ALK1 and its family members like ALK1 and ALK5, Axl, Aurora A and B, Btk, Dyrk2, EGFR, Erk, Ephrin receptors like EphA2, FAK, FGF receptors like FGFR3, insulin receptor IR and insulin like growth factor receptor IGF1R, IKK2, Jak2, JNK3, cKit, LimK, VEGF receptors 1, 2, and 3, Mek1, Met, P70s6K, PDGFR, PDK1, PI3K, Plk1, PKD1, bRaf, RSK1, Src and its family members, TAK1, Trk A, B, C, Zap70. The different kinases can be described under several synonyms, well known to the one skilled in the art and accessible in data bases like Kinweb to find a gene and protein report with alternative names, classification, gene annotation, sequence and gene structure, and links to the pdb 3D structure information. Similarly, proteomics server will give access to a lot of information and analysis and prediction tools for genes and proteins, including kinases.

As a mechanistic part of the hallmarks of cancer, Ser/Thr kinases and receptor tyrosine kinases (RTK) are phosphorylating enzymes essential in cellular signaling. Cell cycle, survival, proliferation and cell death are cellular processes, regulated by cell signaling, to permit tissue to grow, to regenerate and to be in homeostasis, or to regress. Some kinases are therefore exquisite targets for mammalian therapy.

Of the different families of kinases, which are part of the human kinome the receptor tyrosine kinase KDR, also called VEGF receptor 2, can stimulate endothelial cell survival and proliferation if ligated extra cellular by VEGF. Ligand binding can then lead to intracellular phosphorylation events, a signaling cascade and ultimately to proliferation. Inhibition of this KDR signaling is attempted by various therapies.

Other kinases and ligands important for function of endothelial cells are TIE2 kinase and the angiopoietins, PDGF receptor and PDGF as well as PDGF. Ephrin receptor kinase and ephrins, especially EphB4 and ephrin-B2. In addition, the ligand TGFβ and its receptors TGFβR, i.e. Alk1/Alk5 play an important role in maintenance of vascular integrity. By binding to the TGFβ type II receptor TGFβ can activate 2 distinct type I receptors in endothelial cells, i.e. the EC-restricted ALK1 and the broadly expressed ALK5 with opposite effects on EC behavior. ALK1 stimulates EC proliferation and migration via Smad1/5 transcription factors, ALK5 inhibits those functions via Smad2/3 transcription factors. One example for an Alk5 kinase inhibitor that facilitates EC proliferation and sheet formation is SB-431542. Ligand binding inhibition might be an additional approach to modulate TGFβ receptor signaling also in angiogenesis. This was shown with 2 peptides and also discussed for soluble TGFβ receptors TβR-Fc. Use of anti-TGFβ antibodies, even a TGFβ trap, would be another strategy to inhibit TGFβ signaling.

The TGFβ proteins comprise a family of conserved dimeric proteins with a molecular weight of ~25 kDa, which are ubiquitously expressed and secreted in an inactive form. Local proteolysis in response to appropriate stimuli leads to active TGFβ ligands. TGFβ signaling is implicated in numerous conditions and diseases, including cancer, cardiovascular, bone, CNS, PNS, inflammatory and neurodegenerative disorders.

In epithelial cells, TGFβ inhibits cell proliferation. The transition of normal epithelial cell into carcinoma cells is accompanied by down-regulation of the growth-inhibition response to TGFβ, allowing the cells to escape the autocrine tumor suppressor activities of TGFβ signaling. The increased production of TGFβ by carcinoma cells contributes to the invasive and metastatic behavior of the cancer cells. TGFβ can induce an epithelial-to-mesenchymal transition (EMT) that allows the cells to become invasive and migratory. In addition, the increased TGFβ production exerts effects on stromal and immune cells to provide a favorable microenvironment for cancer progression. TGFβ proteins signal through TβR-I/II receptor kinases and their Smad substrates, but can also signal independent of Smads, such as ERK MAP kinases, PI3 kinase, Rho-like GTPases, protein phosphatase 2A, and Par6. Activated type I TβR kinases enhance survival of cells and can accelerate pathological cell progression.

TGFβ receptor type I and II (TβR I, TβR II) are single-pass transmembrane-spanning intracellular serine/threonine kinases presenting extracellular ligand (TGFβ) binding receptors. Intra-cellular signaling proceeds via auto-phosphorylation, trans-phosphorylation and substrate phosphorylation, leading to modulation of target gene expression. Cloning and genomic organization of TβR proteins is well-known. TβR sequences are deposited in www.uniprot.org as TGFR1_human with accession number P36897, and as TGFβR2_human with accession number P37173. On protein level, type I TβR is described to contain a region rich in Gly and Ser (GS domain) preceeding the receptor kinase domain.

TβR II is in its auto/phosphorylated state a constitutively active kinase which binds to the type I receptor and phosphorylates it in the GS domain.

TβReceptor, a ligand TGFβ-bound (activated) tetrameric complex of 2 TβR 1 and 2 TβR II units, is able to phosphorylate Smads (Smad 2 and Smad 3) in their C-terminal SSXS motifs as substrates which in turn are bound to/by Smad4 to be translocated to the cell nucleus, where they modulate TGFβ responsive genes. The different domains which regulate homomeric and heteromeric complex formation among type I and type II TβRs are known. Mutations in the GS domain of TβR I can be constitutively activating. Kinase inactivating mutation were found with K232R for type I and K277R for type II TβR. Inactivating or attenuating mutations in the genes for Type I and Type II TβR genes are found in a variety of cancers. In addition, signaling of TβRs is regulated by phosphorylation and dephosphorylation mechanisms, ubiquitinylation and sumoylation, and by endocytosis and by TACE-mediated ectodomain shedding of type I, but not type II receptors TACE, aka ADAM-17, which mediates shedding of cytokines, GF receptors, and adhesion proteins and is highly expressed in cancers.

The X-ray co-crystal structure of TβR I and FKBP12 has been described, and the kinase activation process was discussed. Meanwhile, several crystal structures can be found in the PDB data base: 1B6C, 1IAS, 1 PY5, 1 RW8, 1VJY, 2PJY, and a model 1TBI. For TβR II only X-ray studies for the extracellular ligand binding domain are known to the public: 1KTZ, 1M9Z, and 1PLO (NMR), but none of the kinase domain.

TGFβ signal transduction involves Smads, the only substrates for TβR type I receptor kinases. The human genome encodes eight Smads from 3 subfamilies (R-, Co-, I-Smads), which are ubiquitously expressed throughout development and in adult tissue. Smads not only are phosphorylated by Type I TGFβ receptor kinases but they are also regulated by oligomerisation, ubiquitinylation and degradation, and nucleoplasmatic shuttling.

It was shown that VEGF release is regulated by ALK1 and ALK5, whereas TGFβ enhanced and BMP-9 suppressed expression of VEGF.

Studies with truncated ALK4 isoforms suggest involvement of this type I kinase in growth and development of pituitary tumors, by a dominant negative inhibition of activin signaling. Studies of the spatiotemporal window of roles of ALK4 in embryonic development, regulation of the mesoderm induction, primitive streak formation, gastrulation, primary axis formation and left-right axis determination are still not clarifying the role of ALK4 in adult. In a large scale human candidate screen it was found that dominant-negative ALK2 alleles are associated with congenital heart disease, like improper atrioventrikular septum development.

ALK1 binds TβR-II and Endoglin/CD105/TβR-III and phosphorylates SMAD-1 and -5. The role of endoglin and especially the differential modulation of TGFβ signaling by two variants, L- and S-endoglin, have been shown. ALK1 functions in vascular remodeling and is found with ALK5 in balancing the activation state of endothelium in inflamed tissue, wounds and tumor. ALK1 is expressed in lung, placenta, and other highly vascularized tissue, and is selectively found on ECs. In addition, ALK1 was detected on neurons.

Loss of expression of type II TβR correlates with high tumor grade in human breast carcinomas, indicating a contribution to beast cancer progression. Tumor growth can be characterized by deregulated i.e. autonomous cell growth due to perturbation of RTK signaling by mutations or other genetic alterations. Of the 32000 human coding genes which are involved in signal transduction, more than 520 protein kinases and 130 protein phosphatases exert tight and reversible control on protein phosphorylation. Selectivity is found for tyrosine and for serine/threonine phosphorylation. There are more than 90 known PTK genes in the human genome, more than 50 encode transmembrane RPTKs distributed in 20 subfamilies, and 32 encode cytoplasmic, non-receptor PTKs in 10 subfamilies. For example Trk A has an important role in thyroid carcinomas and neuroblastomas, EphB2 and B4 are over-expressed in carcinomas, Axl and Lck are over-expressed in leukemia.

TGFβ inhibitors for the treatment of cancer were reviewed. There are further indications and pathologies, indirect targeting cancer, wound healing and inflammation via anti-angiogenesis, blood vessel formation, stabilization, maintenance and regression.

Angiogenesis, the development of new vessels from pre-existing vessels, is critical in vascular development in embryogenesis, organogenesis, and wound healing. In addition to those physiological processes, angiogenesis is important for tumor growth, metastasis and inflammation, resulting in diseases like tumors of the breast, uterine cervix, uterine corpus (endometrium), ovary, lung, bronchus, liver, kidney, skin, oral cavity and pharynx, prostate, pancreas, urinary bladder, blood cells, colon, rectum, bone, brain, central and peripheral nervous system, exemplified as breast cancer, colorectal cancer, gliomas, lymphomas, and so on, and of inflammatory diseases like rheumatoid arthritis and psoriasis, or diseases of the eye, like macula degeneration, and diabetic retinopathy. Molecular mechanisms of blood vessel formation and the angiogenic switch in tumorigenesis were recently discussed. Vascular patterning is regulated by Eph receptor tyrosine kinases and ephrin ligands, e.g. ephrin-B2 signaling via Eph B4 and Eph B1. EphB4 controls vascular morphogenesis during postnatal angiogenesis. The maturation of nascent vasculature, formed by angiogenesis or vasculogenesis, requires mural cells (pericytes, smooth muscle cells), generation of extracellular matrix and specialization of the vessel wall for structural support and regulation of vessel function. Regulation of those processes and interaction between endothelial cells and their mural cells involves several ligand kinase pairs, like VEGF/VEGFR1, VEGFR2, EphrinB2/EphB4, PDGFR/PDGFRβ, Angiopoietins/TIE2, TGFβ/TGFβR-ALK1/ALK5. Vessel assembly, capillary formation, sprouting, stabilization and destabilization, even regression, is regulated by a functional balance of those kinases and ligands. Lymphangiogenesis is regulated via VEGF receptor 3 and its ligands VEGF C, and D, as well as TIE2 and its ligands angiopoietins 1, 2. Inhibition of VEGFR3 and/or TIE2 signaling and therefore inhibition of formation of lymphatic vessels can be a mean to stop metastasis of tumor cells. The whole body of information about pathological vascularisation leads to the assumption for inhibition of angiogenesis being a promising strategy for treatment of cancer and other disorders.

The importance of TGFβ receptors for angiogenic processes is shown by Alk1, endoglin, Alk5 and TβRII KO mice all exhibiting an embryonic lethal phenotype due to vascular defects. In addition, in ECs TGFβ ligands are able to stimulate two pathways, with Smad 1/5/8 phosphorylation downstream of Alk1 and Smad2/3 phosphorylation downstream of Alk5. Both pathways cross-talk with each other. Alk5 knock-in mice with L45 loop mutations show defective Smad activation. TGFβ/Alk5 signaling is antagonized by ALK1 in ECs.

TGFβ exists in at least five isoforms (TGFβ1-5), which are not related to TGFa, with TGFβ1 as the prevalent form. TGFβ is a ubiquitous and essential regulator of cellular and physiological processes including proliferation, differentiation, migration, cell survival, angiogenesis and immunosurveillance.

Since cancer cells express tumor-specific antigens they normally would be recognized by the immune system and would be destroyed. During tumorigenesis cancer cells acquire the ability to evade this immunosurveillance by multiple mechanisms. A major mechanism is cancer cell mediated immunosuppression by secretion of TGFβ, a potent immuno-suppressive cytokine. TGFβ has the potential to switch from being a tumor suppressor to a tumor promoter and prometastatic factor. TGFβ function is transmitted by a tetrameric receptor complex, consisting of two groups of transmembrane serine-threonine kinase receptors, called type I and type II receptors, which are activated following engagement of members of the TGFβ superfamily of ligands, which is divided in 2 groups, the TGFβ/Activin and BMP/GDF branches. TGFβ1, 2, and 3 belong to the TGFβ/Activin branch of ligands. These binding events specify downstream responses that are differentially regulated in different cell types.

Importance of fibroblasts in mesenchymal-epithelial interaction in skin during wound repair was described in an inducible postnatal deletion of TGFβ RII in skin fibroblasts. During wound repair, expression of the ligand TGFβ and its receptor types RI and RII are timely and spatially regulated. CD109, a GPI linked cell surface antigen, expressed by CD34+ acute myeloid leukemia cell lines, ECs, activated platelets and T-cells are part of the TβR system in human keratinocytes. Follicle Stem Cells (FSCs) in the bulge region of hair follicle can give rise to multiple lineages during hair cycle and wound healing. Smad4, a common mediator of TGFβ signaling is part of FSCs maintenance. Smad4 KO studies in mouse skin showed hair follicle defects and squamous cell carcinoma formation. The potential suppression of TGFβ delayed catagen progression in hair follicles. The well described role of TGFβ in keratinocyte apoptosis during catagen phase is likely to involve anagen-specific hair follicle components also involving co-localized TβRI and TβRII.

Abnormal activity of TGFβ in fibrosis of several organs, such as skin, kidney, heart and liver, is known, being a rational for use of TβR inhibitors in fibrotic diseases. Systemic sclerosis (scleroderma), a complex disorder of connective tissue leading to fibrosis of the skin and inner organs, was shown to be TGFβ/receptor RI dependent. Pulmonary arterial hypertension (PAH) is a condition potentially treatable with ALK5 inhibitors because abnormal proliferation of peripheral arterial smooth muscle cells is driven by activated TGFβ receptors. Treatment in rats was successful with SB525334. Benefit in rat was also shown with IN-1233. Renal fibrosis can lead to diabetes.

Beneficial side effects of TβR kinase inhibitor derivatives and a connection between TGFβ signaling and hepatitis C virus (HCV) replication is known. TGFβ signaling is discussed as an emerging stem cell target in metastatic breast cancer. TGFβ1, 2, 3 and their receptors are expressed in neurons, astrocytes and microglia. Improvement of pathological outcome with TGFβ signaling modulators can be expected. The TGFβ superfamily in cardiovascular disease, like atherosclerosis, myocardial ischemia and cardiac remodeling is focus of an issue of cardiovascular research.

Further details on the biochemistry of TGFβ are disclosed in WO 2009/004753, which is incorporated in its entirety by reference in the disclosure of the invention hereby.

In addition, RON kinase is a valuable target in tumor biology (Wagh et al. (2008) Adv Cancer Res. 100:1-33). The Met-related receptor tyrosine kinase RON is involved in tumor growth and metastasis. The RON receptor is a member of the Met family of cell surface receptor tyrosine kinases and is primarily expressed on epithelial cells and macrophages. The biological response of RON is mediated by binding of its ligand, hepatocyte growth factor-like protein/macrophage stimulating-protein (HGFL). HGFL is primarily synthesized and secreted from hepatocytes as an inactive precursor and is activated at the cell surface. Binding of HGFL to RON activates RON and leads to the induction of a variety of intracellular signaling cascades that leads to cellular growth, motility and invasion. Recent studies have documented RON overexpression in a variety of human cancers including breast, colon, liver, pancreas, and bladder. Moreover, clinical studies have also shown that RON overexpression is associated with both worse patient outcomes as well as metastasis. Forced overexpression of RON in transgenic mice leads to tumorigenesis in both the lung and the mammary gland and is associated with metastatic dissemination. While RON overexpression appears to be a hallmark of many human cancers, the mechanisms by which RON induces tumorigenesis and metastasis are still unclear. Several strategies are currently being undertaken to inhibit RON as a potential therapeutic target; current strategies include the use of RON blocking proteins, small interfering RNA (siRNA), monoclonal antibodies, and small molecule inhibitors. In total, these data suggest that RON is a critical factor in tumorigenesis and that inhibition of this protein, alone or in combination with current therapies, may prove beneficial in the treatment of cancer patients.

In addition, TAK1, or CHK2 are valuable targets in immunity and cellular damage response pathways (Delaney & Mlodzik (2006) Cell Cycle 5(24): 2852-5, describing TGF-beta activated kinase-1 and new insights into the diverse roles of TAK1 in development and immunity. A number of recent publications have examined the role of TAK1 in model systems ranging from fly to mouse. Rather than fit into a clearly defined linear molecular pathway, TAK1 seems to act in a signaling nexus that responds to a variety of upstream signals, including inflammatory molecules and developmental cues. TAK1 then influences a number of downstream processes ranging from innate immune responses to patterning and differentiation via JNK, NFkappaB and TCFbeta-catenin signaling. These differences in function are not simply a matter of cell type. For example, NFkappaB signaling in a particular cell may or may not require TAK1 depending on the nature of the activating signal. Interestingly, the multi-task functionality of TAK1 is conserved between vertebrate and invertebrate species. Studies of TAK1 in multiple experimental systems are likely to reveal more roles for this kinase and also elucidate mechanisms by which other signaling molecules fulfill diverse signaling roles.

Furthermore, the checkpoint kinases, Chk1 and Chk2 are Ser/Thr protein kinases, which function as key regulatory kinases in cellular DNA damage response pathways limiting cell-cycle progression in the presence of DNA damage. The development of checkpoint kinase inhibitors for the treatment of cancer has been a major objective in drug discovery over the past decade, as evidenced by three checkpoint kinase inhibitors entering clinic trials since late 2005. A large number of chemically diverse Chk1 and Chk2 kinase inhibitors have appeared in the recent patent literature. Common structural motifs of the checkpoint kinase inhibitors were identified. There are currently three checkpoint kinase inhibitors in clinical development, a continuing effort by the pharmaceutical industry to identify novel scaffolds for checkpoint kinase inhibition (Janetka & Ashwell (2009) Expert Opin Ther Pat. 2009 19(2): 165-97).

Several TGF-beta receptor kinase inhibitors (TβR inhibitors) and compounds series are described to the public from non-clinical studies and several inhibitors are known by code in public domain. In particular, several new chemical entities are known from patent literature, in which they are claimed to be inhibitors of TGFβ receptor kinases. WO 2009/133070 describes imidazopyridines, WO 2009/124653 teaches thienopyrimidines, WO 2009/087225 concerns pyrrolopyridines/pyrimidines and WO 2009/049743 relates to thienopyridines. None of the references is directed to the synthesis and use of compounds of formula (I) as described below.

The invention had the object of finding novel compounds having valuable properties, in particular those which can be used for the preparation of medicaments.

It has been surprisingly found that the compounds according to the invention and salts thereof have very valuable pharmacological properties while being well tolerated. In particular, they exhibit TGF-β receptor I kinase-inhibiting properties. The invention relates to compounds of formula (I)

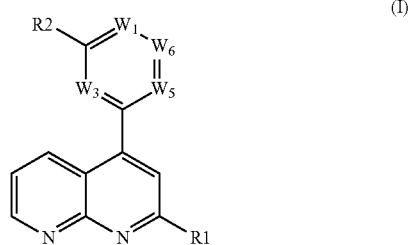

wherein
$W_1$, $W_3$ denotes independently from one another N, NO or CR3;
$W_5$, $W_6$ denotes independently from one another N, NO or CR4;
under the proviso that at least one of $W_1$, $W_3$, $W_5$ or $W_6$ denotes N;
R1 denotes a monocyclic carboaryl having 5-8 C atoms, Het$^1$ or a monocyclic heteroaryl having 2-7 C atoms and 1-4 N, O and/or S atoms, each of which can be substituted by at least one substituent selected from the group of Y, Hal, CN, OY;
R2 denotes Ar, Het$^1$ or Het$^2$,
each of which can be substituted by R5;
R3, R4 denotes independently from one another H, NYY, —NY—COY, A, OY or COOA;
R2, R3 together also denote Alk under the proviso that R2 and at most one R2-adjacent R3 are together;
R5 denotes Hal, A, —(CYY)$_n$—OY, —(CYY)$_n$—NYY, (CYY)$_n$-Het$^3$, SY, NO$_2$, CN, COOY, —CO—NYY, —NY—COA, —NY—SO$_2$A, —SO$_2$—NYY, S(O)$_m$A, —CO-Het$^3$, —O(CYY)$_n$—NYY, —O(CYY)$_n$-Het$^3$, —NH—COOA, —NH—CO—NYY, —NH—COO—(CYY)$_n$—NYY, —NH—COO—(CYY)$_n$-Het$^3$, —NH—CO—NH—(CYY)$_n$—NYY, —NH—CO—NH(CYY)$_n$-Het$^3$, —COO—NH—(CYY)$_n$—NYY, —OCO—NH—(CYY)$_n$-Het$^3$, CHO, COA, =S, =NY, =O, Alk-OH, —CO—NY—(CYY)$_n$—NYY, —CO—NY-Het$^3$ or —SO$_2$-Het$^3$;
Y denotes H or A;
A denotes unbranched or branched alkyl having 1-10 C atoms,
in which 1-7 H atoms can be replaced independently from one another by Hal and/or in which one or two adjacent CH$_2$ groups can be replaced independently of one another by a O, S, SO, SO$_2$, a —CY=CY— group and/or
a —C≡C— group;
Alk denotes unbranched alkylene, alkenyl or alkynyl having 2-5 C atoms, in which 1-2 H atoms can be replaced independently from one another by R5 and/or in which 1-4 C atoms can be replaced independently from one another by N, O and/or S;
Ar denotes a saturated, unsaturated or aromatic, mono- or bicyclic carbocycle having 6-10 C atoms;
Het$^1$ denotes a saturated or unsaturated, mono, bi- or tricyclic heterocycle having 2-19 C atoms and 1-5 N, O and/or S atoms;
Het$^2$ denotes a mono, bi- or tricyclic heteroaryl having 2-19 C atoms and 1-5 N, O and/or S atoms;
Het$^3$ denotes a saturated, unsaturated or aromatic, mono-, bi- or tricyclic heterocycle having 2-19 C atoms and 1-5 N, O and/or S atoms,
which can be substituted by at least one substituent selected from the group of Hal, A, —(CYY)$_n$—OY, —(CYY)$_n$—NYY, SY, NO$_2$, CN, COOY, —CO—NYY, —NY—COA, —NY—SO$_2$A, —SO$_2$—NYY, S(O)$_m$A, —NH—COOA, —NH—CO—NYY, CHO, COA, =S, =NY, =O;
Hal denotes F, Cl, Br or I;
m denotes 0, 1 or 2; and
n denotes 0, 1, 2, 3 or 4;
and/or physiologically acceptable salts thereof.

In the meaning of the present invention, the compound is defined to include pharmaceutically usable derivatives, solvates, prodrugs, tautomers, enantiomers, racemates and stereoisomers thereof, including mixtures thereof in all ratios.

The term "pharmaceutically usable derivatives" is taken to mean, for example, the salts of the compounds according to the invention and also so-called prodrug compounds. The term "solvates" of the compounds is taken to mean adductions of inert solvent molecules onto the compounds, which are formed owing to their mutual attractive force. Solvates are, for example, mono- or dihydrates or alkoxides. The term "prodrug" is taken to mean compounds according to the invention which have been modified by means of, for example, alkyl or acyl groups, sugars or oligopeptides and which are rapidly cleaved in the organism to form the effective compounds according to the invention. These also include biodegradable polymer derivatives of the compounds according to the invention, as described, for example, in Int. J. Pharm. 115, 61-67 (1995). It is likewise possible for the compounds of the invention to be in the form of any desired prodrugs such as, for example, esters, carbonates, carbamates, ureas, amides or phosphates, in which cases the actually biologically active form is released only through metabolism. Any compound that can be converted in-vivo to provide the bioactive agent (i.e. compounds of the invention) is a prodrug within the scope and spirit of the invention. Various forms of prodrugs are well known in the art and are described (e.g. Wermuth C G et al., Chapter 31: 671-696, The Practice of Medicinal Chemistry, Academic Press 1996; Bundgaard H, Design of Prodrugs, Elsevier 1985; Bundgaard H, Chapter 5: 131-191, A Textbook of Drug Design and Development, Harwood Academic Publishers 1991). Said references are incorporated herein by reference. It is further known that chemical substances are converted in the body into metabolites which may where appropriate likewise elicit the desired biological effect—in some circumstances even in more pronounced form. Any biologically active compound that was converted in-vivo by metabolism from any of the compounds of the invention is a metabolite within the scope and spirit of the invention.

The compounds of the invention may be present in the form of their double bond isomers as "pure" E or Z isomers, or in the form of mixtures of these double bond isomers. Where possible, the compounds of the invention may be in the form of the tautomers, such as keto-enol tautomers. All stereoisomers of the compounds of the invention are contemplated, either in a mixture or in pure or substantially pure form. The compounds of the invention can have asymmetric centers at any of the carbon atoms. Consequently, they can exist in the form of their racemates, in the form of the pure enantiomers and/or diastereomers or in the form of mixtures of these enantiomers and/or diastereomers. The mixtures may have any desired mixing ratio of the stereoisomers. Thus, for example, the compounds of the invention which have one or more centers of chirality and which occur as racemates or as diastereomer mixtures can be fractionated by methods known per se into their optical pure isomers, i.e. enantiomers or diastereomers. The separation of the compounds of the invention can take place by column separation on chiral or non-chiral phases or by recrystallization from an optionally optically active solvent or with use of an optically active acid or base or by derivatization with an optically active reagent such as, for example, an optically active alcohol, and subsequent elimination of the radical.

The invention also relates to the use of mixtures of the compounds according to the invention, for example mixtures of two diastereomers, for example in the ratio 1:1, 1:2, 1:3, 1:4, 1:5, 1:10, 1:100 or 1:1000. These are particularly preferably mixtures of stereoisomeric compounds.

The nomenclature as used herein for defining compounds, especially the compounds according to the invention, is in general based on the rules of the IUPAC-organization for chemical compounds and especially organic compounds. The terms indicated for explanation of the above compounds of the invention always, unless indicated otherwise in the description or in the claims, have the following meanings:

The term "unsubstituted" means that the corresponding radical, group or moiety has no substituents. The term "substituted" means that the corresponding radical, group or moiety has one or more substituents. Where a radical has a plurality of substituents, and a selection of various substituents is specified, the substituents are selected independently of one another and do not need to be identical. Even though a radical has a plurality of a specific-designated substituent (e.g. YY) the expression of such substituent may differ from each other (e.g. methyl and ethyl). It shall be understood accordingly that a multiple substitution of any radical of the invention may involve identical or different radicals. Hence, if individual radicals occur a number of times within a compound, the radicals adopt the meanings indicated, independently of one another (e.g. R3 in formula (II)).

The terms "alkyl" or "A" refer to acyclic saturated or unsaturated hydrocarbon radicals, which may be branched or straight-chain and preferably have 1, 2, 3, 4, 5, 6, 7, 8, 9 or 10 carbon atoms, i.e. $C_1$-$C_{10}$-alkanyls. Examples of suitable alkyl radicals are methyl, ethyl, n-propyl, isopropyl, 1,1-, 1,2- or 2,2-dimethylpropyl, 1-ethylpropyl, 1-ethyl-1-methylpropyl, 1-ethyl-2-methylpropyl, 1,1,2- or 1,2,2-trimethylpropyl, n-butyl, isobutyl, sec-butyl, tert-butyl, 1-, 2- or 3-methylbutyl, 1,1-, 1,2-, 1,3-, 2,2-, 2,3- or 3,3-dimethylbutyl, 1- or 2-ethylbutyl, n-pentyl, iso-pentyl, neo-pentyl, tert-pentyl, 1-, 2-, 3- or -methyl-pentyl, n-hexyl, 2-hexyl, isohexyl, n-heptyl, n-octyl, n-nonyl, n-decyl, n-undecyl, n-dodecyl, n-tetradecyl, n-hexadecyl, n-octadecyl, n-icosanyl, n-docosanyl.

In a preferred embodiment of the invention, "A" denotes unbranched or branched alkyl having 1-10 C atoms, in which 1-7 H atoms may be replaced by Hal and/or in which one or two adjacent $CH_2$ groups can be replaced independently of one another by a O, S, SO, $SO_2$, a —CY=CY— group and/or a —C≡C— group. A more preferred "A" denotes unbranched or branched alkyl having 1-4 C atoms, in which 1-5 atoms may be replaced by F and/or Cl. A $C_{1-4}$-alkyl radical is for example a methyl, ethyl, propyl, isopropyl, butyl, isobutyl, tert-butyl, sec-butyl, tert-butyl, fluoromethyl, difluoromethyl, trifluoromethyl, pentafluoroethyl, 1,1,1-trifluoroethyl or bromomethyl, especially methyl, ethyl, propyl or trifluoromethyl. Most preferred is $C_{1-3}$-alkyl. It shall be understood that the respective denotation of "A" is independently of one another in the radicals R5, Y and $Het^3$.

The terms "cycloalkyl" or "eye" for the purposes of this invention refers to saturated and partially unsaturated non-aromatic cyclic hydrocarbon groups/radicals, having 1 to 3 rings, that contain 3 to 20, preferably 3 to 12, more preferably 3 to 9 carbon atoms. The cycloalkyl radical may also be part of a bi- or polycyclic system, where, for example, the cycloalkyl radical is fused to an aryl, heteroaryl or heterocyclyl radical as defined herein by any possible and desired ring member(s). The bonding to the compounds of the general formula (I) can be effected via any possible ring member of the cycloalkyl radical. Examples of suitable cycloalkyl radicals are cyclopropyl, cyclobutyl, cyclopentyl, cyclohexyl, cycloheptyl, cyclooctyl, cyclodecyl, cyclohexenyl, cyclopentenyl and cyclooctadienyl.

In a preferred embodiment of the invention, "Cyc" denotes cycloalkyl having 3-7 C atoms, in which 1-4 H atoms may be replaced independently of one another by A, Hal and/or OY. More preferred is $C_5$-$C_7$-cycloalkyl, in which one H atom may be replaced by A, Hal, OH or OA. A highly preferred $C_5$-$C_7$-cycloalkyl radical is unsubstituted, i.e. cyclopentyl, cyclohexyl or cycloheptyl. Moreover, the definition of "A" shall also comprise cycloalkyls and it is to be applied mutatis mutandis to "Cyc".

The term "Alk" refers to unbranched or branched alkylene, alkenyl or alkynyl having 1, 2, 3, 4, 5 or 6 C atoms, i.e. $C_1$-$C_6$-alkylenes, $C_2$-$C_6$-alkenyls and $C_2$-$C_6$-alkynyls. Alkenyls have at least one C—C double bond and alkynyls at least one C—C triple bond. Alkynyls may additionally have at least one C—C double bond. Example of suitable alkylene radicals are methylene, ethylene, propylene, butylene, pentylene, hexylene, isopropylene, isobutylene, sec-butylene, 1-2- or 3-methylbutylene, 1,1-, 1,2- or 2,2-dimethylpropylene, 1-ethylpropylene, 1-, 2-, 3- or 4-methylpentylene, 1,1-, 1,2-, 1,3-, 2,2-, 2,3- or 3,3-dimethyl-butylene, 1- or 2-ethylbutylene, 1-ethyl-1-methylpropylene, 1-ethyl-2-methylpropylene, 1,1,2- or 1,2,2-trimethylpropylene. Example of suitable alkenyls are allyl, vinyl, propenyl (—$CH_2$CH=$CH_2$; —CH=CH—$CH_3$; —C(=$CH_2$)—$CH_3$), 1-, 2- or 3-butenyl, isobutenyl, 2-methyl-1- or 2-butenyl, 3-methyl-1-butenyl, 1,3-butadienyl, 2-methyl-1,3-butadienyl, 2,3-dimethyl-1,3-butadienyl, 1-, 2-, 3- or 4-pentenyl and hexenyl. Example of suitable alkynyls are ethynyl, propynyl (—$CH_2$—C≡CH; —C≡C—$CH_3$), 1-, 2- or 3-butynyl, pentynyl, hexynyl and or pent-3-en-1-in-yl, particularly propynyl.

In a preferred embodiment of the invention, "Alk" denotes unbranched alkylene, alkenyl or alkynyl having 2-5 C atoms, in which 1-2 H atoms may be replaced independently of one another by R5 and/or in which 1-4 C atoms can be replaced independently from one another by N, O and/or S. A more preferred "Alk" denotes unbranched alkylene having 3-4 C atoms, i.e. propylene or butylene, which can be monosubstituted by R5 and/or in which 1-2 C atoms may be replaced by independently from one another by N, O and/or S. Most preferred is $C_4$-alkylene (—C=C—C=C—).

The term "aryl" or "carboaryl" for the purposes of this invention refers to a mono- or polycyclic aromatic hydrocarbon systems having 3 to 14, preferably 4 to 10, more preferably 5 to 8 carbon atoms, which can be optionally substituted. The term "aryl" also includes systems in which the aromatic cycle is part of a bi- or polycyclic saturated, partially unsaturated and/or aromatic system, such as where the aromatic cycle is fused to an "aryl", "cycloalkyl", "heteroaryl" or "heterocyclyl" group as defined herein via any desired and possible ring member of the aryl radical. The bonding to the compounds of the general formula (I) can be effected via any possible ring member of the aryl radical. Examples of suitable "aryl" radicals are phenyl, biphenyl, naphthyl, 1-naphthyl, 2-naphthyl and anthracenyl, but likewise in-danyl, indenyl or 1,2,3,4-tetrahydronaphthyl.

Preferred "carboaryls" of the invention are optionally substituted phenyl, naphthyl and biphenyl, more preferably optionally substituted monocyclic carboaryl having 5-8 C atoms, most preferably optionally substituted phenyl, and highly preferably optionally substituted phenyl if defined in terms of R1 radical. The preferred carboaryls of the invention can be mono-, di- or trisubstituted by at least one substituent selected from the group of Y, Hal, CN and OY.

The term "heteroaryl" for the purposes of this invention refers to a 3-20, preferably 3-9, most preferably 5-, 6- or 7-membered mono- or polycyclic aromatic hydrocarbon radical which comprises at least 1, where appropriate also 2, 3, 4 or 5 heteroatoms, preferably nitrogen, oxygen and/or sulfur, where the heteroatoms are identical or different. The number of nitrogen atoms is preferably 0, 1, 2, 3 or 4, and that of the oxygen and sulfur atoms is independently 0 or 1. The term "heteroaryl" also includes systems in which the aromatic cycle is part of a bi- or polycyclic saturated, partially unsaturated and/or aromatic system, such as where the aromatic cycle is fused to an "aryl", "cycloalkyl", "heteroaryl" or "heterocyclyl" group as defined herein via any desired and possible ring member of the heteroaryl radical. The bonding to the compounds of the general formula (I) can be effected via any possible ring member of the heteroaryl radical. Examples of suitable "heteroaryl" are pyrrolyl, thienyl, furyl, imidazolyl, thiazolyl, isothiazolyl, oxazolyl, oxadiazolyl, isoxazolyl, pyrazolyl, pyridinyl, pyrimidinyl, pyridazinyl, pyrazinyl, indolyl, quinolinyl, isoquinolinyl, imidazolyl, triazolyl, triazinyl, tetrazolyl, phthalazinyl, indazolyl, indolizinyl, quinoxalinyl, quinazolinyl, pteridinyl, carbazolyl, phenazinyl, phenoxazinyl, phenothiazinyl and acridinyl. It is preferred that "heteroaryl" in the realms of R1 radical represents a monocyclic heteroaryl having 2-7 C atoms and 1 to 4 N, O and/or S atoms, which can be substituted by at least one substituent selected from the group of Y, Hal, CN, and OY. It is also preferred that "carboaryl" in the realms of R1 radical represents a monocyclic carboaryl having 5-8 C atoms, which can be monosubstituted by at least one substituent selected from the group of Y, Hal, CN and OY. It is additionally preferred that R1 denotes $Het^1$. Hence, the aforementioned heteroaryl, carboaryl and $Het^1$ shall represent the preferred Markush group for the radical R1.

In a more preferred embodiment of the invention, the R1 radical denotes phenyl or a monocyclic 4-8 membered heteroaryl including 1-3 N atoms, each of which can be mono-, di- or trisubstituted by at least one substituent selected from the group of A, Hal, CN and OA. Herein, particular preference is given to the heteroaryls pyrrolyl, imidazolyl, pyrazolyl, pyridinyl, pyrimidinyl, pyrazinyl, triazinyl or pyrazolyl, each of which can be substituted as defined above. Subject to other substitutions, R1 denotes most preferably phenyl or pyridin-2-, 3-, 4- or 5-yl, each of which can be mono- di- or trisubstituted by at least one substituent selected from the group of F, Cl, Br, CN, $CH_3$, $CF_3$, CN, $OCH_3$ or $OCF_3$. It is highly preferred that R1 is phenyl, pyridin-2-yl, 2-fluoro-phenyl, 4-fluoro-phenyl, 2-fluoro-5-fluoro-phenyl, 2,4,5-trifluoro-phenyl, 2-fluoro-5-chloro-phenyl, 2-fluoro-5-trifluoromethyl-phenyl, 3-chloro-phenyl, 3-trifluoromethyl-phenyl, 2-cyano-phenyl or 6-methyl-pyridin-2-yl.

It is preferred that "heteroaryl" in the realms of "$Het^2$" represents a mono-, di- or tricyclic heteroaryl having 2-19 C atoms and 1-5 N, S and/or O atoms, which can be substituted by R5. In a more preferred embodiment of the invention, $Het^2$ denotes an unsubstituted or mono-, di- or trisubstituted, monocyclic heteroaryl having 2-5 C atoms and 1-3 N and/or O atoms, which can be substituted by R5. $Het^2$ denotes most preferably an unsubstituted or mono- or disubstituted pyrazolyl, furanyl, triazolyl or pyridinyl.

The terms "heterocycle" or "heterocyclyl" for the purposes of this invention refers to a mono- or polycyclic system of 3 to 20 ring atoms, preferably 3 to 14 ring atoms, more preferably 3 to 10 ring atoms, comprising 2 to 19 carbon atoms and 1, 2, 3, 4 or 5 heteroatoms, which are identical or different, in particular nitrogen, oxygen and/or sulfur. The cyclic system may be saturated or mono- or poly-unsaturated or aromatic. In the case of a cyclic system consisting of at least two rings the rings may be fused or spiro or otherwise connected. Such "heterocyclyl" radicals can be linked via any ring member. The term "heterocyclyl" also includes systems in which the heterocycle is part of a bi- or polycyclic saturated, partially unsaturated and/or aromatic system, such as where the heterocycle is fused to an "aryl", "cycloalkyl", "heteroaryl" or "heterocyclyl" group as defined herein via any desired and possible ring member of the heterocyclyl radical. The bonding to the compounds of the general formula (I) can be effected via any possible ring member of the heterocyclyl radical. Examples of suitable saturated and unsaturated "heterocyclyl" radicals are pyrrolidinyl, thiapyrrolidinyl, piperidinyl, piperazinyl, oxapiperazinyl, oxapiperidinyl, oxadiazolyl, tetrahydrofuryl, imidazolidinyl, thiazolidinyl, tetrahydropyranyl, morpholinyl, tetrahydrothiophenyl, dihydropyranyl.

In an aspect of the invention, "$Het^1$" denotes a saturated or unsaturated, mono-, bi- or tricyclic heterocycle having 2-19 C atoms and 1-5 N, O and/or S atoms, which can be substituted by at least one substituent selected from the group of Y, Hal, CN and OY if defined in terms of R1 radical, or which can be substituted by R5 if defined in terms of R2 radical. In a preferred embodiment of the invention, $Het^1$ denotes an unsubstituted or mono-, di- or trisubstituted, saturated or unsaturated, monocyclic heterocycle having 2-7 C atoms and 1-4 N, O and/or S atoms, wherein the substitution is defined as above. In a more preferred embodiment of the invention, $Het^1$ denotes an unsubstituted or mono-, di- or trisubstituted, unsaturated monocyclic heterocycle having 2-6 C atoms and 1-3 N, O and/or S atoms. In another preferred embodiment of the invention, $Het^1$ denotes an unsubstituted or mono- or disubstituted, unsaturated, bicyclic heterocycle having 7-9 C atoms and 1-2 N and/or O atoms, which can be substituted by R5. It shall be understood that the respective denotation of "$Het^1$" is independently of one another in the radicals R1 and R2.

It is preferred that "heterocycle" in the realms of "$Het^3$" represents a saturated, unsaturated or aromatic, mono-, bi- or tricyclic heterocycle having 2-19 C atoms and 1-5 N, S and/or O atoms, which can be substituted by at least one substituent selected from the group of Hal, A, —$(CYY)_n$—OY, —$(CYY)_n$—NYY, SY, $NO_2$, CN, COOY, —CO—NYY, —NY—COA, —NY—$SO_2$A, —$SO_2$—NYY, $S(O)_m$A, —NH—COOA, —NH—CO—NYY, CHO, COA, =S, =NY and =O. It is more preferred that $Het^3$ denotes a saturated monocyclic heterocycle having 2-7 C atoms and 1-4 N, O and/or S atoms, which can be mono, di- or trisubstituted by at least one substituent selected from the group of Hal, A, —$(CYY)_n$—OY, —$(CYY)_n$—NYY. In a most preferred embidiment of the invention, $Het^3$ is a saturated monocyclic heterocycle having 3-6 C atoms and 1-2 N and/or O atoms, which can be mono- or disubstituted by Hal or A. Highly preferred are pyrrolidinyl, morpholinyl, piperidinyl, piperazinyl, which can be monosubstituted by A.

In another embodiment of the invention, a "carbocycle", including, but not limited to, carboaryl, is defined as "Ar", which denotes a saturated, unsaturated or aromatic, mono- or bicyclic carbocycle having 3-10 C atoms, which can be substituted by R5. Examples of suitable "Ar" radicals are phenyl, o-, m- or p-tolyl, o-, m- or p-ethylphenyl, o-, m- or p-propylphenyl, o-, m- or p-isopropylphenyl, o-, m- or p-tert.-butylphenyl, o-, m- or p-hydroxyphenyl, o-, m- or p-methoxyphenyl, o-, m- or p-ethoxyphenyl, o-, m- or p-fluoro-phenyl, o-, m- or p-bromophenyl, o-, m- or p-chlorophenyl, o-, m- or p-sulfonamidophenyl, o-, m- or p-(N-methyl-sulfonamido) phenyl, o-, m- or p-(N,N-dimethyl-sulfonamido)phenyl, o-, m- or p-(N-ethyl-N-methyl-sulfonamido)phenyl, o-, m- or p-(N,N-diethyl-sulfonamido)-phenyl, particularly 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,3,4-, 2,3,5-, 2,3,6-, 2,4,6- or 3,4,5-trichlorophenyl, 2,4,6-trimethoxyphenyl, 2-hydroxy-3,5-dichlorophenyl, p-iodophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl or 2,5-dimethyl-4-chlorophenyl.

In another preferred embodiment of the invention, the "Ar" radical denotes a saturated, unsaturated or aromatic, mono- or bicyclic carbocycle having 6-10 C atoms, which can be substituted by at least one substituent by R5. In a more preferred embodiment of the invention, Ar denotes an unsubstituted or mono-, di- or trisubstituted, monocyclic carboaryl having 5-8 C atoms, which can be substituted by R5. In a most preferred embodiment of the invention, Ar denotes phenyl, which can be monosubstituted by R5. Highly preferred is phenyl.

The term "halogen", "halogen atom", "halogen substituent" or "Hal" for the purposes of this invention refers to one or, where appropriate, a plurality of fluorine (F, fluoro), bromine (Br, bromo), chlorine (Cl, chloro) or iodine (I, iodo) atoms. The designations "dihalogen", "trihalogen" and "perhalogen" refer respectively to two, three and four substituents, where each substituent can be selected independently from the group consisting of fluorine, chlorine, bromine and iodine. "Halogen" preferably means a fluorine, chlorine or bromine atom. Fluorine and chlorine are more preferred, when the halogens are substituted on an alkyl (haloalkyl) or alkoxy group (e.g. $CF_3$ and $CF_3O$).

It is a preferred embodiment of the invention that the heteroaryl sub-structure

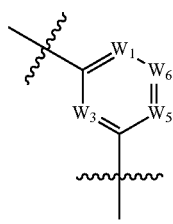

denotes pyridinyl, pyrimidinyl, triazinyl or pyridazinyl, each of which can be substituted by R3 and/or R4 in addition to R2. In addition, each nitrogen atom may bear an oxygen atom resulting in an N-oxide derivative. N-oxides can be prepared chemically or can be metabolites in vitro and in-vivo. Those skilled in the art may know other N-heteroaryl rings that can also be active in the meaning of the invention. It goes without saying that R3 and/or R4 are absent if $W_1$, $W_3$, $W_5$ and/or $W_6$ denote N. For the sake of clarity, R3 is the substituent in position 1 if $W_1$ is CR3, R3 is the substituent in position 3 if $W_3$ is CR3, R4 is the substituent in position 5 if $W_5$ is CR4, and R4 is the substituent in position 6 if $W_6$ is CR4.

The denotation of $W_1$, $W_3$, $W_5$ and $W_6$ can be easily assigned by the skilled artisan to each N-heteroaryl in the meaning of the invention. In a particular embodiment of the invention, for example, $W_1$ and $W_3$ are independently from one another N or CR3 and/or $W_5$ and $W_6$ are independently from one another N or CR4. It is especially preferred that at most two of $W_1$, $W_3$, $W_5$ and $W_6$ are CR3 and/or CR4, wherein CH shall be excluded. In a more particular embodiment of the invention, $W_1$ and $W_3$ are CR3, $W_5$ is CH and/or $W_6$ is N, which most particularly corresponds to pyridin-3-yl substituted by R2.

It is a preferred embodiment of the R2 radical according to the present invention to be Ar or $Het^2$, each of which can be substituted by R5. In another preferred embodiment of the invention, the R2 radical denotes, together with one adjacent R3, an annellated cyclic ring system, which can be unsubstituted or mono- or disubstituted by R5. Said ring system particularly relates to an annellated alicyclic or heterocyclic ring system, which is more particularly 5- or 6-membered, most particularly an annellated phenyl ring, each of which can be substituted as defined above.

It is a preferred embodiment of the R3 and R4 radical according to the present invention to be independently from one another H, NHY, —NH—COY, A or OA, more preferably H, NHY or —NH—COY.

It is a preferred embodiment according to the present invention that R5 denotes Hal, A, —(CYY)$_n$—OY, —(CYY)$_n$—NYY, (CYY)$_n$-$Het^3$, —NY—COA, —CO—NY—(CYY)$_n$—NYY, —O(CYY)$_n$-$Het^3$, =O, —SO$_2$—NYY, —O(CYY)$_n$—CO—NYY, —O(CYY)$_n$—NYY, —(CYY)$_n$—NYY or COA, more preferably Hal, A, —(CYY)$_n$—OY, —(CYY)$_n$—NYY or (CYY)$_n$-$Het^3$.

Accordingly, the subject-matter of the invention relates to compounds of formula (I), in which at least one of the aforementioned radicals has any meaning, particularly realize any preferred embodiment, as described above. Radicals, which are not explicitly specified in the context of any embodiment of formula (I), sub-formulae thereof or other radicals thereto, shall be construed to represent any respective denotations according to formula (I) as disclosed hereunder for solving the problem of the invention. That means, the aforementioned radicals may adopt all designated meanings as each described in the prior or following course of the present specification, irrespective of the context to be found, including, but not limited to, any preferred embodiments. It shall be particularly understood that any embodiment of a certain radical can be combined with any embodiment of one or more other radicals.

In a more preferred embodiment of the present invention, hetaryl-[1,8]naphthyridine derivatives of formula (II) are provided,

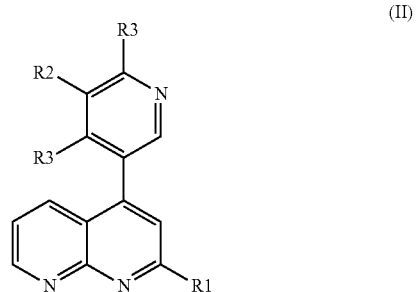

wherein
R1 denotes phenyl or a monocyclic heteroaryl having 3-5 C-atoms and 1-3 N atoms, each of which can be mono-, di- or trisubstituted by at least one substituent selected from the group of A, Hal, CN and OA;
R2 denotes phenyl, a monocyclic heteroaryl having 2-5 C atoms and 1-3 N and/or O atoms, or an unsaturated bicyclic heterocycle having 7-9 C atoms and 1-2 N and/or O atoms, each of which can be mono- or disubstituted by at least one substituent selected from the group of Hal, A, —(CYY)$_n$—OY, —(CYY)$_n$—NYY, (CYY)$_n$-Het$^3$, —NY—COA, —CO—NY—(CYY)$_n$—NYY, —O(CYY)$_n$-Het$^3$, =O, —SO$_2$—NYY, —O(CYY)$_n$—CO—NYY, —O(CYY)$_n$—NYY, —(CYY)$_n$—NYY, COA;
R3 denotes independently from one another H, NHY or —NH—COY;
R2, R3 together also denote unbranched alkenyl having 3-4 C atoms, which can be monosubstituted by R5 and/or in which 1-2 C atoms can be replaced independently from one another by N, O and/or S, under the proviso that R2 and at most one R2-adjacent R3 are together;
R5 denotes Hal, A, —(CYY)$_n$—OY, —(CYY)$_n$—NYY, (CYY)$_n$-Het$^3$, —NY—COA, —CO—NY—(CYY)$_n$—NYY, —O(CYY)$_n$-Het$^3$, =O, —SO$_2$—NYY, —O(CYY)$_n$—CO—NYY, —O(CYY)$_n$—NYY, —(CYY)$_n$—NYY or COA;
Y denotes H or A;
A denotes 1-4 C atoms, in which 1-5 atoms may be replaced by F and/or Cl;
Het$^3$ denotes a saturated monocyclic heterocycle having 3-6 C atoms and 1-2 N and/or O atoms, which can be mono- or disubstituted by at least one substituent selected from the group of Hal, A, —(CYY)$_n$—OY, —(CYY)$_n$—NYY,
Hal denotes F, Cl, Br or I; and
n denotes 0, 1, 2, 3 or 4;
and/or physiologically acceptable salts thereof.

Most preferred embodiments are those compounds of formulae (I) and/or (II) as listed in Table 1.

TABLE 1

Compounds of formulae (I), (II)

| No. | Structure | Name; Mass | HPLC/MS R$_t$ [min] | HPLC/MS [M + H] | TβR activity (Example 36)  0 / + / ++ / +++ | TβR activity (Example 35A) >10 μM / 1-10 μM / 0.1-1 μM / <0.1 μM |
|---|---|---|---|---|---|---|
| 1 | Quinoline control | 2-(5-Chloro-2-fluoro-phenyl)-4-isoquinolin-4-yl-quinoline M 384.84 | 2.94 | 385 | + | + |
| 2 | 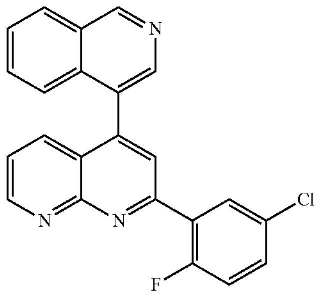 [SMILES: Fc1ccc(Cl)cc1-c1cc(-c2cncc3ccccc23)c2cccnc2n1] | 2-(5-Chloro-2-fluoro-phenyl)-4-isoquinolin-4-yl-[1,8]naphthyridine M 385.83 | 2.22 | 386 | ++ | + |

TABLE 1-continued

Compounds of formulae (I), (II)

| No. | Structure | Name; Mass | HPLC/MS R$_t$ [min] | HPLC/MS [M + H] | TβR activity (Example 36) 0 + ++ +++ | TβR activity (Example 35A) >10 μM 1-10 μM 0.1-1 μM <0.1 μM |
|---|---|---|---|---|---|---|
| 3 | 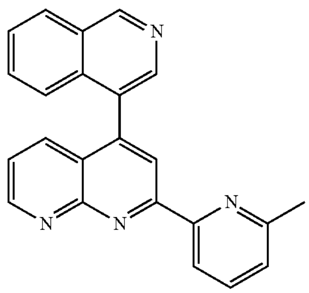 [SMILES: Cc1cccc(-c2cc(-c3cncc4ccccc34)c3cccnc3n2)n1] | 4-Isoquinolin-4-yl-2-(6-methyl-pyridin-2-yl)-[1,8]naphthyridine M 348.41 | 1.76 | 349 | + | 0 |
| 4 | 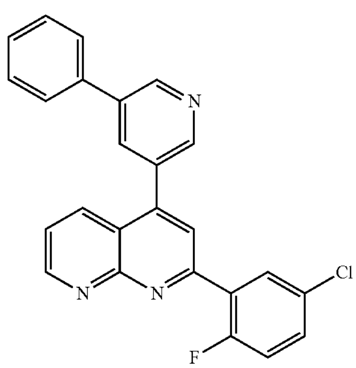 [SMILES: Fc1ccc(Cl)cc1-c1cc(-c2cncc(-c3ccccc3)c2)c2cccnc2n1] | 2-(5-Chloro-2-fluoro-phenyl)-4-(5-phenyl-pyridin-3-yl)-[1,8]naphthyridine M 411.87 | 2.53 | 412 | ++ | ++ |
| 5 | 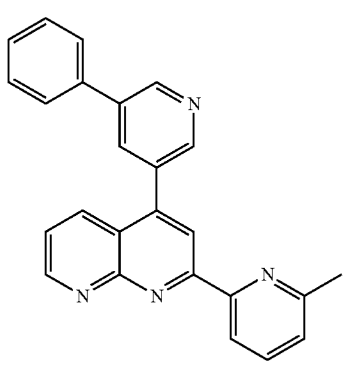 [SMILES: Cc1cccc(-c2cc(-c3cncc(-c4ccccc4)c3)c3cccnc3n2)n1] | 2-(6-Methyl-pyridin-2-yl)-4-(5-phenyl-pyridin-3-yl)-[1,8]naphthyridine M 374.45 | 2.18 | 375 | ++ | + |

TABLE 1-continued

Compounds of formulae (I), (II)

| | | | HPLC/ MS $R_t$ [min] | HPLC/ MS [M + H] | TβR activity (Example 36) 0 + ++ +++ | TβR activity (Example 35A) >10 μM 1-10 μM 0.1-1 μM <0.1 μM |
|---|---|---|---|---|---|---|
| No. | Structure | Name; Mass | | | | |
| 6 | quinoline control | 2-(5-Chloro-2-fluoro-phenyl)-4-(5-phenyl-pyridin-3-yl)-quinoline M 410.88 | 2.20 | 411 | + | 0 |
| 7 | | 2-(5-Chloro-2-fluoro-phenyl)-4-[5-(1-methyl-1H-pyrazol-4-yl)-pyridin-3-yl]-[1,8]naphthyridine | 2.09 | 416 | +++ | ++ |
| 8 | | 2-(2-Fluoro-5-trifluoromethyl-phenyl)-4-[5-(1-methyl-1H-pyrazol-4-yl)-pyridin-3-yl]-[1,8]naphthyridine | 2.17 | 450 | +++ | ++ |

TABLE 1-continued

Compounds of formulae (I), (II)

| No. | Structure | Name; Mass | HPLC/MS R_t [min] | HPLC/MS [M + H] | TβR activity (Example 36)  0   + ++ +++ | TβR activity (Example 35A) >10 μM 1-10 μM 0.1-1 μM <0.1 μM |
|---|---|---|---|---|---|---|
| 9 | 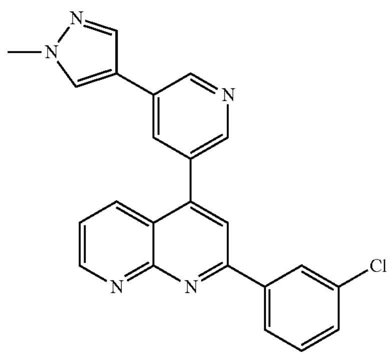 [SMILES: Cn1cc(-c2cncc(-c3cc(-c4cccc(Cl)c4)nc4ncccc34)c2)cn1] | 2-(3-Chloro-phenyl)-4-[5-(1-methyl-1H-pyrazol-4-yl)-pyridin-3-yl]-[1,8]naphthyridine | 2.08 | 398 | ++ | + |
| 10 | 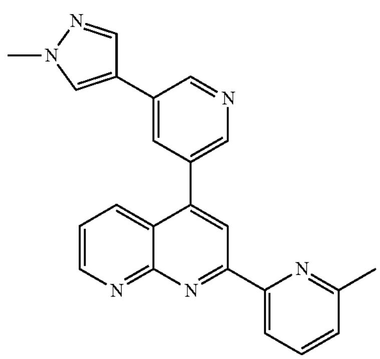 | 4-[5-(1-Methyl-1H-pyrazol-4-yl)-pyridin-3-yl]-2-(6-methyl-pyridin-2-yl)-[1,8]naphthyridine | 1.68 | 379 | ++ | + |
| 11 | 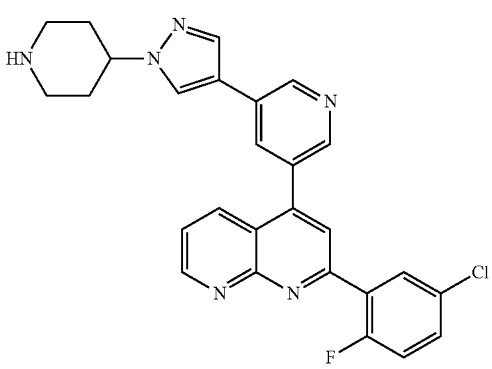 [SMILES: Fc1ccc(Cl)cc1-c1cc(-c2cncc(-c3cnn(C4CCNCC4)c3)c2)c2cccnc2n1] | 2-(5-Chloro-2-fluoro-phenyl)-4-[5-(1-piperidin-4-yl-1H-pyrazol-4-yl)-pyridin-3-yl]-[1,8]naphthyridine dihydrochloride | 1.65 | 485 | +++ | +++ |

TABLE 1-continued

Compounds of formulae (I), (II)

| No. | Structure | Name; Mass | HPLC/MS R$_t$ [min] | HPLC/MS [M + H] | TβR activity (Example 36) 0 + ++ +++ | TβR activity (Example 35A) >10 μM 1-10 μM 0.1-1 μM <0.1 μM |
|---|---|---|---|---|---|---|
| 12 | 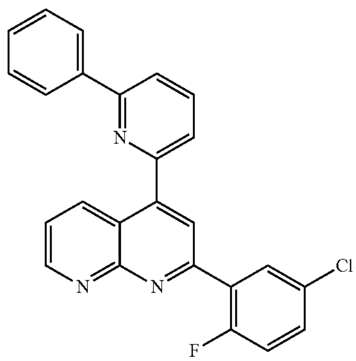 [SMILES: Fc1ccc(Cl)cc1-c1cc(-c2cccc(-c3ccccc3)n2)c2cccnc2n1] | 2-(5-Chloro-2-fluoro-phenyl)-4-(6-phenyl-pyridin-2-yl)-[1,8]naphthyridine | 2.73 | 412 | 0 | 0 |
| 13 | 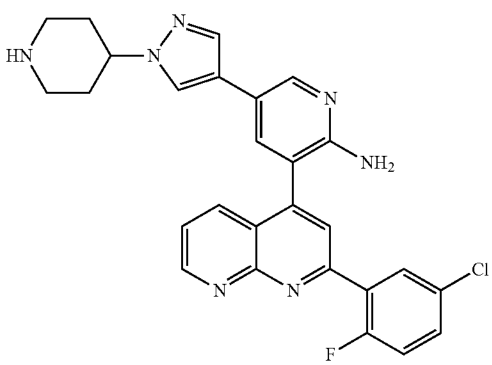 [SMILES: Nc1ncc(-c2cnn(C3CCNCC3)c2)cc1-c1cc(-c2cc(Cl)ccc2F)nc2ncccc12] | 3-[2-(5-Chloro-2-fluoro-phenyl)-[1,8]naphthyridin-4-yl]-5-(1-piperidin-4-yl-1H-pyrazol-4-yl)-pyridin-2-ylamine dihydrochloride | 1.35 | 500 | +++ | +++ |
| 14 | 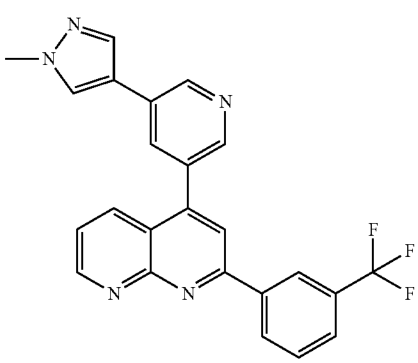 [SMILES: Cn1cc(-c2cncc(-c3cc(-c4cccc(C(F)(F)F)c4)nc4ncccc34)c2)cn1] | 4-[5-(1-Methyl-1H-pyrazol-4-yl)-pyridin-3-yl]-2-(3-trifluoromethyl-phenyl)-[1,8]naphthyridine | 2.17 | 432 | ++ | + |

TABLE 1-continued

Compounds of formulae (I), (II)

| No. | Structure | Name; Mass | HPLC/MS R$_t$ [min] | HPLC/MS [M + H] | TβR activity (Example 36) 0 + ++ +++ | TβR activity (Example 35A) >10 μM 1-10 μM 0.1-1 μM <0.1 μM |
|---|---|---|---|---|---|---|
| 15 | 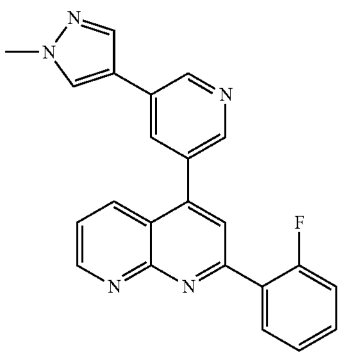 [SMILES: Cn1cc(-c2cncc(-c3cc(-c4ccccc4F)nc4ncccc34)c2)cn1] | 2-(2-Fluoro-phenyl)-4-[5-(1-methyl-1H-pyrazol-4-yl)-pyridin-3-yl]-[1,8]naphthyridine | 1.90 | 382 | +++ | ++ |
| 16 | 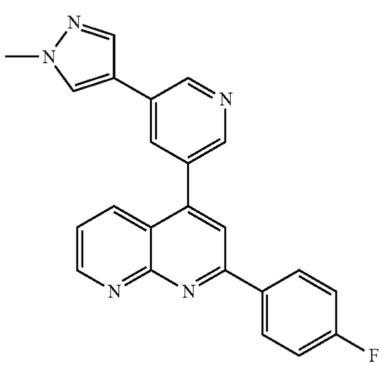 [SMILES: Cn1cc(-c2cncc(-c3cc(-c4ccc(F)cc4)nc4ncccc34)c2)cn1] | 2-(4-Fluoro-phenyl)-4-[5-(1-methyl-1H-pyrazol-4-yl)-pyridin-3-yl]-[1,8]naphthyridine | 1.93 | 382 | ++ | + |
| 17 | 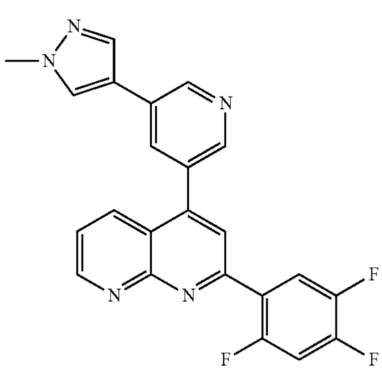 [SMILES: Cn1cc(-c2cncc(-c3cc(-c4cc(F)c(F)cc4F)nc4ncccc34)c2)cn1] | 4-[5-(1-Methyl-1H-pyrazol-4-yl)-pyridin-3-yl]-2-(2,4,5-trifluoro-phenyl)-[1,8]naphthyridine | 2.04 | 418 | ++ | + |

TABLE 1-continued

Compounds of formulae (I), (II)

| No. | Structure | Name; Mass | HPLC/MS R$_t$ [min] | HPLC/MS [M + H] | TβR activity (Example 36) 0 + ++ +++ | TβR activity (Example 35A) >10 μM 1-10 μM 0.1-1 μM <0.1 μM |
|---|---|---|---|---|---|---|
| 18 | 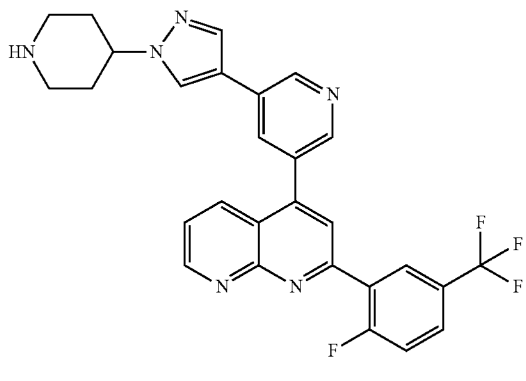 [SMILES: Fc1ccc(C(F)(F)F)cc1-c1cc(-c2cncc(-c3cnn(C4CCNCC4)c3)c2)c2cccnc2n1] | 2-(2-Fluoro-5-trifluoromethyl-phenyl)-4-[5-(1-piperidin-4-yl)-1H-pyrazol-4-yl)-pyridin-3-yl]-[1,8]naphthyridine dihydrochloride | 1.73 | 499 | +++ | +++ |
| 19 | 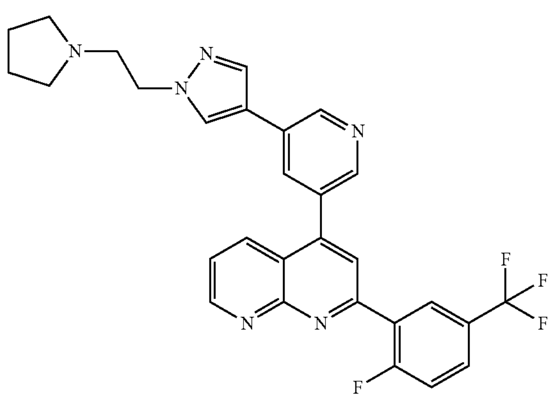 [SMILES: Fc1ccc(C(F)(F)F)cc1-c1cc(-c2cncc(-c3cnn(CCN4CCCC4)c3)c2)c2cccnc2n1] | 2-(2-Fluoro-5-trifluoromethyl-phenyl)-4-{5-[1-(2-pyrrolidin-1-yl-ethyl)-1H-pyrazol-4-yl]-pyridin-3-yl}-[1,8]naphthyridine | 1.74 | 533 | +++ | +++ |
| 20 | 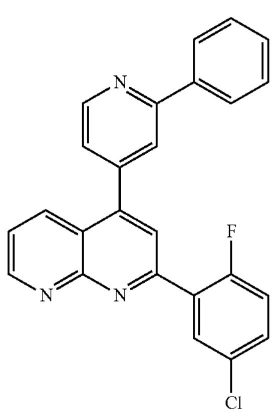 [SMILES: Fc1ccc(Cl)cc1-c1cc(-c2ccnc(-c3ccccc3)c2)c2cccnc2n1] | 2-(5-Chloro-2-fluoro-phenyl)-4-(2-phenyl-pyridin-4-yl)-[1,8]naphthyridine M 411.87 | 2.55 | 412 | 0 | 0 |

TABLE 1-continued

Compounds of formulae (I), (II)

| No. | Structure | Name; Mass | HPLC/MS R_t [min] | HPLC/MS [M + H] | TβR activity (Example 36)  0  +  ++  +++ | TβR activity (Example 35A) >10 μM 1-10 μM 0.1-1 μM <0.1 μM |
|---|---|---|---|---|---|---|
| 21 | 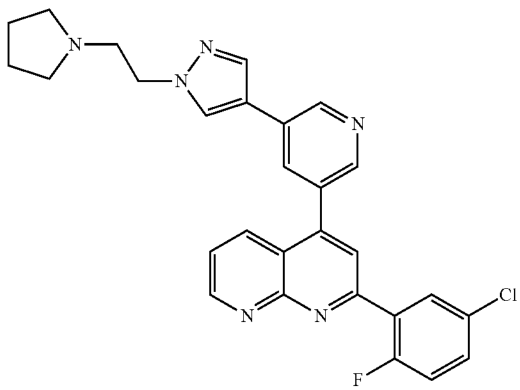 [SMILES: Fc1ccc(Cl)cc1-c1cc(-c2cncc(-c3cnn(CCN4CCCC4)c3)c2)c2cccnc2n1] | 2-(5-Chloro-2-fluoro-phenyl)-4-{5-[1-(2-pyrrolidin-1-yl-ethyl)-1H-pyrazol-4-yl]-pyridin-3-yl}-[1,8]naphthyridine | 1.67 | 499 | +++ | +++ |
| 22 | 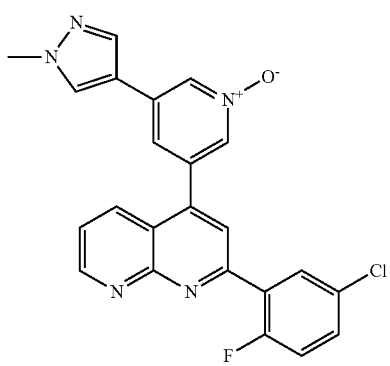 [SMILES: Cn1cc(-c2cc(-c3cc(-c4cc(Cl)ccc4F)nc4ncccc34)c[n+]([O-])c2)cn1] | 2-(5-Chloro-2-fluoro-phenyl)-4-[5-(1-methyl-1H-pyrazol-4-yl)-1-oxy-pyridin-3-yl]-[1,8]naphthyridine | 1.86 | 432 | + | + |
| 23 | 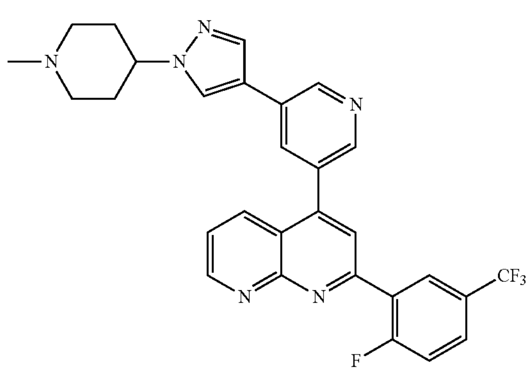 [SMILES: CN1CCC(n2cc(-c3cncc(-c4cc(-c5cc(C(F)(F)F)ccc5F)nc5ncccc45)c3)cn2)CC1] | 2-(2-Fluoro-5-trifluoromethyl-phenyl)-4-{5-[1-(1-methyl-piperidin-4-yl)-1H-pyrazol-4-yl]-pyridin-3-yl}-[1,8]naphthyridine | 1.72 | 533 | +++ | +++ |

TABLE 1-continued

Compounds of formulae (I), (II)

| No. | Structure | Name; Mass | HPLC/MS R$_t$ [min] | HPLC/MS [M + H] | TβR activity (Example 36) 0 + ++ +++ | TβR activity (Example 35A) >10 μM 1-10 μM 0.1-1 μM <0.1 μM |
|---|---|---|---|---|---|---|
| 24 | 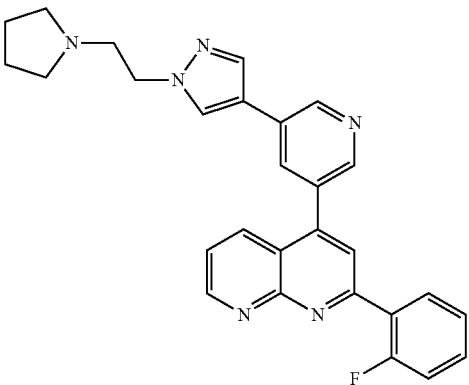 [SMILES: Fc1ccccc1-c1cc(-c2cncc(-c3cnn(CCN4CCCC4)c3)c2)c2cccnc2n1] | 2-(2-Fluoro-phenyl)-4-{5-[1-(2-pyrrolidin-1-yl-ethyl)-1H-pyrazol-4-yl]-pyridin-3-yl}-[1,8]naphthyridine | 1.51 | 465 | +++ | +++ |
| 25 | 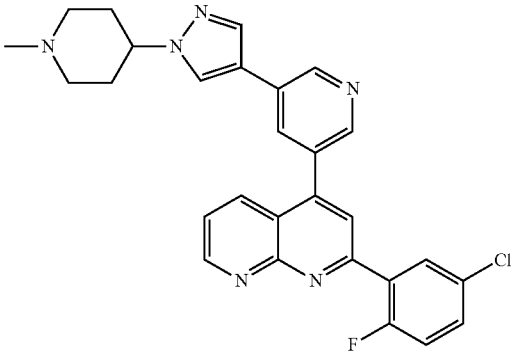 | 2-(5-Chloro-2-fluoro-phenyl)-4-{5-[1-(1-methyl-piperidin-4-yl)-1H-pyrazol-4-yl]-pyridin-3-yl}-[1,8]naphthyridine formate | 1.61 | 499 | +++ | +++ |
| 26 | 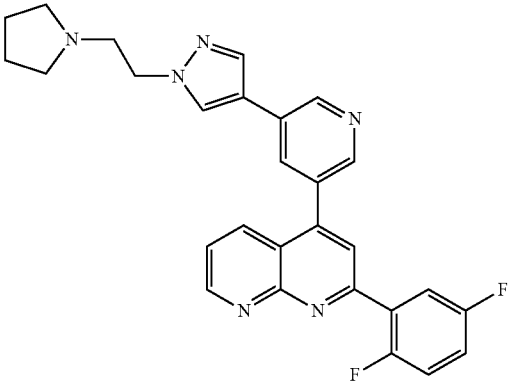 [SMILES: Fc1ccc(F)c(-c2cc(-c3cncc(-c4cnn(CCN5CCCC5)c4)c3)c3cccnc3n2)c1] | 2-(2,5-Difluoro-phenyl)-4-{5-[1-(2-pyrrolidin-1-yl-ethyl)-1H-pyrazol-4-yl]-pyridin-3-yl}-[1,8]naphthyridine | 1.47 | 483 | +++ | +++ |

TABLE 1-continued

Compounds of formulae (I), (II)

| No. | Structure | Name; Mass | HPLC/MS R_t [min] | HPLC/MS [M + H] | TβR activity (Example 36) 0 + ++ +++ | TβR activity (Example 35A) >10 μM 1-10 μM 0.1-1 μM <0.1 μM |
|-----|-----------|------------|-------|---------|-----|-----|
| 27 | 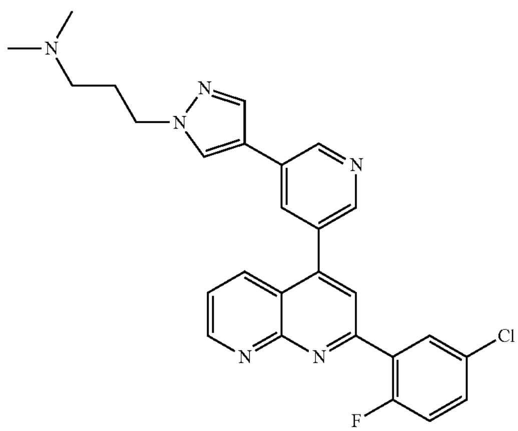 [SMILES: CN(C)CCCn1cc(-c2cncc(-c3cc(-c4cc(Cl)ccc4F)nc4ncccc34)c2)cn1] | [3-(4-{5-[2-(5-Chloro-2-fluoro-phenyl)-[1,8]naphthyridin-4-yl]-pyridin-3-yl}-pyrazol-1-yl)-propyl]-dimethyl-amine | 1.64 | 487 | +++ | +++ |
| 28 | 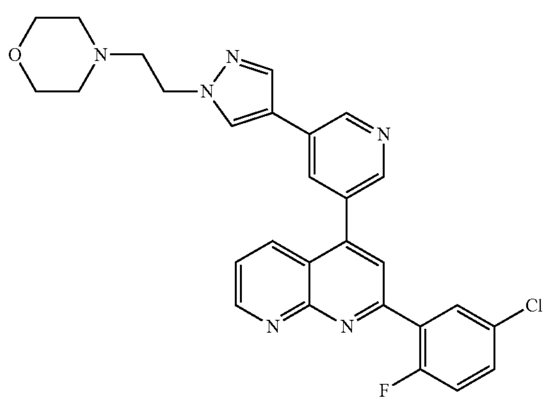 [SMILES: Fc1ccc(Cl)cc1-c1cc(-c2cncc(-c3cnn(CCN4CCOCC4)c3)c2)c2cccnc2n1] | 2-(5-Chloro-2-fluoro-phenyl)-4-{5-[1-(2-morpholin-4-yl-ethyl)-1H-pyrazol-4-yl]-pyridin-3-yl}-[1,8]naphthyridine | 1.66 | 515 | +++ | +++ |
| 29 | 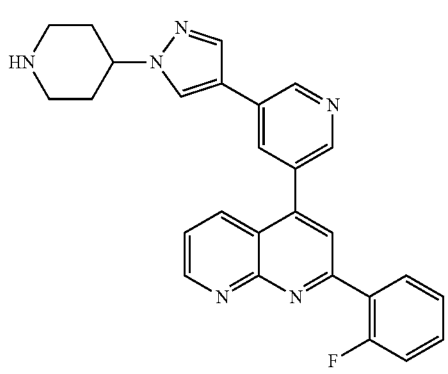 [SMILES: Fc1ccccc1-c1cc(-c2cncc(-c3cnn(C4CCNCC4)c3)c2)c2cccnc2n1] | 2-(2-Fluoro-phenyl)-4-[5-(1-piperidin-4-yl-1H-pyrazol-4-yl)-pyridin-3-yl]-[1,8]naphthyridine dihydrochloride | 1.52 | 451 | +++ | +++ |

TABLE 1-continued

Compounds of formulae (I), (II)

| No. | Structure | Name; Mass | HPLC/MS R$_t$ [min] | HPLC/MS [M + H] | TβR activity (Example 36) 0 + ++ +++ | TβR activity (Example 35A) >10 μM 1-10 μM 0.1-1 μM <0.1 μM |
|---|---|---|---|---|---|---|
| 30 | 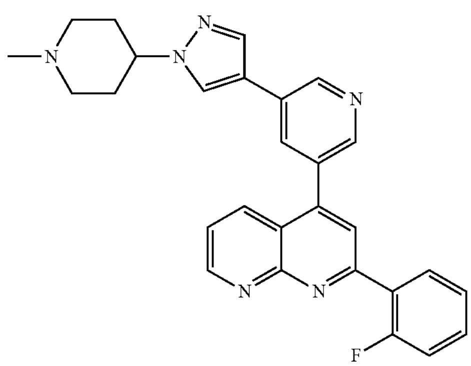 | 2-(2-Fluoro-phenyl)-4-{5-[1-(1-methyl-piperidin-4-yl)-1H-pyrazol-4-yl]-pyridin-3-yl}-[1,8]naphthyridine | 1.37 | 465 | +++ | +++ |
| 31 | 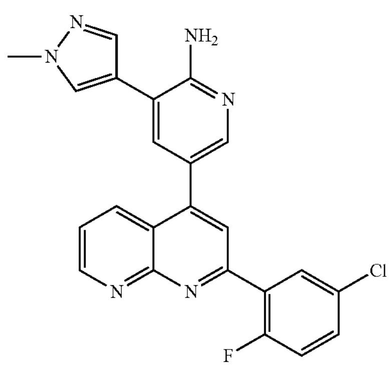 [SMILES: Cn1cc(-c2cc(-c3cc(-c4cc(Cl)ccc4F)nc4ncccc34)cnc2N)cn1] | 5-[2-(5-Chloro-2-fluoro-phenyl)-[1,8]naphthyridin-4-yl]-3-(1-methyl-1H-pyrazol-4-yl)-pyridin-2-ylamine | 1.56 | 431 | + | 0 |
| 32 | 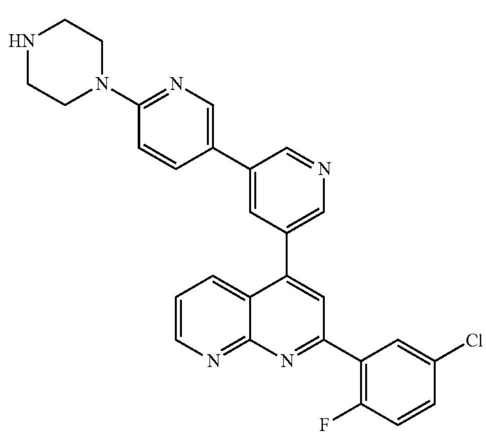 [SMILES: Fc1ccc(Cl)cc1-c1cc(-c2cncc(-c3ccc(N4CCNCC4)nc3)c2)c2cccnc2n1] | 2-(5-Chloro-2-fluoro-phenyl)-4-(6'-piperazin-1-yl-[3,3']bipyridinyl-5-yl)-[1,8]naphthyridine | 1.66 | 497 | +++ | ++ |

TABLE 1-continued

Compounds of formulae (I), (II)

| No. | Structure | Name; Mass | HPLC/ MS R_t [min] | HPLC/ MS [M + H] | TβR activity (Example 36) 0 + ++ +++ | TβR activity (Example 35A) >10 μM 1-10 μM 0.1-1 μM <0.1 μM |
|---|---|---|---|---|---|---|
| 33 | 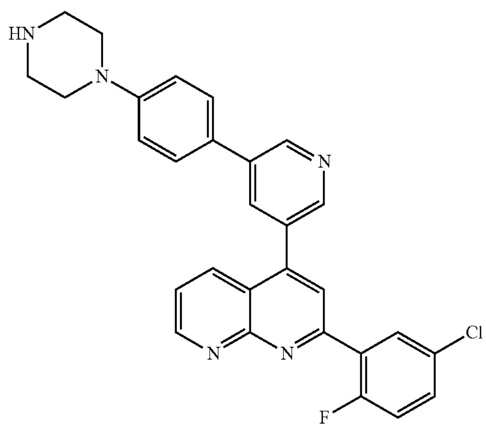 [SMILES: Fc1ccc(Cl)cc1-c1cc(-c2cncc(-c3ccc(N4CCNCC4)cc3)c2)c2cccnc2n1] | 2-(5-Chloro-2-fluoro-phenyl)-4-[5-(4-piperazin-1-yl-phenyl)-pyridin-3-yl]-[1,8]naphthyridine | 1.66 | 496 | +++ | +++ |
| 34 | 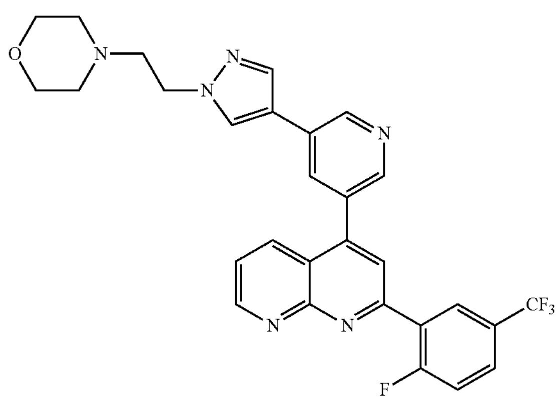 [SMILES: Fc1ccc(C(F)(F)F)cc1-c1cc(-c2cncc(-c3cnn(CCN4CCOCC4)c3)c2)c2cccnc2n1] | 2-(2-Fluoro-5-trifluoromethyl-phenyl)-4-{5-[1-(2-morpholin-4-yl-ethyl)-1H-pyrazol-4-yl]-pyridin-3-yl}-[1,8]naphthyridine | 1.66 | 549 | +++ | ++ |
| 35 | 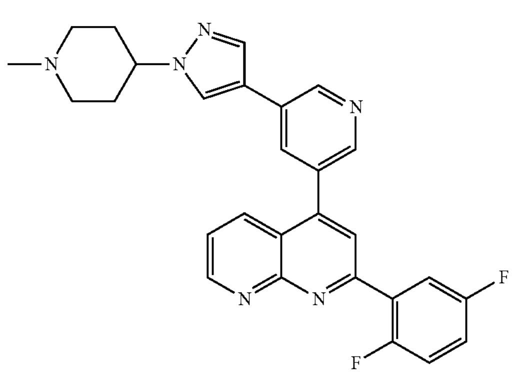 [SMILES: CN1CCC(n2cc(-c3cncc(-c4cc(-c5cc(F)ccc5F)nc5ncccc45)c3)cn2)CC1] | 2-(2,5-Difluoro-phenyl)-4-{5-[1-(1-methyl-piperidin-4-yl)-1H-pyrazol-4-yl]-pyridin-3-yl}-[1,8]naphthyridine | 1.42 | 483 | +++ | +++ |

TABLE 1-continued

Compounds of formulae (I), (II)

|  |  |  |  |  | TβR activity (Example 36) | TβR activity (Example 35A) |
|---|---|---|---|---|---|---|
|  |  |  | HPLC/ MS |  | 0 | >10 μM |
|  |  |  | MS | HPLC/ | + | 1-10 μM |
|  |  | Name; | R$_t$ | MS | ++ | 0.1-1 μM |
| No. | Structure | Mass | [min] | [M + H] | +++ | <0.1 μM |
| 36 |  | 2-(5-Chloro-2-fluoro-phenyl)-4-[6'-(4-methyl-piperazin-1-yl)-[3,3']bipyridinyl-5-yl]-[1,8]naphthyridine | 1.55 | 511 | +++ | +++ |
| 37 |  | 2-(4-{5-[2-(2-Fluoro-5-trifluoromethyl-phenyl)-[1,8]naphthyridin-4-yl]-pyridin-3-yl}-pyrazol-1-yl)-ethanol | 1.97 | 480 | +++ | ++ |
| 38 |  | 2-(5-Chloro-2-fluoro-phenyl)-4-{5-[4-(4-methyl-piperazin-1-yl)-phenyl]-pyridin-3-yl}-[1,8]naphthyridine | 1.68 | 510 | +++ | +++ |

TABLE 1-continued

Compounds of formulae (I), (II)

| | | | | | TβR activity (Example 36) | TβR activity (Example 35A) |
|---|---|---|---|---|---|---|
| | | | HPLC/ MS | | 0 | >10 μM |
| | | | R$_t$ | HPLC/ MS | + | 1-10 μM |
| | | Name; | | | ++ | 0.1-1 μM |
| No. | Structure | Mass | [min] | [M + H] | +++ | <0.1 μM |
| 39 | | 2-(4-{5-[2-(5-Chloro-2-fluoro-phenyl)-[1,8]naphthyridin-4-yl]-pyridin-3-yl}-pyrazol-1-yl)-ethanol | 1.88 | 446 | | +++ |
| 40 | | 2-(4-{5-[2-(2-Fluoro-phenyl)-[1,8]naphthyridin-4-yl]-pyridin-3-yl}-pyrazol-1-yl)-ethanol | 1.70 | 412 | | ++ |
| 41 | | 2-(2-Fluoro-phenyl)-4-{5-[1-(2-morpholin-4-yl-ethyl)-1H-pyrazol-4-yl]-pyridin-3-yl}-[1,8]naphthyridine | 1.47 | 481 | | ++ |

TABLE 1-continued

Compounds of formulae (I), (II)

| No. | Structure | Name; Mass | HPLC/ MS R<sub>t</sub> [min] | HPLC/ MS [M + H] | TβR activity (Example 36) 0 + ++ +++ | TβR activity (Example 35A) >10 μM 1-10 μM 0.1-1 μM <0.1 μM |
|---|---|---|---|---|---|---|
| 42 | 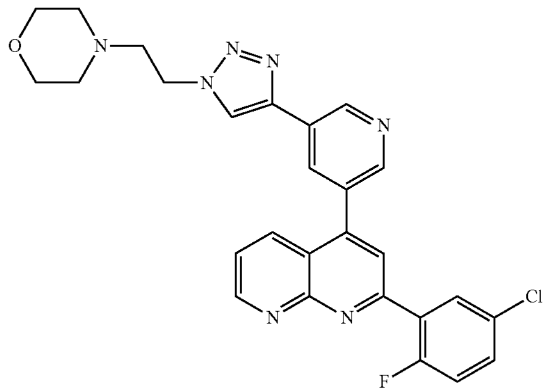 [SMILES: Fc1ccc(Cl)cc1-c1cc(-c2cncc(-c3cn(CCN4CCOCC4)nn3)c2)c2cccnc2n1] | 2-(5-Chloro-2-fluoro-phenyl)-4-{5-[1-(2-morpholin-4-yl-ethyl)-1H-[1,2,3]triazol-4-yl]-pyridin-3-yl}-[1,8]naphthyridine | 1.50 | 516 | ++ | |
| 43 | 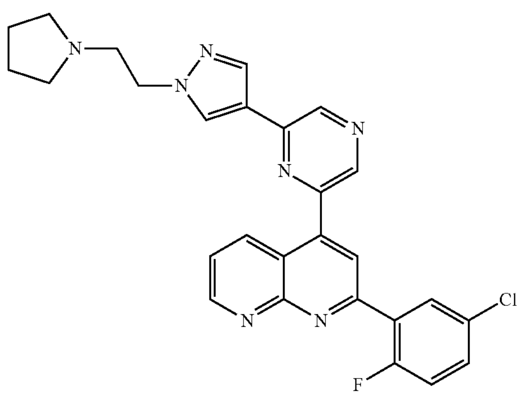 [SMILES: Fc1ccc(Cl)cc1-c1cc(-c2cncc(-c3cnn(CCN4CCCC4)c3)n2)c2cccnc2n1] | 2-(5-Chloro-2-fluoro-phenyl)-4-{6-[1-(2-pyrrolidin-1-yl-ethyl)-1H-pyrazol-4-yl]-pyrazin-2-yl}-[1,8]naphthyridine | 1.52 | 500 | | |
| 44 | 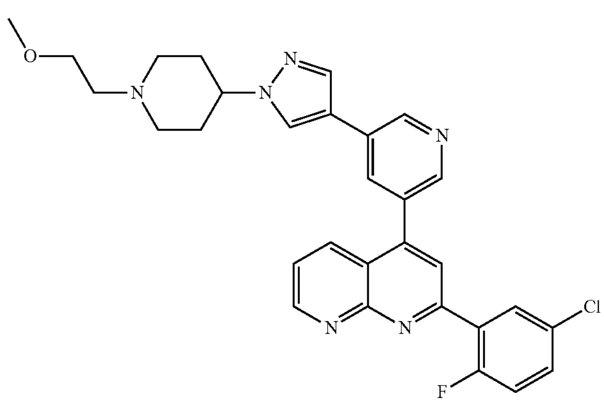 [SMILES: COCCN1CCC(n2cc(-c3cncc(-c4cc(-c5cc(Cl)ccc5F)nc5ncccc45)c3)cn2)CC1] | 2-(5-Chloro-2-fluoro-phenyl)-4-(5-{1-[1-(2-methoxy-ethyl)-piperidin-4-yl]-1H-pyrazol-4-yl}-pyridin-3-yl)-[1,8]naphthyridine | 1.65 | 543 | +++ | +++ |

TABLE 1-continued

Compounds of formulae (I), (II)

| No. | Structure | Name; Mass | HPLC/MS R_t [min] | HPLC/MS [M + H] | TβR activity (Example 36) 0 + ++ +++ | TβR activity (Example 35A) >10 μM 1-10 μM 0.1-1 μM <0.1 μM |
|---|---|---|---|---|---|---|
| 45 | 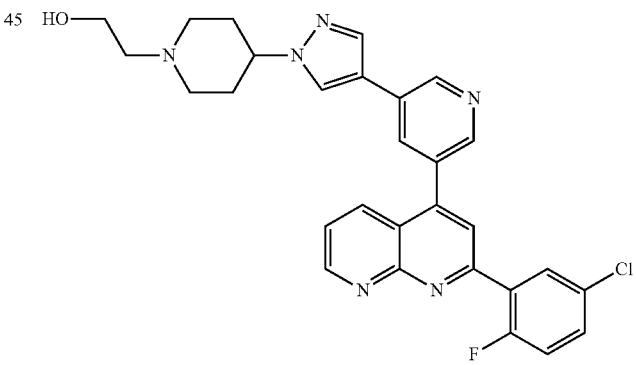 | 2-[4-(4-{5-[2-(5-Chloro-2-fluoro-phenyl)-[1,8]naphthyridin-4-yl]-pyridin-3-yl}-pyrazol-1-yl)-piperidin-1-yl]-ethanol | 1.60 | 529 | +++ | +++ |
| 46 | 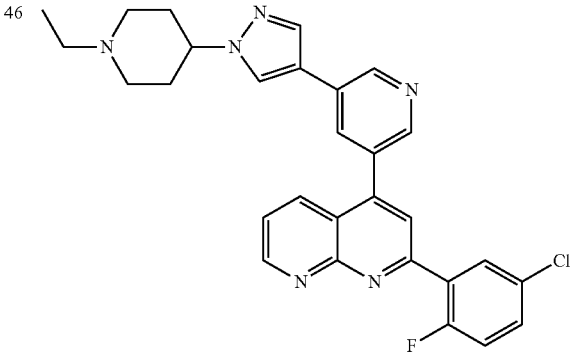 | 2-(5-Chloro-2-fluoro-phenyl)-4-{5-[1-(1-ethyl-piperidin-4-yl)-1H-pyrazol-4-yl]-pyridin-3-yl}-[1,8]naphthyridine | 2.00 | 513 | +++ | +++ |
| 47 | 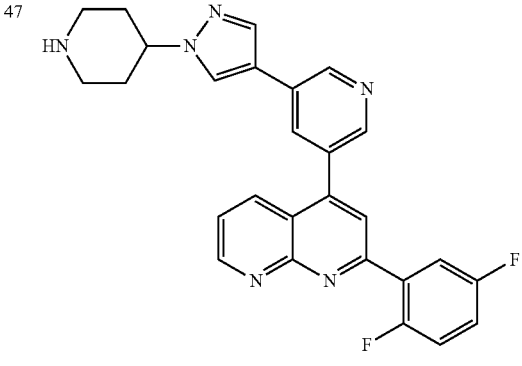 [SMILES: CCN1CCC(n2cc(-c3cncc(-c4cc(-c5cc(Cl)ccc5F)nc5ncccc45)c3)cn2)CC1] | 2-(2,5-Difluoro-phenyl)-4-[5-(1-piperidin-4-yl-1H-pyrazol-4-yl)-pyridin-3-yl]-[1,8]naphthyridine | 1.54 | 469 | +++ | +++ |

TABLE 1-continued

Compounds of formulae (I), (II)

| No. | Structure | Name; Mass | HPLC/ MS R_t [min] | HPLC/ MS [M + H] | TβR activity (Example 36) 0 + ++ +++ | TβR activity (Example 35A) >10 μM 1-10 μM 0.1-1 μM <0.1 μM |
|---|---|---|---|---|---|---|
| 48 | 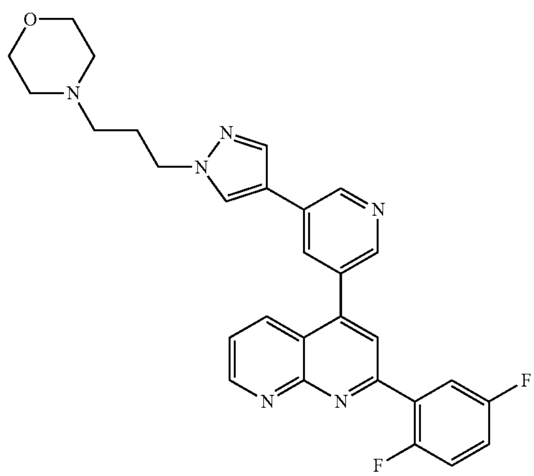 [SMILES: Fc1ccc(F)c(-c2cc(-c3cncc(-c4cnn(CCCN5CCOCC5)c4)c3)c3cccnc3n2)c1] | 2-(2,5-Difluoro-phenyl)-4-{5-[1-(3-morpholin-4-yl-propyl)-1H-pyrazol-4-yl]-pyridin-3-yl}-[1,8]naphthyridine | 1.51 | 513 | +++ | ++ |
| 49 | 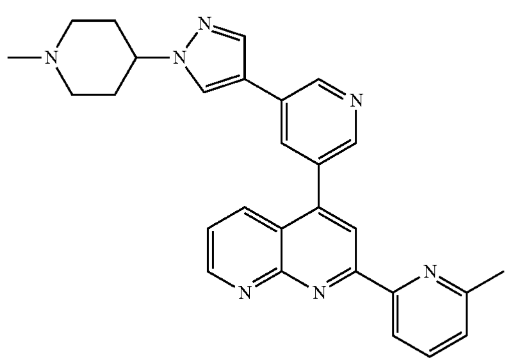 | 4-{5-[1-(1-Methyl-piperidin-4-yl)-1H-pyrazol-4-yl]-pyridin-3-yl}-2-(6-methyl-pyridin-2-yl)-[1,8]naphthyridine | 1.31 | 462 | +++ | +++ |
| 50 | 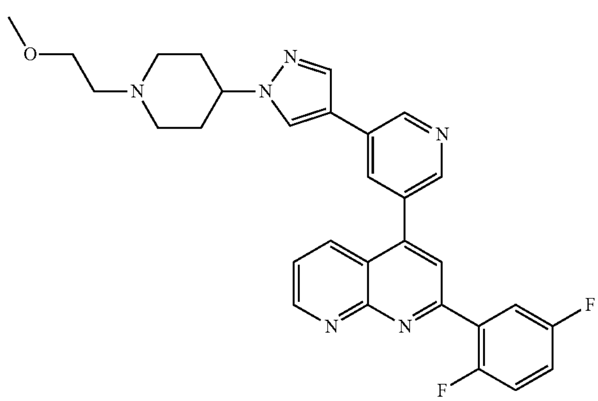 [SMILES: COCCN1CCC(n2cc(-c3cncc(-c4cc(-c5cc(F)ccc5F)nc5ncccc45)c3)cn2)CC1] | 2-(2,5-Difluoro-phenyl)-4-(5-{1-[1-(2-methoxy-ethyl)-piperidin-4-yl]-1H-pyrazol-4-yl}-pyridin-3-yl)-[1,8]naphthyridine | 1.61 | 527 | +++ | +++ |

TABLE 1-continued

Compounds of formulae (I), (II)

| No. | Structure | Name; Mass | HPLC/ MS R$_t$ [min] | HPLC/ MS [M + H] | TβR activity (Example 36) 0 + ++ +++ | TβR activity (Example 35A) >10 μM 1-10 μM 0.1-1 μM <0.1 μM |
|---|---|---|---|---|---|---|
| 51 | 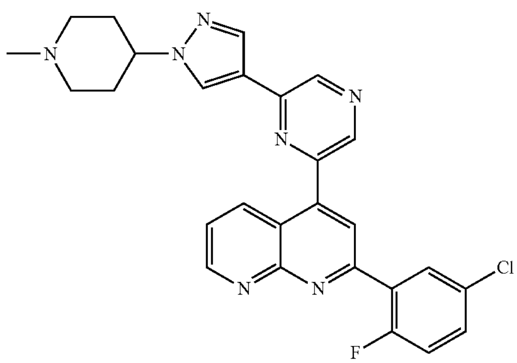 [SMILES: CN1CCC(n2cc(-c3cncc(-c4cc(-c5cc(Cl)ccc5F)nc5ncccc45)n3)cn2)CC1] | 2-(5-Chloro-2-fluoro-phenyl)-4-{6-[1-(1-methyl-piperidin-4-yl)-1H-pyrazol-4-yl]-pyrazin-2-yl}-[1,8]naphthyridine | 1.57 | 500 | +++ | +++ |
| 52 | 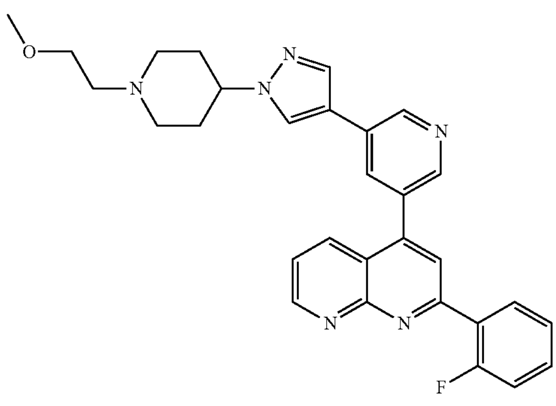 [SMILES: COCCN1CCC(n2cc(-c3cncc(-c4cc(-c5ccccc5F)nc5ncccc45)c3)cn2)CC1] | 2-(2-Fluoro-phenyl)-4-(5-{1-[1-(2-methoxy-ethyl)-piperidin-4-yl]-1H-pyrazol-4-yl}-pyridin-3-yl)-[1,8]naphthyridine | 1.55 | 509 | +++ | +++ |
| 53 | 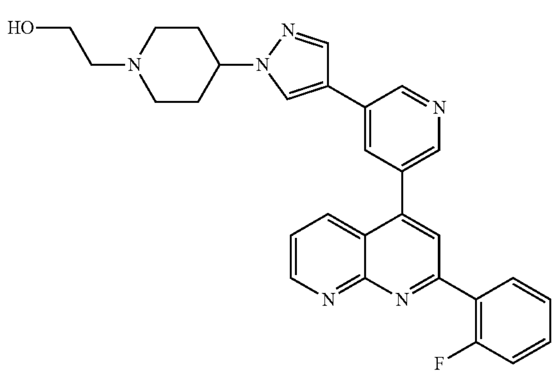 [SMILES: OCCN1CCC(n2cc(-c3cncc(-c4cc(-c5ccccc5F)nc5ncccc45)c3)cn2)CC1] | 2-[4-(4-{5-[2-(2-Fluoro-phenyl)-[1,8]naphthyridin-4-yl]-pyridin-3-yl}-pyrazol-1-yl)-piperidin-1-yl]-ethanol | 1.47 | 495 | +++ | +++ |

TABLE 1-continued

Compounds of formulae (I), (II)

| No. | Structure | Name; Mass | HPLC/MS R$_t$ [min] | HPLC/MS [M + H] | TβR activity (Example 36) 0 + ++ +++ | TβR activity (Example 35A) >10 μM 1-10 μM 0.1-1 μM <0.1 μM |
|---|---|---|---|---|---|---|
| 54 | 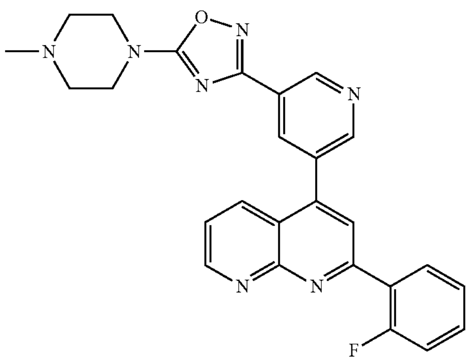 [SMILES: CN1CCN(c2nc(-c3cncc(-c4cc(-c5ccccc5F)nc5ncccc45)c3)no2)CC1] | 2-(2-Fluoro-phenyl)-4-{5-[5-(4-methyl-piperazin-1-yl)-[1,2,4]oxadiazol-3-yl]-pyridin-3-yl}-[1,8]naphthyridine | 1.43 | 468 | +++ | + |
| 55 | 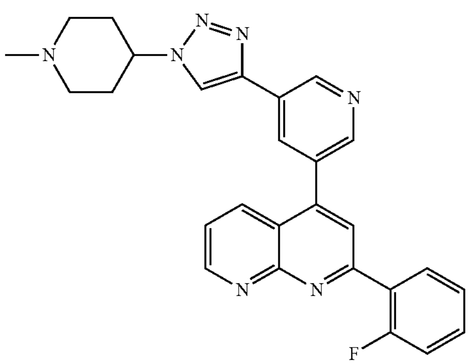 [SMILES: CN1CCC(n2cc(-c3cncc(-c4cc(-c5ccccc5F)nc5ncccc45)c3)nn2)CC1] | 2-(2-Fluoro-phenyl)-4-{5-[1-(1-methyl-piperidin-4-yl)-1H-[1,2,3]triazol-4-yl]-pyridin-3-yl}-[1,8]naphthyridine | 1.36 | 466 | +++ | +++ |
| 56 | 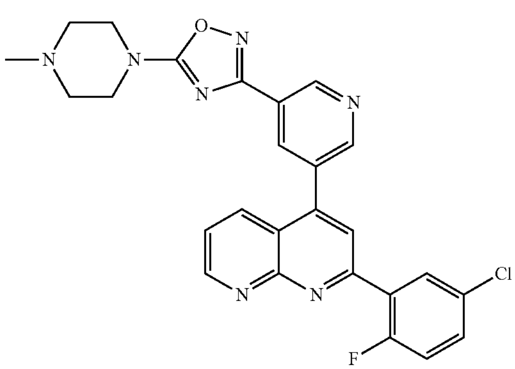 [SMILES: CN1CCN(c2nc(-c3cncc(-c4cc(-c5cc(Cl)ccc5F)nc5ncccc45)c3)no2)CC1] | 2-(5-Chloro-2-fluoro-phenyl)-4-{5-[5-(4-methyl-piperazin-1-yl)-[1,2,4]oxadiazol-3-yl]-pyridin-3-yl}-[1,8]naphthyridine | 1.55 | 502 | +++ | ++ |

TABLE 1-continued

Compounds of formulae (I), (II)

| No. | Structure | Name; Mass | HPLC/MS R_t [min] | HPLC/MS [M + H] | TβR activity (Example 36) 0 / + / ++ / +++ | TβR activity (Example 35A) >10 μM / 1-10 μM / 0.1-1 μM / <0.1 μM |
|---|---|---|---|---|---|---|
| 57 | 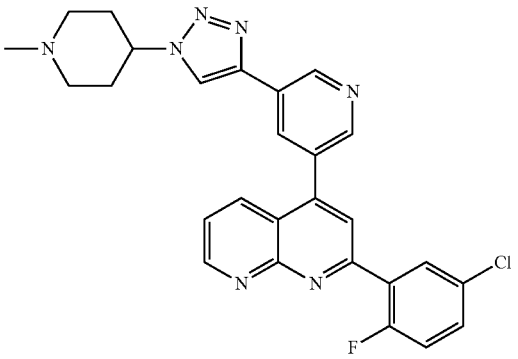 | 2-(5-Chloro-2-fluoro-phenyl)-4-{5-[1-(1-methyl-piperidin-4-yl)-1H-[1,2,3]triazol-4-yl]-pyridin-3-yl}-[1,8]naphthyridine | 1.47 | 500 | +++ | +++ |
| 58 | 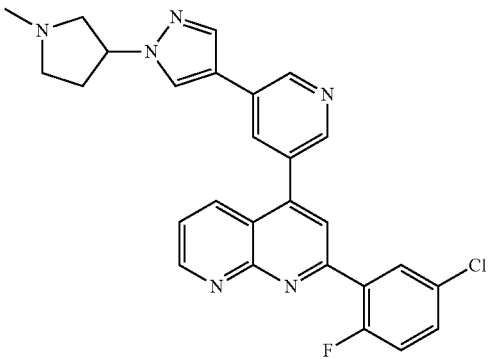 [SMILES: CN1CCC(n2cc(-c3cncc(-c4cc(-c5cc(Cl)ccc5F)nc5ncccc45)c3)cn2)C1] | 2-(5-Chloro-2-fluoro-phenyl)-4-{5-[1-(1-methyl-pyrrolidin-3-yl)-1H-pyrazol-4-yl]-pyridin-3-yl}-[1,8]naphthyridine | 1.51 | 485 | +++ | +++ |
| 59 | 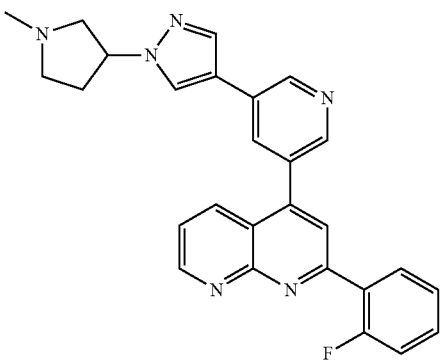 [SMILES: CN1CCC(n2cc(-c3cncc(-c4cc(-c5ccccc5F)nc5ncccc45)c3)cn2)C1] | 2-(2-Fluoro-phenyl)-4-{5-[1-(1-methyl-pyrrolidin-3-yl)-1H-pyrazol-4-yl]-pyridin-3-yl}-[1,8]naphthyridine | 1.39 | 451 | +++ | +++ |

TABLE 1-continued

Compounds of formulae (I), (II)

| No. | Structure | Name; Mass | HPLC/ MS R$_t$ [min] | HPLC/ MS [M + H] | TβR activity (Example 36) 0 + ++ +++ | TβR activity (Example 35A) >10 μM 1-10 μM 0.1-1 μM <0.1 μM |
|---|---|---|---|---|---|---|
| 60 | 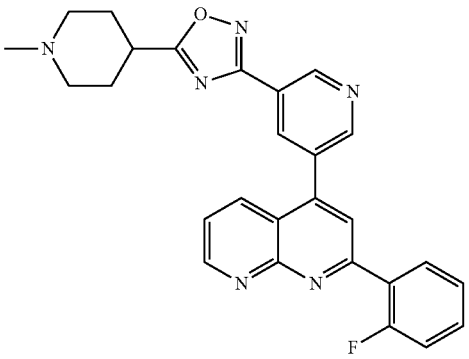 [SMILES: CN1CCC(c2nc(-c3cncc(-c4cc(-c5ccccc5F)nc5ncccc45)c3)no2)CC1] | 2-(2-Fluoro-phenyl)-4-{5-[5-(1-methyl-piperidin-4-yl)-[1,2,4]oxadiazol-3-yl]-pyridin-3-yl}-[1,8]naphthyridine | 1.46 | 467 | ++ | |
| 61 | 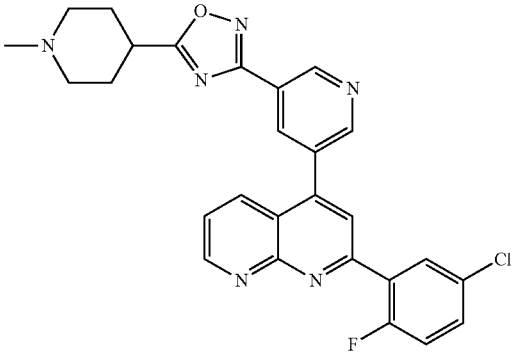 [SMILES: CN1CCC(c2nc(-c3cncc(-c4cc(-c5cc(Cl)ccc5F)nc5ncccc45)c3)no2)CC1] | 2-(5-Chloro-2-fluoro-phenyl)-4-{5-[5-(1-methyl-piperidin-4-yl)-[1,2,4]oxadiazol-3-yl]-pyridin-3-yl}-[1,8]naphthyridine | 1.56 | 501 | +++ | ++ |
| 62 | 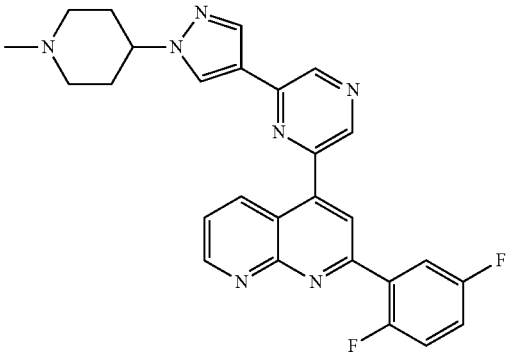 | 2-(2,5-Difluoro-phenyl)-4-{6-[1-(1-methyl-piperidin-4-yl)-1H-pyrazol-4-yl]-pyrazin-2-yl}-[1,8]naphthyridine | 1.52 | 484 | +++ | +++ |

TABLE 1-continued

Compounds of formulae (I), (II)

| No. | Structure | Name; Mass | HPLC/MS R$_t$ [min] | HPLC/MS [M + H] | TβR activity (Example 36) 0 + ++ +++ | TβR activity (Example 35A) >10 μM 1-10 μM 0.1-1 μM <0.1 μM |
|---|---|---|---|---|---|---|
| 63 | 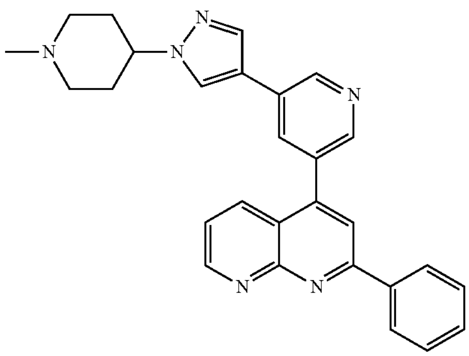 [SMILES: CN1CCC(n2cc(-c3cncc(-c4cc(-c5ccccc5)nc5ncccc45)c3)cn2)CC1] | 4-{5-[1-(1-Methyl-piperidin-4-yl)-1H-pyrazol-4-yl]-pyridin-3-yl}-2-phenyl-[1,8]naphthyridine | 1.47 | 447 | +++ | ++ |
| 64 | 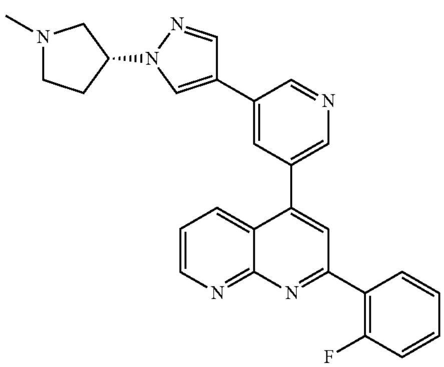 | 2-(2-Fluoro-phenyl)-4-{5-[1-((R)-1-methyl-pyrrolidin-3-yl)-1H-pyrazol-4-yl]-pyridin-3-yl}-[1,8]naphthyridine | 1.36 | 451 | +++ | +++ |
| 65 | 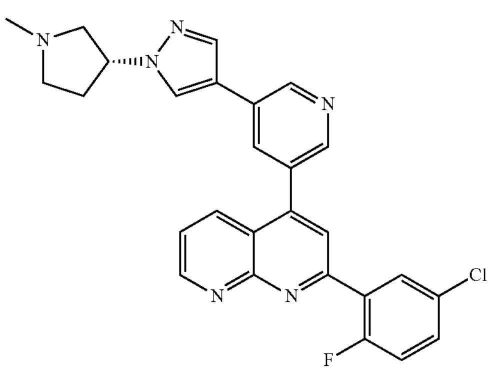 [SMILES: CN1CC[C@@H](n2cc(-c3cncc(-c4cc(-c5cc(Cl)ccc5F)nc5ncccc45)c3)cn2)C1] | 2-(5-Chloro-2-fluoro-phenyl)-4-{5-[1-((R)-1-ethyl-pyrrolidin-3-yl)-1H-pyrazol-4-yl]-pyridin-3-yl}-[1,8]naphthyridine | 1.55 | 485 | +++ | +++ |

TABLE 1-continued

Compounds of formulae (I), (II)

| No. | Structure | Name; Mass | HPLC/MS R$_t$ [min] | HPLC/MS [M + H] | TβR activity (Example 36) 0 + ++ +++ | TβR activity (Example 35A) >10 μM 1-10 μM 0.1-1 μM <0.1 μM |
|---|---|---|---|---|---|---|
| 66 | 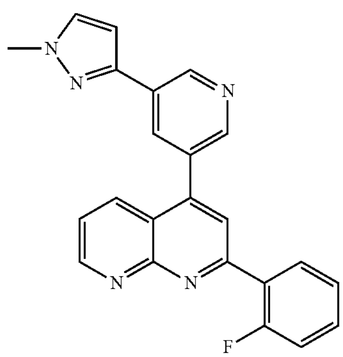 [SMILES: Cn1ccc(-c2cncc(-c3cc(-c4ccccc4F)nc4ncccc34)c2)n1] | 2-(2-Fluoro-phenyl)-4-[5-(1-methyl-1H-pyrazol-3-yl)-pyridin-3-yl]-[1,8]naphthyridine | 2.33 | 382 | | + |
| 67 | 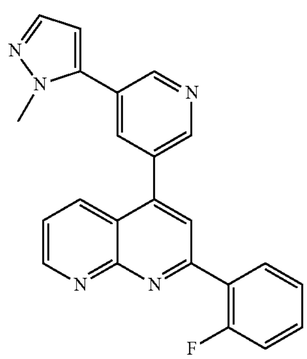 [SMILES: Cn1nccc1-c1cncc(-c2cc(-c3ccccc3F)nc3ncccc23)c1] | 2-(2-Fluoro-phenyl)-4-[5-(2-methyl-2H-pyrazol-3-yl)-pyridin-3-yl]-[1,8]naphthyridine | 2.33 | 382 | | + |
| 68 | 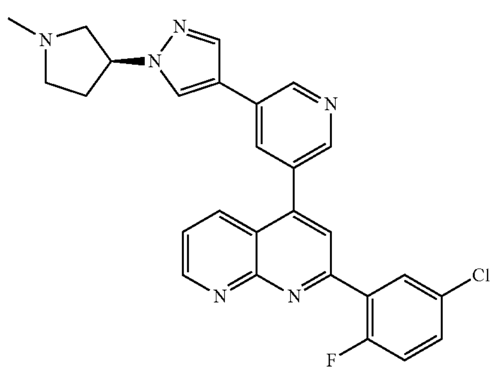 [SMILES: CN1CC[C@H](n2cc(-c3cncc(-c4cc(-c5cc(Cl)ccc5F)nc5ncccc45)c3)cn2)C1] | 2-(5-Chloro-2-fluoro-phenyl)-4-{5-[1-((S)-1-methyl-pyrrolidin-3-yl)-1H-pyrazol-4-yl]-pyridin-3-yl}-[1,8]naphthyridine | 1.59 | 485 | +++ | +++ |

TABLE 1-continued

Compounds of formulae (I), (II)

| No. | Structure | Name; Mass | HPLC/ MS R$_t$ [min] | HPLC/ MS [M + H] | TβR activity (Example 36) 0 + ++ +++ | TβR activity (Example 35A) >10 μM 1-10 μM 0.1-1 μM <0.1 μM |
|---|---|---|---|---|---|---|
| 69 | 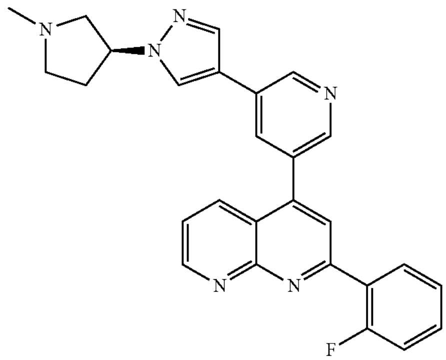 [SMILES: CN1CC[C@H](n2cc(-c3cncc(-c4cc(-c5ccccc5F)nc5ncccc45)c3)cn2)C1] | 2-(2-Fluoro-phenyl)-4-{5-[1-((S)-1-methyl-pyrrolidin-3-yl)-1H-pyrazol-4-yl]-pyridin-3-yl}-[1,8]naphthyridine | 1.36 | 451 | +++ | +++ |
| 70 | 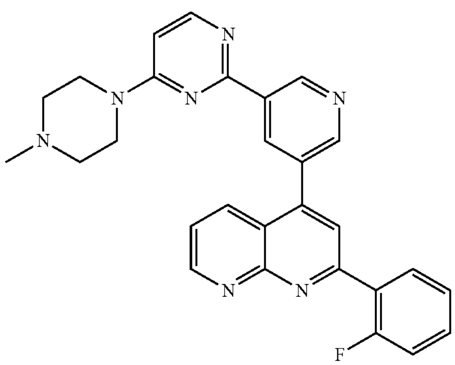 [SMILES: CN1CCN(c2ccnc(-c3cncc(-c4cc(-c5ccccc5F)nc5ncccc45)c3)n2)CC1] | 2-(2-Fluoro-phenyl)-4-{5-[4-(4-methyl-piperazin-1-yl)-pyrimidin-2-yl]-pyridin-3-yl}-[1,8]naphthyridine | 1.47 | 478 | ++ | |
| 71 | 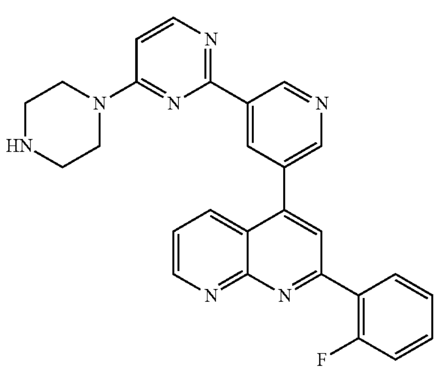 [SMILES: Fc1ccccc1-c1cc(-c2cncc(-c3nccc(N4CCNCC4)n3)c2)c2cccnc2n1] | 2-(2-Fluoro-phenyl)-4-[5-(4-piperazin-1-yl-pyrimidin-2-yl)-pyridin-3-yl]-[1,8]naphthyridine | 1.52 | 464 | +++ | + |

TABLE 1-continued

Compounds of formulae (I), (II)

| No. | Structure | Name; Mass | HPLC/ MS R_t [min] | HPLC/ MS [M + H] | TβR activity (Example 36) 0 + ++ +++ | TβR activity (Example 35A) >10 μM 1-10 μM 0.1-1 μM <0.1 μM |
|---|---|---|---|---|---|---|
| 72 | 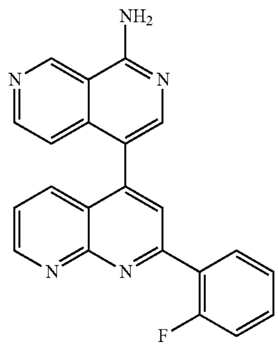 [SMILES: Nc1ncc(-c2cc(-c3ccccc3F)nc3ncccc23)c2ccncc12] | 4-[2-(2-Fluoro-phenyl)-[1,8]naphthyridin-4-yl]-[2,7]naphthyridin-1-ylamine | 1.40 | 368 | +++ | ++ |
| 73 | 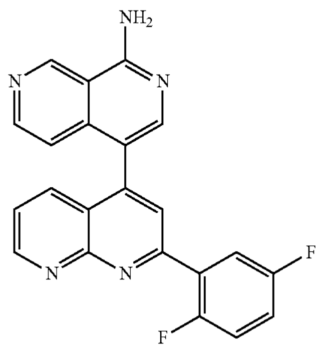 [SMILES: Nc1ncc(-c2cc(-c3cc(F)ccc3F)nc3ncccc23)c2ccncc12] | 4-[2-(2,5-Difluoro-phenyl)-[1,8]naphthyridin-4-yl]-[2,7]naphthyridin-1-ylamine | 1.47 | 386 | +++ | +++ |
| 74 | 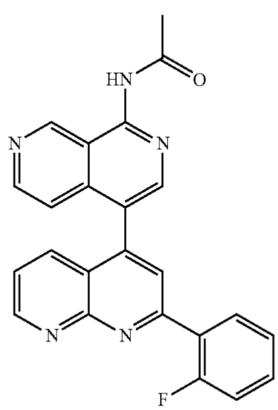 [SMILES: CC(=O)Nc1ncc(-c2cc(-c3ccccc3F)nc3ncccc23)c2ccncc12] | N-{4-[2-(2-Fluoro-phenyl)-[1,8]naphthyridin-4-yl]-[2,7]naphthyridin-1-yl}-acetamide | 1.64 | 369 | ++ | + |
| 75 | 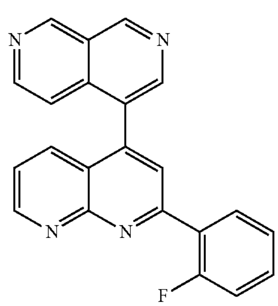 [SMILES: Fc1ccccc1-c1cc(-c2cncc3cnccc23)c2cccnc2n1] | 2-(2-Fluoro-phenyl)-4-[2,7]naphthyridin-4-yl-[1,8]naphthyridine | | | | |

TABLE 1-continued

Compounds of formulae (I), (II)

| No. | Structure | Name; Mass | HPLC/ MS R$_t$ [min] | HPLC/ MS [M + H] | TβR activity (Example 36) HPLC/MS 0 + ++ +++ | TβR activity (Example 35A) >10 μM 1-10 μM 0.1-1 μM <0.1 μM |
|---|---|---|---|---|---|---|
| 76 | 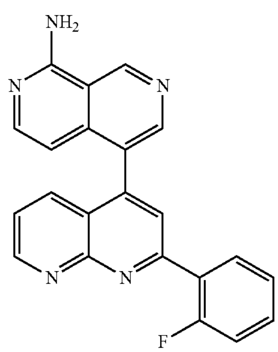 [SMILES: Nc1nccc2c(-c3cc(-c4ccccc4F)nc4ncccc34)cncc12] | 5-[2-(2-Fluoro-phenyl)-[1,8]naphthyridin-4-yl]-[2,7]naphthyridin-1-ylamine | | | | |
| 77 | 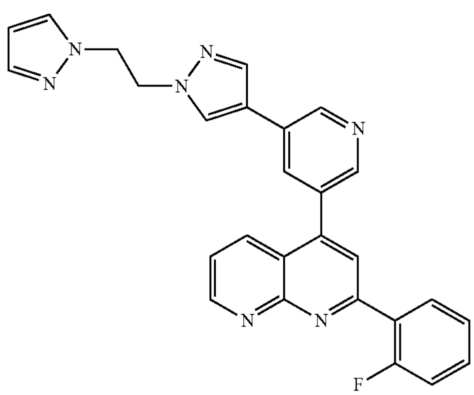 [SMILES: Fc1ccccc1-c1cc(-c2cncc(-c3cnn(CCn4cccn4)c3)c2)c2cccnc2n1] | 2-(2-Fluoro-phenyl)-4-{5-[1-(2-pyrazol-1-yl-ethyl)-1H-pyrazol-4-yl]-pyridin-3-yl}-[1,8]naphthyridine M 461.5 | 1.89 | 462 | ++ | + |
| 78 | 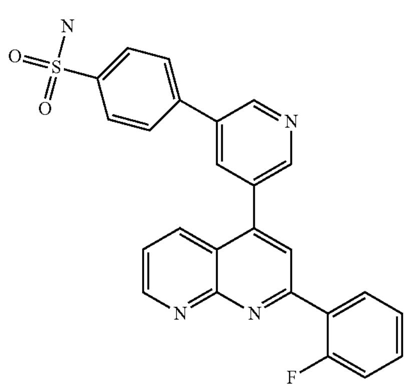 [SMILES: NS(=O)(=O)c1ccc(-c2cncc(-c3cc(-c4ccccc4F)nc4ncccc34)c2)cc1] | 4-{5-[2-(2-Fluoro-phenyl)-[1,8]naphthyridin-4-yl]-pyridin-3-yl}-benzene-sulfonamide M 456.5 | 1.89 | 457 | +++ | ++ |

TABLE 1-continued

Compounds of formulae (I), (II)

| No. | Structure | Name; Mass | HPLC/MS R$_t$ [min] | HPLC/MS [M + H] | TβR activity (Example 36) 0 >10 μM + 1-10 μM ++ 0.1-1 μM +++ <0.1 μM | TβR activity (Example 35A) |
|---|---|---|---|---|---|---|
| 79 | 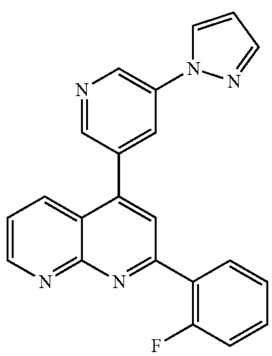 [SMILES: Fc1ccccc1-c1cc(-c2cncc(-n3cccn3)c2)c2cccnc2n1] | 2-(2-Fluoro-phenyl)-4-(5-pyrazol-1-yl-pyridin-3-yl)-[1,8]naphthyridine M 367.4 | 2.08 | 368 | ++ | + |
| 80 | 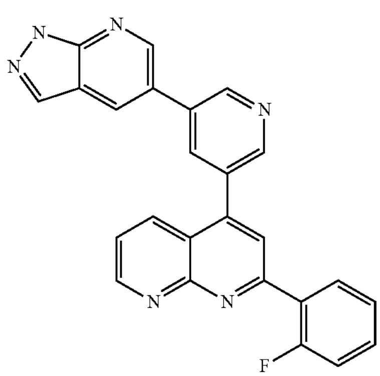 [SMILES: Fc1ccccc1-c1cc(-c2cncc(-c3cnc4[nH]ncc4c3)c2)c2cccnc2n1] | 2-(2-Fluoro-phenyl)-4-[5-(1H-pyrazolo[3,4-b]pyridin-5-yl)-pyridin-3-yl]-[1,8]naphthyridine M 418.4 | 1.87 | 419 | ++ | ++ |
| 81 | 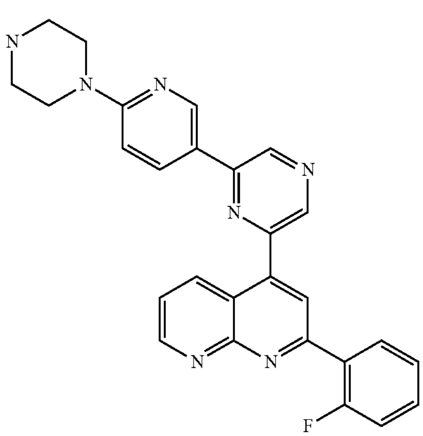 [SMILES: Fc1ccccc1-c1cc(-c2cncc(-c3ccc(N4CCNCC4)nc3)n2)c2cccnc2n1] | 2-(2-Fluoro-phenyl)-4-[6-(6-piperazin-1-yl-pyridin-3-yl)-pyrazin-2-yl]-[1,8]naphthyridine M 463.5 | 1.56 | 464 | +++ | ++ |

TABLE 1-continued

Compounds of formulae (I), (II)

| No. | Structure | Name; Mass | HPLC/ MS R_t [min] | HPLC/ MS [M + H] | TβR activity (Example 36) 0 / + / ++ / +++ | TβR activity (Example 35A) >10 µM / 1-10 µM / 0.1-1 µM / <0.1 µM |
|---|---|---|---|---|---|---|
| 82 | 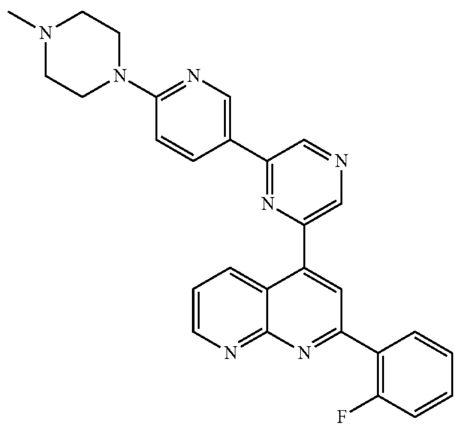 [SMILES: CN1CCN(c2ccc(-c3cncc(-c4cc(-c5ccccc5F)nc5ncccc45)n3)cn2)CC1] | 2-(2-Fluoro-phenyl)-4-{6-[6-(4-methyl-piperazin-1-yl)-pyridin-3-yl]-pyrazin-2-yl}-[1,8]naphthyridine M 477.5 | 1.50 | 478 | +++ | ++ |
| 83 | 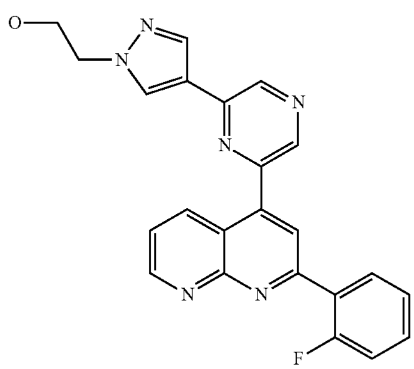 [SMILES: OCCn1cc(-c2cncc(-c3cc(-c4ccccc4F)nc4ncccc34)n2)cn1] | 2-(4-{6-[2-(2-Fluoro-phenyl)-[1,8]naphthyridin-4-yl]-pyrazin-2-yl}-pyrazol-1-yl)-ethanol M 412.4 | 1.78 | 413 | +++ | + |
| 84 | 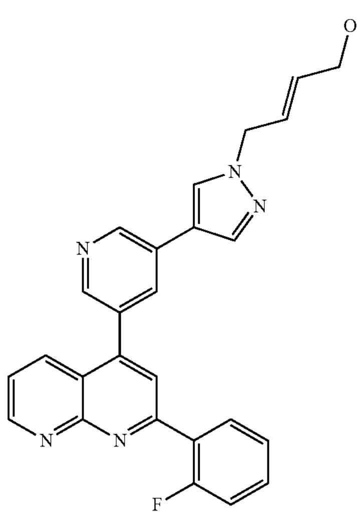 [SMILES: OC/C=C/Cn1cc(-c2cncc(-c3cc(-c4ccccc4F)nc4ncccc34)c2)cn1] | (E)-4-(4-{5-[2-(2-Fluoro-phenyl)-[1,8]naphthyridin-4-yl]-pyridin-3-yl}-pyrazol-1-yl)-but-2-en-1-ol M 437.5 | 1.79 | 438 | +++ | ++ |

TABLE 1-continued

Compounds of formulae (I), (II)

| No. | Structure | Name; Mass | HPLC/ MS $R_t$ [min] | HPLC/ MS [M + H] | TβR activity (Example 36) 0 + ++ +++ | TβR activity (Example 35A) >10 μM 1-10 μM 0.1-1 μM <0.1 μM |
|---|---|---|---|---|---|---|
| 85 | 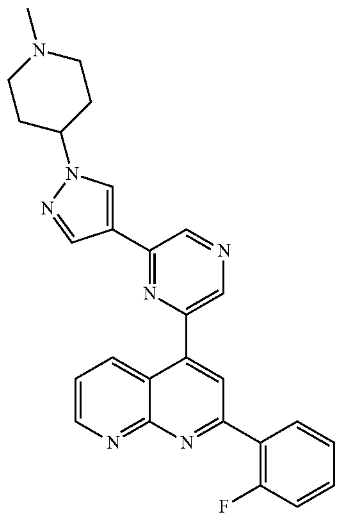 [SMILES: CN1CCC(n2cc(-c3cncc(-c4cc(-c5ccccc5F)nc5ncccc45)n3)cn2)CC1] | 2-(2-Fluoro-phenyl)-4-{6-[1-(1-methyl-piperidin-4-yl)-1H-pyrazol-4-yl]-pyrazin-2-yl}-[1,8]naphthyridine M 465.5 | 1.51 | 466 | +++ | ++ |
| 86 | 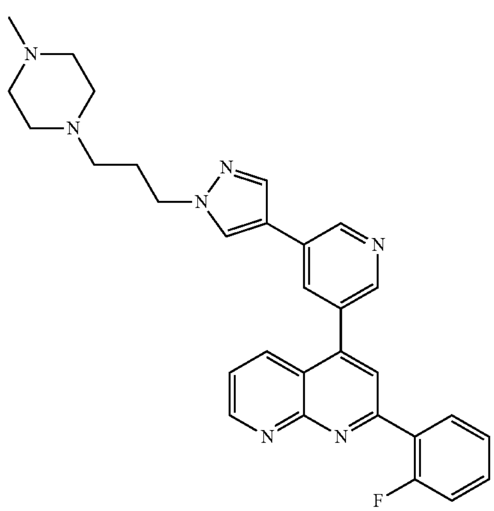 [SMILES: CN1CCN(CCCn2cc(-c3cncc(-c4cc(-c5ccccc5F)nc5ncccc45)c3)cn2)CC1] | 2-(2-Fluoro-phenyl)-4-(5-{1-[3-(4-methyl-piperazin-1-yl)-propyl]-1H-pyrazol-4-yl}-pyridin-3-yl)-[1,8]naphthyridine M 507.6 | 1.47 | 508 | +++ | ++ |

TABLE 1-continued

Compounds of formulae (I), (II)

| No. | Structure | Name; Mass | HPLC/ MS $R_t$ [min] | HPLC/ MS [M + H] | TβR activity (Example 36) 0 + ++ +++ | TβR activity (Example 35A) >10 μM 1-10 μM 0.1-1 μM <0.1 μM |
|---|---|---|---|---|---|---|
| 87 | 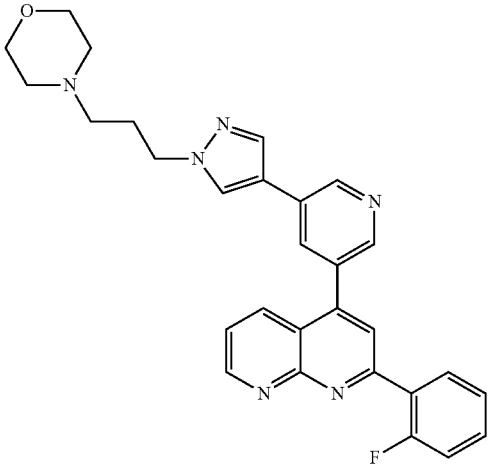 [SMILES: Fc1ccccc1-c1cc(-c2cncc(-c3cnn(CCCN4CCOCC4)c3)c2)c2cccnc2n1] | 2-(2-Fluoro-phenyl)-4-{5-[1-(3-morpholin-4-yl-propyl)-1H-pyrazo l-4-yl]-pyridin-3-yl}-[1,8]naphthyridine M 494.6 | 1.44 | 495 | +++ | ++ |
| 88 | 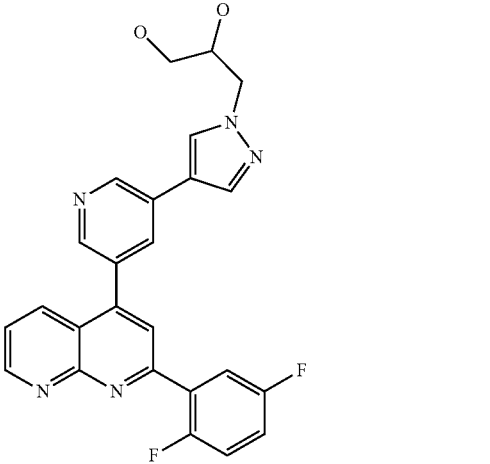 [SMILES: OCC(O)Cn1cc(-c2cncc(-c3cc(-c4cc(F)ccc4F)nc4ncccc34)c2)cn1] | 3-(4-{5-[2-(2,5-Difluoro-phenyl)-[1,8]naphthyridin-4-yl]-pyridin-3-yl}-pyrazol-1-yl)-propane-1,2-diol M 459.5 | 1.70 | 460 | +++ | + |
| 89 | 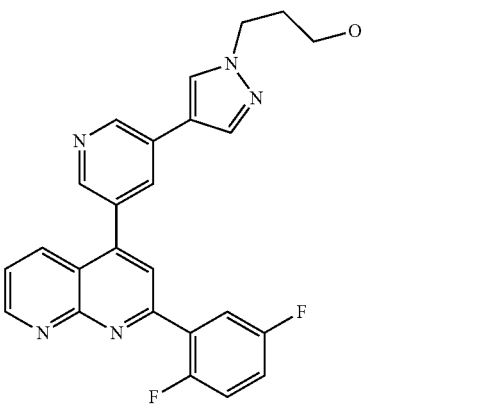 [SMILES: OCCCn1cc(-c2cncc(-c3cc(-c4cc(F)ccc4F)nc4ncccc34)c2)cn1] | 3-(4-{5-[2-(2,5-Difluoro-phenyl)-[1,8]naphthyridin-4-yl]-pyridin-3-yl}-pyrazol-1-yl)-propan-1-ol M 443.5 | 1.82 | 444 | +++ | ++ |

TABLE 1-continued

Compounds of formulae (I), (II)

| | | | | | TβR activity (Example 36) | TβR activity (Example 35A) |
|---|---|---|---|---|---|---|
| | | | HPLC/ MS | | 0 | >10 μM |
| | | | $R_t$ | HPLC/ MS | + | 1-10 μM |
| | | Name; | | | ++ | 0.1-1 μM |
| No. | Structure | Mass | [min] | [M + H] | +++ | <0.1 μM |
| 90 | | 2-(2,5-Difluoro-phenyl)-4-{5-[1-(3-morpholin-4-yl-propyl)-1H-pyrazol-4-yl]-pyridin-3-yl}-[1,8]naphthyridine M 512.6 | 1.46 | 513 | +++ | ++ |
| 91 | | 2-(4-{5-[2-(5-Chloro-2-fluoro-phenyl)-[1,8]naphthyridin-4-yl]-pyridin-3-yl}-pyrazol-1-yl)-ethanol M 445.9 | 1.88 | 446 | +++ | +++ |

TABLE 1-continued

Compounds of formulae (I), (II)

| No. | Structure | Name; Mass | HPLC/ MS R$_t$ [min] | HPLC/ MS [M + H] | TβR activity (Example 36) 0 + ++ +++ | TβR activity (Example 35A) >10 μM 1-10 μM 0.1-1 μM <0.1 μM |
|---|---|---|---|---|---|---|
| 92 | 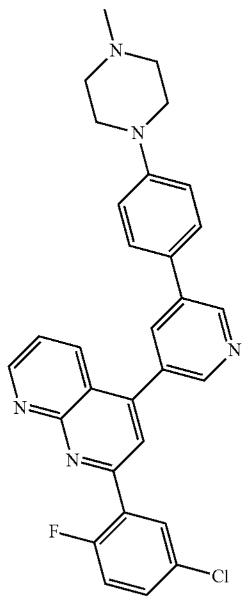 | 2-(5-Chloro-2-fluoro-phenyl)-4-{5-[4-(4-methyl-piperazin-1-yl)-phenyl]-pyridin-3-yl}-[1,8]naphthyridine M 510.0 | 1.56 | 511 | +++ | +++ |
| 93 | 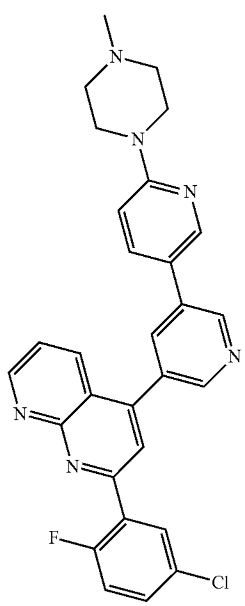 [SMILES: CN1CCN(c2ccc(-c3cncc(-c4cc(-c5cc(Cl)ccc5F)nc5ncccc45)c3)cn2)CC1] | 2-(5-Chloro-2-fluoro-phenyl)-4-[6'-(4-methyl-piperazin-1-yl)-[3,3']bipyridinyl-5-yl]-[1,8]naphthyridine M 511.0 | 1.55 | 512 | +++ | +++ |

TABLE 1-continued

Compounds of formulae (I), (II)

| No. | Structure | Name; Mass | HPLC/MS R$_t$ [min] | HPLC/MS [M + H] | TβR activity (Example 36) | TβR activity (Example 35A) |
|---|---|---|---|---|---|---|
| | | | | | 0 | >10 μM |
| | | | | | + | 1-10 μM |
| | | | | | ++ | 0.1-1 μM |
| | | | | | +++ | <0.1 μM |
| 94 | 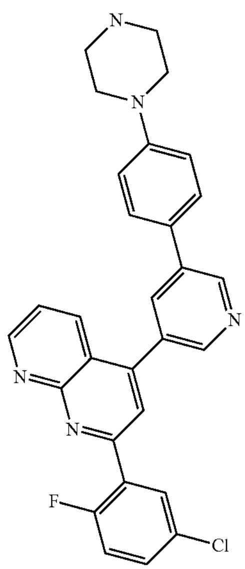 [SMILES: Fc1ccc(Cl)cc1-c1cc(-c2cncc(-c3ccc(N4CCNCC4)cc3)c2)c2cccnc2n1] | 2-(5-Chloro-2-fluoro-phenyl)-4-[5-(4-piperazin-1-yl-phenyl)-pyridin-3-yl]-[1,8]naphthyridine M 496.0 | 1.62 | 497 | +++ | +++ |
| 95 | 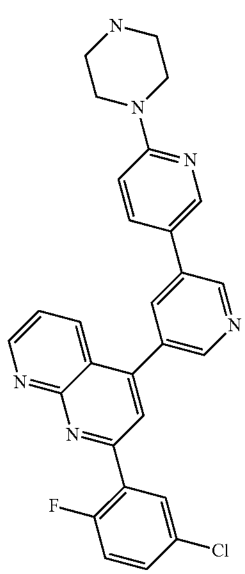 [SMILES: Fc1ccc(Cl)cc1-c1cc(-c2cncc(-c3ccc(N4CCNCC4)nc3)c2)c2cccnc2n1] | 2-(5-Chloro-2-fluoro-phenyl)-4-(6'-piperazin-1-yl-[3,3']bipyridinyl-5-yl)-[1,8]naphthyridine M 497.0 | 1.66 | 498 | +++ | ++ |

TABLE 1-continued

Compounds of formulae (I), (II)

|  |  |  |  |  | TβR activity (Example 36) | TβR activity (Example 35A) |
|---|---|---|---|---|---|---|
|  |  |  | HPLC/ MS |  | 0 | >10 μM |
|  |  |  | MS | HPLC/ | + | 1-10 μM |
|  |  | Name; | R$_t$ | MS | ++ | 0.1-1 μM |
| No. | Structure | Mass | [min] | [M + H] | +++ | <0.1 μM |
| 96 |  | 2-(5-Chloro-2-fluoro-phenyl)-4-{5-[1-(2-morpholin-4-yl-ethyl)-1H-pyrazol-4 yl]-pyridin-3-yl}-[1,8]naphthyridine M 515.0 | 1.66 | 516 | +++ | +++ |
| 97 |  | [3-(4-{5-[2-(5-Chloro-2-fluoro-phenyl)-[1,8]naphthyridin-4-yl]-pyridin-3-yl}-pyrazol-1-yl)-propyl]-dimethyl-amine M 487.0 | 1.64 | 488 | +++ | +++ |

TABLE 1-continued
Compounds of formulae (I), (II)
| No. | Structure | Name; Mass | HPLC/ MS R$_t$ [min] | HPLC/ MS [M + H] | TβR activity (Example 36) 0 + ++ +++ | TβR activity (Example 35A) >10 μM 1-10 μM 0.1-1 μM <0.1 μM |
|---|---|---|---|---|---|---|
| 98 control | 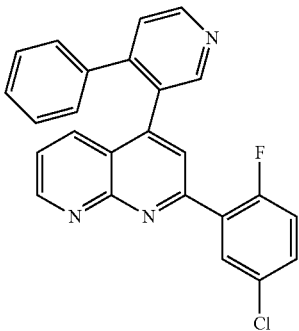 | 2-(5-Chloro-2-fluoro-phenyl)-4-(4-phenyl-pyridin-3-yl)-[1,8]naphthyridine M 411.9 | 2.30 | 412 | + | + |
| 5599 control | 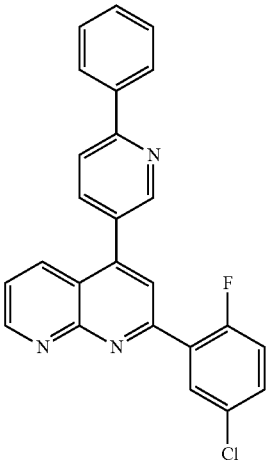 | 2-(5-Chloro-2-fluoro-phenyl)-4-(6-phenyl-pyridin-3-yl)-[1,8]naphthyridine M 411.9 | 2.70 | 412 | 0 | 0 |
| 100 | 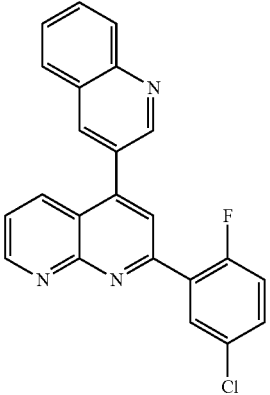 [SMILES: Fc1ccc(Cl)cc1-c1cc(-c2cnc3ccccc3c2)c2cccnc2n1] | 2-(5-Chloro-2-fluoro-phenyl)-4-quinolin-3-yl-[1,8]naphthyridine M 385.8 | 2.37 | 386 | + | 0 |

TABLE 1-continued
Compounds of formulae (I), (II)
| No. | Structure | Name; Mass | HPLC/ MS $R_t$ [min] | HPLC/ MS [M + H] | TβR activity (Example 36) 0 / + / ++ / +++ | TβR activity (Example 35A) >10 μM / 1-10 μM / 0.1-1 μM / <0.1 μM |
|---|---|---|---|---|---|---|
| 101 | 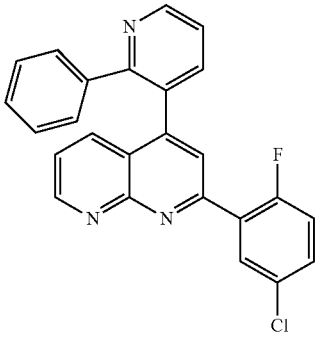 control | 2-(5-Chloro-2-fluoro-phenyl)-4-(2-phenyl-pyridin-3-yl)-[1,8]naphthyridine M 411.9 | 2.29 | 412 | 0 | 0 |
| 102 | 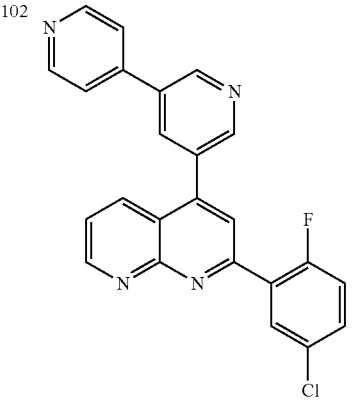 | 4-[3,4']Bipyridinyl-5-yl-2-(5-chloro-2-fluoro-phenyl)-[1,8]naphthyridine M 412.9 | 1.75 | 413 | +++ | ++ |
| 103 | 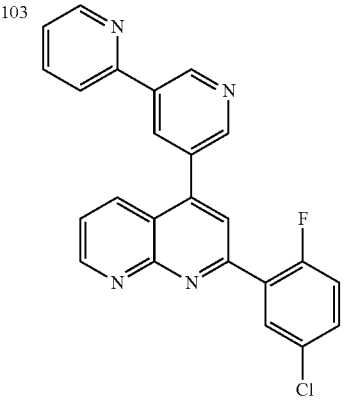 | 4-[2,3']Bipyridinyl-5'-yl-2-(5-chloro-2-fluoro-phenyl)-[1,8]naphthyridine M 412.9 | 2.20 | 413 | +++ | ++ |

TABLE 1-continued

Compounds of formulae (I), (II)

| No. | Structure | Name; Mass | HPLC/MS R$_t$ [min] | HPLC/MS [M + H] | TβR activity (Example 36) 0 + ++ +++ | TβR activity (Example 35A) >10 μM 1-10 μM 0.1-1 μM <0.1 μM |
|---|---|---|---|---|---|---|
| 104 | 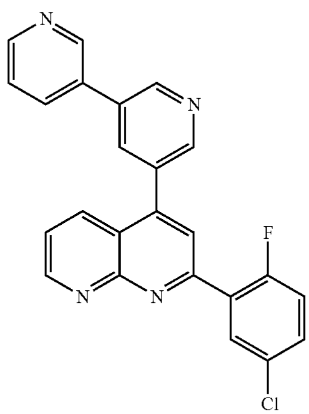 [SMILES: Fc1ccc(Cl)cc1-c1cc(-c2cncc(-c3cccnc3)c2)c2cccnc2n1] | 4-[3,3']Bipyridinyl-5-yl-2-(5-chloro-2-fluoro-phenyl)-[1,8]naphthyridine M 412.9 | 1.92 | 413 | +++ | ++ |
| 105 | 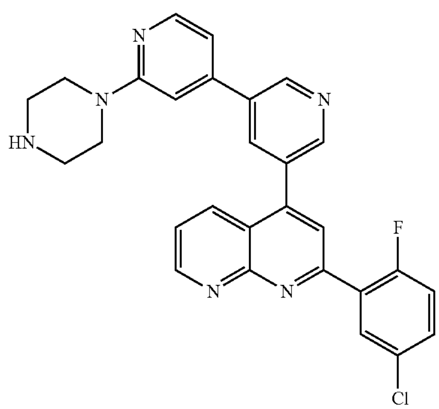 [SMILES: Fc1ccc(Cl)cc1-c1cc(-c2cncc(-c3ccnc(N4CCNCC4)c3)c2)c2cccnc2n1] | 2-(5-Chloro-2-fluoro-phenyl)-4-(2'-piperazin-1-yl-[3,4']bipyridinyl-5-yl)-[1,8]naphthyridine M 497.0 | 1.61 | 497 | +++ | +++ |
| 106 | 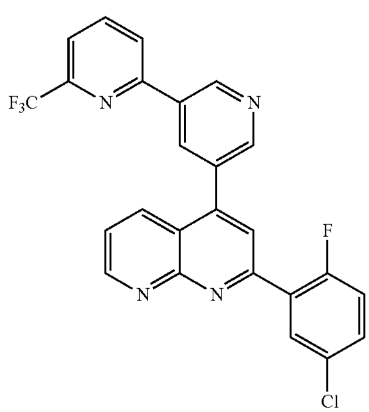 [SMILES: Fc1ccc(Cl)cc1-c1cc(-c2cncc(-c3cccc(C(F)(F)F)n3)c2)c2cccnc2n1] | 2-(5-Chloro-2-fluoro-phenyl)-4-(6-trifluoromethyl-[2,3']bipyridinyl-5'-yl)-[1,8]naphthyridine M 480.9 | 2.57 | 481 | ++ | 0 |

TABLE 1-continued

Compounds of formulae (I), (II)

| No. | Structure | Name; Mass | HPLC/MS R_t [min] | HPLC/MS [M + H] | TβR activity (Example 36) 0 / + / ++ / +++ | TβR activity (Example 35A) >10 μM / 1-10 μM / 0.1-1 μM / <0.1 μM |
|---|---|---|---|---|---|---|
| 107 | 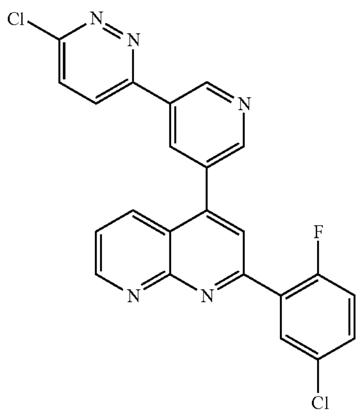 [SMILES: Fc1ccc(Cl)cc1-c1cc(-c2cncc(-c3ccc(Cl)nn3)c2)c2cccnc2n1] | 2-(5-Chloro-2-fluoro-phenyl)-4-[5-(6-chloro-pyridazin-3-yl)-pyridin-3-yl]-[1,8]naphthyridine M 448.3 | 2.16 | 448 | ++ | + |
| 108 | 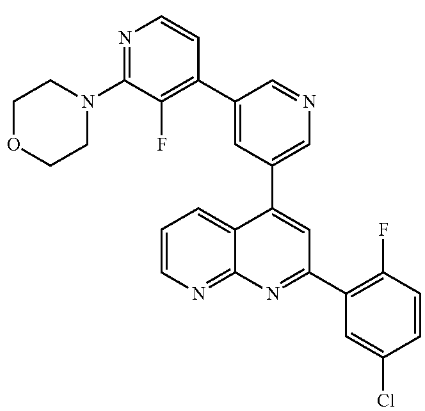 [SMILES: Fc1ccc(Cl)cc1-c1cc(-c2cncc(-c3ccnc(N4CCOCC4)c3F)c2)c2cccnc2n1] | 2-(5-Chloro-2-fluoro-phenyl)-4-(3'-fluoro-2'-morpholin-4-yl-[3,4']bipyridinyl-5-yl)-[1,8]naphthyridine M 515.9 | 2.35 | 516 | ++ | ++ |
| 109 | 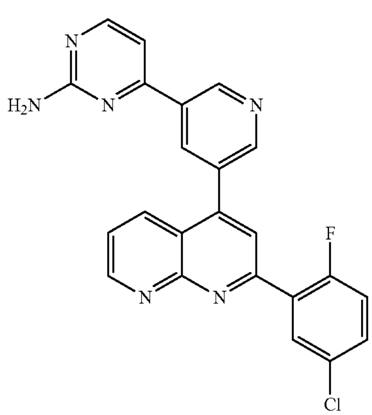 [SMILES: Nc1nccc(-c2cncc(-c3cc(-c4cc(Cl)ccc4F)nc4ncccc34)c2)n1] | 4-{5-[2-(5-Chloro-2-fluoro-phenyl)-[1,8]naphthyridin-4-yl]-pyridin-3-yl}-pyrimidin-2-ylamine M 428.9 | 1.86 | 429 | +++ | ++ |

TABLE 1-continued

Compounds of formulae (I), (II)

| No. | Structure | Name; Mass | HPLC/ MS R$_t$ [min] | HPLC/ MS [M + H] | TβR activity (Example 36) 0 + ++ +++ | TβR activity (Example 35A) >10 μM 1-10 μM 0.1-1 μM <0.1 μM |
|---|---|---|---|---|---|---|
| 110 | 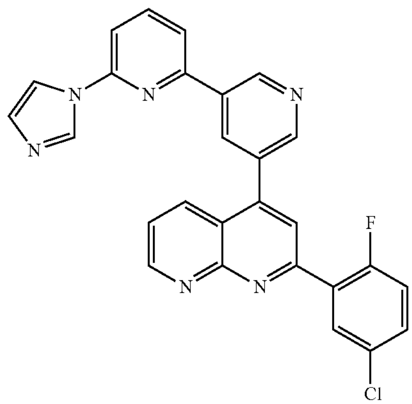 [SMILES: Fc1ccc(Cl)cc1-c1cc(-c2cncc(-c3cccc(-n4ccnc4)n3)c2)c2cccnc2n1] | 2-(5-Chloro-2-fluoro-phenyl)-4-(6-imidazol-1-yl-[2,3']bipyridinyl-5'-yl)-[1,8]naphthyridine M 478.9 | 1.69 | 479 | 0 | 0 |
| 111 | 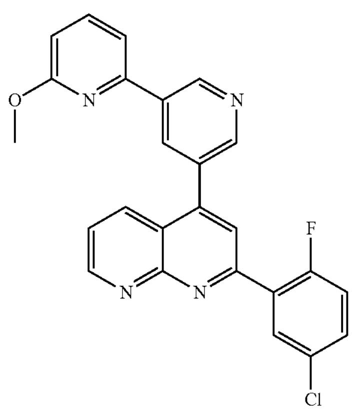 [SMILES: COc1cccc(-c2cncc(-c3cc(-c4cc(Cl)ccc4F)nc4ncccc34)c2)n1] | 2-(5-Chloro-2-fluoro-phenyl)-4-(6-methoxy-[2,3']bipyridinyl-5'-yl)-[1,8]naphthyridine M 442.9 | 2.57 | 443 | ++ | ++ |
| 112 | 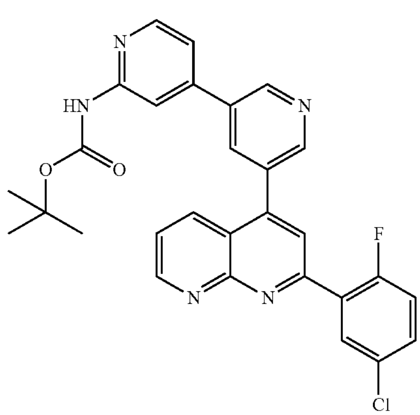 [SMILES: CC(C)(C)OC(=O)Nc1cc(-c2cncc(-c3cc(-c4cc(Cl)ccc4F)nc4ncccc34)c2)ccn1] | {5-[2-(5-Chloro-2-fluoro-phenyl)[1,8]naphthyridin-4-yl]-[3,4']bipyridinyl-2'-yl}-carbamic acid tert-butyl ester M 528.0 | 2.48 | 528 | ++ | ++ |

TABLE 1-continued

Compounds of formulae (I), (II)

| No. | Structure | Name; Mass | HPLC/ MS R_t [min] | HPLC/ MS [M + H] | TβR activity (Example 36) 0 + ++ +++ | TβR activity (Example 35A) >10 μM 1-10 μM 0.1-1 μM <0.1 μM |
|---|---|---|---|---|---|---|
| 113 | 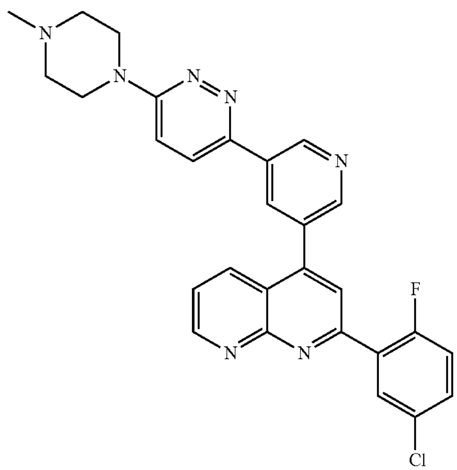 | 2-(5-Chloro-2-fluoro-phenyl)-4-{5-[6-(4-methyl-piperazin-1-yl)-pyridazin-3-yl]-pyridin-3-yl}-[1,8]naphthyridine M 512.0 | 1.51 | 512 | +++ | +++ |
| 114 | 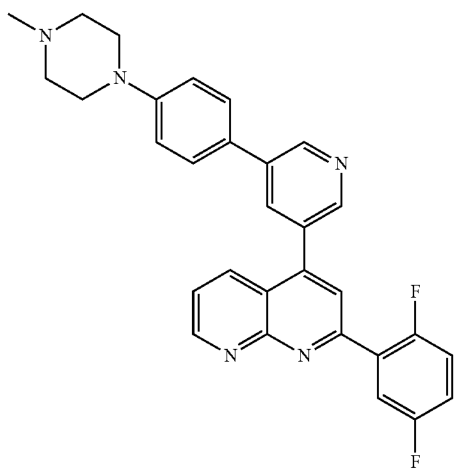 [SMILES: CN1CCN(c2ccc(-c3cncc(-c4cc(-c5cc(F)ccc5F)nc5ncccc45)c3)cc2)CC1] | 2-(2,5-Difluoro-phenyl)-4-{5-[4-(4-methyl-piperazin-1-yl)-phenyl]-pyridin-3-yl}-[1,8]naphthyridine M 493.6 | 1.57 | 494 | +++ | +++ |
| 115 | 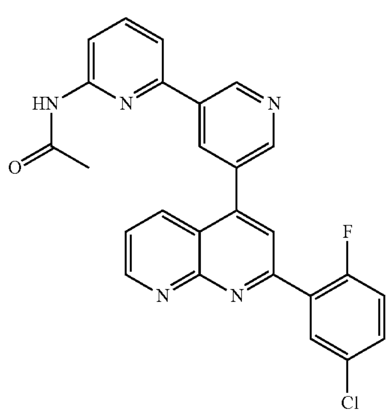 [SMILES: CC(=O)Nc1cccc(-c2cncc(-c3cc(-c4cc(Cl)ccc4F)nc4ncccc34)c2)n1] | N-{5'-[2-(5-Chloro-2-fluoro-phenyl)-[1,8]naphthyridin-4-yl]-[2,3']bipyridinyl-6-yl}-acetamide M 469.9 | 2.10 | 470 | +++ | ++ |

TABLE 1-continued

Compounds of formulae (I), (II)

| No. | Structure | Name; Mass | HPLC/ MS R$_t$ [min] | HPLC/ MS [M + H] | TβR activity (Example 36) 0 + ++ +++ | TβR activity (Example 35A) >10 μM 1-10 μM 0.1-1 μM <0.1 μM |
|---|---|---|---|---|---|---|
| 116 | 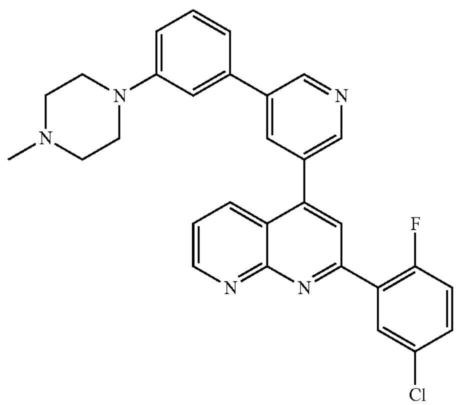 [SMILES: CN1CCN(c2cccc(-c3cncc(-c4cc(-c5cc(Cl)ccc5F)nc5ncccc45)c3)c2)CC1] | 2-(5-Chloro-2-fluoro-phenyl)-4-{5-[3-(4-methyl-piperazin-1-yl)-phenyl]-pyridin-3-yl}-[1,8]naphthyridine M 510.0 | 1.72 | 510 | +++ | +++ |
| 117 | 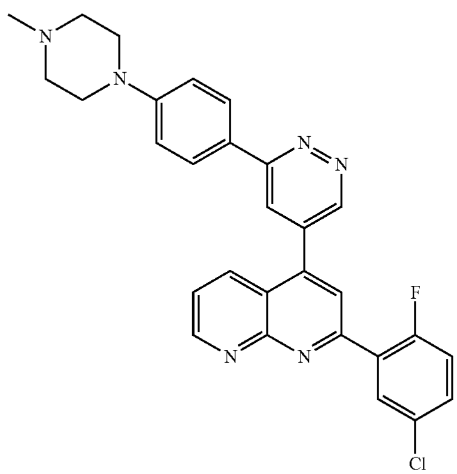 [SMILES: CN1CCN(c2ccc(-c3cc(-c4cc(-c5cc(Cl)ccc5F)nc5ncccc45)cnn3)cc2)CC1] | 2-(5-Chloro-2-fluoro-phenyl)-4-{6-[4-(4-methyl-piperazin-1-yl)-phenyl]-pyridazin-4-yl}-[1,8]naphthyridine M 511.0 | 1.58 | 511 | ++ | ++ |
| 118 | 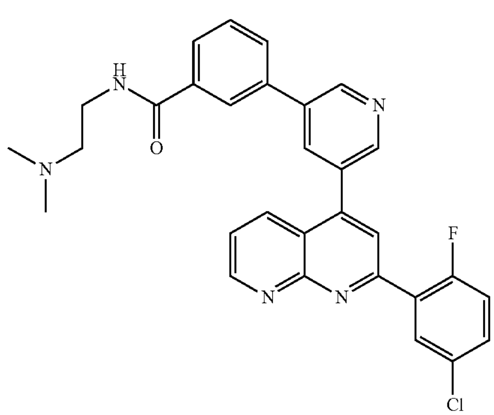 [SMILES: CN(C)CCNC(=O)c1cccc(-c2cncc(-c3cc(-c4cc(Cl)ccc4F)nc4ncccc34)c2)c1] | 3-{5-[2-(5-Chloro-2-fluoro-phenyl)-[1,8]naphthyridin-4-yl]-pyridin-3-yl}-N-(2-dimethylamino-ethyl)-benzamide M 526.0 | 1.62 | 526 | +++ | ++ |

TABLE 1-continued

Compounds of formulae (I), (II)

| No. | Structure | Name; Mass | HPLC/ MS R_t [min] | HPLC/ MS [M + H] | TβR activity (Example 36) 0 / + / ++ / +++ | TβR activity (Example 35A) >10 μM / 1-10 μM / 0.1-1 μM / <0.1 μM |
|---|---|---|---|---|---|---|
| 119 | 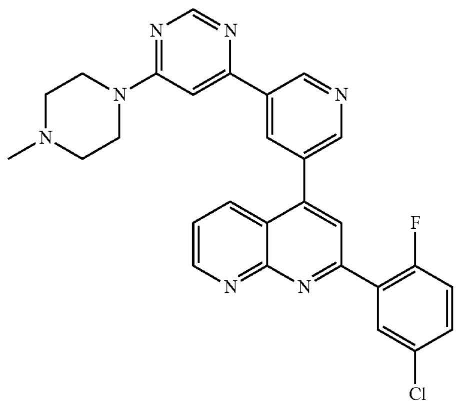 [SMILES: CN1CCN(c2cc(-c3cncc(-c4cc(-c5cc(Cl)ccc5F)nc5ncccc45)c3)ncn2)CC1] | 2-(5-Chloro-2-fluorophenyl)-4-{5-[6-(4-methyl-piperazin-1-yl)-pyrimidin-4-yl]-pyridin-3-yl}-[1,8]naphthyridine M 512.0 | 1.57 | 512 | ++ | ++ |
| 120 | 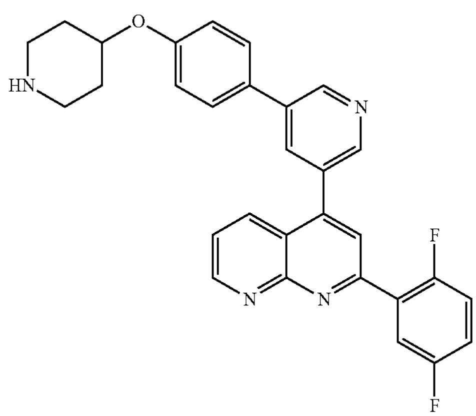 [SMILES: Fc1ccc(F)c(-c2cc(-c3cncc(-c4ccc(OC5CCNCC5)cc4)c3)c3cccnc3n2)c1] | 2-(2,5-Difluorophenyl)-4-{5-[4-(piperidin-4-yloxy)-phenyl]-pyridin-3-yl}-[1,8]naphthyridine M 494.5 | 1.55 | 495 | +++ | +++ |
| 121 | 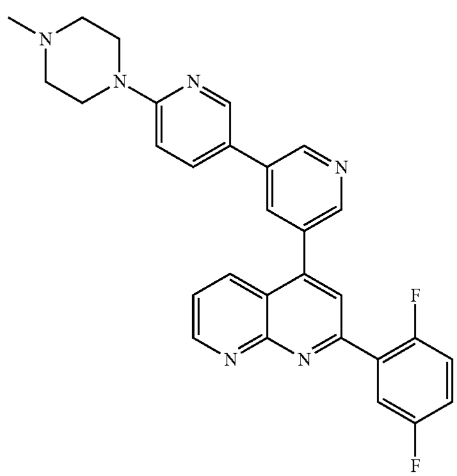 [SMILES: CN1CCN(c2ccc(-c3cncc(-c4cc(-c5cc(F)ccc5F)nc5ncccc45)c3)cn2)CC1] | 2-(2,5-Difluorophenyl)-4-[6'-(4-methyl-piperazin-1-yl)-[3,3']bipyridinyl-5-yl]-[1,8]naphthyridine M 494.5 | 1.47 | 495 | +++ | ++ |

TABLE 1-continued

Compounds of formulae (I), (II)

| No. | Structure | Name; Mass | HPLC/MS R$_t$ [min] | HPLC/MS [M + H] | TβR activity (Example 36) 0 + ++ +++ | TβR activity (Example 35A) >10 μM 1-10 μM 0.1-1 μM <0.1 μM |
|---|---|---|---|---|---|---|
| 122 | 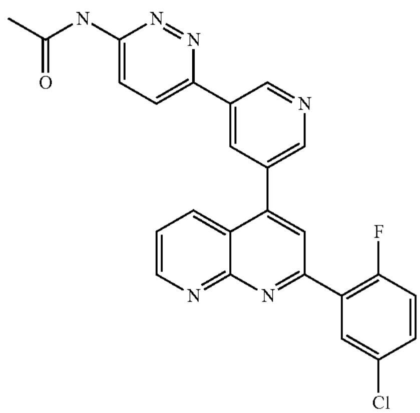 [SMILES: CC(=O)Nc1ccc(-c2cncc(-c3cc(-c4cc(Cl)ccc4F)nc4ncccc34)c2)nn1] | N-(6-{5-[2-(5-Chloro-2-fluoro-phenyl)-[1,8]naphthyridin-4-yl]-pyridin-3-yl}-pyridazin-3-yl)-acetamide M 470.9 | 1.91 | 471 | ++ | ++ |
| 123 | 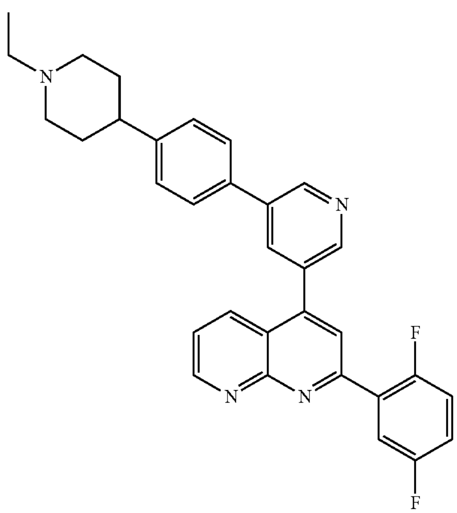 [SMILES: CCN1CCC(c2ccc(-c3cncc(-c4cc(-c5cc(F)ccc5F)nc5ncccc45)c3)cc2)CC1] | 2-(2,5-Difluoro-phenyl)-4-{5-[4-(1-ethyl-piperidin-4-yl)-phenyl]-pyridin-3-yl}-[1,8]naphthyridine M 506.6 | 1.58 | 507 | +++ | +++ |
| 124 | 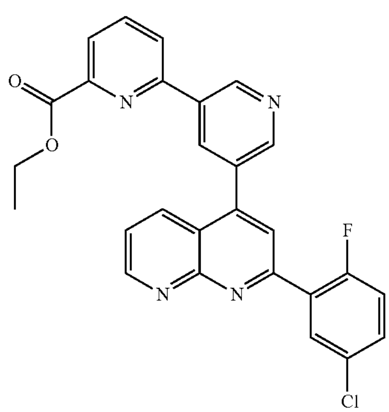 [SMILES: CCOC(=O)c1cccc(-c2cncc(-c3cc(-c4cc(Cl)ccc4F)nc4ncccc34)c2)n1] | 5'-[2-(5-Chloro-2-fluoro-phenyl)-[1,8]naphthyridin-4-yl]-[2,3']bipyridinyl-6-carboxylic acid ethyl ester M 484.9 | 2.34 | 485 | + | ++ |

TABLE 1-continued

Compounds of formulae (I), (II)

| No. | Structure | Name; Mass | HPLC/ MS R_t [min] | HPLC/ MS [M + H] | TβR activity (Example 36) 0 + ++ +++ | TβR activity (Example 35A) >10 μM 1-10 μM 0.1-1 μM <0.1 μM |
|---|---|---|---|---|---|---|
| 125 | 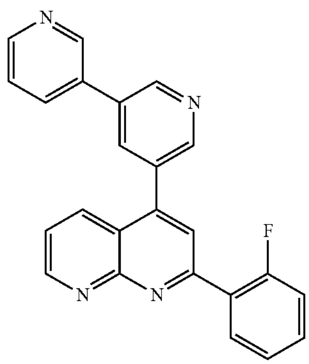 [SMILES: Fc1ccccc1-c1cc(-c2cncc(-c3cccnc3)c2)c2cccnc2n1] | 4-[3,3']Bipyridinyl-5-yl-2-(2-fluoro-phenyl)-[1,8]naphthyridine M 378.4 | 1.71 | 379 | + | + |
| 126 | 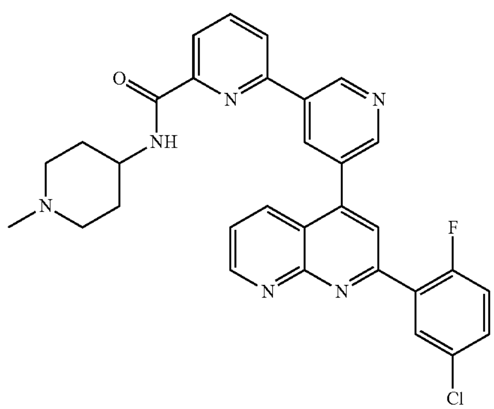 [SMILES: CN1CCC(NC(=O)c2cccc(-c3cncc(-c4cc(-c5cc(Cl)ccc5F)nc5ncccc45)c3)n2)CC1] | 3-{5-[2-(5-Chloro-2-fluoro-phenyl)-[1,8]naphthyridin-4-yl]-pyridin-3-yl}-N-(1-methyl-piperidin-4-yl)-benzamide M 552.1 | 1.64 | 552 | ++ | ++ |
| 127 | 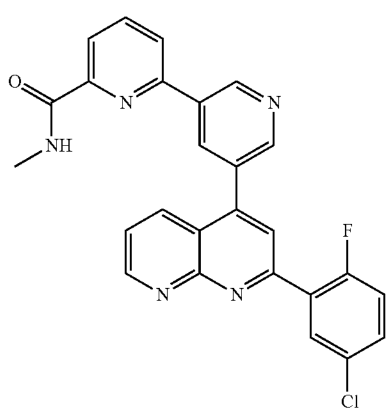 [SMILES: CNC(=O)c1cccc(-c2cncc(-c3cc(-c4cc(Cl)ccc4F)nc4ncccc34)c2)n1] | 5'-[2-(5-Chloro-2-fluoro-phenyl)-[1,8]naphthyridin-4-yl]-[2,3']bipyridinyl-6-carboxylic acid methylamide M 469.9 | 2.08 | 470 | + | 0 |

TABLE 1-continued

Compounds of formulae (I), (II)

| No. | Structure | Name; Mass | HPLC/MS R$_t$ [min] | HPLC/MS [M + H] | TβR activity (Example 36) 0 + ++ +++ | TβR activity (Example 35A) >10 μM 1-10 μM 0.1-1 μM <0.1 μM |
|---|---|---|---|---|---|---|
| 128 | 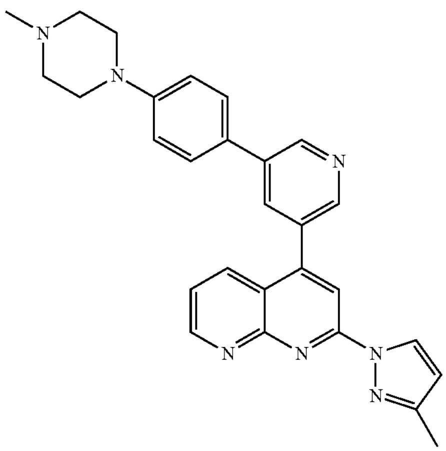 [SMILES: Cc1ccn(-c2cc(-c3cncc(-c4ccc(N5CCN(C)CC5)cc4)c3)c3cccnc3n2)n1] | 4-{5-[4-(4-Methyl-piperazin-1-yl)-phenyl]-pyridin-3-yl}-2-(3-methyl-pyrazol-1-yl)-[1,8]naphthyridine<br>M 461.6 | 1.48 | 462 | + | + |
| 129 | 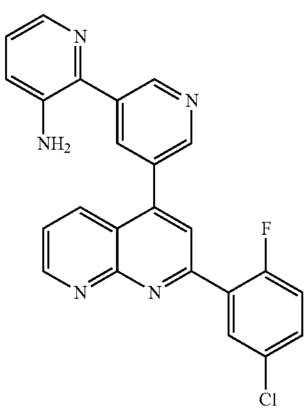 [SMILES: Nc1cccnc1-c1cncc(-c2cc(-c3cc(Cl)ccc3F)nc3ncccc23)c1] | 5'-[2-(5-Chloro-2-fluoro-phenyl)-[1,8]naphthyridin-4-yl]-[2,3']bipyridinyl-3-ylamine<br>M 427.9 | 1.60 | 428 | 0 | 0 |
| 130 | 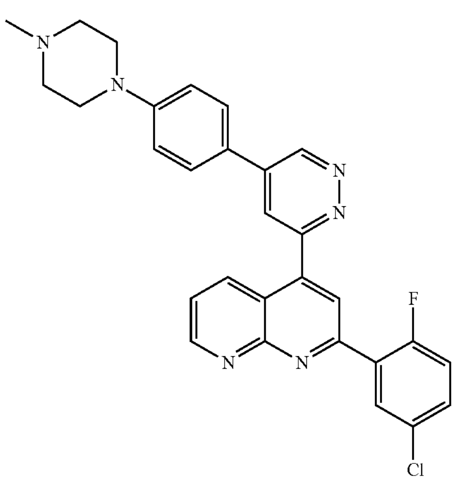 [SMILES: CN1CCN(c2ccc(-c3cnnc(-c4cc(-c5cc(Cl)ccc5F)nc5ncccc45)c3)cc2)CC1] | 2-(5-Chloro-2-fluoro-phenyl)-4-{5-[4-(4-methyl-piperazin-1-yl)-phenyl]-pyridazin-3-yl}-[1,8]naphthyridine<br>M 511.0 | 1.62 | 511 | + | + |

TABLE 1-continued

Compounds of formulae (I), (II)

| No. | Structure | Name; Mass | HPLC/MS R_t [min] | HPLC/MS [M + H] | TβR activity (Example 36)  0 +  ++  +++ | TβR activity (Example 35A)  >10 µM  1-10 µM  0.1-1 µM  <0.1 µM |
|---|---|---|---|---|---|---|
| 131 | 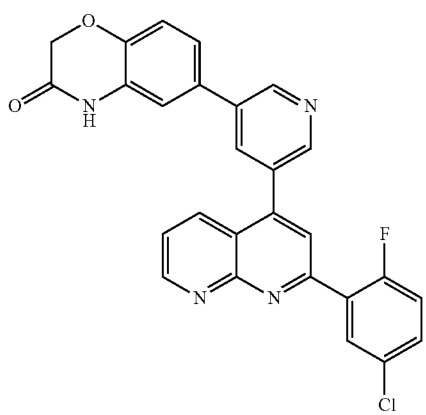 [SMILES: O=C1COc2ccc(-c3cncc(-c4cc(-c5cc(Cl)ccc5F)nc5ncccc45)c3)cc2N1] | 6-{5-[2-(5-Chloro-2-fluoro-phenyl)-[1,8]naphthyridin-4-yl]-pyridin-3-yl}-4H-benzo[1,4]oxazin-3-one<br>M 482.9 | 2.09 | 483 | +++ | ++ |
| 132 | 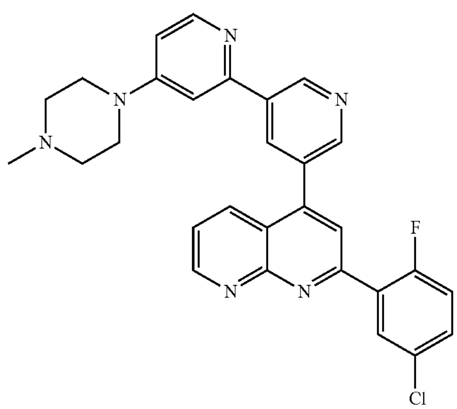 [SMILES: CN1CCN(c2ccnc(-c3cncc(-c4cc(-c5cc(Cl)ccc5F)nc5ncccc45)c3)c2)CC1] | 2-(5-Chloro-2-fluoro-phenyl)-4-[4-(4-methyl-piperazin-1-yl)-[2,3']bipyridinyl-5'-yl]-[1,8]naphthyridine<br>M 511.0 | 1.28 | 511 | +++ | +++ |
| 133 | 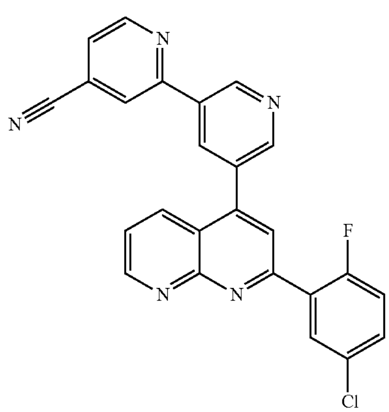 [SMILES: N#Cc1ccnc(-c2cncc(-c3cc(-c4cc(Cl)ccc4F)nc4ncccc34)c2)c1] | 5'-[2-(5-Chloro-2-fluoro-phenyl)-[1,8]naphthyridin-4-yl]-[2,3']bipyridinyl-4-carbonitrile<br>M 437.9 | 2.26 | 438 | 0 | 0 |

TABLE 1-continued

Compounds of formulae (I), (II)

| | | | | | TβR activity (Example 36) | TβR activity (Example 35A) |
|---|---|---|---|---|---|---|
| | | | HPLC/ MS | | 0 | >10 μM |
| | | Name; | R$_t$ | HPLC/ MS | + | 1-10 μM |
| No. | Structure | Mass | [min] | [M + H] | ++ +++ | 0.1-1 μM <0.1 μM |
| 134 | 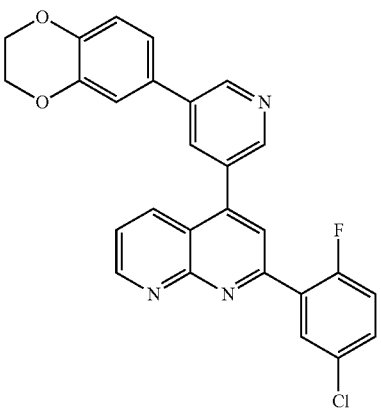 [SMILES: Fc1ccc(Cl)cc1-c1cc(-c2cncc(-c3ccc4c(c3)OCCO4)c2)c2cccnc2n1] | 2-(5-Chloro-2-fluoro-phenyl)-4-[5-(2,3-dihydro-benzo[1,4]dioxin-6-yl)-pyridin-3-yl]-[1,8]naphthyridine M 469.9 | 2.46 | 470 | ++ | +++ |
| 135 | 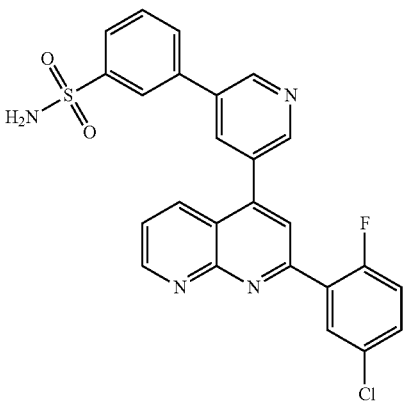 [SMILES: NS(=O)(=O)c1cccc(-c2cncc(-c3cc(-c4cc(Cl)ccc4F)nc4ncccc34)c2)c1] | 3-{5-[2-(5-Chloro-2-fluoro-phenyl)-[1,8]naphthyridin-4-yl]-pyridin-3-yl}-benzene-sulfonamide M 490.9 | 2.02 | 491 | +++ | ++ |
| 136 | 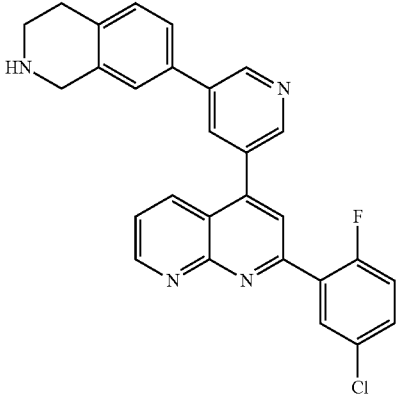 [SMILES: Fc1ccc(Cl)cc1-c1cc(-c2cncc(-c3ccc4c(c3)CNCC4)c2)c2cccnc2n1] | 2-(5-Chloro-2-fluoro-phenyl)-4-[5-(1,2,3,4-tetrahydro-isoquinolin-7-yl)-pyridin-3-yl]-[1,8]naphthyridine M 466.9 | 1.53 | 467 | +++ | +++ |

TABLE 1-continued

Compounds of formulae (I), (II)

| No. | Structure | Name; Mass | HPLC/MS R_t [min] | HPLC/MS [M + H] | TβR activity (Example 36) 0 + ++ +++ | TβR activity (Example 35A) >10 μM 1-10 μM 0.1-1 μM <0.1 μM |
|---|---|---|---|---|---|---|
| 137 | control | 2-(2,5-Difluoro-phenyl)-4-pyridin-3-yl-[1,8]naphthyridine M 319.3 | 1.78 | 320 | + | 0 |
| 138 | 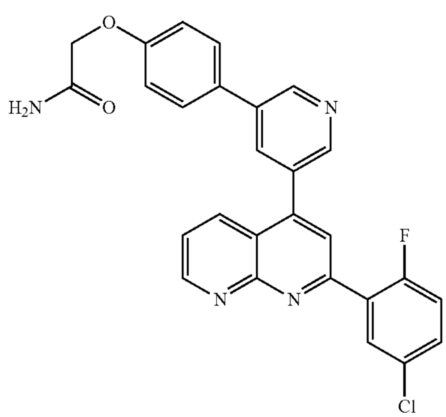 [SMILES: NC(=O)COc1ccc(-c2cncc(-c3cc(-c4cc(Cl)ccc4F)nc4ncccc34)c2)cc1] | 2-(4-{5-[2-(5-Chloro-2-fluoro-phenyl)-[1,8]naphthyridin-4-yl]-pyridin-3-yl}-phenoxy)-acetamide M 484.9 | 1.95 | 485 | +++ | ++ |
| 139 | 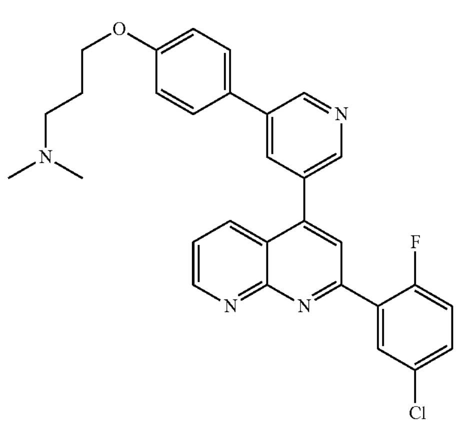 [SMILES: CN(C)CCCOc1ccc(-c2cncc(-c3cc(-c4cc(Cl)ccc4F)nc4ncccc34)c2)cc1] | [3-(4-{5-[2-(5-Chloro-2-fluoro-phenyl)-[1,8]naphthyridin-4-yl]-pyridin-3-yl}-phenoxy)-propyl]-dimethyl-amine M 513.0 | 1.72 | 513 | +++ | +++ |

TABLE 1-continued

Compounds of formulae (I), (II)

| No. | Structure | Name; Mass | HPLC/MS R$_t$ [min] | HPLC/MS [M + H] | TβR activity (Example 36) 0 + ++ +++ | TβR activity (Example 35A) >10 μM 1-10 μM 0.1-1 μM <0.1 μM |
|---|---|---|---|---|---|---|
| 140 | 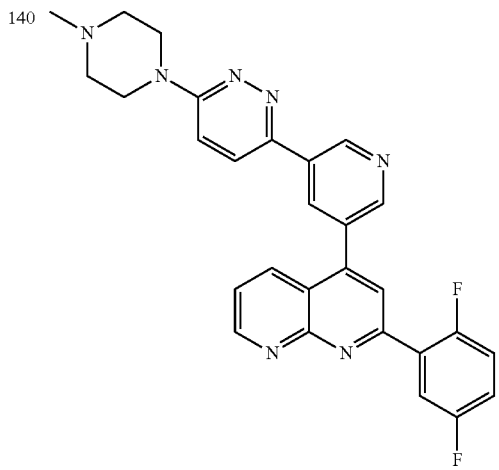 | 2-(2,5-Difluoro-phenyl)-4-{5-[6-(4-methyl-piperazin-1-yl)-pyridazin-3-yl]-pyridin-3-yl}-[1,8]naphthyridine M 495.5 | 1.46 | 496 | ++ | + |
| 141 | 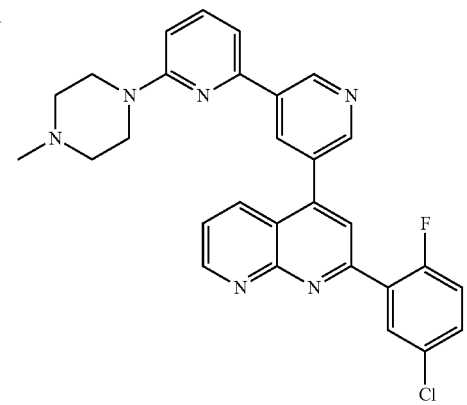 [SMILES: CN1CCN(c2cccc(-c3cncc(-c4cc(-c5cc(Cl)ccc5F)nc5ncccc45)c3)n2)CC1] | 2-(5-Chloro-2-fluoro-phenyl)-4-[6-(4-methyl-piperazin-1-yl)-[2,3']bipyridinyl-5'-yl]-[1,8]naphthyridine M 511.0 | 1.60 | 511 | ++ | ++ |
| 142 | 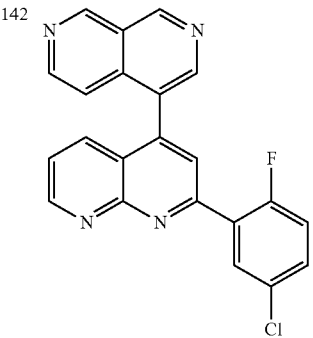 | 5-[2-(5-Chloro-2-fluoro-phenyl)-[1,8]naphthyridin-4-yl]-[1,7]naphthyridine M 386.8 | 2.01 | 387 | ++ | + |

TABLE 1-continued

Compounds of formulae (I), (II)

| No. | Structure | Name; Mass | HPLC/MS R_t [min] | HPLC/MS [M + H] | TβR activity (Example 36)<br>0 +<br>+ ++<br>++ +++<br>+++ | TβR activity (Example 35A)<br>>10 μM<br>1-10 μM<br>0.1-1 μM<br><0.1 μM |
|---|---|---|---|---|---|---|
| 143 | 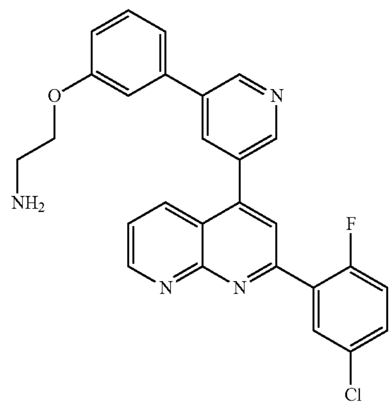 [SMILES: NCCOc1cccc(-c2cncc(-c3cc(-c4cc(Cl)ccc4F)nc4ncccc34)c2)c1] | 2-(3-{5-[2-(5-Chloro-2-fluoro-phenyl)-[1,8]naphthyridin-4-yl]-pyridin-3-yl}-phenoxy)-ethylamine<br>M 470.9 | 1.57 | 471 | +++ | ++ |
| 144 | 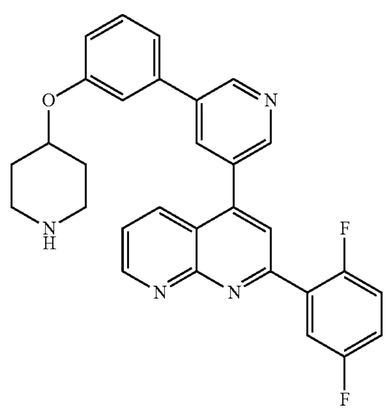 [SMILES: Fc1ccc(F)c(-c2cc(-c3cncc(-c4cccc(OC5CCNCC5)c4)c3)c3cccnc3n2)c1] | 2-(2,5-Difluoro-phenyl)-4-{5-[3-(piperidin-4-yloxy)-phenyl]-pyridin-3-yl}-[1,8]naphthyridine<br>M 494.5 | 1.59 | 495 | +++ | ++ |
| 145 | 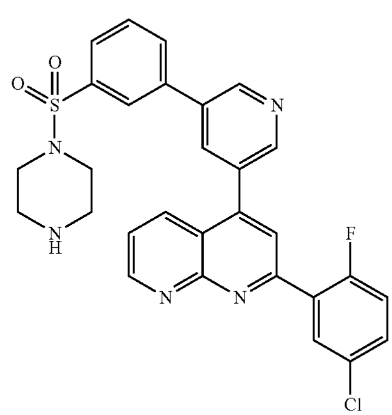 [SMILES: O=S(=O)(c1cccc(-c2cncc(-c3cc(-c4cc(Cl)ccc4F)nc4ncccc34)c2)c1)N1CCNCC1] | 2-(5-Chloro-2-fluoro-phenyl)-4-{5-[3-(piperazine-1-sulfonyl)-phenyl]-pyridin-3-yl}-[1,8]naphthyridine<br>M 560.1 | 1.68 | 560 | ++ | + |

TABLE 1-continued

Compounds of formulae (I), (II)

| No. | Structure | Name; Mass | HPLC/MS R$_t$ [min] | HPLC/MS [M + H] | TβR activity (Example 36) 0 + ++ +++ | TβR activity (Example 35A) >10 μM 1-10 μM 0.1-1 μM <0.1 μM |
|---|---|---|---|---|---|---|
| 146 | 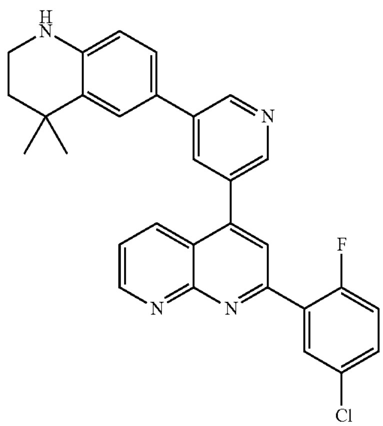 [SMILES: CC1(C)CCNc2ccc(-c3cncc(-c4cc(-c5cc(Cl)ccc5F)nc5ncccc45)c3)cc21] | 2-(5-Chloro-2-fluoro-phenyl)-4-[5-(4,4-dimethyl-1,2,3,4-tetrahydro-quinolin-6-yl)-pyridin-3-yl]-[1,8]naphthyridine M 495.0 | 2.55 | 495 | ++ | ++ |
| 147 | 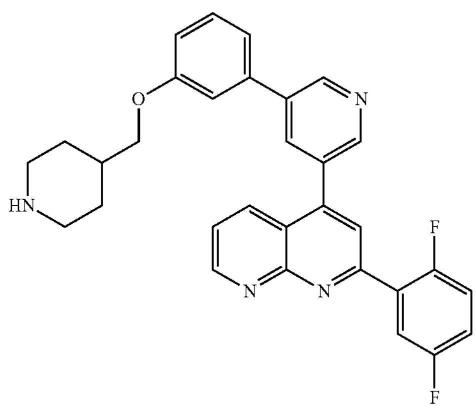 [SMILES: Fc1ccc(F)c(-c2cc(-c3cncc(-c4cccc(OCC5CCNCC5)c4)c3)c3cccnc3n2)c1] | 2-(2,5-Difluoro-phenyl)-4-{5-[3-(piperidin-4-ylmethoxy)-phenyl]-pyridin-3-yl}-[1,8]naphthyridine M 508.6 | 1.70 | 509 | ++ | + |
| 148 | 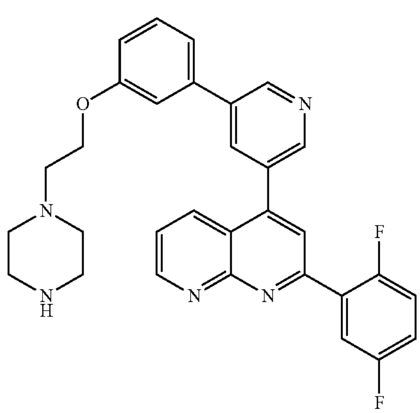 [SMILES: Fc1ccc(F)c(-c2cc(-c3cncc(-c4cccc(OCCN5CCNCC5)c4)c3)c3cccnc3n2)c1] | 2-(2,5-Difluoro-phenyl)-4-{5-[3-(2-piperazin-1-yl-ethoxy)-phenyl]-pyridin-3-yl}-[1,8]naphthyridine M 523.6 | 1.50 | 524 | +++ | +++ |

TABLE 1-continued

Compounds of formulae (I), (II)

|  |  |  |  | TβR activity (Example 36) | TβR activity (Example 35A) |
|---|---|---|---|---|---|
|  |  |  |  | 0 | >10 μM |
|  |  |  | HPLC/ |  | 1-10 μM |
|  |  |  | MS | + |  |
|  |  | HPLC/ | R_t | ++ | 0.1-1 μM |
|  | Name; | MS |  |  |  |
| No. | Structure | Mass | [min] | [M + H] | +++ | <0.1 μM |

| No. | Structure | Name; Mass | HPLC/MS R_t [min] | HPLC/MS [M + H] | TβR activity (Example 36) | TβR activity (Example 35A) |
|---|---|---|---|---|---|---|
| 149 | 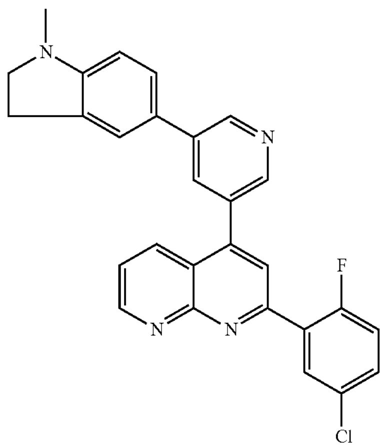 [SMILES: CN1CCc2cc(-c3cncc(-c4cc(-c5cc(Cl)ccc5F)nc5ncccc45)c3)ccc21] | 2-(5-Chloro-2-fluorophenyl)-4-[5-(1-methyl-2,3-dihydro-1H-indol-5-yl)-pyridin-3-yl]-[1,8]naphthyridine M 466.9 | 2.63 | 467 | ++ | +++ |
| 150 | 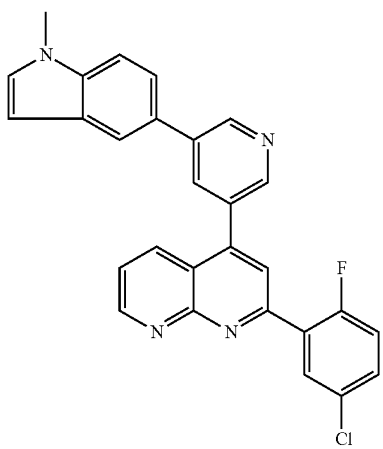 [SMILES: Cn1ccc2cc(-c3cncc(-c4cc(-c5cc(Cl)ccc5F)nc5ncccc45)c3)ccc21] | 2-(5-Chloro-2-fluorophenyl)-4-[5-(1-methyl-1H-indol-5-yl)-pyridin-3-yl]-[1,8]naphthyridine M 464.9 | 2.54 | 465 | ++ | +++ |
| 151 | 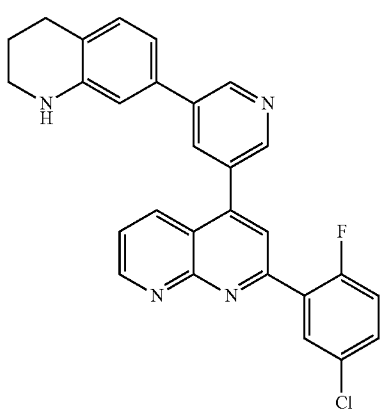 [SMILES: Fc1ccc(Cl)cc1-c1cc(-c2cncc(-c3ccc4c(c3)NCCC4)c2)c2cccnc2n1] | 2-(5-Chloro-2-fluorophenyl)-4-[5-(1,2,3,4-tetrahydroquinolin-7-yl)-pyridin-3-yl]-[1,8]naphthyridine M 466.9 | 2.46 | 467 | ++ | +++ |

TABLE 1-continued

Compounds of formulae (I), (II)

| | | | | | TβR activity (Example 36) | TβR activity (Example 35A) |
|---|---|---|---|---|---|---|
| | | | HPLC/ MS | | 0 | >10 μM |
| | | | R_t | HPLC/ MS | + | 1-10 μM |
| | | Name; | | | ++ | 0.1-1 μM |
| No. | Structure | Mass | [min] | [M + H] | +++ | <0.1 μM |
| 152 | | 2-(2-{5-[2-(5-Chloro-2-fluoro-phenyl)-[1,8]naphthyridin-4-yl]-pyridin-3-yl}-phenyl)-ethylamine M 454.9 | 1.65 | 455 | + | + |
| 153 | | 2-(5-Chloro-2-fluoro-phenyl)-4-{5-[4-(2-morpholin-4-yl-ethyl)-phenyl]-pyridin-3-yl}-[1,8]naphthyridine M 525.0 | 1.63 | 525 | +++ | +++ |
| 154 | | 2-(5-Chloro-2-fluoro-phenyl)-4-[5-(2,3-dihydro-1H-indol-5-yl)-pyridin-3-yl]-[1,8]naphthyridine M 452.9 | 1.97 | 453 | ++ | + |

TABLE 1-continued

Compounds of formulae (I), (II)

| | | | | | TβR activity (Example 36) | TβR activity (Example 35A) |
|---|---|---|---|---|---|---|
| | | | HPLC/ MS | HPLC/ MS | 0 + ++ +++ | >10 μM 1-10 μM 0.1-1 μM <0.1 μM |
| No. | Structure | Name; Mass | R_t [min] | [M + H] | | |
| 155 | | 2-(5-Chloro-2-fluoro-phenyl)-4-[5-(1,2,3,4-tetrahydro-isoquinolin-6-yl)-pyridin-3-yl]-[1,8]naphthyridine M 466.9 | 1.56 | 467 | +++ | +++ |
| 156 | | 2-(5-Chloro-2-fluoro-phenyl)-4-{5-[4-(2-pyrrolidin-1-yl-ethoxy)-phenyl]-pyridin-3-yl}-[1,8]naphthyridine M 525.0 | 1.61 | 525 | +++ | +++ |
| 157 | | 6-{5-[2-(5-Chloro-2-fluoro-phenyl)-[1,8]naphthyridin-4-yl]-pyridin-3-yl}-4,4-dimethyl-3,4-dihydro-1H-quinolin-2-one M 509.0 | 2.19 | 509 | ++ | ++ |

TABLE 1-continued

Compounds of formulae (I), (II)

| | | | | | TβR activity (Example 36) | TβR activity (Example 35A) |
|---|---|---|---|---|---|---|
| | | | HPLC/ MS | | 0 | >10 μM |
| | | | $R_t$ | HPLC/ MS | + | 1-10 μM |
| | | Name; | | | ++ | 0.1-1 μM |
| No. | Structure | Mass | [min] | [M + H] | +++ | <0.1 μM |
| 158 | | 2-(5-Chloro-2-fluoro-phenyl)-4-{5-[3-(2-pyrrolidin-1-yl-ethoxy)-phenyl]-pyridin-3-yl}-[1,8]naphthyridine M 525.0 | 1.70 | 525 | +++ | +++ |
| 159 | | 2-(5-Chloro-2-fluoro-phenyl)-4-[5-(3-piperidin-4-yl-phenyl)-pyridin-3-yl]-[1,8]naphthyridine M 495.0 | 1.67 | 495 | +++ | ++ |
| 160 | | 5'-[2-(5-Chloro-2-fluoro-phenyl)-[1,8]naphthyridin-4-yl]-[2,3']bipyridinyl-6-carbonitrile M 437.9 | 2.27 | 438 | 0 | 0 |

TABLE 1-continued

Compounds of formulae (I), (II)

| No. | Structure | Name; Mass | HPLC/MS R$_t$ [min] | HPLC/MS [M + H] | TβR activity (Example 36) 0 + ++ +++ | TβR activity (Example 35A) >10 μM 1-10 μM 0.1-1 μM <0.1 μM |
|---|---|---|---|---|---|---|
| 161 | 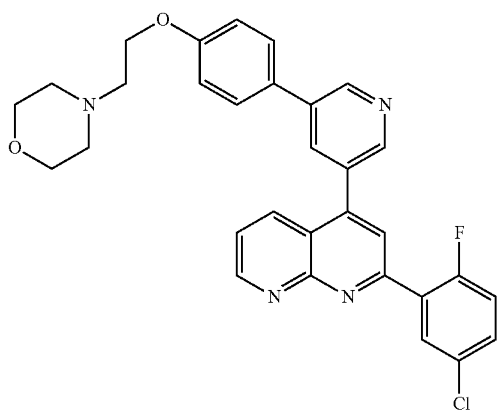 [SMILES: Fc1ccc(Cl)cc1-c1cc(-c2cncc(-c3ccc(OCCN4CCOCC4)cc3)c2)c2cccnc2n1] | 2-(5-Chloro-2-fluoro-phenyl)-4-{5-[4-(2-morpholin-4-yl-ethoxy)-phenyl]-pyridin-3-yl}-[1,8]naphthyridine M 541.0 | 1.68 | 541 | +++ | +++ |
| 162 | 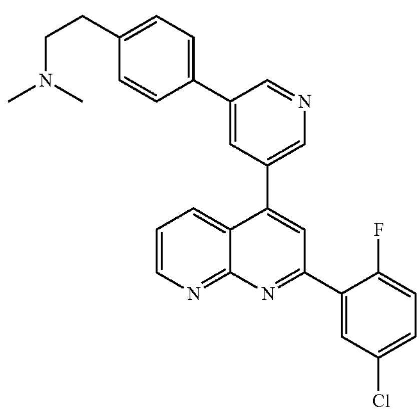 [SMILES: CN(C)CCc1ccc(-c2cncc(-c3cc(-c4cc(Cl)ccc4F)nc4ncccc34)c2)cc1] | [2-(4-{5-[2-(5-Chloro-2-fluoro-phenyl)-[1,8]naphthyridin-4-yl]-pyridin-3-yl}-phenyl)-ethyl]-dimethyl-amine M 483.0 | 1.65 | 483 | +++ | +++ |
| 163 | 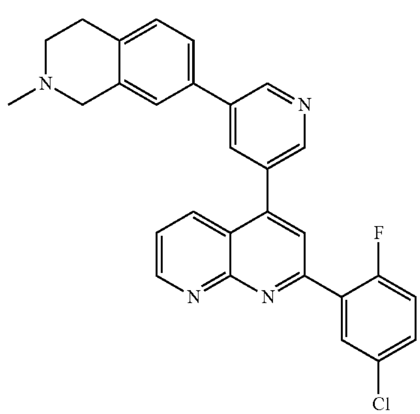 [SMILES: CN1CCc2ccc(-c3cncc(-c4cc(-c5cc(Cl)ccc5F)nc5ncccc45)c3)cc2C1] | 2-(5-Chloro-2-fluoro-phenyl)-4-[5-(2-methyl-1,2,3,4-tetrahydro-isoquinolin-7-yl)-pyridin-3-yl]-[1,8]naphthyridine M 481.0 | 1.58 | 481 | +++ | +++ |

TABLE 1-continued

Compounds of formulae (I), (II)

| No. | Structure | Name; Mass | HPLC/ MS R$_t$ [min] | HPLC/ MS [M + H] | TβR activity (Example 36) 0 + ++ +++ | TβR activity (Example 35A) >10 μM 1-10 μM 0.1-1 μM <0.1 μM |
|---|---|---|---|---|---|---|
| 164 | 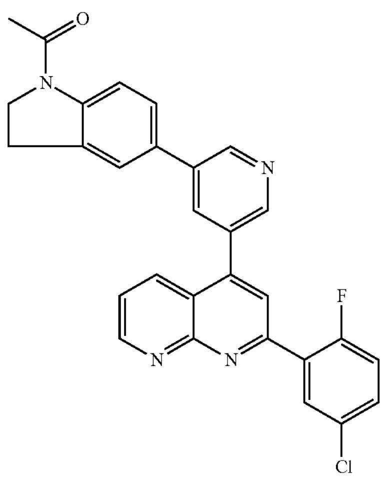 [SMILES: CC(=O)N1CCc2cc(-c3cncc(-c4cc(-c5cc(Cl)ccc5F)nc5ncccc45)c3)ccc21] | 1-(5-{5-[2-(5-Chloro-2-fluoro-phenyl)-[1,8]naphthyridin-4-yl]-pyridin-3-yl}-2,3-dihydro-indol-1-yl)-ethanone M 495.0 | 2.19 | 495 | +++ | +++ |
| 165 | 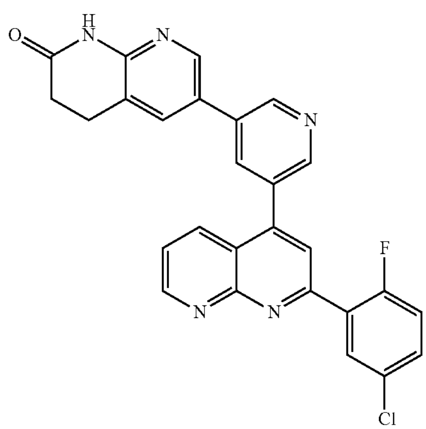 [SMILES: O=C1CCc2cc(-c3cncc(-c4cc(-c5cc(Cl)ccc5F)nc5ncccc45)c3)cnc2N1] | 6-{5-[2-(5-Chloro-2-fluoro-phenyl)-[1,8]naphthyridin-4-yl]-pyridin-3-yl}-3,4-dihydro-1H-[1,8]naphthyridin-2-one M 481.9 | 1.92 | 482 | +++ | +++ |
| 166 | 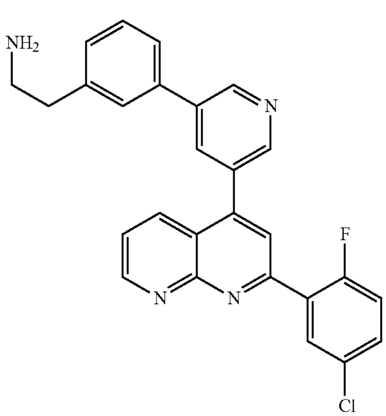 [SMILES: NCCc1cccc(-c2cncc(-c3cc(-c4cc(Cl)ccc4F)nc4ncccc34)c2)c1] | 2-(3-{5-[2-(5-Chloro-2-fluoro-phenyl)-[1,8]naphthyridin-4-yl]-pyridin-3-yl}-phenyl)-ethylamine M 454.9 | 1.58 | 455 | +++ | +++ |

TABLE 1-continued

Compounds of formulae (I), (II)

| No. | Structure | Name; Mass | HPLC/MS R$_t$ [min] | HPLC/MS [M + H] | TβR activity (Example 36) 0 + ++ +++ | TβR activity (Example 35A) >10 μM 1-10 μM 0.1-1 μM <0.1 μM |
|---|---|---|---|---|---|---|
| 167 | 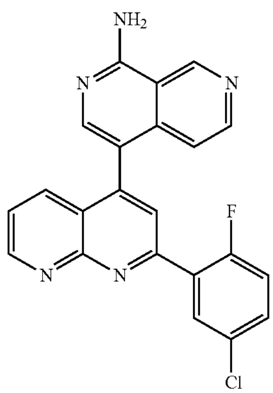 [SMILES: Nc1ncc(-c2cc(-c3cc(Cl)ccc3F)nc3ncccc23)c2ccncc12] | 4-[2-(5-Chloro-2-fluoro-phenyl)-[1,8]naphthyridin-4-yl]-[2,7]naphthyridin-1-ylamine M 401.8 | 1.59 | 402 | +++ | +++ |
| 168 | 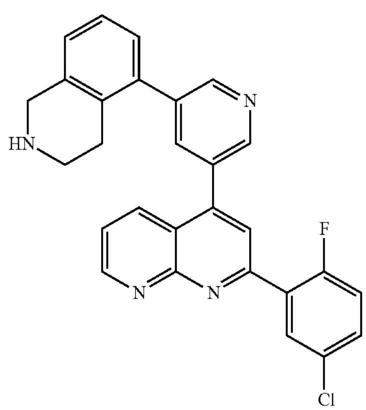 [SMILES: Fc1ccc(Cl)cc1-c1cc(-c2cncc(-c3cccc4c3CCNC4)c2)c2cccnc2n1] | 2-(5-Chloro-2-fluoro-phenyl)-4-[5-(1,2,3,4-tetrahydro-isoquinolin-5-yl)-pyridin-3-yl]-[1,8]naphthyridine M 466.9 | 1.55 | 467 | + | + |
| 169 | 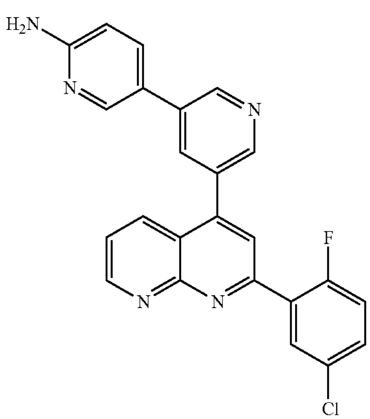 [SMILES: Nc1ccc(-c2cncc(-c3cc(-c4cc(Cl)ccc4F)nc4ncccc34)c2)cn1] | 5'-[2-(5-Chloro-2-fluoro-phenyl)-[1,8]naphthyridin-4-yl]-[3,3']bipyridinyl-6-ylamine M 427.9 | 1.52 | 428 | +++ | ++ |

TABLE 1-continued

Compounds of formulae (I), (II)

| | | | | TβR activity (Example 36) | TβR activity (Example 35A) |
|---|---|---|---|---|---|
| | | HPLC/ MS | | 0 | >10 μM |
| | | | HPLC/ | + | 1-10 μM |
| | Name; | R$_t$ | MS | ++ | 0.1-1 μM |
| No. Structure | Mass | [min] | [M + H] | +++ | <0.1 μM |

| 170 | 2-[{5'-[2-(5-Chloro-2-fluoro-phenyl)-[1,8]naphthyridin-4-yl]-[2,3']bipyridinyl-6-yl}-(2-hydroxy-ethyl)amino]-ethanol<br>M 516.0 | 1.86 | 516 | +++ | ++ |
| 171 | 2-(5-Chloro-2-fluoro-phenyl)-4-[5'-(4-methyl-piperazin-1-yl)-[3,3']bipyridinyl-5 yl]-[1,8]naphthyridine<br>M 511.0 | 1.47 | 511 | +++ | +++ |
| 172 | 2-(5-Chloro-2-fluoro-phenyl)-4-{5-[4-(2-pyrrolidin-1-yl-ethyl)-phenyl]-pyridin-3-yl}-[1,8]naphthyridine<br>M 509.0 | 1.67 | 509 | +++ | +++ |

TABLE 1-continued

Compounds of formulae (I), (II)

| No. | Structure | Name; Mass | HPLC/ MS R$_t$ [min] | HPLC/ MS [M + H] | TβR activity (Example 36) 0 + ++ +++ | TβR activity (Example 35A) >10 μM 1-10 μM 0.1-1 μM <0.1 μM |
|---|---|---|---|---|---|---|
| 173 | 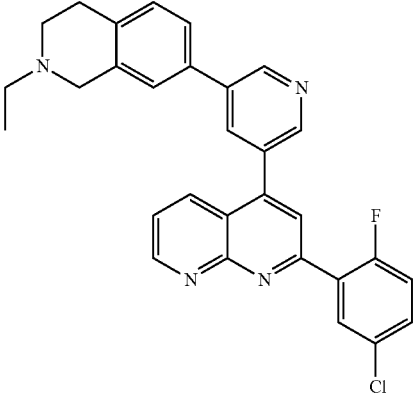 [SMILES: CCN1CCc2ccc(-c3cncc(-c4cc(-c5cc(Cl)ccc5F)nc5ncccc45)c3)cc2C1] | 2-(5-Chloro-2-fluoro-phenyl)-4-[5-(2-ethyl-1,2,3,4-tetrahydro-isoquinolin-7-yl)-pyridin-3-yl]-[1,8]naphthyridine M 495.0 | 1.65 | 495 | +++ | +++ |
| 174 | 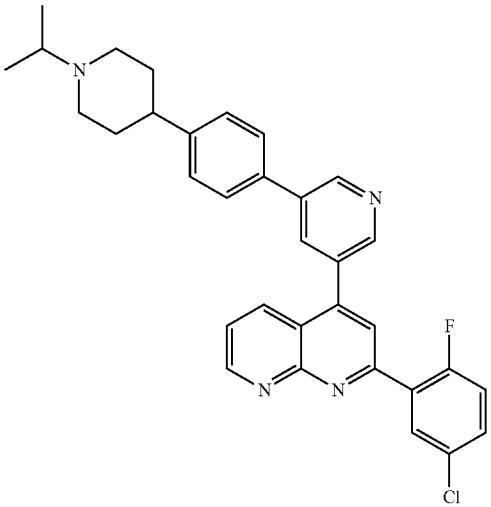 [SMILES: CC(C)N1CCC(c2ccc(-c3cncc(-c4cc(-c5cc(Cl)ccc5F)nc5ncccc45)c3)cc2)CC1] | 2-(5-Chloro-2-fluoro-phenyl)-4-{5-[4-(1-isopropyl-piperidin-4-yl)-phenyl]-pyridin-3-yl}-[1,8]naphthyridine M 537.1 | 1.72 | 537 | +++ | +++ |
| 175 | 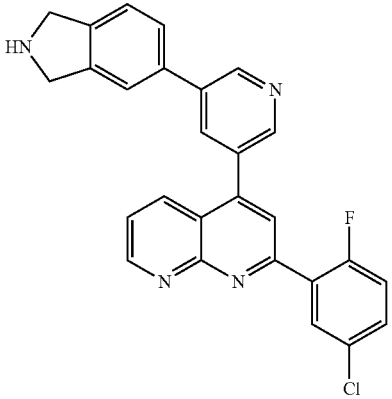 [SMILES: Fc1ccc(Cl)cc1-c1cc(-c2cncc(-c3ccc4c(c3)CNC4)c2)c2cccnc2n1] | 2-(5-Chloro-2-fluoro-phenyl)-4-[5-(2,3-dihydro-1H-isoindol-5-yl)-pyridin-3-yl]-[1,8]naphthyridine M 452.9 | 1.55 | 453 | +++ | +++ |

TABLE 1-continued

Compounds of formulae (I), (II)

| No. | Structure | Name; Mass | HPLC/ MS R$_t$ [min] | HPLC/ MS [M + H] | TβR activity (Example 36) 0 + ++ +++ | TβR activity (Example 35A) >10 μM 1-10 μM 0.1-1 μM <0.1 μM |
|---|---|---|---|---|---|---|
| 176 | 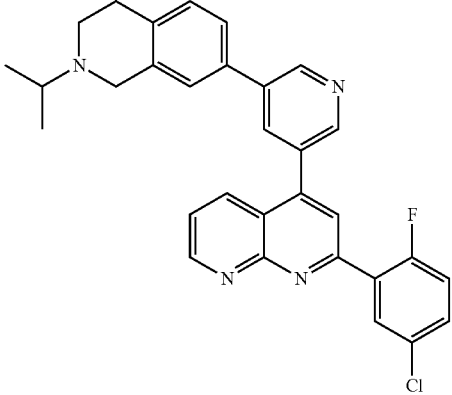 [SMILES: CC(C)N1CCc2ccc(-c3cncc(-c4cc(-c5cc(Cl)ccc5F)nc5ncccc45)c3)cc2C1] | 2-(5-Chloro-2-fluoro-phenyl)-4-[5-(2-isopropyl-1,2,3,4-tetrahydro-isoquinolin-7-yl)-pyridin-3-yl]-[1,8]naphthyridine M 509.0 | 1.67 | 509 | +++ | +++ |
| 177 | 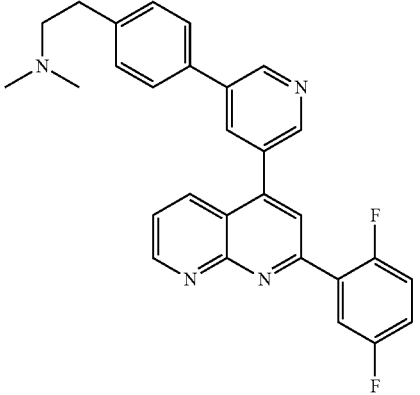 [SMILES: CN(C)CCc1ccc(-c2cncc(-c3cc(-c4cc(F)ccc4F)nc4ncccc34)c2)cc1] | [2-(4-{5-[2-(2,5-Difluoro-phenyl)-[1,8]naphthyridin-4-yl]-pyridin-3-yl}-phenyl)-ethyl]-dimethyl-amine M 466.5 | 1.54 | 467 | +++ | +++ |
| 178 | 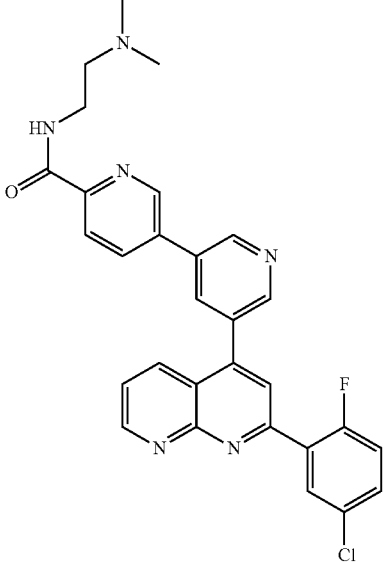 [SMILES: CN(C)CCNC(=O)c1ccc(-c2cncc(-c3cc(-c4cc(Cl)ccc4F)nc4ncccc34)c2)cn1] | 5'-[2-(5-Chloro-2-fluoro-phenyl)-[1,8]naphthyridin-4-yl]-[3,3']bipyridinyl-6-carboxylic acid (2-dimethylamino-ethyl)-amide M 527.0 | 1.55 | 527 | ++ | ++ |

TABLE 1-continued

Compounds of formulae (I), (II)

| | | | | TβR activity (Example 36) | TβR activity (Example 35A) |
|---|---|---|---|---|---|
| | | HPLC/ MS | | 0 | >10 μM |
| | | R$_t$ | HPLC/ MS | + | 1-10 μM |
| | Name; | | | ++ | 0.1-1 μM |
| No. Structure | Mass | [min] | [M + H] | +++ | <0.1 μM |

179

5-[2-(5-Chloro-2-fluoro-phenyl)-[1,8]naphthyridin-4-yl]-5-trifluoromethyl-[3,3']bipyridinyl-2-ylamine
M 495.9

180

2-(5-Chloro-2-fluoro-phenyl)-4-{5-[3-(2-pyrrolidin-1-yl-ethyl)-phenyl]-pyridin-3-yl}-[1,8]naphthyridine
M 509.0

181

TABLE 1-continued
Compounds of formulae (I), (II)
| No. | Structure | Name; Mass | HPLC/ MS R_t [min] | HPLC/ MS [M + H] | TβR activity (Example 36) 0 + ++ +++ | TβR activity (Example 35A) >10 μM 1-10 μM 0.1-1 μM <0.1 μM |
|---|---|---|---|---|---|---|
182
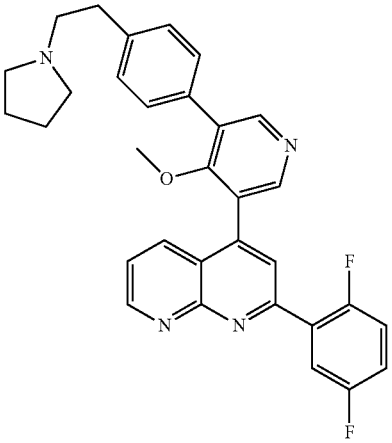 [SMILES: COc1c(-c2ccc(CCN3CCCC3)cc2)cncc1-c1cc(-c2cc(F)ccc2F)nc2ncccc12]
183
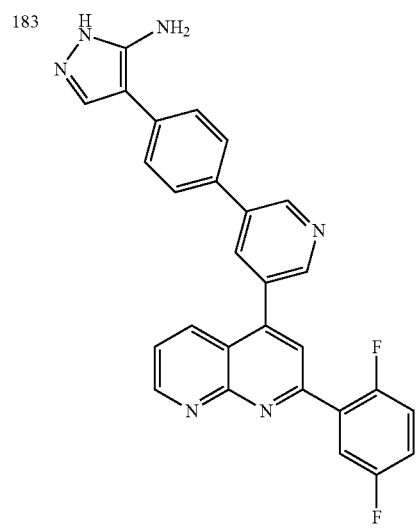

TABLE 1-continued

Compounds of formulae (I), (II)

| No. | Structure | Name; Mass | HPLC/ MS R$_t$ [min] | HPLC/ MS [M + H] | TβR activity (Example 36) 0 + ++ +++ | TβR activity (Example 35A) >10 μM 1-10 μM 0.1-1 μM <0.1 μM |
|-----|-----------|------------|----------------------|------------------|--------------------------------------|------------------------------------------------------------|
| 184 | 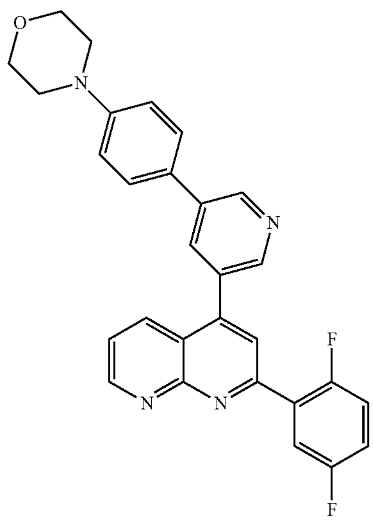 [SMILES: Fc1ccc(F)c(-c2cc(-c3cncc(-c4ccc(N5CCOCC5)cc4)c3)c3cccnc3n2)c1] | | | | | |
| 185 | 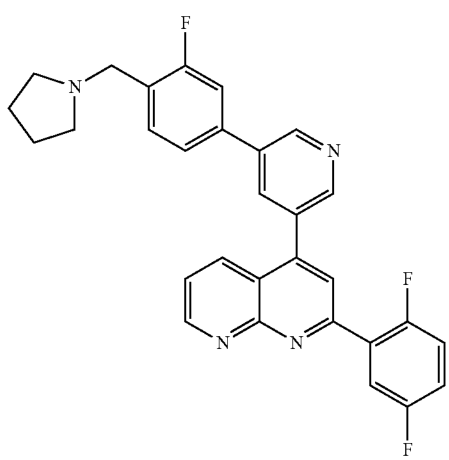 [SMILES: Fc1ccc(F)c(-c2cc(-c3cncc(-c4ccc(CN5CCCC5)c(F)c4)c3)c3cccnc3n2)c1] | | | | | |

TABLE 1-continued

Compounds of formulae (I), (II)

| No. | Structure | Name; Mass | HPLC/ MS R$_t$ [min] | HPLC/ MS [M + H] | TβR activity (Example 36) 0 + ++ +++ | TβR activity (Example 35A) >10 μM 1-10 μM 0.1-1 μM <0.1 μM |
|---|---|---|---|---|---|---|
| 186 | 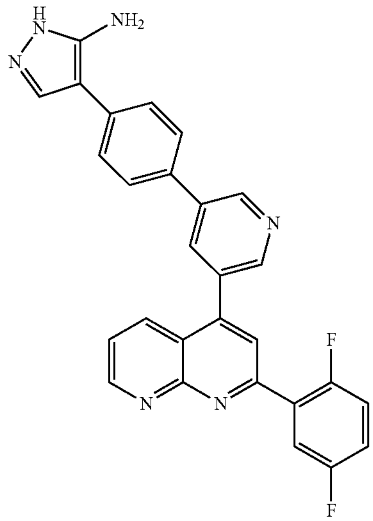 [SMILES: Nc1[nH]ncc1-c1ccc(-c2cncc(-c3cc(-c4cc(F)ccc4F)nc4ncccc34)c2)cc1] | | | | | |
| 187 | 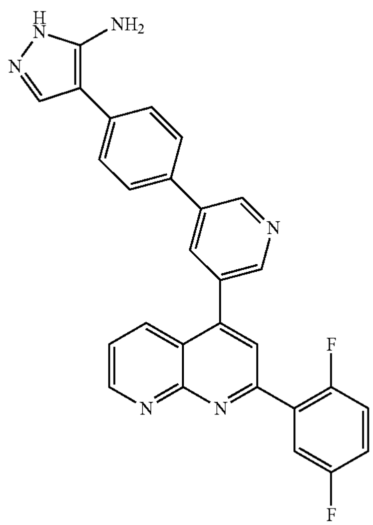 [SMILES: Nc1[nH]ncc1-c1ccc(-c2cncc(-c3cc(-c4cc(F)ccc4F)nc4ncccc34)c2)cc1] | | | | | |

Highly preferred embodiments are those compounds of formulae (I) and/or (II) with the nos. 7, 8, 11, 13, 15, 18, 19, 21, 23, 24, 25, 26, 27, 28, 29, 30, 32, 33, 34, 35, 36, 37, 38, 44, 45, 46, 47, 48, 49, 50, 51, 52, 53, 54, 55, 56, 57, 58, 59, 61, 62, 63, 64, 65, 68, 69, 71, 72, 73, 78, 81, 82, 83, 84, 85, 86, 87, 88, 89, 90, 91, 92, 93, 94, 95, 96, 97, 102, 103, 104, 105, 109, 113, 114, 115, 116, 118, 120, 121, 123, 131, 132, 135, 136, 138, 139, 143, 144, 148, 153, 155, 156, 158, 159, 161, 162, 163, 164, 165, 166, 167, 169, 170, 171, 172, 173, 174, 175, 176, 177.

The hetaryl-[1,8]naphthyridine derivatives according to formula (I) and the starting materials for its preparation, respectively, are produced by methods known per se, as described in the literature (for example in standard works, such as Houben-Weyl, Methoden der organischen Chemie [Methods of Organic Chemistry], Georg-Thieme-Verlag, Stuttgart), i.e. under reaction conditions that are known and suitable for said reactions.

Use can also be made of variants that are known per se, but are not mentioned in greater detail herein. If desired, the starting materials can also be formed in-situ by leaving them in the un-isolated status in the crude reaction mixture, but immediately converting them further into the compound according to the invention. On the other hand, it is possible to carry out the reaction stepwise.

The reactions are preferably performed under basic conditions. Suitable bases are metal oxides, e.g. aluminum oxide, alkaline metal hydroxide (potassium hydroxide, sodium hydroxide and lithium hydroxide, inter alia), alkaline earth metal hydroxide (barium hydroxide and calcium hydroxide, inter alia), alkaline metal alcoholates (potassium ethanolate and sodium propanolate, inter alia) and several organic bases (piperidine or diethanolamine, inter alia).

The reactions are generally carried out in an inert solvent. Suitable inert solvents are, for example, hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents. Particular preference is given to water, THF, tert. butanol, tert. amylalcohol, NMP, triethylamine and/or dioxane.

Depending on the conditions used, the reaction time is between a few minutes and 14 days, the reaction temperature is between about −30° C. and 150° C., normally from 0° C. to 140° C., particularly preferably from 70° C. to 130° C.

The present invention also relates to a process for manufacturing a compound of formula (I) comprising the steps of:

(a) reacting a compound of formula (III)

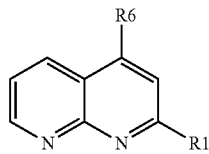

wherein

R6 denotes Hal, OH or $B(OH)_2$, preferably Hal or $B(OH)_2$, and

R1 and Hal have the meaning as defined above, with a compound of formula (IV)

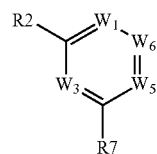

wherein

R7 denotes Hal, OH, boronic acid or a ester of boronic acid (e.g. pinacol ester, such as 4,4,5,5-tetramethyl-[1,3,2] dioxaborolan-2-yl), preferably Hal, boronic acid or a ester of boronic acid, and $R2, W_1, W_3, W_5, W_6$ and Hal have the meaning as defined above, to yield the compound of formula (I)

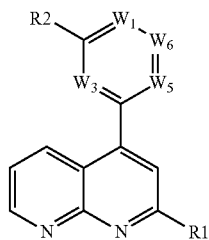

wherein R1, R2, $W_1$, $W_3$, $W_5$ and $W_6$ have the meaning as defined above, or (b) reacting a compound of formula (V)

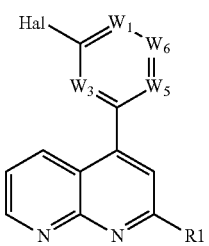

wherein R1, Hal, $W_1$, $W_3$, $W_5$ and $W_6$ have the meaning as defined above, with a compound of formula (VI) or a ester thereof

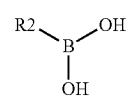

wherein R2 has the meaning as defined above, to yield the compound of formula (I)

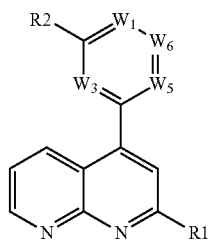

wherein R1, R2, $W_1$, $W_3$, $W_5$ and $W_6$ have the meaning as defined above, and optionally (c) converting a base or an acid of the compound of formula (I) into a salt thereof.

The hetaryl-[1,8]naphthyridine derivatives of formula (I) are accessible via the route above. The starting materials, including the compounds of formulae (III), (IV), (V) and (VI) are usually known to the skilled artisan, or they can be easily prepared by known methods. In a variant i) of way b), Hal is substituted by boronic acid or boronic ester or a derivative thereof in the compound of formula (V) and the boronic acid/boronic ester derivative is subsequently reacted with R2-Hal to yield the compound of formula (I). In another variant ii) of way b), the compound of formula (V), preferably a bromine derivative, is converted with aromatics, which are functionalized in a suitable manner, into the compound of formula (I).

Particularly, the compounds of formula (III) are accessible via two different routes. In a first embodiment of the synthesis routes, the compounds of formula (III) can be prepared by a process (A) comprising the steps of:

(a) reacting 1-(2-amino-3-pyridin-3-yl)-ethanone in an alkaline milieu with a compound of formula (VII)

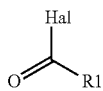
(VII)

wherein R1 and Hal have the meaning as defined above, to yield a compound of formula (VIII)

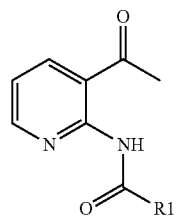
(VIII)

wherein R1 has the meaning as defined above, (b) reacting the compound of formula (VIII) in an alkaline milieu to yield a compound of formula (IX)

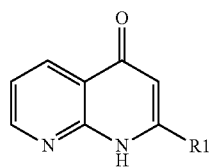
(IX)

wherein R1 has the meaning as defined above, (c) reacting the compound of formula (IX) with a halogenating agent to yield a compound of formula (III-A)

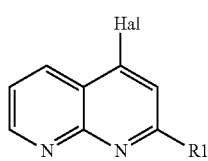
(III-A)

wherein R1 and Hal have the meaning as defined above, and optionally (d) reacting the compound of formula (III-A) with bis-pinacolato-diboron to yield a compound of formula (III-B)

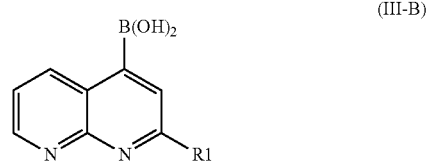
(III-B)

wherein R1 has the meaning as defined above, and optionally (e) converting a base or an acid of the compound of formulae (III-A), (III-B) into a salt thereof.

In more detail, starting from 2-amino-3-acetyl pyridine by acetylating reaction with a benzoic aryl/hetaryl derivative of formula (VII), like 6-methylpyridine-2-carboxylic acid chloride, an 2-aroylamido-3-acetyl pyridine of formula (VIII), like 6-methyl-pyridine-2-carboxylic acid-(3-acetyl-pyridin-2-yl)-amide, is obtained, which cyclizes under treatment with a strong base, preferably KOBut, to give 2-aryl/hetaryl-[1,8] naphtyridine-4-ones of formula (IX), like 2-(6-Methyl-pyridin-2-yl)-1H-[1,8]naphthyridin-4-one. Halogenation with $SOHal_2$, $SO_2Hal_2$, $POHal_3$ and/or $PHal_5$, wherein Hal has the meaning as defined above, preferably Cl or Br, more preferably $POCl_3$, gives a reactive intermediate of formula (III-A).

In a second embodiment of the synthesis routes, the compound of formula (III) can be prepared by another process (B) comprising the steps of:

(a) reacting a halogenating agent with a compound of formula (X)

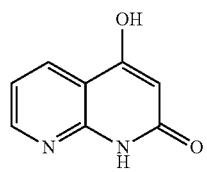
(X)

to yield a compound of formula (XI)

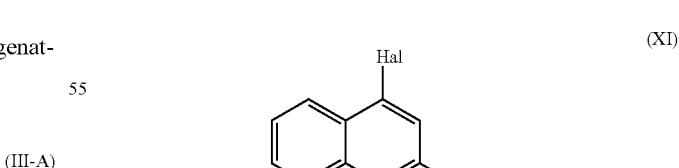
(XI)

wherein Hal has the meaning as defined above, (b) reacting the compound of formula (XI) with a compound selected from the group of boronic acid, boronic ester, tin organics, zinc organics and boron triflates, each of which is substituted by R2 having the meaning as defined above (e.g. the compound of formula (VI)), to yield a compound of formula (III-A)

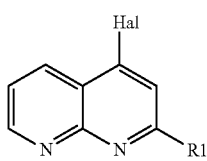
(III-A)

wherein R1 and Hal have the meaning as defined above, and optionally
(c) reacting the compound of formula (III-A) with bis-pinacolato-diboron to yield a compound of formula (III-B)

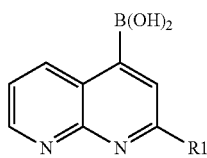
(III-B)

wherein R1 has the meaning as defined above,
and optionally
(d) converting a base or an acid of the compound of formulae (III-A), (III-B) into a salt thereof.

In more detail, 4-hydroxy-[1,8]naphthyridinone of formula (X), or its tautomers, is transferred to 2,4-halo-[1,8]naphthyridine of formula (XI) by treatment with one or more halogenating agents, preferably $POCl_3$ or $POBr_3$ and/or the corresponding $PHal_5$, wherein Hal has the meaning as defined above. Treatment of 2,4-dihalo-[1,8]naphthyridine of formula (X) using Pd0 catalysis with a boronic acid or boronic ester type (i), or similar chemistries with tin organics type (ii), or boron triflates type (iii), yields a 2-aryl/hetaryl-4-halo-[1,8]naphthyridine of formula (III-A).

The starting materials of process (B), including the compound of formula (X), are usually known to the skilled artisan, or they can be easily prepared by known methods. In particular, the compounds of formula (X) are accessible via two different routes. In a first embodiment of the synthesis routes, the compounds of formula (X) can be prepared by a process (C) comprising the steps of:
(a) reacting an acetylating agent with a compound of formula (XII)

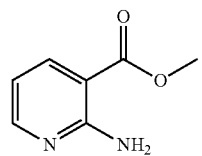
(XII)

to yield a compound of formula (XIII)

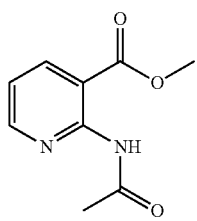
(XIII)

(b) reacting the compound of formula (XIII) under basic conditions to yield a compound of formula (X) or a tautomer of formula (X-A)

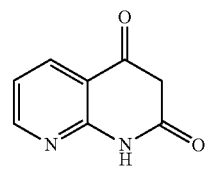
(X-A)

and optionally
(c) converting a base or an acid of the compound of formula (X-A) into a salt thereof.

In more detail, starting from nicotinic esters of formula (XII), prepared from nicotinic acid by esterification, by reaction with acetylating agents, preferably AcOEt, AcCl, $Ac_2O$, Ac-imidazole, acetyl morpholine, Ac—CN or acetic acid, under coupling (dehydrating) conditions, acetamido nicotinic ester derivatives of formula (XIII) are obtained, which can be cyclized under basic conditions, e.g. by use of $KN(SiMe_3)_2$ in a solvent like THF and/or toluene, to yield tetrahydro-[1,8]naphthyridine-2,4-diones of formula (X), or tautomeric forms of formula (X-A) to be processed further like in process B.

The esters of formula (XII) can be produced via alcoholysis of a compound of formula (XXIII),

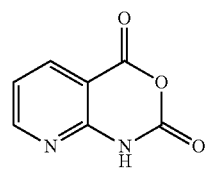
(XXIII)

which can be generated from acids by phosgenation techniques.

In a second embodiment of the synthesis routes, the compounds of formula (X) can be prepared by a process (D) comprising the steps of:
(a) reacting a compound of formula (XII)

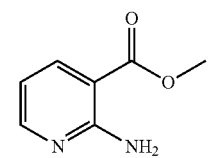
(XII)

with a compound of formula (XIV)

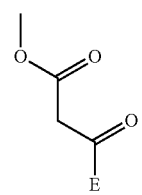
(XIV)

wherein
E denotes OY or NYY, and
Y has the meaning as defined above, to yield a compound of formula (XV)

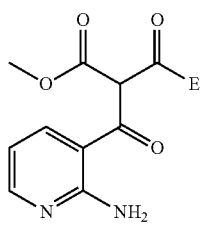

(XV)

wherein
E denotes OY or NYY; and
Y has the meaning as defined above,
(b) reacting the compound of formula (XV) in a solvent and under alkaline condition to yield a compound of formula (XVI)

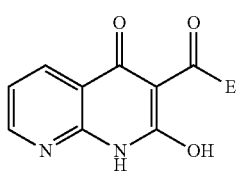

(XVI)

wherein E denotes OY or NYY; and
Y has the meaning as defined above,
(c) reacting the compound of formula (XVI) under acidic or alkaline conditions to yield the compound of formula (X) or a tautomer of formula (X-B)

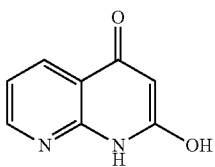

(X-B)

and optionally
(d) converting a base or an acid of the compound of formula (X-B) into a salt thereof.

In more detail, starting from nicotinic acid ester of formula (XII) and reaction with malonic acid derivatives of formula (XIV) in the presence of a solvent and a base, acyl malonic acid derivatives of formula (XV) are formed, which can be cyclized under basic conditions in a solvent to form tetrahydro-[1,8]naphthyridine-2,4-dione-3-carboxylic acid derivatives or its tautomeric forms of formula (XVI). After acidic or alkaline hydrolysis/saponification and decarboxylation, 2-hydroxy-[1,8]naphthyridine-4-one of formula (X-B), or its tautomers, is formed, which can be further processed like in method B.

Alternatively, the naphthyridine-ones of formulae (X), (X-A) and (X-B) can be obtained from reaction of a corresponding pyridin-4-yl-amine with malonic acid ester chloride (i.e. MeOCOCH$_2$COCl) or diethyl malonate (i.e. CH$_2$(COOEt)$_2$), followed by saponification, e.g. with NaOH, and cyclization mediated by polyphosphoric acid (PPA).

In another aspect of manufacturing the naphthyridine derivative of formula (I), the compound of formula (IV) is accessible by a process (E) comprising the steps of:

(a) reacting the compound of formula (VI) with a compound of formula (XVII)

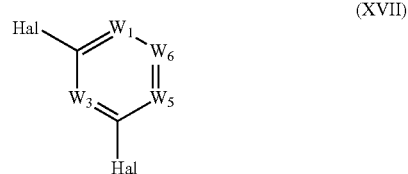

(XVII)

wherein Hal has the meaning as defined above under the proviso that both Hal radicals adopt different meanings,
to yield the compound of formula (IV)

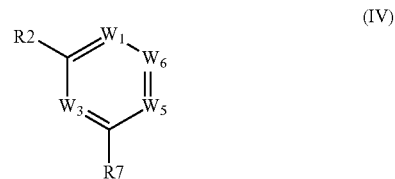

(IV)

wherein R2, R7, W$_1$, W$_3$, W$_5$ and W$_6$ have the meaning as defined above,
and optionally
(b) converting a base or an acid of the compound of formula (IV) into a salt thereof.

In still another aspect of manufacturing the naphthyridine derivative of formula (I), the compound of formula (V) is accessible by a process (F) comprising the steps of:

(a) reacting a compound of formula (III)

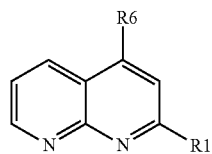

(III)

wherein
R6 denotes B(OH)$_2$, and
R1 and Hal have the meaning as defined above,
with a compound of formula (XVII)

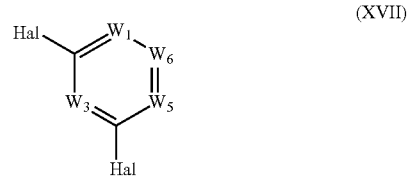

(XVII)

wherein Hal has the meaning as defined above, to yield the compound of formula (V)

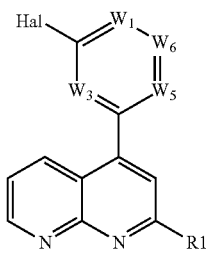
(V)

and optionally
(c) converting a base or an acid of the compound of formula (V) into a salt thereof.

Accordingly, any compound of formulae (IV) to (XVII) can be purified, provided as intermediate product and used as starting material for the preparation of compounds of formula (I). It is preferred, however, that the compounds of formulae (III), (IV), (V), (VI), (VIII), (IX), (X), (XI), (XIII) and/or (XV) are provided as intermediate product and used as starting material for the preparation of compounds of formula (I), more preferably the compounds of formulae (III), (IV), (V), (VI), (VIII), (IX) and/or (XI). In a most preferred aspect of the invention, intermediate compounds of formulae (III), (IV), (V) and/or (VIII) are provided

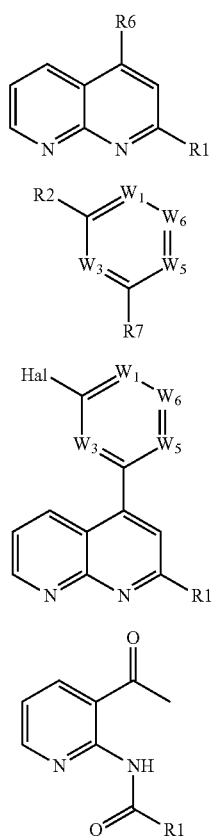

wherein
R6 denotes Hal, OH or $B(OH)_2$,
R7 denotes Hal, OH, boronic acid or a ester of boronic acid, and R1, R2, $W_1$, $W_3$, $W_5$, $W_6$ and Hal have the meaning as defined above;
and/or physiologically acceptable salts thereof.

Highly preferred template intermediates for producing the compounds of formula (I) are selected from the group of:

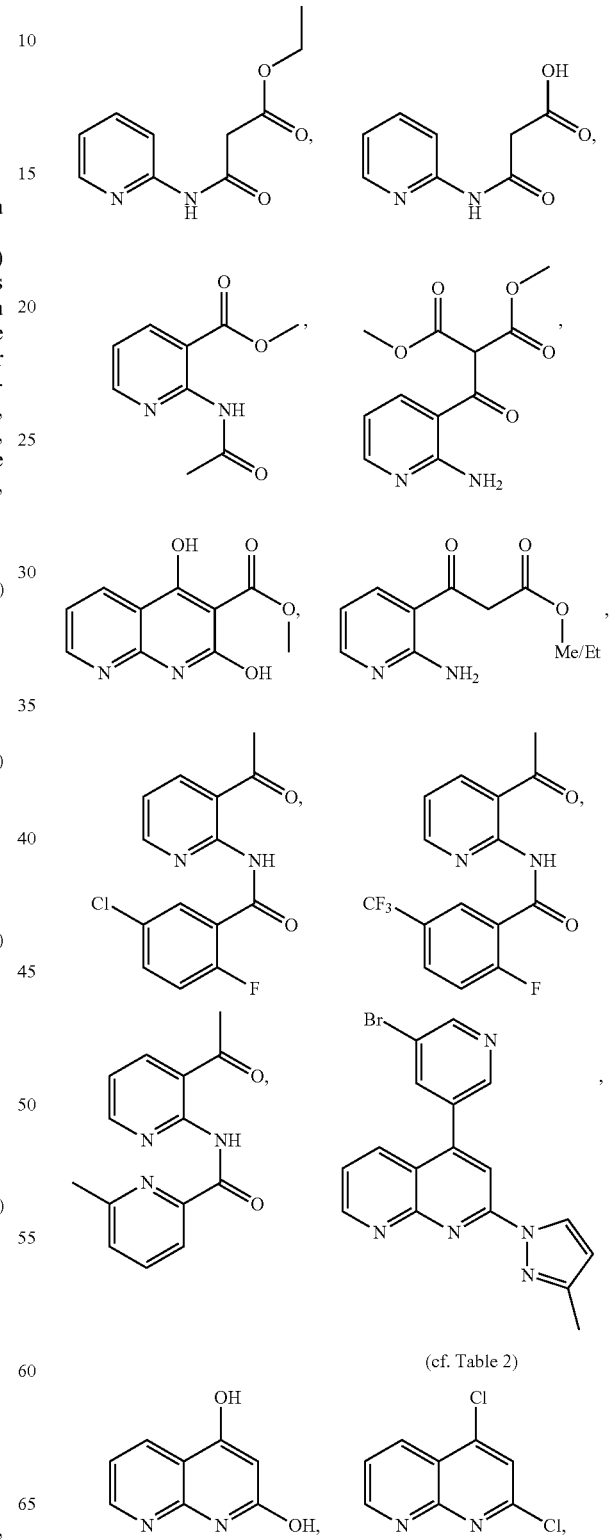

(cf. Table 2)

155
-continued
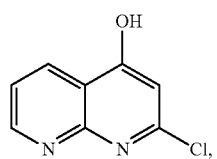
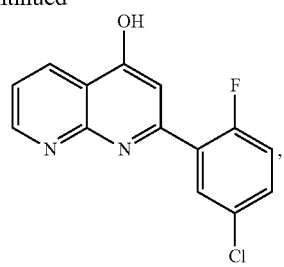
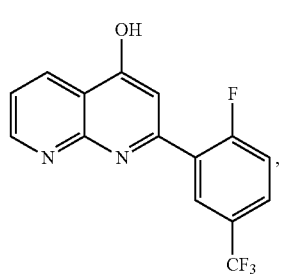
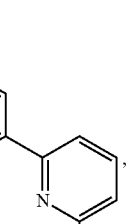
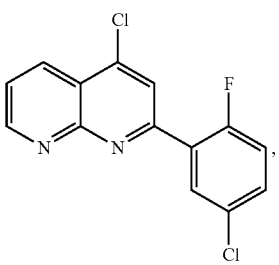
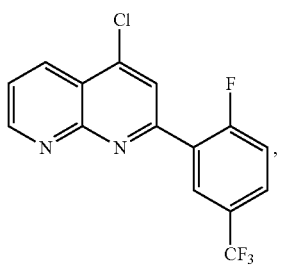
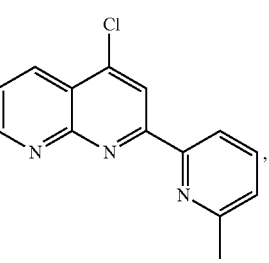
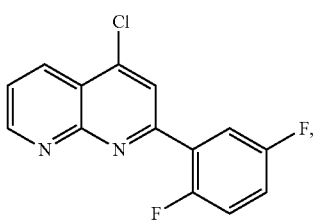
156
-continued
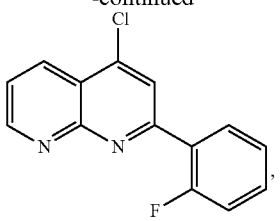
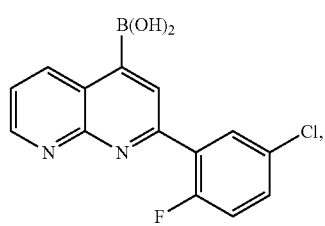
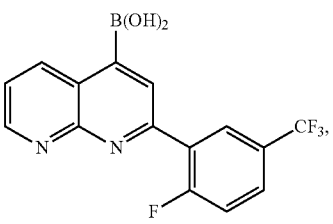
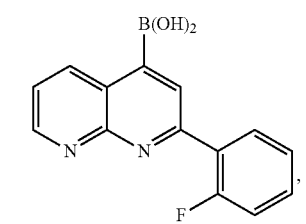
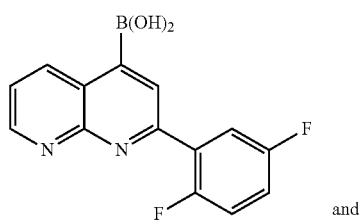
and
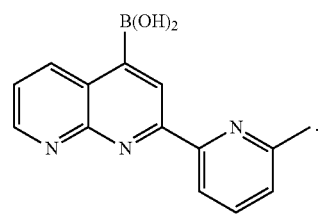

TABLE 2

Characteristics of preferred intermediate 4-(5-bromo-pyridin-3-yl)-2-(3-methyl-pyrazol-1-yl)-[1,8]naphthyridine

| Structure | Name; Mass | HPLC/MS $R_t$ [min] | HPLC/MS [M + H] | TβR activity (Example 36) | TβR activity (Example 35A) |
|---|---|---|---|---|---|
| (structure) | 4-(5-Bromo-pyridin-3-yl)-2-(3-methyl-pyrazol-1-yl)-[1,8]naphthyridine M 366.2 | 2.04 | 366 | >10 μM | >10 μM |

The compounds of formula (I) can be modified, like hydrogenated or metal-reduced, to remove the chlorine, or put into a substitution reaction, and/or to be transformed with an acid or base into a salt, preferably with a strong acid. Numerous papers and methods are available and useful for the one skilled in the art in respect for organic chemistry, chemical strategies and tactics, synthetic routes, protection of intermediates, cleavage and purification procedure, isolation and characterization. General chemical modifications are known to the one skilled in the art. Halogenation of aryls or hydroxy substitution by halogens of acids, alcohols, phenols, and their tautomeric structures can be preferably carried out by use of $POCl_3$, or $SOCl_2$, $PCl_5$, $SO_2Cl_2$. In some instances oxalyl chloride is also useful. Temperatures can vary from 0° C. to reflux depending on the task to halogenate a pyridone structure or a carboxylic acid or a sulfonic acid. Time will also be adjusted from minutes to several hours or even over night. Similarly, alkylation, ether formation, ester formation, amide formation are known to the one skilled in the art. Arylation with aryl boronic acids can be performed in presence of a Pd catalyst, appropriate ligand and base, preferably a carbonate, phosphate, borate salt of sodium, potassium or cesium. Organic bases, like $Et_3N$, DIPEA or the more basic DBU can also be used. Solvents can vary too, from toluene, dioxane, THF, diglyme, monoglyme, alcohols, DMF, DMA, NMP, acetonitrile, in some cases even water, and others. Commonly used catalysts like Pd $(PPh_3)_4$, or $Pd(OAc)_2$, $PdCl_2$ type precursors of Pd0 catalysts have advanced to more complex ones with more efficient ligands. In C—C arylations instead of boronic acids and esters (Stille coupling), aryl-trifluoroborate potassium salts (Suzuki-Miyaura coupling), organo silanes (Hiyama coupling), Grignard reagents (Kumada), zinc organyles (Negishi coupling) and tin organyles (Stille coupling) are useful. This experience can be transferred to N- and O-arylations. Numerous papers and methods are available and useful for the one skilled in the art in respect of N-arylation and even of electron deficient anilines (Biscoe et al. JACS 130: 6686 (2008)), and with aryl chlorides and anilines (Fors et al. JACS 130: 13552 (2008) as well as for O-arylation by using Cu catalysis and Pd catalysis.

In the final step of the processes above, a salt of the compound according to formulae (I) to (XVII), preferably formula (I), is optionally provided. The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds according to the invention are for the most part prepared by conventional methods. If the compound according to the invention contains a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline earth metal hydroxides, such as barium hydroxide and calcium hydroxide; alkali metal alkoxides, for example potassium ethoxide and sodium propoxide; and various organic bases, such as piperidine, diethanolamine and N-methylglutamine. The aluminum salts of the compounds according to the invention are likewise included. In the case of certain compounds according to the invention, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds according to the invention include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulf ate, ethanesulfonate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

With regard to that stated above, it can be seen that the expressions "pharmaceutically acceptable salt" and "physiologically acceptable salt", which are used interchangeable herein, in the present connection are taken to mean an active ingredient which comprises a compound according to the invention in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

Object of the present invention is also the use of compounds according to formula (I) and/or physiologically acceptable salts thereof for inhibiting ATP consuming proteins, particularly kinases. The term "inhibition" denotes any reduction in kinase activity, which is based on the action of the specific inventive compounds capable to interact with the target kinase in such a manner that makes recognition, binding and blocking possible. The compounds are characterized by such a high affinity to at least one kinase, which ensures a reliable binding and preferably a complete blocking of kinase activity. More preferably, the substances are mono-specific in order to guarantee an exclusive and directed recognition with the chosen single kinase target. In the context of the present invention, the term "recognition"—without being limited thereto—relates to any type of interaction between the specific substances and the target, particularly covalent or non-covalent binding or association, such as a covalent bond, hydrophobic/hydrophilic interactions, van der Waals forces, ion pairs, hydrogen bonds, ligand-receptor interactions, and the like. Such association may also encompass the presence of other molecules such as peptides, proteins or nucleotide sequences. The present receptor/ligand-interaction is characterized by high affinity, high selectivity and minimal or even lacking cross-reactivity to other target molecules to exclude unhealthy and harmful impacts to the treated subject.

In an embodiment of the present invention, the kinases either belong to the group of tyrosine kinases and serine/threonine kinases. In a preferred embodiment of the invention, the kinases are selected form the group of TGF-beta, RON, TAK1, CHK2, PDK1, Met, PKD1, MINK1, SAPK2-alpha, SAPK2-beta, MKK1, GCK, HER4, ALK1, ALK2, ALK4, ALK5 and TbR type II. It is more preferred to inhibit serine/threonine kinases. Most preferred kinases to be inhibited are TGF-beta receptor kinase, RON, TAK1 and/or CHK2, highly preferably TGF-beta receptor kinase.

The kinase are especially half inhibited if the concentration of the compounds amounts to less than 10 µM, preferably less than 1 µM, more preferably less than 0.1 µM. Such concentration is also referred to as $IC_{50}$.

The compounds according to the invention preferably exhibit an advantageous biological activity, which is easily demonstrated in enzyme-based assays, for example assays as described herein. In such enzyme-based assays, the compounds according to the invention preferably exhibit and cause an inhibiting effect, which is usually documented by $IC_{50}$ values in a suitable range, preferably in the micromolar range and more preferably in the nanomolar range.

As discussed herein, these signaling pathways are relevant for various diseases. Accordingly, the compounds according to the invention are useful in the prophylaxis and/or treatment of diseases that are dependent on the said signaling pathways by interaction with one or more of the said signaling pathways. The present invention therefore relates to compounds according to the invention as promoters or inhibitors, preferably as inhibitors, of the signaling pathways described herein, particularly the TGF-β□ signaling pathway.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of human disease.

The susceptibility of a particular cell to treatment with the compounds according to the invention can be determined by in vitro tests. Typically, a culture of the cell is combined with a compound according to the invention at various concentrations for a period of time which is sufficient to allow the active agents to induce cell death or to inhibit migration, usually between about one hour and one week. In vitro testing can be carried out using cultivated cells from a biopsy sample. The viable cells remaining after the treatment are then counted.

For identification of a signal transduction pathway and for detection of interactions between various signal transduction pathways, various scientists have developed suitable models or model systems, for example cell culture models (for example Khwaja et al., EMBO, 1997, 16, 2783-93) and models of transgenic animals (for example White et al., Oncogene, 2001, 20, 7064-7072). For the determination of certain stages in the signal transduction cascade, interacting compounds can be utilized in order to modulate the signal (e.g. Stephens et al., Biochemical J., 2000, 351, 95-105). The compounds according to the invention can also be used as reagents for testing kinase-dependent signal transduction pathways in animals and/or cell culture models or in the clinical diseases mentioned in this application.

Measurement of the kinase activity is a technique which is well known to the person skilled in the art. Generic test systems for the determination of the kinase activity using substrates, for example histone (for example Alessi et al., FEBS Lett. 1996, 399, 3, pages 333-338) or the basic myelin protein, are described in the literature (for example Campos-González, R. and Glenney, Jr., J. R. 1992, J. Biol. Chem. 267, page 14535).

For the identification of kinase inhibitors, various assay systems are available. In scintillation proximity assay (Sorg et al., J. of. Biomolecular Screening, 2002, 7, 11-19) and flashplate assay, the radioactive phosphorylation of a protein or peptide as substrate with γATP is measured. In the presence of an inhibitory compound, a decreased radioactive signal, or none at all, is detectable. Furthermore, homogeneous time-resolved fluorescence resonance energy transfer (HTR-FRET) and fluorescence polarisation (FP) technologies are suitable as assay methods (Sills et al., J. of Biomolecular Screening, 2002, 191-214). Other non-radioactive ELISA assay methods use specific phospho-antibodies (phospho-ABs). The phospho-AB binds only the phosphorylated substrate. This binding can be detected by chemiluminescence using a second peroxidase-conjugated anti-sheep antibody.

The use according to the previous paragraphs of the specification may be either performed in-vitro or in-vivo models. The inhibition can be monitored by the techniques described in the course of the present specification. The in-vitro use is preferably applied to samples of humans suffering from cancer, tumor growth, metastatic growth, fibrosis, restenosis, HIV infection, neurodegenerative disorders, e.g. Alzheimer's disease, atherosclerosis, inflammation and disorders of wound healing, angiogenesis, cardiovascular system, bone, CNS and/or PNS. Testing of several specific compounds and/or derivatives thereof makes the selection of that active ingredient possible that is best suited for the treatment of the human subject. The in-vivo dose rate of the chosen derivative is advantageously pre-adjusted to the kinase susceptibility and/or severity of disease of the respective subject with regard to the in-vitro data. Therefore, the therapeutic efficacy is remarkably enhanced. Moreover, the subsequent teaching of the present specification concerning the use of the compounds according to formula (I) and its derivatives for the production of a medicament for the prophylactic or therapeutic treatment and/or monitoring is considered as valid and applicable without restrictions to the use of the compound for the inhibition of kinase activity if expedient.

The invention furthermore relates to a medicament comprising at least one compound according to the invention and/or pharmaceutically usable derivatives, salts, solvates and stereoisomers thereof, including mixtures thereof in all ratios, and optionally excipients and/or adjuvants.

In the meaning of the invention, an "adjuvant" denotes every substance that enables, intensifies or modifies a specific response against the active ingredient of the invention if administered simultaneously, contemporarily or sequentially. Known adjuvants for injection solutions are, for example, aluminum compositions, such as aluminum hydroxide or aluminum phosphate, saponins, such as QS21, muramyldipeptide or muramyltripeptide, proteins, such as gamma-interferon or TNF, M59, squalen or polyols.

Consequently, the invention also relates to a pharmaceutical composition comprising as active ingredient an effective amount of at least one compound according to formula (I) and/or physiologically acceptable salts thereof together with pharmaceutically tolerable adjuvants.

A "medicament", "pharmaceutical composition" or "pharmaceutical formulation" in the meaning of the invention is any agent in the field of medicine, which comprises one or more compounds of formula (I) or preparations thereof and can be used in prophylaxis, therapy, follow-up or aftercare of patients who suffer from diseases, which are associated with kinase activity, in such a way that a pathogenic modification of their overall condition or of the condition of particular regions of the organism could establish at least temporarily.

Furthermore, the active ingredient may be administered alone or in combination with other treatments. A synergistic effect may be achieved by using more than one compound in the pharmaceutical composition, i.e. the compound of formula (I) is combined with at least another agent as active ingredient, which is either another compound of formula (I) or a compound of different structural scaffold. The active ingredients can be used either simultaneously or sequentially.

The present compounds are suitable for combination with known anticancer agents. These known anticancer agents include the following: (1) estrogen receptor modulators, (2) androgen receptor modulators, (3) retinoid receptor modulators, (4) cytotoxic agents, (5) antiproliferative agents, (6) prenyl-protein transferase inhibitors, (7) HMG-CoA reductase inhibitors, (8) HIV protease inhibitors, (9) reverse transcriptase inhibitors and (10) further angiogenesis inhibitors. The present compounds are particularly suitable for administration at the same time as radiotherapy. The synergistic effects of inhibiting VEGF in combination with radiotherapy have been described in the art (see WO 00/61186).

The invention also relates to a set (kit) consisting of separate packs of an effective amount of a compound according to the invention and/or pharmaceutically acceptable salts, derivatives, solvates and stereoisomers thereof, including mixtures thereof in all ratios, and an effective amount of a further medicament active ingredient. The set comprises suitable containers, such as boxes, individual bottles, bags or ampoules. The set may, for example, comprise separate ampoules, each containing an effective amount of a compound according to the invention and/or pharmaceutically acceptable salts, derivatives, solvates and stereoisomers thereof, including mixtures thereof in all ratios, and an effective amount of a further medicament active ingredient in dissolved or lyophilized form.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

The pharmaceutical composition of the invention is produced in a known way using common solid or liquid carriers, diluents and/or additives and usual adjuvants for pharmaceutical engineering and with an appropriate dosage. The amount of excipient material that is combined with the active ingredient to produce a single dosage form varies depending upon the host treated and the particular mode of administration. Suitable excipients include organic or inorganic substances that are suitable for the different routes of administration, such as enteral (e.g. oral), parenteral or topical application, and which do not react with compounds of formula (I) or salts thereof. Examples of suitable excipients are water, vegetable oils, benzyl alcohols, alkylene glycols, polyethylene glycols, glycerol triacetate, gelatin, carbohydrates, such as lactose or starch, magnesium stearate, talc, and petroleum jelly.

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multi-dose containers, for example sealed ampoules and vials, and stored in freeze-dried (lyophilized) state, so that only the addition of the sterile carrier liquid, for example water for injection purposes, immediately before use is necessary. Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavors.

In a preferred embodiment of the present invention, the pharmaceutical composition is orally or parenterally administered, more preferably orally. In particular, the active ingredient is provided in a water-soluble form, such as a pharmaceutically acceptable salt, which is meant to include both acid and base addition salts. Furthermore, the compounds of formula (I) and salts thereof, may be lyophilized and the resulting lyophilizates used, for example, to produce preparations for injection. The preparations indicated may be sterilized and/or may comprise auxiliaries, such as carrier proteins (e.g. serum albumin), lubricants, preservatives, stabilizers, fillers, chelating agents, antioxidants, solvents, bonding agents, suspending agents, wetting agents, emulsifiers, salts (for influencing the osmotic pressure), buffer substances, colorants, flavorings and one or more further active substances, for example one or more vitamins. Additives are well known in the art, and they are used in a variety of formulations.

The terms "effective amount" or "effective dose" or "dose" are interchangeably used herein and denote an amount of the pharmaceutical compound having a prophylactically or therapeutically relevant effect on a disease or pathological conditions, i.e. which causes in a tissue, system, animal or human a biological or medical response which is sought or desired, for example, by a researcher or physician. A "prophylactic effect" reduces the likelihood of developing a disease or even prevents the onset of a disease. A "therapeutically relevant effect" relieves to some extent one or more symptoms of a disease or returns to normality either partially or completely one or more physiological or biochemical parameters associated with or causative of the disease or pathological conditions. In addition, the expression "therapeutically effective amount" denotes an amount which, compared with a corresponding subject who has not received this amount, has the following consequence: improved treatment, healing, prevention or elimination of a disease, syndrome, condition, complaint, disorder or side-effects or also the reduction in the advance of a disease, complaint or disorder. The expression "therapeutically effective amount" also encompasses the amounts which are effective for increasing normal physiological function.

The respective dose or dosage range for administering the pharmaceutical composition according to the invention is sufficiently high in order to achieve the desired prophylactic or therapeutic effect of reducing symptoms of the aforementioned diseases, cancer and/or fibrotic diseases. It will be understood that the specific dose level, frequency and period of administration to any particular human will depend upon a variety of factors including the activity of the specific compound employed, the age, body weight, general state of health, gender, diet, time and route of administration, rate of excretion, drug combination and the severity of the particular disease to which the specific therapy is applied. Using well-known means and methods, the exact dose can be determined by one of skill in the art as a matter of routine experimentation. The prior teaching of the present specification is valid and applicable without restrictions to the pharmaceutical composition comprising the compounds of formula (I) if expedient.

Pharmaceutical formulations can be administered in the form of dosage units which comprise a predetermined amount of active ingredient per dosage unit. The concentration of the prophylactically or therapeutically active ingredient in the formulation may vary from about 0.1 to 100 wt %. Preferably, the compound of formula (I) or the pharmaceutically acceptable salts thereof are administered in doses of approximately 0.5 to 1000 mg, more preferably between 1 and 700 mg, most preferably 5 and 100 mg per dose unit. Generally, such a dose range is appropriate for total daily incorporation. In other terms, the daily dose is preferably between approximately 0.02 and 100 mg/kg of body weight. The specific dose for each patient depends, however, on a wide variety of factors as already described in the present specification (e.g. depending on the condition treated, the method of administration and the age, weight and condition of the patient). Preferred dosage unit formulations are those which comprise a daily dose or part-dose, as indicated above, or a corresponding fraction thereof of an active ingredient. Furthermore, pharmaceutical formulations of this type can be prepared using a process which is generally known in the pharmaceutical art.

Although a therapeutically effective amount of a compound according to the invention has to be ultimately determined by the treating doctor or vet by considering a number of factors (e.g. the age and weight of the animal, the precise condition that requires treatment, severity of condition, the nature of the formulation and the method of administration), an effective amount of a compound according to the invention for the treatment of neoplastic growth, for example colon or breast carcinoma, is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as a single dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

The pharmaceutical composition of the invention can be employed as medicament in human and veterinary medicine. According to the invention, the compounds of formula (I) and/or physiologically salts thereof are suited for the prophylactic or therapeutic treatment and/or monitoring of diseases that are caused, mediated and/or propagated by kinase activity. It is particularly preferred that the diseases are selected from the group of cancer, tumor growth, metastatic growth, fibrosis, restenosis, HIV infection, neurodegenerative disorders, atherosclerosis, inflammation and disorders of wound healing, angiogenesis, cardiovascular system, bone, CNS and/or PNS. It shall be understood that the host of the compound is included in the present scope of protection according to the present invention.

Particular preference is given to the treatment and/or monitoring of a tumor and/or cancer disease. The tumor is preferably selected from the group of tumors of the squamous epithelium, bladder, stomach, kidneys, head, neck, esophagus, cervix, thyroid, intestine, liver, brain, prostate, urogenital tract, lymphatic system, larynx and/or lung.

The tumor is furthermore preferably selected from the group of lung adenocarcinoma, small-cell lung carcinomas, pancreatic cancer, glioblastomas, colon carcinoma and breast carcinoma. In addition, preference is given to the treatment and/or monitoring of a tumor of the blood and immune system, more preferably for the treatment and/or monitoring of a tumor selected from the group of acute myeloid leukemia, chronic myeloid leukemia, acute lymphatic leukemia and/or chronic lymphatic leukemia. Such tumors can also be designated as cancers in the meaning of the invention.

In a more preferred embodiment of the invention, the aforementioned tumors are solid tumors.

In another preferred embodiment of the invention, the compounds of formula (I) are applied for the prophylactic or therapeutic treatment and/or monitoring of retroviral diseases or for the manufacture of a medicament for the prophylactic or therapeutic treatment and/or monitoring of retroviral diseases, respectively, preferably of retroviral immune diseases, more preferably an HIV infection. The agent can be either administered to reducing the likelihood of infection or to prevent the infection of a mammal with a retrovirus and the onset of the disease in advance, or to treat the disease caused by the infectious agent. Particularly, later stages of virus internalization can be reduced and/or prevented. It is the intention of a prophylactic inoculation to reduce the likelihood of infection or to prevent the infection with a retrovirus after the infiltration of single viral representatives, e.g. into a wound, such that the subsequent propagation of the virus is strictly diminished, or it is even completely inactivated. If an infection of the patient is already given, a therapeutic administration is performed in order to inactivate the retrovirus being present in the body or to stop its propagation. Numerous retroviral diseases can be successfully combated by applying the inventive compounds, particularly AIDS caused by HIV.

The naphthyridine compounds according to the present invention are also useful against diseases selected from the group of cardiovascular diseases, kidney diseases, hepatic diseases, syndromes associated with pulmonary fibrosis, collagen vascular disorders, eye diseases, excessive or hypertrophic scar formation in the dermis, disorders of the gastrointestinal tract, chronic scarring of the peritoneum, neurological conditions, diseases of the joints, diseases that benefit from the improvement of lung function and diseases from a proinflammation response, fibroproliferative response or both.

The invention also relates to the use of compounds according to formula (I) and/or physiologically acceptable salts thereof for the prophylactic or therapeutic treatment and/or monitoring of diseases that are caused, mediated and/or propagated by kinase activity. Furthermore, the invention relates to the use of compounds according to formula (I) and/or physiologically acceptable salts thereof for the production of a medicament for the prophylactic or therapeutic treatment and/or monitoring of diseases that are caused, mediated and/or propagated by kinase activity. Compounds of formula (I) and/or a physiologically acceptable salt thereof can furthermore be employed as intermediate for the preparation of further medicament active ingredients. The medicament is preferably prepared in a non-chemical manner, e.g. by combining the active ingredient with at least one solid, fluid and/or semi-fluid carrier or excipient, and optionally in conjunction with a single or more other active substances in an appropriate dosage form.

In another embodiment of the present invention, the compounds according to formula (I) and/or physiologically acceptable salts thereof are used for the production of a combination preparation for the prophylactic or therapeutic treatment and/or monitoring of solid tumors, wherein the combination preparation comprises an effective amount of an active ingredient selected from the group of (1) oestrogen receptor modulators, (2) androgen receptor modulators, (3) retinoid receptor modulators, (4) cytotoxic agents, (5) antiproliferative agents, (6) prenyl-protein transferase inhibitors, (7) HMG-CoA reductase inhibitors, (8) HIV protease inhibitors, (9) reverse transcriptase inhibitors and (10) further angiogenesis inhibitors.

The compounds of formula (I) according to the invention can be administered before or following an onset of disease once or several times acting as therapy. The aforementioned medical products of the inventive use are particularly used for the therapeutic treatment. A therapeutically relevant effect relieves to some extent one or more symptoms of an autoimmune disease, or returns to normality, either partially or completely, one or more physiological or biochemical parameters associated with or causative of the disease or pathological conditions. Monitoring is considered as a kind of treatment provided that the compounds are administered in distinct intervals, e.g. in order to booster the response and eradicate the pathogens and/or symptoms of the disease completely. Either the identical compound or different compounds can be applied. The medicament can also be used to reducing the likelihood of developing a disease or even prevent the initiation of diseases associated with increased kinase activity in advance or to treat the arising and continuing symptoms. The diseases as concerned by the invention are preferably cancer and/or fibrotic diseases. In the meaning of the invention, prophylactic treatment is advisable if the subject possesses any preconditions for the aforementioned physiological or pathological conditions, such as a familial disposition, a genetic defect, or a previously passed disease.

The prior teaching of the present specification concerning the pharmaceutical composition is valid and applicable without restrictions to the use of compounds according to formula (I) and their salts for the production of a medicament and/or combination preparation for prophylaxis and therapy of said diseases.

It is another object of the invention to provide a method for treating diseases that are caused, mediated and/or propagated by kinase activity, wherein an effective amount of at least one compound according to formula (I) and/or physiologically acceptable salts thereof is administered to a mammal in need of such treatment. The preferred treatment is an oral or parenteral administration. The treatment of the patients with cancer, tumor growth, metastatic growth, fibrosis, restenosis, HIV infection, neurodegenerative disorders, atherosclerosis, inflammation and disorders of wound healing, angiogenesis, cardiovascular system, bone, CNS and/or PNS, or people bearing a risk of developing such diseases or disorders on the basis of existing preconditions by means of the compounds of formula (I) improves the whole-body state of health and ameliorates symptoms in these individuals. The inventive method is particularly suitable for treating solid tumors.

In a preferred embodiment of the method, the treatment with the present compounds is combined with radiotherapy. It is even more preferred to administer a therapeutically effective amount of a compound according formula (I) in combination with radiotherapy and another compound from the groups (1) to (10) as defined above. The synergistic effects of inhibiting VEGF in combination with radiotherapy have already been described.

The prior teaching of the invention and its embodiments is valid and applicable without restrictions to the method of treatment if expedient.

In the scope of the present invention, novel hetaryl-[1,8] naphthyridine compounds of formula (I) are provided for the first time. The inventive compounds strongly and/or selectively target ATP consuming proteins like kinases, particularly TGF-β receptor kinases. The compounds of formula (I) and derivatives thereof are characterized by a high specificity and stability; low manufacturing costs and convenient handling. These features form the basis for a reproducible action, wherein the lack of cross-reactivity is included, and for a reliable and safe interaction with their matching target structures. The current invention also comprises the use of present hetaryl-[1,8]naphthyridine derivatives in the inhibition, the regulation and/or modulation of the signal cascade of kinases, especially the TGF-β receptor kinases, which can be advantageously applied as research and/or diagnostic tool.

Furthermore, medicaments and pharmaceutical compositions containing said compounds and the use of said compounds to treat kinase-mediated conditions is a promising, novel approach for a broad spectrum of therapies causing a direct and immediate reduction of symptoms in man and animal. The impact is of special benefit to efficiently combat severe diseases, such as cancer, inflammation and/or fibrotic diseases, either alone or in combination with other anti-cancer, anti-inflammatory or anti-fibrotic treatments. In addition to the aforementioned clinical pictures, the compounds of formula (I), their salts, isomers, tautomers, enantiomeric forms, diastereomers, racemates, derivatives, prodrugs and/or metabolites are also useful for the diagnosis and treatment of any illnesses arising from TGF-β kinase signaling, particularly associated with cell proliferation and cell migration to be inhibited. The low molecular weight inhibitors are applied either themselves and/or in combination with physical measurements for diagnostics of effectiveness of any method of treatment, such as surgery, immune-, radio- and/or chemotherapy; the latter means a targeted therapy with any NME (i.e. NCE and/or NBE) as mono- and/or on-target/off-target combination therapy.

Due to their surprisingly strong and/or selective inhibition of enzymes, which regulate cellular processes by transferring phosphate groups from ATP to protein, the compounds of the invention can be advantageously administered at lower doses compared to other less potent or selective inhibitors of the prior art while still achieving equivalent or even superior desired biological effects. In addition, such a dose reduction may advantageously lead to less or even no medicinal adverse effects. Further, the high inhibition selectivity of the compounds of the invention may translate into a decrease of undesired side effects on its own regardless of the dose applied.

All the references cited herein are incorporated by reference in the disclosure of the invention hereby.

It is to be understood that this invention is not limited to the particular compounds, pharmaceutical compositions, uses and methods described herein, as such matter may, of course, vary. It is also to be understood that the terminology used herein is for the purpose of describing particular embodiments only and is not intended to limit the scope of the present invention, which is only defined by the appended claims. As used herein, including the appended claims, singular forms of words such as "a," "an," and "the" include their corresponding plural referents unless the context clearly dictates otherwise. Thus, e.g., reference to "a compound" includes a single or several different compounds, and reference to "a method" includes reference to equivalent steps and methods known to a person of ordinary skill in the art, and so forth. Unless otherwise defined, all technical and scientific terms used herein have the same meaning as commonly understood by a person of ordinary skill in the art to which this invention belongs.

The techniques that are essential according to the invention are described in detail in the specification. Other techniques which are not described in detail correspond to known standard methods that are well known to a person skilled in the art, or the techniques are described in more detail in cited references, patent applications or standard literature. Although methods and materials similar or equivalent to those described herein can be used in the practice or testing of the present invention, suitable examples are described below. The following examples are provided by way of illustration and not by way of limitation. Within the examples, standard reagents and buffers that are free from contaminating activities (whenever practical) are used. The example are particularly to be construed such that they are not limited to the explicitly demonstrated combinations of features, but the exemplified features may be unrestrictedly combined again if the technical problem of the invention is solved.

In the following examples, "conventional workup" means: water was added if necessary, the pH was adjusted, if necessary, to a value of between 2 and 10, depending on the constitution of the end product, the mixture was extracted with ethyl acetate or dichloromethane, the phases were separated, the organic phase was dried over sodium sulfate and evaporated, and the product was purified by chromatography on silica gel and/or by crystallization. $R_f$ values were determined on silica gel. The eluent was ethyl acetate/methanol 9:1. Above and below, all temperatures were indicated in ° C.

Retention time $R_t$ [min] determination was carried out by HPLC:
Column: Chromolith SpeedROD RP-18e, 50×4.6 mm$^2$
Gradient: A:B=96:4 to 0:100
Flow rate: 2.4 ml/min
Eluent A: water+0.05% formic acid,
Eluent B: acetonitrile+0.04% formic acid
Wavelength: 220 nm

EXAMPLE 1

Synthesis of 4-chloro-2-(5-chloro-2-fluoro-phenyl)-[1,8]naphthyridine

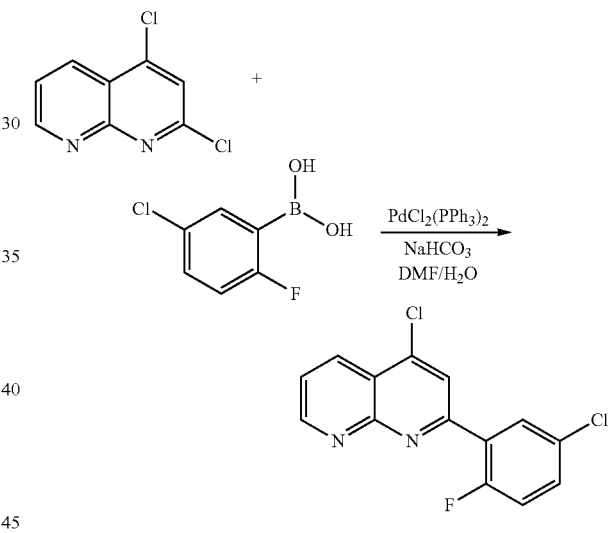

A solution of 9.95 g (50.0 mmol) 2,4-dichloro-[1,8]naphthyridine (described by Koller, Chemische Berichte 60: 407 (1927)), 8.72 g (50.0 mmol) 5-chloro-2-fluorophenylboronic acid und 5.04 g (60.0 mmol) sodium hydrogencarbonate in 100 ml DMF und 50 ml water was heated to 80° C. under nitrogen. 701 mg (1.0 mmol) bis-(triphenylphosphine)-palladium(II)-chloride were added and the mixture was stirred for 16 hrs at 80° C. Water was added to the reaction mixture and the precipitate was filtered off, dried in vacuum and recrystallized from 2-propanol. This yielded 4-chloro-2-(5-chloro-2-fluoro-phenyl)-[1,8]naphthyridine as yellowish crystals; HPLC-MS: 2.49 min, [M+H] 293.

$^1$H NMR (400 MHz, CDCl$_3$) δ [ppm]=9.14 (dd, J=4.2, 1.9, 1H), 8.56 (dd, J=8.3, 1.9, 1H), 8.37 (dd, J=6.8, 2.7, 1H), 8.10 (d, J=1.6, 1H), 7.56 (dd, J=8.4, 4.2, 1H), 7.36 (ddd, J=8.7, 4.2, 2.8, 1H), 7.10 (dd, J=10.9, 8.8, 1H).

The following compounds were similarly produced:
4-Chloro-2-(2-fluoro-phenyl)-[1,8]naphthyridine; HPLC-MS: 2.30 min, [M+H] 259
4-Chloro-2-(4-fluoro-phenyl)-[1,8]naphthyridine; HPLC-MS: 2.29 min, [M+H] 259

4-Chloro-2-(3-chloro-phenyl)-[1,8]naphthyridine; HPLC-MS: 2.44 min, [M+H] 275

4-Chloro-2-(3-trifluoromethyl-phenyl)-[1,8]naphthyridine; HPLC-MS: 2.49 min, [M+H] 309

4-Chloro-2-(2-fluoro-5-trifluoromethyl-phenyl)-[1,8]naphthyridine; HPLC-MS: 2.52 min, [M+H] 327

4-Chloro-2-(2,4,5-trifluoro-phenyl)-[1,8]naphthyridine; HPLC-MS: 2.45 min, [M+H] 295

4-Chloro-2-(2-fluoro-5-trifluoromethoxy-phenyl)-[1,8]naphthyridine; HPLC-MS: 2.63 min, [M+H] 343

4-Chloro-2-(2,5-difluoro-phenyl)-[1,8]naphthyridine; HPLC-MS: 2.32 min, [M+H] 277

EXAMPLE 2

Synthesis of 2-(4-chloro-[1,8]naphthyridin-2-yl)-benzonitrile

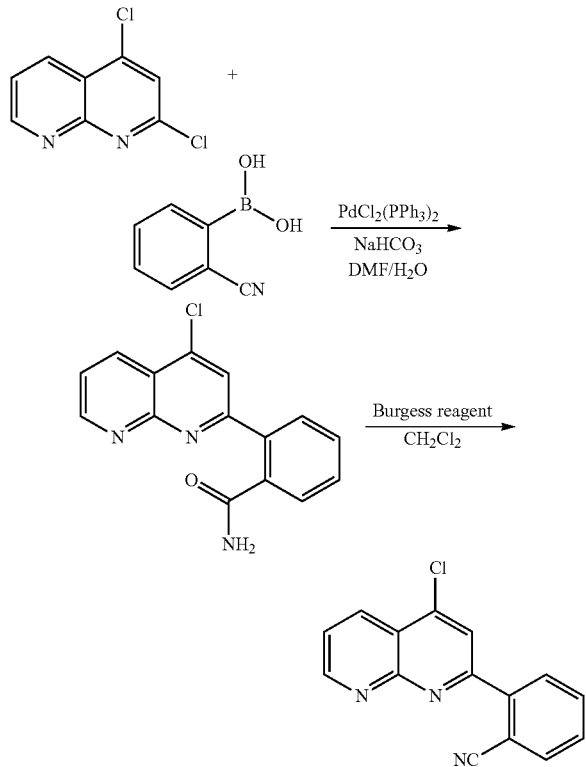

A solution of 1.99 g (10.0 mmol) 2,4-dichloro-[1,8]naphthyridine, 1.47 g (10.0 mmol) 2-cyanobenzeneboronic acid and 1.01 g (120.0 mmol) sodium bicarbonate in 100 ml DMF and 50 ml water was heated to 80° C. under nitrogen. 140 mg (0.20 mmol) bis-(triphenyl-phosphine)-palladium(II)-chloride were added and the mixture was stirred for 16 hrs at 80° C. Water was added to the reaction mixture and the resulting precipitate was filtered off and washed well with water. The residue was dried in vacuum yielding 2-(4-chloro-[1,8]naphthyridin-2-yl)-benzamide as yellow crystals; HPLC-MS: 1.55 min, [M+H] 284.

To a slurry of 970 mg (3.42 mmol) 2-(4-chloro-[1,8]naphthyridin-2-yl)-benzamide in 10 ml dichloromethane 2.85 g (12.0 mmol) 1.26 g (5.27 mmol) methoxycarbonylsulfamoyl-triethylammonium hydroxide, inner salt, (Burgess reagent) was added. The reaction mixture was stirred for 4 hours at room temperature. The reaction mixture was partitioned between water and dichloromethane. The organic phase was dried over sodium sulfate and evaporated. The residue was crystallized from isopropanol yielding 2-(4-chloro-[1,8]naphthyridin-2-yl)-benzonitrile as colourless crystals; HPLC-MS: 1.94 min, [M+H] 266.

EXAMPLE 3

Synthesis of 4-chloro-2-(6-methylpyridin-2-yl)-[1,8]naphthyridine

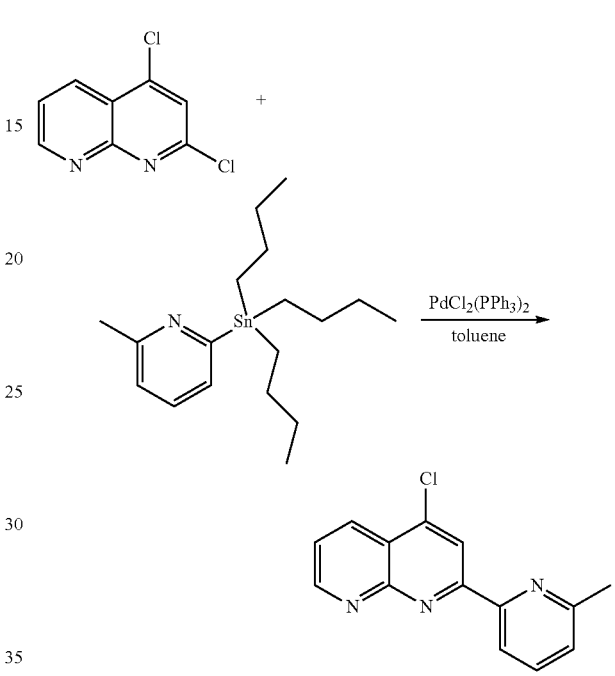

A solution of 1.69 g (8.47 mmol) 2,4-dichloro-[1,8]naphthyridine and 3.24 g (8.47 mmol) 6-methyl-2-(tributylstannyl)-pyridine in 8.5 ml toluene under nitrogen was heated to 80° C. Then 178 mg (0.254 mmol) bis-(triphenylphosphine)-palladium(II)-chloride were added. The mixture was stirred for 16 hrs at 80° C. and then cooled to 0° C. in an ice bath. The precipitate was filtered off, washed with ice cold toluene and petrolether and dried in vacuum. This yielded 4-chloro-2-(6-methylpyridin-2-yl)-[1,8]naphthyridine as gray felted needles; HPLC-MS: 2.25 min, [M+H] 256.

$^1$H-NMR (CDCl$_3$): δ [ppm]=2.71 (s, 3H), 7.29 (d, J=7.3 Hz, 1H), 7.61 (dd, J$_1$=8.3 Hz, J$_2$=4.1 Hz, 1H), 7.80 (t, J=7.7 Hz, 1H), 8.66 (dd, J$_1$=8.1 Hz, J$_2$=2.0 Hz, 1H), 8.67 (d, J=7.8 Hz, 1H), 8.9 (s, 1H), 9.2 (dd, J$_1$=4.1 Hz, J$_2$=1.9 Hz, 1H).

EXAMPLE 4

Synthesis of 2-(5-chloro-2-fluoro-phenyl)-[1,8]naphthyridine-4-boronic acid

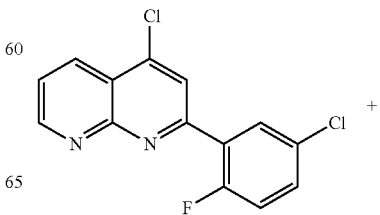

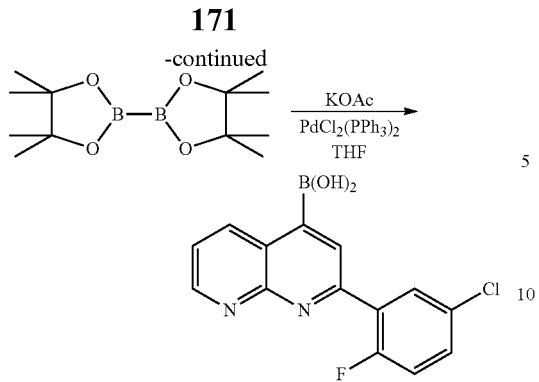

A slurry of 2.93 g (10.0 mmol) 4-chloro-2-(5-chloro-2-fluoro-phenyl)-[1,8]naphthyridine, 3.30 g (13.0 mmol) bis-pinacolato-diboron and 2.94 g (30.0 mmol) potassium acetate in 40 ml THF was heated to 80° C. under nitrogen. Then 140 mg (0.20 mmol) bis-(triphenyl-phosphine)-palladium(II)-chloride were added and the reaction mixture was stirred for 16 hours at 80° C. The mixture was cooled to room temperature and saturated sodium chloride solution was added. The mixture was stirred for some minutes at room temperature. The precipitate thus formed was filtered with suction, washed with water and THF and dried in vacuo yielding 2-(5-chloro-2-fluoro-phenyl)-[1,8]naphthyridine-4-boronic acid as grey solid; HPLC-MS: [M+H] 303.

$^1$H NMR (400 MHz, DMSO) δ=9.12 (dd, J=4.1, 1.9, 1H), 8.95 (s, 2H), 8.85 (dd, J=8.3, 1.8, 1H), 8.20 (d, J=2.3, 1H), 8.11 (dd, J=6.6, 2.7, 1H), 7.67 (m, 2H), 7.51 (dd, J=10.6, 8.9, 1H).

In the reaction described above, the corresponding pinacol ester is the primary product.

The following compounds were synthesized in an analogous manner:
2-(6-Methylpyridin-2-yl)-[1,8]naphthyridine-4-boronic acid; HPLC-MS: 1.07 min, [M+H] 266
2-(2-Fluoro-5-trifluoromethyl-phenyl)-[1,8]naphthyridine-4-boronic acid; [M+H] 337
2-(2,5-Difluoro-phenyl)-[1,8]naphthyridine-4-boronic acid; HPLC-MS; 1.42 min, [M+H] 287
2-(2-Fluoro-phenyl)-[1,8]naphthyridine-4-boronic acid; HPLC-MS: [M+H] 269
2-(2-Cyano-phenyl)-[1,8]naphthyridine-4-boronic acid

EXAMPLE 5

Synthesis of 4-(5-Bromo-pyridin-3-yl)-2-(5-chloro-2-fluoro-phenyl)-[1,8]naphthyridine

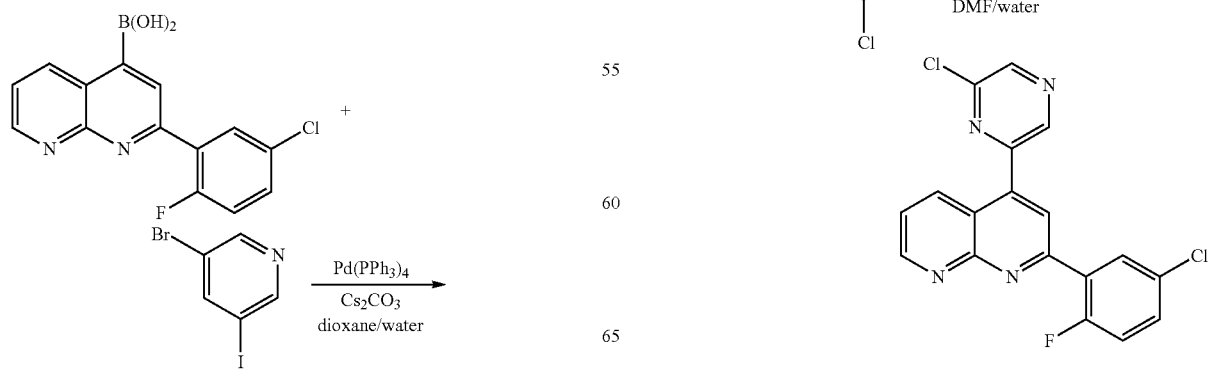

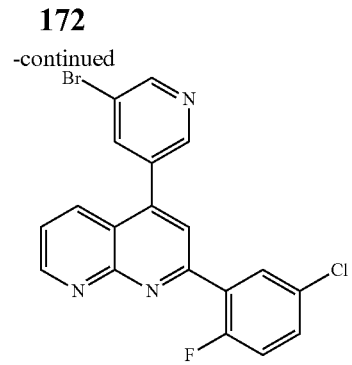

A slurry of 4.04 g (14.2 mmol) 2-bromo-5-iodo-pyridine, 4.74 g (15.7 mmol) 2-(5-chloro-2-fluoro-phenyl)-[1,8]naphthyridine-4-boronic acid and 9.27 g (28.5 mmol) cesium carbonate in 70 ml dioxane and 14 ml water was heated to 80° C. under nitrogen. Then 822 mg (0.71 mmol) tetrakis-(triphenylphosphine)-palladium(0) were added and the reaction mixture was stirred for 2 hours at 100° C. The reaction mixture was cooled to room temperature and partitioned between water and dichloromethane. The organic phase was dried over sodium sulfate and evaporated. The residue was chromatographed on a silica gel column with dichloromethane/methanol as eluent yielding 4-(5-Bromo-pyridin-3-yl)-2-(5-chloro-2-fluoro-phenyl)-[1,8]naphthyridine as light-yellow crystals; HPLC-MS: 2.28 min, [M+H] 416.

$^1$H NMR (500 MHz, DMSO) δ=9.22 (s, 1H), 8.94 (d, J=1.9, 1H), 8.84 (s, 1H), 8.44 (s, 1), 8.34 (d, J=8.0, 1H), 8.14 (m, 1H), 8.06 (m, 1H), 7.72 (dd, J=8.3, 4.1, 1H), 7.69 (m, 1H), 7.52 (t, J=9.7, 1H).

EXAMPLE 5A

Synthesis of 2-(5-Chloro-2-fluoro-phenyl)-4-(6-chloro-pyrazin-2-yl)-[1,8]naphthyridine

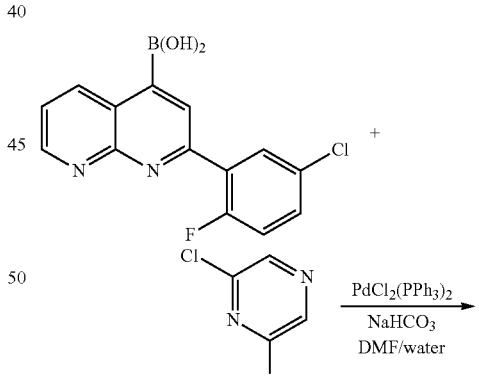

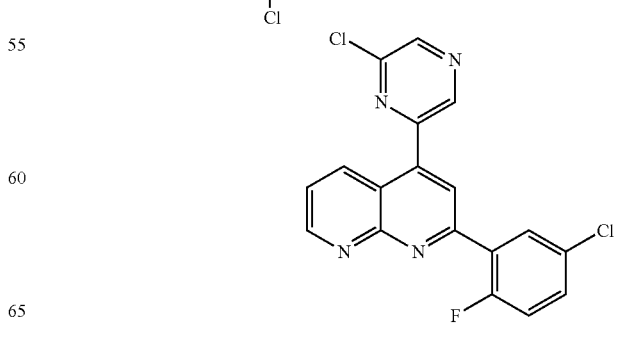

A solution of 302 mg (1.00 mmol) 2-(5-chloro-2-fluoro-phenyl)-[1,8]naphthyridine-4-boronic acid, 194 mg (1.30 mmol) 2,6-dichloropyrazine and 101 mg (1.2 mmol) sodium bicarbonate in 4 ml DMF and 1 ml water was heated to 80° C. under nitrogen. Then 14.0 mg (0.02 mmol) bis-(triphenylphosphine)-palladium(II)-chloride were added and the reaction mixture was stirred for 16 hours at 80° C. Water was added to the reaction mixture and the resulting precipitate was filtered off. The residue was chromatographed on a silica gel column with dichloromethane/methanol as eluent yielding 2-(5-chloro-2-fluoro-phenyl)-4-(6-chloro-pyrazin-2-yl)-[1,8]naphthyridine as colourless crystals; HPLC-MS: 2.35 min, [M+H] 371.

EXAMPLE 6

Synthesis of 3-Bromo-5-[2-(5-chloro-2-fluoro-phenyl)-[1,8]naphthyridin-4-yl]-pyridin-2-ylamine

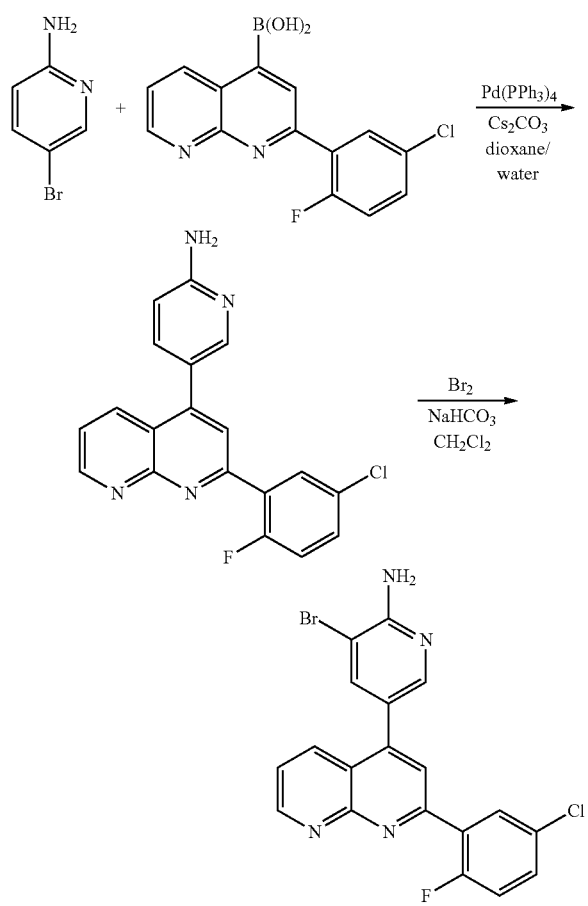

A slurry of 352 mg (2.04 mmol) 2-amino-5-bromo-pyridine, 678 mg (2.24 mmol) 2-(5-chloro-2-fluoro-phenyl)-[1,8]naphthyridine-4-boronic acid and 1.33 g (4.07 mmol) cesium carbonate in 10 ml dioxane and 2 ml water was heated to 80° C. under nitrogen. Then 118 mg (0.10 mmol) tetrakis-(triphenylphosphine)-palladium(0) were added and the reaction mixture was stirred for 1 hour at 100° C. The reaction mixture was cooled to room temperature and water and dichloromethane were added. The resulting precipitate was filtered off, washed with water and dried in vacuo yielding 5-[2-(5-chloro-2-fluoro-phenyl)-[1,8]naphthyridin-4-yl]-pyridin-2-ylamine as brown crystals; HPLC-MS: 1.43 min, [M+H] 351.

To a solution of 429 mg (1.22 mmol) 5-[2-(5-Chloro-2-fluoro-phenyl)-[1,8]naphthyridin-4-yl]-pyridin-2-ylamine in 5 ml dichloromethane 195 mg (1.84 mmol) sodium bicarbonate was added. Then 94 µl (1.84 mmol) bromine were added slowly. The reaction mixture was stirred for 1 hour at room temperature and subsequently was partitioned between water and dichloromethane. The organic phase was dried over sodium sulfate and evaporated yielding 3-bromo-5-[2-(5-chloro-2-fluoro-phenyl)-[1,8]naphthyridin-4-yl]-pyridin-2-ylamine as brown amorphous solid; HPLC-MS: 2.18 min, [M+H] 431.

$^1$H NMR (400 MHz, DMSO) δ=9.16 (dd, J=4.1, 1.9, 1H), 8.45 (dd, J=8.4, 1.9, 1H), 8.24 (d, J=2.1, 1H), 8.13 (dd, J=6.6, 2.8, 1H), 8.10 (d, J=2.1, 1H), 7.96 (d, J=2.0, 1H), 7.69 (dd, J=8.4, 4.1, 2H), 7.65 (m, 1H), 7.50 (dd, J=10.7, 8.9, 1H), 6.72 (s, 2H).

EXAMPLE 7

Synthesis of 2-(5-chloro-2-fluoro-phenyl)-4-[5-(1-methyl-1H-pyrazol-4-yl)-pyridin-3-yl]-[1,8]naphthyridine (no. 7)

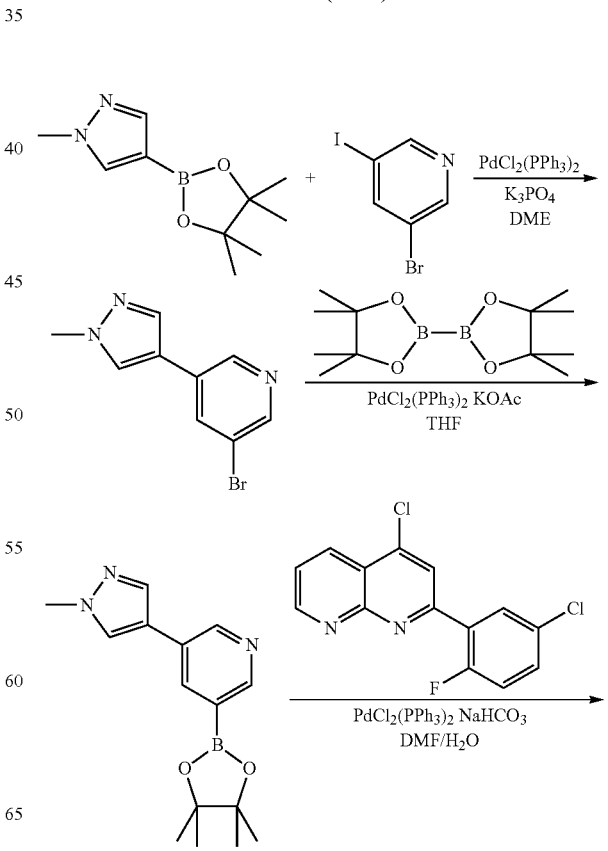

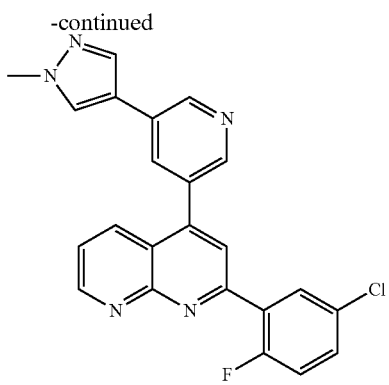

A slurry of 4.33 g (15.3 mmol) 3-bromo-5-iodo-pyridine, 3.49 g (16.8 mmol) 1-methyl-4-(4,4,5,5-tetramethyl-[1,3,2]dioxaborolan-2-yl)-1H-pyrazol and 6.48 g (30.5 mmol) tri-potassium-phosphate-trihydrate in 30 ml 1,2-dimethoxy-ethane was heated to 80° C. under nitrogen. Then 321 mg (0.46 mmol) bis-(triphenylphosphine)-palladium(II)-chloride were added. The reaction mixture was stirred for 16 hours at 80° C. The reaction mixture was evaporated. The residue was chromatographed on a silica gel column with dichloromethane/methanol as eluent yielding 3-bromo-5-(1-methyl-1H-pyrazol-4-yl)-pyridine als slightly yellow crystals; HPLC-MS: [M+H] 238/234.

A slurry of 1.04 g (4.39 mmol) 3-bromo-5-(1-methyl-1H-pyrazol-4-yl)-pyridine, 1.48 g (5.70 mmol) bis(pinacolato)diboron and 1.29 g (13.2 mmol) potassium acetate in 9 ml THF was heated to 80° C. under nitrogen. Then 92 mg (0.13 mmol) Bis-(triphenylphosphine)-palladium(II)-chloride were added. The reaction mixture was stirred for 16 hours at 80° C. The reaction mixture was cooled to room temperature, filtered over a pad of celite and the filtrate was extracted with brine. The organic phase was dried over sodium sulfate and evaporated. The residue was crystallized from tert.butyl-methyl-ether yielding 3-(1-methyl-1H-pyrazol-4-yl)-5-(4,4,5,5-tetramethyl-[1,3,2]dioxaborolan-2-yl)-pyridine as slightly yellow solid.

$^1$H NMR (400 MHz, DMSO) δ=8.92 (d, J=2.4, 1H), 8.58 (d, J=1.6, 1H), 8.33 (s, 1H), 8.08 (dd, J=2.4, 1.7, 1H), 7.99 (d, J=0.7, 1H), 3.87 (s, 3H), 1.33 (s, 12H).

A slurry of 147 mg (0.5 mmol) 4-chloro-2-(5-chloro-2-fluoro-phenyl)-[1,8]naphthyridine, 171 mg (0.6 mmol) 3-(1-methyl-1H-pyrazol-4-yl)-5-(4,4,5,5-tetramethyl-[1,3,2]di-oxaborolan-2-yl)-pyridine and 50.4 mg (0.6 mmol) sodium bicarbonate in 1 ml DMF and 0.5 ml water was heated to 80° C. under nitrogen. Then 7.0 mg (0.01 mmol) bis-(triphenylphosphine)-palladium(II)-chloride were added. The reaction mixture was stirred for 16 hours at 80° C. Water was then added to the reaction mixture and the resulting precipitate was filtered off. The residue was chromatographed on a silica gel column with dichloromethane/methanol as eluent yielding 2-(5-chloro-2-fluoro-phenyl)-4-[5-(1-methyl-1H-pyrazol-4-yl)-pyridin-3-yl]-[1,8]naphthyridine als yellow crystals; HPLC-MS: 2.09 min, [M+H] 416.

$^1$H NMR (500 MHz, d$^6$-DMSO): δ [ppm]=9.21 (dd, J=4.1, 1.8, 1H), 9.04 (d, J=2.1, 1H), 8.64 (d, J=2.0, 1H), 8.38 (m, 2H), 8.27 (t, J=2.1, 1H), 8.17 (dd, J=6.6, 2.8, 1H), 8.10 (d, J=1.8, 1H), 8.08 (s, 1H), 7.71 (dd, J=8.4, 4.1, 1H), 7.68 (ddd, J=6.9, 4.6, 3.5, 1H), 7.52 (dd, J=10.6, 8.9, 1H), 3.89 (s, 3H).

The following compounds were synthesized analogously:

2-(2-Fluoro-5-trifluoromethyl-phenyl)-4-[5-(1-methyl-1H-pyrazol-4-yl)-pyridin-3-yl]-[1,8]naphthyridine (no. 8); HPLC-MS: 2.17 min, [M+H] 450

2-(3-Chloro-phenyl)-4-[5-(1-methyl-1H-pyrazol-4-yl)-pyridin-3-yl]-[1,8]naphthyridine (no. 9); HPLC-MS: 2.08 min, [M+H] 398

4-[5-(1-Methyl-1H-pyrazol-4-yl)-pyridin-3-yl]-2-(6-methyl-pyridin-2-yl)-[1,8]naphthyridine (no. 10); HPLC-MS: 1.68 min, [M+H] 379

4-[5-(1-Methyl-1H-pyrazol-4-yl)-pyridin-3-yl]-2-(3-trifluoromethyl-phenyl)-[1,8]naphthyridine (no. 14); HPLC-MS: 2.17 min, [M+H] 432

2-(2-Fluoro-phenyl)-4-[5-(1-methyl-1H-pyrazol-4-yl)-pyridin-3-yl]-[1,8]naphthyridine (no. 15); HPLC-MS: 1.90 min, [M+H] 382

2-(4-Fluoro-phenyl)-4-[5-(1-methyl-1H-pyrazol-4-yl)-pyridin-3-yl]-[1,8]naphthyridine (no. 16); HPLC-MS: 1.93 min, [M+H] 382

4-[5-(1-Methyl-1H-pyrazol-4-yl)-pyridin-3-yl]-2-(2,4,5-trifluoro-phenyl)-[1,8]naphthyridine (no. 17); HPLC-MS: 2.04 min, [M+H] 418

EXAMPLE 8

Synthesis of 2-(5-chloro-2-fluoro-phenyl)-4-[5-(1-piperidin-4-yl-1H-pyrazol-4-yl)-pyridin-3-yl]-[1,8]naphthyridine dihydrochloride (no. 11)

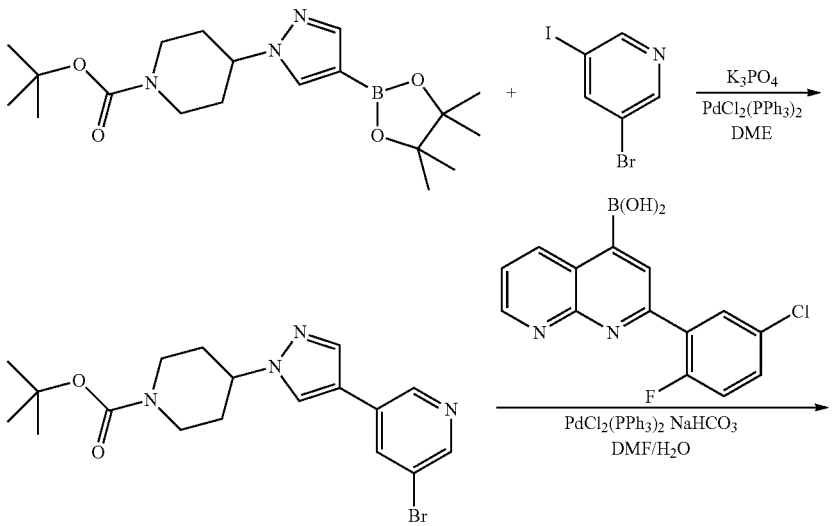

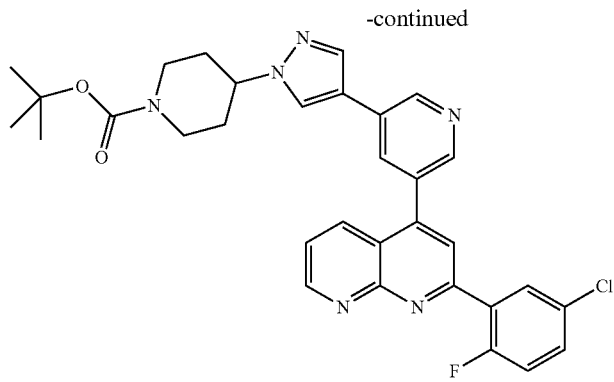

4N HCl in dioxane

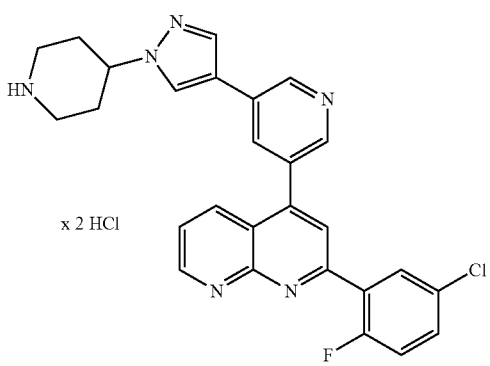

x 2 HCl

A slurry of 2.50 g (8.81 mmol) 3-bromo-5-iodo-pyridine, 3.66 g (9.7 mmol) 4-[4-(4,4,5,5-tetramethyl-[1,3,2]dioxaborolan-2-yl)-pyrazol-1-yl]-piperidin-1-carboxylic acid tert.butyl ester (synthesis described in WO 2007/066187) and 3.74 g (17.6 mmol) tri-potassium-phosphate-trihydrate in 30 ml 1,2-dimethoxyethane was heated to 80° C. under nitrogen. Then 618 mg (0.88 mmol) bis-(triphenylphosphine)-palladium(II)-chloride were added. The reaction mixture was stirred for 16 hours at 80° C. The reaction mixture was partitioned between THF and brine. The organic phase was dried over sodium sulfate and evaporated yielding 4-[4-(5-bromo-pyridin-3-yl)-pyrazol-1-yl]-piperidine-1-carboxylic acid tert-butyl-ester as slightly yellow crystals; HPLC-MS: 2.28 min, [M+H] 407/409.

A slurry of 204 mg (0.50 mmol) 4-[4-(5-bromo-pyridin-3-yl)-pyrazol-1-yl]-piperidine-1-carboxylic acid tert-butyl-ester, 167 mg (0.55 mmol) 2-(5-chloro-2-fluoro-phenyl)-[1,8]naphthyridine-4-boronic acid and 50.4 mg (0.6 mmol) sodium bicarbonate in 2 ml DMF and 0.5 ml water were heated to 80° C. under nitrogen. Then 7.0 mg (0.01 mmol) bis-(triphenylphosphine)-palladium(II)-chloride were added. The reaction mixture was stirred for 40 hours at 80° C. The reaction mixture was partitioned between water and dichloromethane. The organic phase was dried over sodium sulfate and evaporated. The residue was chromatographed on a silica gel column with petrolether/ethylacetate as eluent yielding 4-(4-{5-[2-(5-chloro-2-fluoro-phenyl)-[1,8]naphthyridin-4-yl]-pyridin-3-yl}-pyrazol-1-yl)-piperidine-1-carboxylic acid tert-butyl ester as colourless crystals; HPLC-MS: 2.55 min, [M+H] 585.

A slurry of 155 mg (0.265 mmol) 4-(4-{5-[2-(5-chloro-2-fluoro-phenyl)-[1,8]naphthyridin-4-yl]-pyridin-3-yl}-pyrazol-1-yl)-piperidine-1-carboxylic acid tert-butyl-ester in 1.5 ml 4 N HCl in dioxane was treated with 1 drop of methanol. The solution thus formed was left for 3 hours at room temperature and subsequently evaporated. The residue was treated with tert-butyl-methyl-ether and the solid was filtered off. The residue was dissolved in water and lyophilized yielding 2-(5-chloro-2-fluoro-phenyl)-4-[5-(1-piperidin-4-yl-1H-pyrazol-4-yl)-pyridin-3-yl]-[1,8]naphthyridine dihydrochloride als colourless lyophilisate; HPLC-MS: 1.65 min, [M+H] 485.

$^1$H NMR (400 MHz, DMSO) δ=9.30 (m, 4H), 8.90 (s, 1H), 8.81 (s, 1H), 8.68 (s, 1H), 8.56 (dd, J=8.4, 1.1, 1H), 8.30 (s, 1H), 8.27 (s, 1H), 8.20 (dd, J=6.6, 2.7, 1H), 7.83 (dd, J=8.4, 4.3, 1H), 7.73 (ddd, J=8.8, 4.1, 2.8, 1H), 7.55 (dd, J=10.6, 8.9, 1H), 4.56 (m, 1H), 3.38 (d, J=12.7, 2H), 3.10 (q, J=11.8, 2H), 2.22 (m, 4H).

The following compounds were prepared analogously:

2-(2-Fluoro-5-trifluoromethyl-phenyl)-4-[5-(1-piperidin-4-yl-1H-pyrazol-4-yl)-pyridin-3-yl]-[1,8]naphthyridine dihydrochloride (no. 18); HPLC-MS: 1.73 min, [M+H] 499

3-[2-(5-Chloro-2-fluoro-phenyl)-[1,8]naphthyridin-4-yl]-5-(1-piperidin-4-yl-1H-pyrazol-4-yl)-pyridin-2-ylamine dihydrochloride (no. 13); HPLC-MS: 1.35 min, [M+H] 500, using 4-[4-(6-amino-5-bromo-pyridin-3-yl)-pyrazol-1-yl]-piperidine-1-carboxylic acid tert-butyl-ester (synthesis described in US2009197862)

2-(2-Fluoro-phenyl)-4-[5-(1-piperidin-4-yl-1H-pyrazol-4-yl)-pyridin-3-yl]-[1,8]naphthyridine dihydrochloride (no. 29); HPLC/MS: 1.52 min, [M+H] 451

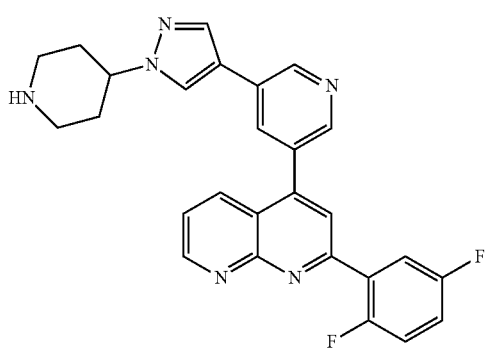 [SMILES: Fc1ccc(F)c(-c2cc(-c3cncc(-c4cnn(C5CCNCC5)c4)c3)c3cccnc3n2)c1]

2-(2,5-Difluoro-phenyl)-4-[5-(1-piperidin-4-yl-1H-pyrazol-4-yl)-pyridin-3-yl]-[1,8]naphthyridine (no. 47); HPLC/MS: 1.54 min, [M+H] 469

EXAMPLE 9

Synthesis of 2-(5-chloro-2-fluoro-phenyl)-4-[5-(1-methyl-1H-pyrazol-4-yl)-1-oxy-pyridin-3-yl]-[1,8]naphthyridine (no. 22)

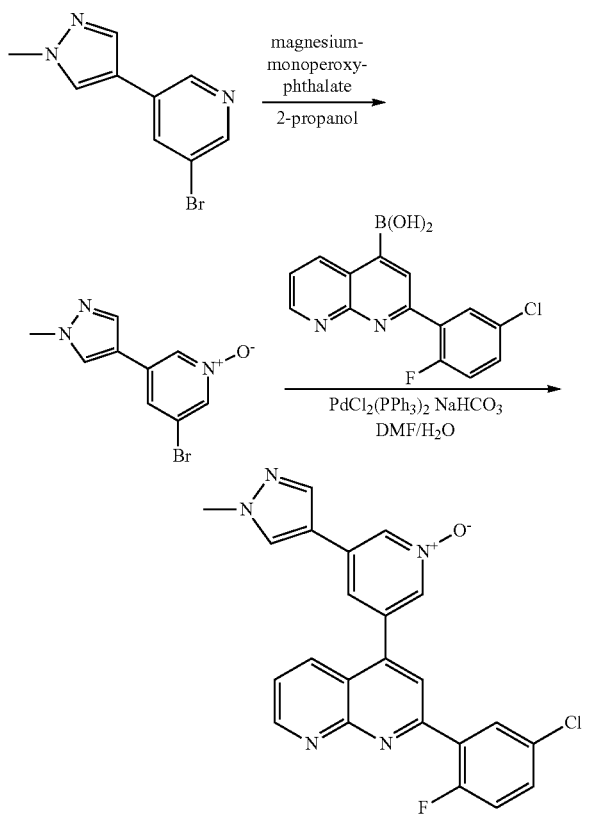

A slurry of 266 mg (1.12 mmol) 3-bromo-5-(1-methyl-1H-pyrazol-4-yl)-pyridine and 1.30 g (2.23 mmol) magnesium monoperoxyphthalate hexahydrate (85%) in 5 ml 2-propanol was stirred for 18 hours at room temperature. The reaction mixture was evaporated and the residue partitioned between saturated sodium bicarbonate solution and dichloromethane. The organic phase was dried over sodium sulfate and evaporated yielding 3-bromo-5-(1-methyl-1H-pyrazol-4-yl)-pyridine 1-oxide as slightly yellow solid; HPLC-MS: 1.34 min, [M+H] 254/256.

A slurry of 125 mg (0.49 mmol) 3-bromo-5-(1-methyl-1H-pyrazol-4-yl)-pyridine 1-oxide, 164 mg (0.54 mmol) 2-(5-chloro-2-fluoro-phenyl)-[1,8]naphthyridine-4-boronic acid and 50.0 mg (0.59 mmol) sodium bicarbonate in 2 ml DMF and 0.5 ml water was heated to 80° C. under nitrogen. Then 6.9 mg (0.01 mmol) bis-(triphenylphosphine)-palladium(II)-chloride were added. The reaction mixture was stirred for 18 hours at 80° C. The reaction mixture was cooled to room temperature. Water was added and the resulting precipitate was filtered off. The residue was chromatographed on a silica gel column with dichloromethane/methanol as eluent yielding 2-(5-chloro-2-fluoro-phenyl)-4-[5-(1-methyl-1H-pyrazol-4-yl)-1-oxy-pyridin-3-yl]-[1,8]naphthyridine as colourless crystals; HPLC-MS: 1.86 min, [M+H] 432.

$^1$H NMR (500 MHz, DMSO) δ=9.21 (dd, J=4.1, 1.9, 1H), 8.78 (t, J=1.4, 1H), 8.44 (dd, J=8.4, 1.8, 1H), 8.40 (s, 1H), 8.36 (t, J=1.4, 1H), 8.17 (dd, J=6.6, 2.8, 1H), 8.12 (d, J=1.6, 1H), 8.10 (s, 1H), 7.83 (t, J=1.3, 1H), 7.72 (dd, J=8.4, 4.1, 1H), 7.68 (ddd, J=8.7, 4.0, 2.9, 1H), 7.52 (dd, J=10.6, 8.9, 1H), 3.87 (s, 3H).

EXAMPLE 10

Synthesis of 2-(5-Chloro-2-fluoro-phenyl)-4-{5-[1-(2-pyrrolidin-1-yl-ethyl)-1H-pyrazol-4-yl]-pyridin-3-yl}-[1,8]naphthyridine (no. 21)

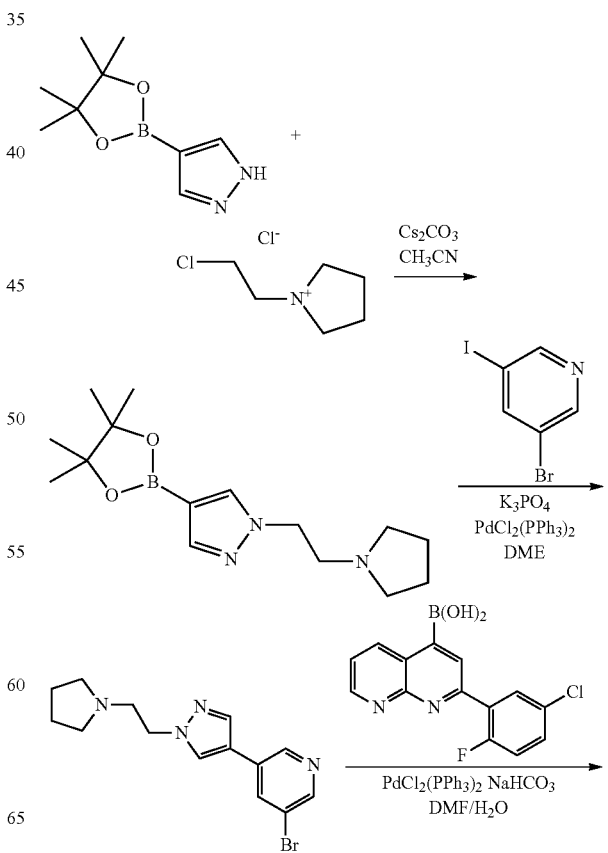

-continued

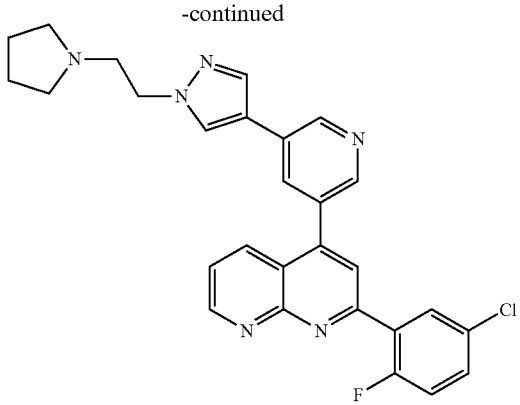

To a solution of 19.4 g (100 mmol) pyrazol-4-boronic acid pinacol-ester in 150 ml acetonitrile were added 32.5 g (191 mmol) N-(2-Chloroethyl)-pyrrolidine hydrochloride and 87.7 g (300 mmol) cesium carbonate. The resulting slurry was stirred for 18 hours at room temperature. The reaction mixture was filtered with suction and the residue was washed well with acetonitrile. The filtrate was evaporated and dissolved in ethyl acetate. This solution was extracted four times with water and finally washed with brine. The organic phase was dried over sodium sulfate and evaporated in vacuo yielding 1-(2-pyrrolidin-1-yl-ethyl)-4-(4,4,5,5-tetramethyl-[1,3,2]dioxaborolan-2-yl)-1H-pyrazol as light-brown oil.

$^1$H-NMR (d$^6$-DMSO): δ=1.25 (s, 12H), 1.65 (m, 4H), 2.44 (m, 4H), 2.79 (t, J=6.8 Hz, 2H), 4.21 (t, J=6.8 Hz, 2H), 7.56 (s, 1H), 7.93 (s, 1H) ppm.

A solution of 5.43 g (19.1 mmol) 3-bromo-5-iodo-pyridine and 6.12 g (21.0 mmol) 1-(2-pyrrolidin-1-yl-ethyl)-4-(4,4,5,5-tetramethyl-[1,3,2]dioxaborolan-2-yl)-1H-pyrazol in 17 ml 1,2-dimethoxyethan was treated with 8.12 g (38.2 mmol) tri-potassium-phosphate-trihydrate and was heated to 80° C. under nitrogen. Then 403 mg (0.57 mmol) bis(triphenylphosphine)palladium(II)-chloride were added. The reaction mixture was stirred for 18 hours at 80° C. The reaction mixture was partitioned between water and dichloromethane. The organic phase was extracted several times with 1 N HCl and was washed with water. The aqueous phases were combined, basified with 50% aqueous NaOH. Brine and THF were added. The organic phase was separated and the aqueous phase was extracted several times with THF. The combined organic phases were dried over sodium sulfate and evaporated. The residue was chromatographed on a silica gel column with dichloromethane/methanol as eluent yielding 3-bromo-5-[1-(2-pyrrolidin-1-yl-ethyl)-1H-pyrazol-4-yl]-pyridine as brown oil; HPLC-MS: 1.29 min, [M+H] 321/323.

$^1$H NMR (400 MHz, DMSO) δ=8.84 (d, J=1.9, 1H), 8.49 (d, J=2.2, 1H), 8.41 (s, 1H), 8.29 (t, J=2.1, 1H), 8.06 (s, 1H), 4.23 (t, J=6.6, 2H), 2.85 (t, J=6.6, 2H), 2.45 (m, 4H), 1.66 (m, 4H).

A slurry of 161 mg (0.50 mmol) 3-bromo-5-[1-(2-pyrrolidin-1-yl-ethyl)-1H-pyrazol-4-yl]-pyridine, 167 mg (0.55 mmol) 2-(5-Chloro-2-fluoro-phenyl)-[1,8]naphthyridine-4-boronic acid and 50.4 mg (0.6 mmol) sodium bicarbonate in 2 ml DMF and 0.5 ml water was heated at 80° C. under nitrogen. Then 7.0 mg (0.01 mmol) bis-(triphenylphosphine)-palladium(II)-chloride were added. The reaction mixture was stirred for 40 hours at 80° C. Water was added, the resulting precipitate was filtered off and washed with water. The residue was chromatographed on a silica gel column with dichloromethane/methanol as eluent yielding 2-(5-Chloro-2-fluoro-phenyl)-4-{5-[1-(2-pyrrolidin-1-yl-ethyl)-1H-pyrazol-4-yl]-pyridin-3-yl}-[1,8]naphthyridine as colourless crystals; HPLC-MS: 1.67 min, [M+H] 499.

$^1$H NMR (500 MHz, DMSO) δ=9.21 (dd, J=4.1, 1.8, 1H), 9.04 (d, J=2.0, 1H), 8.63 (d, J=1.9, 1H), 8.43 (s, 1H), 8.37 (dd, J=8.4, 1.8, 1H), 8.27 (t, J=2.0, 1H), 8.18 (dd, J=6.6, 2.7, 1H), 8.10 (d, J=1.7, 1H), 8.09 (s, 1H), 7.71 (dd, J=8.4, 4.1, 1H), 7.68 (ddd, J=8.7, 4.0, 3.0, 1H), 7.51 (dd, J=10.6, 8.9, 1H), 4.25 (t, J=6.4, 2H), 2.87 (bs, 2H), 2.48 (bs, 4H), 1.66 (bs, 4H).

The following compounds were prepared analogously:

2-(2-Fluoro-5-trifluoromethyl-phenyl)-4-{5-[1-(2-pyrrolidin-1-yl-ethyl)-1H-pyrazol-4-yl]-pyridin-3-yl}-[1,8]naphthyridine (no. 19); HPLC-MS: 1.74 min, [M+H] 533

2-(2-Fluoro-phenyl)-4-{5-[1-(2-pyrrolidin-1-yl-ethyl)-1H-pyrazol-4-yl]-pyridin-3-yl}-[1,8]naphthyridine (no. 24); HPLC-MS: 1.51 min, [M+H] 465

2-(2,5-Difluoro-phenyl)-4-{5-[1-(2-pyrrolidin-1-yl-ethyl)-1H-pyrazol-4-yl]-pyridin-3-yl}-[1,8]naphthyridine (no. 26); HPLC-MS: 1.47 min, [M+H] 483

2-(2-Fluoro-phenyl)-4-{5-[1-(2-pyrazol-1-yl-ethyl)-1H-pyrazol-4-yl]-pyridin-3-yl}-[1,8]naphthyridine (no. 77); HPLC-MS: 1.89 min, [M+H] 462

2-(2-Fluoro-phenyl)-4-(5-pyrazol-1-yl-pyridin-3-yl)-[1,8]naphthyridine (no. 79); HPLC-MS: 2.08 min, [M+H] 369

EXAMPLE 11

Synthesis of 2-(2-fluoro-5-trifluoromethyl-phenyl)-4-{5-[1-(1-methyl-piperidin-4-yl)-1H-pyrazol-4-yl]-pyridin-3-yl}-[1,8]naphthyridine (no. 23)

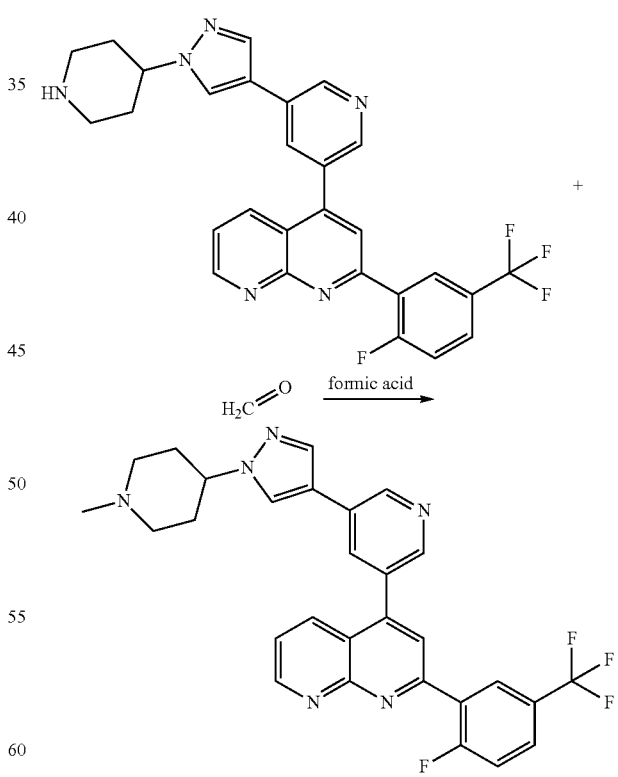

A solution of 110 mg (0.21 mmol) 2-(2-fluoro-5-trifluoromethyl-phenyl)-4-[5-(1-piperidin-4-yl-1H-pyrazol-4-yl)-pyridin-3-yl]-[1,8]naphthyridine (synthesis see example 8) in 1 ml formic acid was treated with 54 mg (0.63 mmol) 35% aqueous formaldehyde solution and heated to 80° C. The reaction mixture was stirred at this temperature for 2 hours. The volume of the reaction mixture was reduced under vacuum and the residue was made strongly alkaline with 2 N NaOH. The resulting precipitate was filtered off, washed with water and dried. The residue was crystallized from tert-butyl-methyl-ether yielding 2-(2-fluoro-5-trifluoromethyl-phenyl)-4-{5-[1-(1-methyl-piperidin-4-yl)-1H-pyrazol-4-yl]-pyridin-3-yl}-[1,8]naphthyridine as colourless crystals. HPLC/MS: 1.72 min, [M+H] 533.

$^1$H NMR (500 MHz, DMSO) δ=9.22 (dd, J=4.0, 1.6, 1H), 9.07 (d, J=1.8, 1H), 8.63 (d, J=1.8, 1H), 8.49 (m, 2H), 8.38 (dd, J=8.4, 1.5, 1H), 8.29 (m, 1H), 8.16 (d, J=1.4, 1H), 8.10 (s, 1H), 8.03 (m, 1H), 7.72 (m, 2H), 4.14 (m, 1H), 3.29 (m, 2H), 2.86 (d, J=11.4, 2H), 2.22 (s, 3H), 2.03 (m, 4H).

EXAMPLE 12

Synthesis of 2-(5-chloro-2-fluoro-phenyl)-4-{5-[1-(1-methyl-piperidin-4-yl)-1H-pyrazol-4-yl]-pyridin-3-yl}-[1,8]naphthyridine (no. 25)

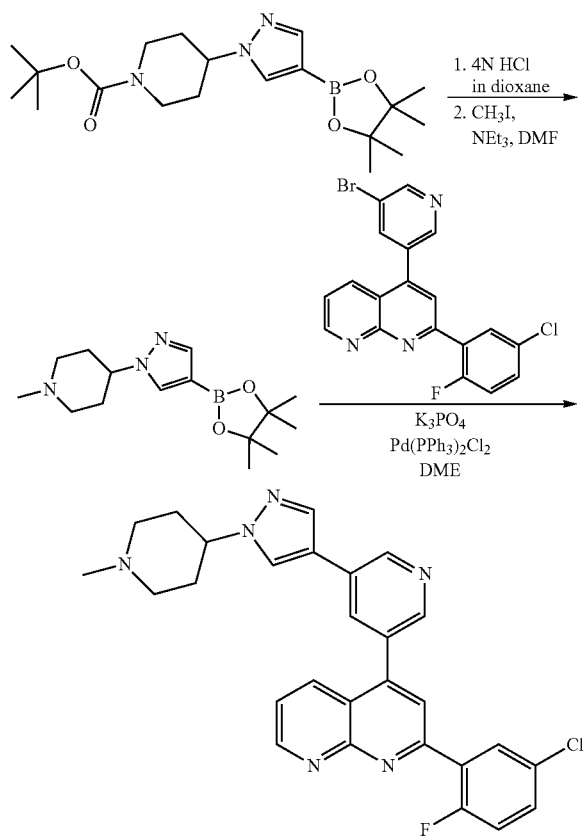

A solution of 5.00 g (13.3 mmol) 4-[4-(4,4,5,5-tetramethyl-[1,3,2]dioxaborolan-2-yl)-pyrazol-1-yl]-piperidine-1-carboxylic acid tert-butyl ester in a 4 N solution of hydrochloric acid in dioxane was stirred at room temperature for 16 hours. The precipitate that has formed was filtered off and the filtrate was evaporated to dryness. This residue was dissolved in 20 ml DMF and 2.6 ml (18.5 mmol) triethylamine and 0.6 ml (9.7 mmol) iodomethane were added. The reaction mixture was stirred for 16 hours at room temperature. The precipitate that had formed was filtered off and the filtrate was evaporated in vacuo. The residue was partitioned between water and dichloromethane. The organic phase was dried over sodium sulphate and evaporated. The residue was chromatographed on a silica gel column with toluene/ethylacetate as eluent yielding 1-methyl-4-[4-(4,4,5,5-tetramethyl-[1,3,2] dioxaborolan-2-yl)-pyrazol-1-yl]-piperidine as colourless crystals; HPLC-MS: 1.29 min, [M+H] 292.

To a solution of 59.7 mg (0.144 mmol) 4-(5-bromo-pyridin-3-yl)-2-(5-chloro-2-fluoro-phenyl)-[1,8]naphthyridine and 55.3 mg (0.190 mmol) 1-methyl-4-[4-(4,4,5,5-tetramethyl-[1,3,2]dioxaborolan-2-yl)-pyrazol-1-yl]-piperidine 67.2 mg (0.316 mmol) tri-potassiumphosphate trihydrate were added. The mixture was heated to 80° C. under nitrogen. Then 5.5 mg (0.008 mmol) bis(triphenylphosphine)palladium(II)-chloride were added. The reaction mixture was stirred for 4 hours at 80° C. The reaction mixture was cooled to room temperature and water was added. The resulting precipitate was filtered off, washed with water and air-dried. The residue was purified by preparative HPLC yielding 2-(5-chloro-2-fluoro-phenyl)-4-{5-[1-(1-methyl-piperidin-4-yl)-1H-pyrazol-4-yl]-pyridin-3-yl}-[1,8]naphthyridine formate as colourless crystals; HPLC-MS: 1.29 min, [M+H] 292.

$^1$H NMR (400 MHz, DMSO) δ=9.22 (dd, J=4.1, 1.9, 1H), 9.07 (d, J=2.1, 1H), 8.63 (d, J=2.1, 1H), 8.50 (s, 1H), 8.38 (dd, J=8.4, 1.9, 1H), 8.30 (t, J=2.1, 1H), 8.18 (m, 2H), 8.11 (d, J=0.5, 1H), 8.10 (d, J=2.0, 1H), 7.70 (m, 2H), 7.53 (dd, J=10.7, 8.9, 1H), 4.15 (m, 1H), 3.4 (m, 2H), 2.88 (d, J=11.7, 2H), 2.23 (s, 3H), 2.03 (m, 4H).

EXAMPLE 13

Synthesis of 2-(2-fluoro-phenyl)-4-{5-[1-(1-methyl-piperidin-4-yl)-1H-pyrazol-4-yl]-pyridin-3-yl}-[1,8] naphthyridine (no. 30)

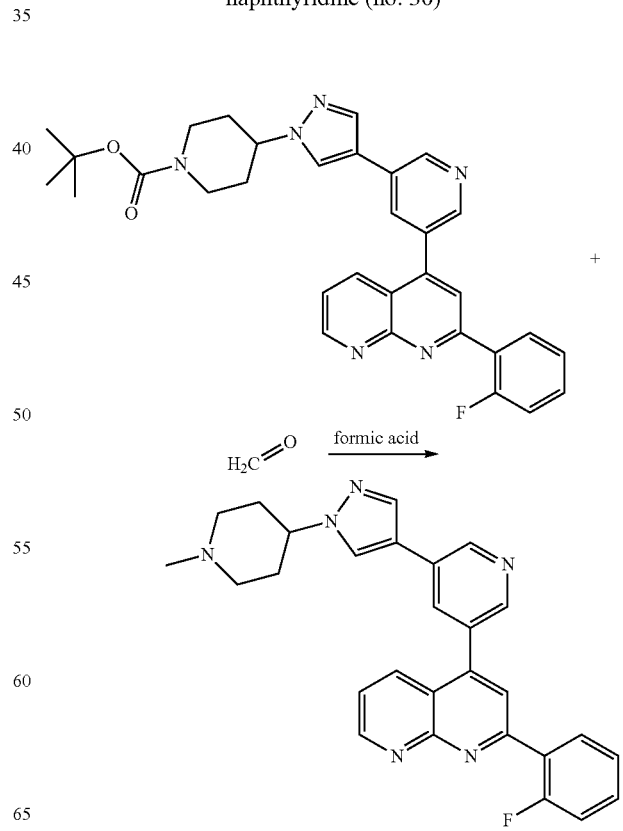

A solution of 286 mg (0.52 mmol) 4-(4-{5-[2-(2-fluoro-phenyl)-[1,8]naphthyridin-4-yl]-pyridin-3-yl}-pyrazol-1-yl)-piperidine-1-carboxylic acid tert-butyl ester (synthesis see example 8) in 1.7 ml formic acid was treated with 124 mg (1.56 mmol) 35% aqueous formaldehyde solution and heated to 80° C. The reaction mixture was stirred at this temperature for two hours. The volume of the reaction mixture was reduced under vacuum and the residue was partitioned between 2 N NaOH and dichloromethane. The organic phase was dried over sodium sulphate and evaporated. The residue was chromatographed on a silica gel column with dichloromethane/methanol as eluent yielding 2-(2-fluoro-phenyl)-4-{5-[1-(1-methyl-piperidin-4-yl)-1H-pyrazol-4-yl]-pyridin-3-yl}-[1,8]naphthyridine as colourless solid; HPLC/MS: 1.37 min, [M+H] 465.

EXAMPLE 14

Alternative synthesis of 2-(5-chloro-2-fluoro-phenyl)-4-{5-[1-(1-methyl-piperidin-4-yl)-1H-pyrazol-4-yl]-pyridin-3-yl}-[1,8]naphthyridine (no. 25)

A slurry of 2.92 g (7.04 mmol) 4-(5-bromo-pyridin-3-yl)-2-(5-chloro-2-fluoro-phenyl)-[1,8]naphthyridine, 2.92 g (7.75 mmol) 4-[4-(4,4,5,5-tetramethyl-[1,3,2]dioxaborolan-2-yl)-pyrazol-1-yl]-piperidine-1-carboxylic acid tert.butyl ester and 2.99 g (14.1 mmol) tri-potassium-phosphate-trihydrate in 30 ml 1,2-dimethoxyethane was heated to 80° C. under nitrogen. Then 247 mg (0.05 mmol) bis-(triphenylphosphine)-palladium(II)-chloride and 0.1 ml triethylamine were added. The reaction mixture was stirred for 16 hours at 80° C. The reaction mixture was partitioned between water and dichloromethane. The organic phase was dried over sodium sulfate and evaporated. The residue was chromatographed on a silica gel column with petrolether/ethylacetate as eluent yielding 4-(4-{5-[2-(5-chloro-2-fluoro-phenyl)-[1,8]naphthyridin-4-yl]-pyridin-3-yl}-pyrazol-1-yl)-piperidine-1-carboxylic acid tert-butyl ester as colourless crystals; HPLC-MS: 2.55 min, [M+H] 585.

The following reaction step was performed as described in example 13.

The following compounds were prepared analogously:

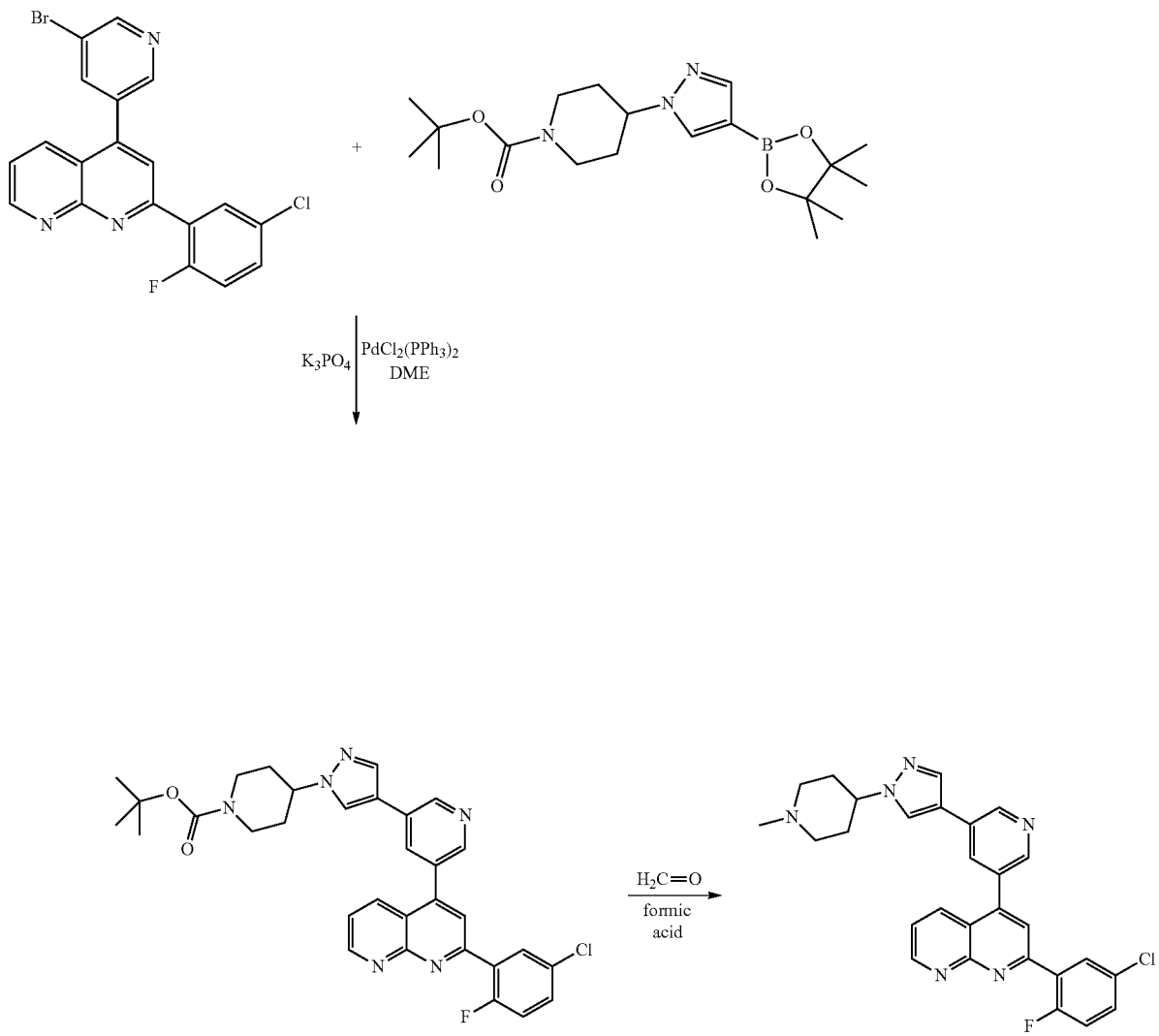

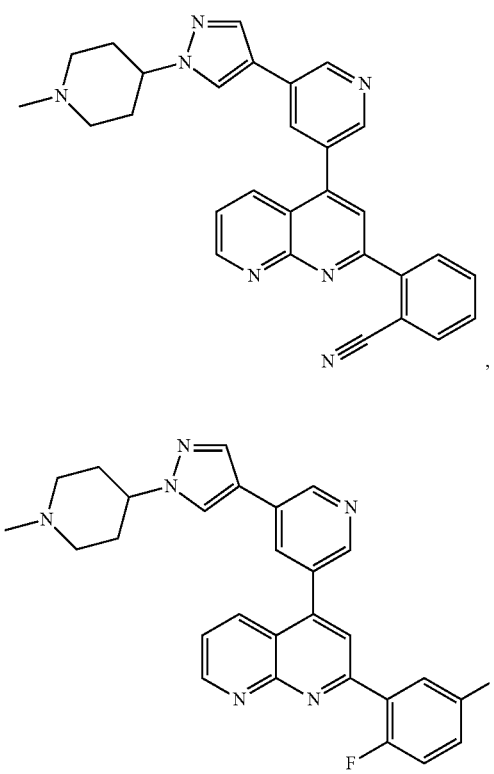

4-{5-[1-(1-Methyl-piperidin-4-yl)-1H-pyrazol-4-yl]-pyridin-3-yl}-2-(6-methyl-pyridin-2-yl)-[1,8]naphthyridine (no. 49); HPLC-MS: 1.31 min, [M+H] 462

2-(5-Chloro-2-fluoro-phenyl)-4-{6-[1-(1-methyl-piperidin-4-yl)-1H-pyrazol-4-yl]-pyrazin-2-yl}-[1,8]naphthyridine (no. 51); HPLC-MS: 1.57 min, [M+H] 500

2-(5-Chloro-2-fluoro-phenyl)-4-{5-[1-(1-methyl-pyrrolidin-3-yl)-1H-pyrazol-4-yl]-pyridin-3-yl}-[1,8]naphthyridine (no. 58); HPLC-MS: 1.51 min, [M+H] 485

2-(2-Fluoro-phenyl)-4-{5-[1-(1-methyl-pyrrolidin-3-yl)-1H-pyrazol-4-yl]-pyridin-3-yl}-[1,8]naphthyridine (no. 59); HPLC-MS: 1.39 min, [M+H] 451

2-(2,5-Difluoro-phenyl)-4-{6-[1-(1-methyl-piperidin-4-yl)-1H-pyrazol-4-yl]-pyrazin-2-yl}-[1,8]naphthyridine (no. 62); HPLC-MS: 1.52 min, [M+H] 484

4-{5-[1-(1-Methyl-piperidin-4-yl)-1H-pyrazol-4-yl]-pyridin-3-yl}-2-phenyl-[1,8]naphthyridine (no. 63); HPLC-MS: 1.47 min, [M+H] 447

2-(2-Fluoro-phenyl)-4-{5-[1-((R)-1-methyl-pyrrolidin-3-yl)-1H-pyrazol-4-yl]-pyridin-3-yl}-[1,8]naphthyridine (no. 64); HPLC-MS: 1.36 min, [M+H] 451

2-(5-Chloro-2-fluoro-phenyl)-4-{5-[1-((R)-1-methyl-pyrrolidin-3-yl)-1H-pyrazol-4-yl]-pyridin-3-yl}-[1,8]naphthyridine (no. 65); HPLC-MS: 1.55 min, [M+H] 485

2-(5-Chloro-2-fluoro-phenyl)-4-{5-[1-((S)-1-methyl-pyrrolidin-3-yl)-1H-pyrazol-4-yl]-pyridin-3-yl}-[1,8]naphthyridine (no. 68); HPLC-MS: 1.59 min, [M+H] 485

2-(2-Fluoro-phenyl)-4-{5-[1-((S)-1-methyl-pyrrolidin-3-yl)-1H-pyrazol-4-yl]-pyridin-3-yl}-[1,8]naphthyridine (no. 69); HPLC-MS: 1.36 min, [M+H] 451

EXAMPLE 15

Synthesis of [3-(4-{5-[2-(5-chloro-2-fluoro-phenyl)-[1,8]naphthyridin-4-yl]-pyridin-3-yl}-pyrazol-1-yl)-propyl]-dimethyl-amine (no. 27)

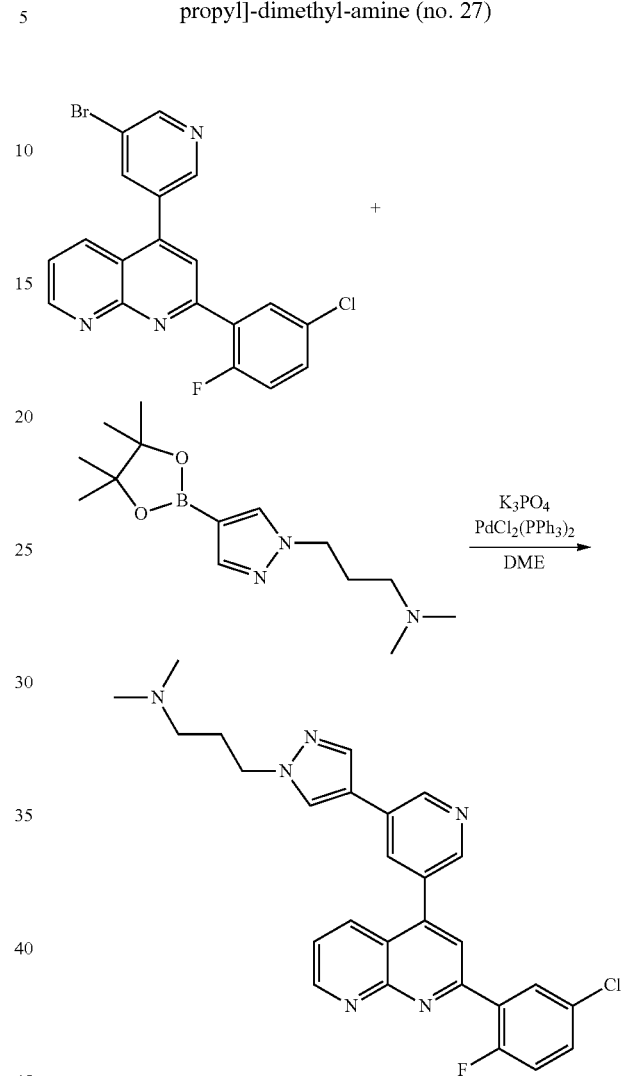

A slurry of 500 mg (1.21 mmol) 4-(5-bromo-pyridin-3-yl)-2-(5-chloro-2-fluoro-phenyl)-[1,8]naphthyridine, 370 mg (1.33 mmol) dimethyl-{3-[4-(4,4,5,5-tetramethyl-[1,3,2]dioxaborolan-2-yl)-pyrazol-1-yl]-propyl}-amine and 512 mg (2.41 mmol) tri-potassium-phosphate-trihydrate in 5 ml 1,2-dimethoxyethane is heated to 85° C. under nitrogen. Then 42.3 mg (0.06 mmol) bis-(triphenylphosphine)-palladium (II)-chloride and 17 μl triethylamine were added. The reaction mixture was stirred for 2 hours at 85° C. The reaction mixture was partitioned between water and dichloromethane. The organic phase was dried over sodium sulfate and evaporated. The residue was crystallized from acetonitrile yielding [3-(4-{5-[2-(5-chloro-2-fluoro-phenyl)-[1,8]naphthyridin-4-yl]-pyridin-3-yl}-pyrazol-1-yl)-propyl]-dimethyl-amine as light grey crystals; HPLC-MS: 1.64 min, [M+H] 487.

$^1$H NMR (500 MHz, DMSO) δ=9.21 (dd, J=4.1, 1.8, 1H), 9.05 (d, J=2.1, 1H), 8.63 (d, J=2.0, 1H), 8.41 (s, 1H), 8.37 (dd, J=8.4, 1.8, 1H), 8.28 (t, J=2.1, 1H), 8.18 (dd, J=6.6, 2.8, 1H), 8.10 (m, 2H), 7.72 (dd, J=8.4, 4.2, 1H), 7.68 (ddd, J=8.7, 4.0, 3.0, 1H), 7.52 (dd, J=10.6, 8.9, 1H), 4.16 (t, J=7.0, 2H), 2.22 (t, J=6.7, 2H), 2.14 (s, 6H), 1.94 (p, J=7.0, 2H).

The following compounds were prepared similarly:

2-(5-Chloro-2-fluoro-phenyl)-4-{5-[1-(2-morpholin-4-yl-ethyl)-1H-pyrazol-4-yl]-pyridin-3-yl}-[1,8]naphthyridine (no. 28); HPLC-MS: 1.66 min, [M+H] 515,

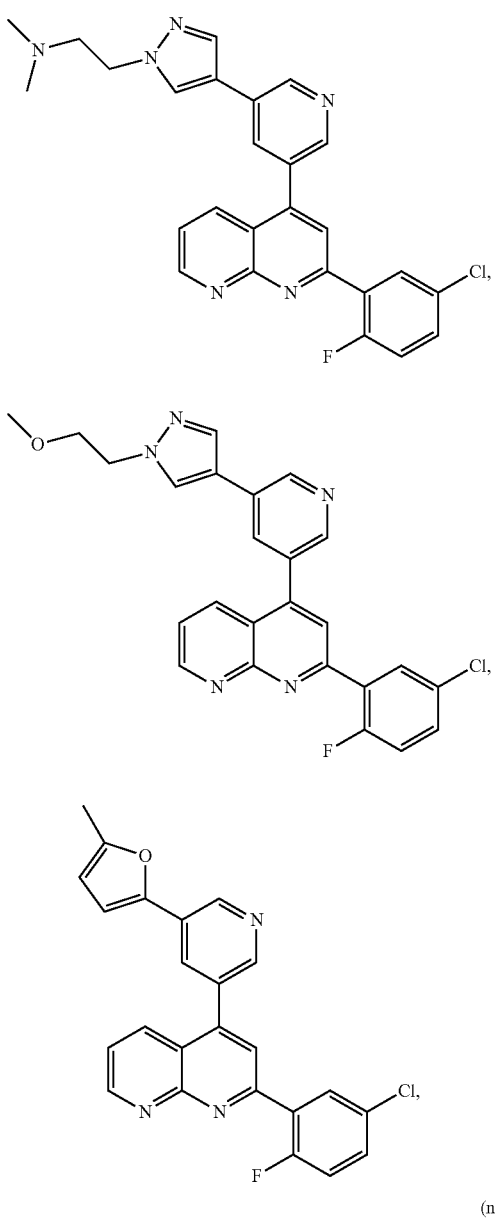

(no. 34)

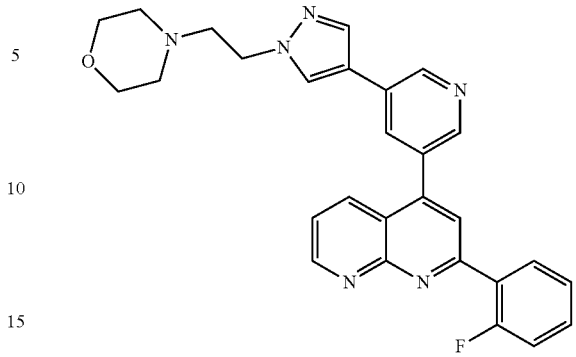

(no. 41)

2-(2,5-Difluoro-phenyl)-4-{5-[1-(3-morpholin-4-yl-propyl)-1H-pyrazol-4-yl]-pyridin-3-yl}-[1,8]naphthyridine (no. 48); HPLC-MS: 1.51 min, [M+H] 513

2-(2-Fluoro-phenyl)-4-[5-(1-methyl-1H-pyrazol-3-yl)-pyridin-3-yl]-[1,8]naphthyridine (no. 66); HPLC-MS: 2.33 min, [M+H] 382

2-(2-Fluoro-phenyl)-4-[5-(2-methyl-2H-pyrazol-3-yl)-pyridin-3-yl]-[1,8]naphthyridine (no. 67); HPLC-MS: 2.33 min, [M+H] 382

4-{5-[2-(2-Fluoro-phenyl)-[1,8]naphthyridin-4-yl]-pyridin-3-yl}-benzenesulfonamide (no. 78); HPLC-MS: 1.89 min, [M+H] 457

2-(2-Fluoro-phenyl)-4-(5-{1-[3-(4-methyl-piperazin-1-yl)-propyl]-1H-pyrazol-4-yl}-pyridin-3-yl)-[1,8]naphthyridine (no. 86); HPLC-MS: 1.47 min, [M+H] 508

2-(2-Fluoro-phenyl)-4-{5-[1-(3-morpholin-4-yl-propyl)-1H-pyrazol-4-yl]-pyridin-3-yl}-[1,8]naphthyridine (no. 87); HPLC-MS: 1.44 min, [M+H] 496

2-(2,5-Difluoro-phenyl)-4-{5-[1-(3-morpholin-4-yl-propyl)-1H-pyrazol-4-yl]-pyridin-3-yl}-[1,8]naphthyridine (no. 90); HPLC-MS: 1.46 min, [M+H] 514

2-(5-Chloro-2-fluoro-phenyl)-4-{5-[1-(2-morpholin-4-yl-ethyl)-1H-pyrazol-4-yl]-pyridin-3-yl}-[1,8]naphthyridine (no. 96); HPLC-MS: 1.66 min, [M+H] 516

[3-(4-{5-[2-(5-Chloro-2-fluoro-phenyl)-[1,8]naphthyridin-4-yl]-pyridin-3-yl}-pyrazol-1-yl)-propyl]-dimethyl-amine (no. 97); HPLC-MS: 1.64 min, [M+H] 488

EXAMPLE 16

Synthesis of 5-[2-(5-chloro-2-fluoro-phenyl)-[1,8]naphthyridin-4-yl]-3-(1-methyl-1H-pyrazol-4-yl)-pyridin-2-ylamine (no. 31)

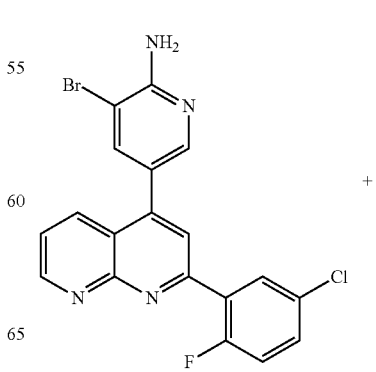

+

-continued

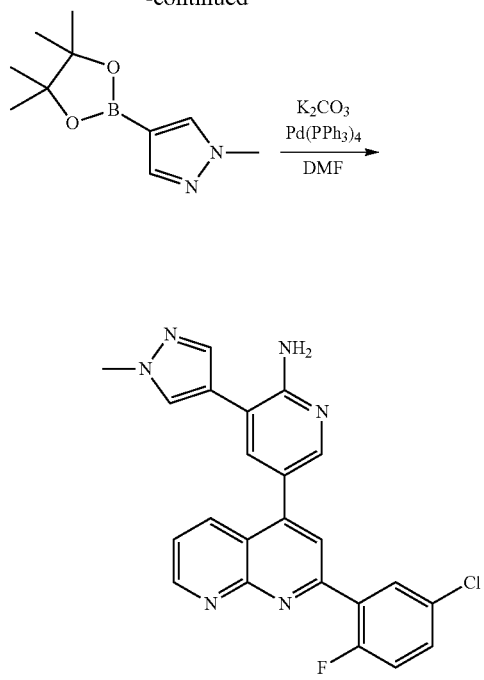

A slurry of 297 mg (0.65 mmol) 3-bromo-5-[2-(5-chloro-2-fluoro-phenyl)-[1,8]naphthyridin-4-yl]-pyridin-2-ylamine, 270 mg (1.30 mmol) 1-methyl-1H-pyrazole-4-boronic acid pinacol ester and 270 mg (1.95 mmol) potassium carbonate in 3 ml DMF was flushed with nitrogen and then 75 mg (0.07 mmol) tetrakis(triphenylphosphine)-palladium were added. This mixture was heated for 30 minutes at a temperature of 130° C. in the microwave. Water was added to the reaction mixture and the resulting precipitate was filtered off and washed with water. The residue was chromatographed on a silica gel column with dichloromethane/methanol as eluent yielding 5-[2-(5-chloro-2-fluoro-phenyl)-[1,8]naphthyridin-4-yl]-3-(1-methyl-1H-pyrazol-4-yl)-pyridin-2-ylamine as yellow crystals; HPLC-MS: 1.57 min, [M+H] 431.

The following compound was prepared similarly:

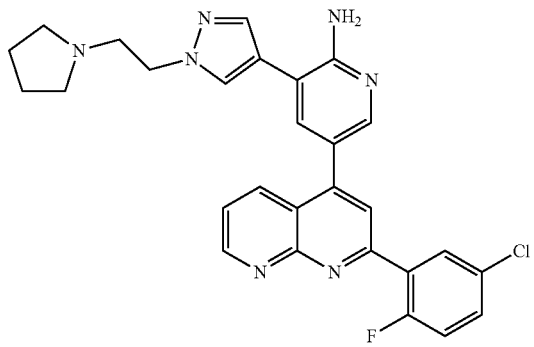 [SMILES: Nc1ncc(-c2cc(-c3cc(Cl)ccc3F)nc3ncccc23)cc1-c1cnn(CCN2CCCC2)c1]

EXAMPLE 17

Synthesis of 2-(4-{5-[2-(2-fluoro-phenyl)-[1,8]naphthyridin-4-yl]-pyridin-3-yl}-pyrazol-1-yl)-ethanol (no. 40)

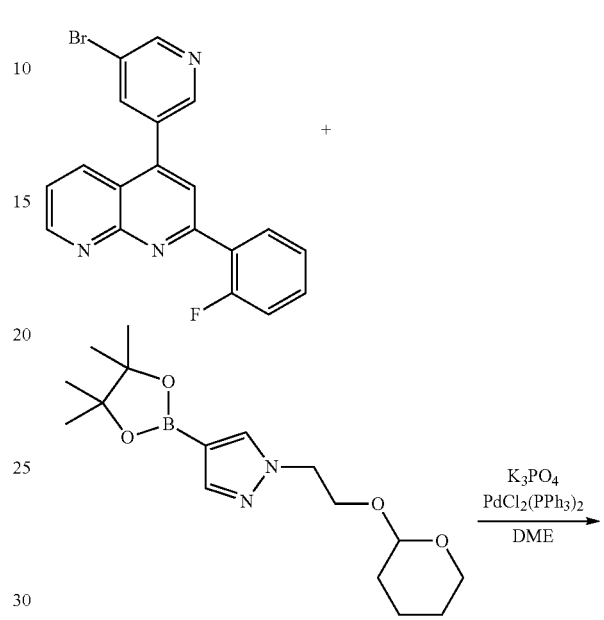

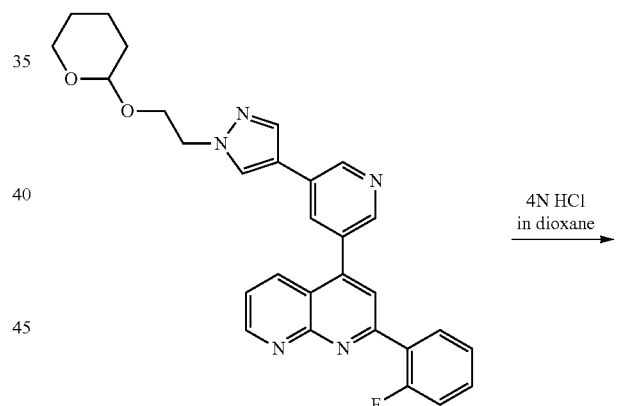

A slurry of 380 mg (1.00 mmol) 4-(5-bromo-pyridin-3-yl)-2-(2-fluoro-phenyl)-[1,8]naphthyridine, 354 mg (1.10 mmol)

1-[2-(tetrahydro-pyran-2-yloxy)-ethyl]-4-(4,4,5,5-tetramethyl-[1,3,2]dioxaborolan-2-yl)-1H-pyrazole (prepared from 4-(4,4,5,5-tetramethyl-[1,3,2]dioxaborolan-2-yl)-1H-pyrazole and 2-(2-bromo-ethoxy)-tetrahydro-pyran (in analogy to example 10) and 425 mg (2.00 mmol) tri-potassium-phosphate-trihydrate in 3 ml 1,2-dimethoxyethane was heated to 85° C. under nitrogen. Then 35.1 mg (0.05 mmol) bis-(triphenylphosphine)-palladium(II)-chloride and 14 µl trimethylamine were added. The reaction mixture was stirred for 16 hours at 85° C. The reaction mixture was cooled to room temperature and partitioned between water and dichloromethane. The organic phase was dried over sodium sulfate and evaporated. The residue was chromatographed on a silica gel column with dichloromethane/methanol as eluent yielding 2-(2-fluoro-phenyl)-4-(5-{1-[2-(tetrahydro-pyran-2-yloxy)-ethyl]-1H-pyrazol-4-yl}-pyridin-3-yl)-[1,8]naphthyridine as yellow solid; HPLC-MS: 2.13 min, [M+H] 496.

A solution of 219 mg (0.44 mmol) 2-(2-fluoro-phenyl)-4-(5-{1-[2-(tetrahydro-pyran-2-yloxy)-ethyl]-1H-pyrazol-4-yl}-pyridin-3-yl)-[1,8]naphthyridine in 7 ml dichloromethane was treated with 0.52 ml of a 4 N solution of hydrochloric acid in dioxane. The reaction mixture was stirred for 60 minutes and the precipitate that had formed was filtered off. The residue was dissolved in water and treated with saturated sodium carbonate solution. The resulting precipitate was filtered off, washed with water and dried under vacuum yielding 2-(4-{5-[2-(2-fluoro-phenyl)-[1,8]naphthyridin-4-yl]-pyridin-3-yl}-pyrazol-1-yl)-ethanol as colorless crystals; HPLC-MS: 1.70 min, [M+H] 412.

¹H NMR (500 MHz, DMSO) δ=9.21 (dd, J=4.0, 1.8, 1H), 9.05 (d, J=2.1, 1H), 8.63 (d, J=2.0, 1H), 8.37 (m, 2H), 8.28 (t, J=2.0, 1H), 8.18 (dd, J=6.6, 2.7, 1H), 8.10 (m, 2H), 7.72 (dd, J=8.4, 4.2, 1H), 7.68 (m, 1H), 7.51 (dd, J=10.5, 8.9, 1H), 4.91 (t, J=5.3, 1H), 4.18 (t, J=5.6, 2H), 3.77 (q, J=5.5, 2H).

The following compounds were prepared similarly:

2-(4-{5-[2-(2-Fluoro-5-trifluoromethyl-phenyl)-[1,8]naphthyridin-4-yl]-pyridin-3-yl}-pyrazol-1-yl)-ethanol (no. 37); HPLC-MS: 1.97 min, [M+H] 480

2-(4-{5-[2-(5-Chloro-2-fluoro-phenyl)-[1,8]naphthyridin-4-yl]-pyridin-3-yl}-pyrazol-1-yl)-ethanol (no. 39); HPLC-MS: 1.88 min, [M+H] 446

¹H NMR (500 MHz, DMSO) δ=9.21 (dd, J=4.0, 1.8, 1H), 9.05 (d, J=2.1, 1H), 8.63 (d, J=2.0, 1H), 8.37 (m, 2H), 8.28 (t, J=2.0, 1H), 8.18 (dd, J=6.6, 2.7, 1H), 8.10 (m, 2H), 7.72 (dd, J=8.4, 4.2, 1H), 7.68 (m, 1H), 7.51 (dd, J=10.5, 8.9, 1H), 4.91 (t, J=5.3, 1H), 4.18 (t, J=5.6, 2H), 3.77 (q, J=5.5, 2H)

E)-4-(4-{5-[2-(2-Fluoro-phenyl)-[1,8]naphthyridin-4-yl]-pyridin-3-yl}-pyrazol-1-yl)-but-2-en-1-ol (no. 84); HPLC-MS: 1.79 min, [M+H] 439

3-(4-{5-[2-(2,5-Difluoro-phenyl)-[1,8]naphthyridin-4-yl]-pyridin-3-yl}-pyrazol-1-yl)-propane-1,2-diol (no. 88); HPLC-MS: 1.70 min, [M+H] 461

3-(4-{5-[2-(2,5-Difluoro-phenyl)-[1,8]naphthyridin-4-yl]-pyridin-3-yl}-pyrazol-1-yl)-propan-1-ol (no. 89); HPLC-MS: 1.82 min, [M+H] 445

2-(4-{5-[2-(5-Chloro-2-fluoro-phenyl)-[1,8]naphthyridin-4-yl]-pyridin-3-yl}-pyrazol-1-yl)-ethanol (no. 91); HPLC-MS: 1.88 min, [M+H] 446

EXAMPLE 18

Synthesis of [2-(4-{5-[2-(5-Chloro-2-fluoro-phenyl)-[1,8]naphthyridin-4-yl]-pyridin-3-yl}-pyrazol-1-yl)-ethyl]-methyl-amine

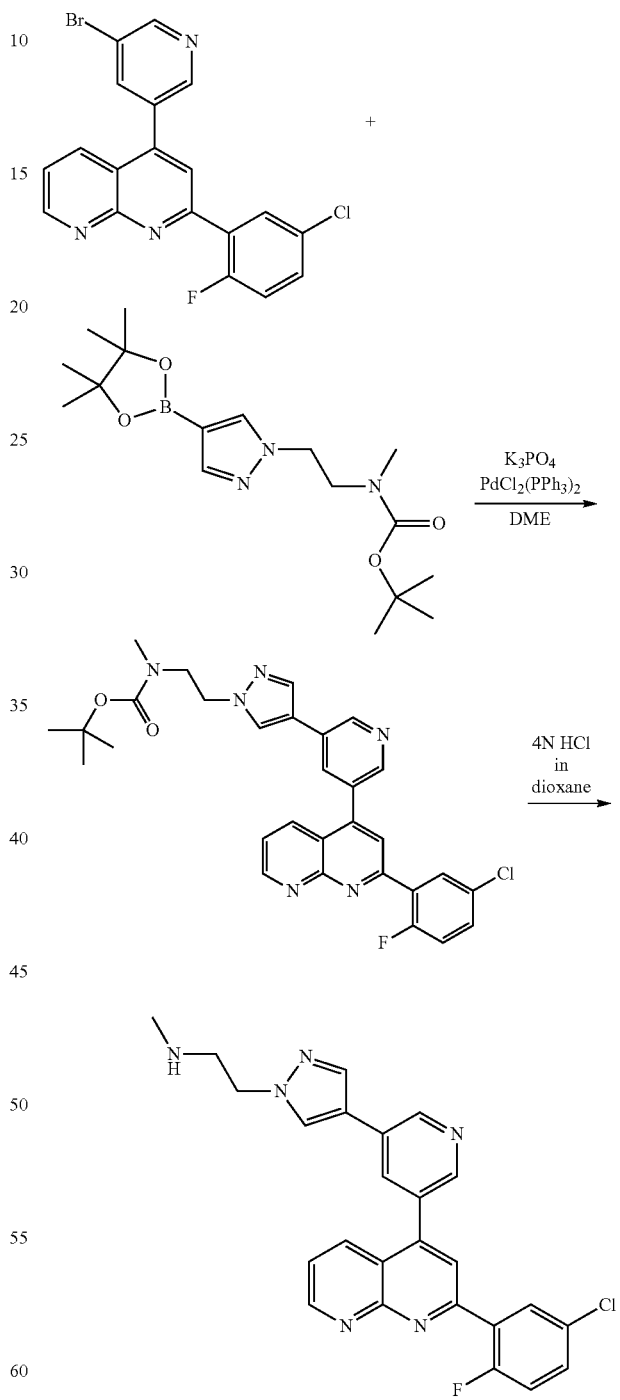

The first reaction step was carried out as in example 14, the second reaction step as in example 8 step 3.

EXAMPLE 19

Synthesis of 2-(5-chloro-2-fluoro-phenyl)-4-{5-[1-(2-morpholin-4-yl-ethyl)-1H-[1,2,3]triazol-4-yl]-pyridin-3-yl}-[1,8]naphthyridine (no. 42)

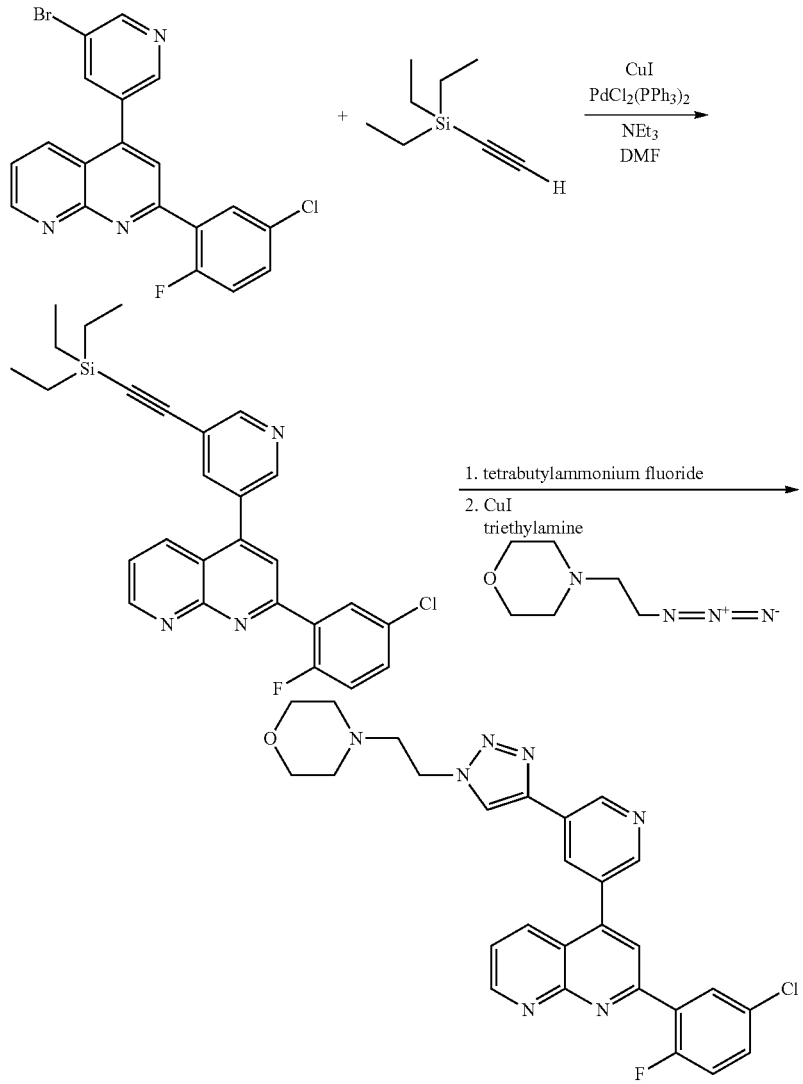

A solution of 415 mg (1.00 mmol) 4-(5-bromo-pyridin-3-yl)-2-(5-chloro-2-fluoro-phenyl)-[1,8]naphthyridine in 5 ml DMF was flushed with nitrogen and subsequently treated with 70 mg (0.10 mmol) bis-(triphenylphosphine)-palladium (II)-chloride, 6.0 mg (0.03 mmol) cuprous iodide, 0.42 ml (3.0 mmol) triethylamine and 450 µl (2.5 mmol) triethylsilyl acetylene. The resulting slurry was stirred at 120° C. for two hours. The reaction mixture was cooled to room temperature and partitioned between ethylacetate and brine. The combined organic phases were dried with sodium sulfate and evaporated yielding 2-(5-chloro-2-fluoro-phenyl)-4-(5-triethylsilanylethynyl-pyridin-3-yl)-[1,8]naphthyridine as brown solid; HPLC-MS: 2.73 min, [M+H] 474.

A solution of 471 mg (0.994 mmol) 2-(5-chloro-2-fluoro-phenyl)-4-(5-triethylsilanylethynyl-pyridin-3-yl)-[1,8]naphthyridine in 6 ml THF was treated with 1.19 ml of a 1 M solution of tetra-n-butylammonium fluoride in THF and stirred for 1 hour at room temperature. Then 276 µl (1.99 mmol) triethylamine, 190 mg (1.21 mmol) 4-(2-azido-ethyl)-morpholine and 9.5 mg (0.05 mmol) cuprous iodide were added. The reaction mixture was stirred for 66 hours at 70° C. The reaction mixture was cooled to room temperature and partitioned between ethylacetate and brine. The organic phase was dried over sodium sulfate and evaporated. The residue was chromatographed on a silica gel column with dichloromethane/methanol as eluent yielding 2-(5-chloro-2-fluoro-phenyl)-4-{5-[1-(2-morpholin-4-yl-ethyl)-1H-[1,2,3]triazol-4-yl]pyridin-3-yl}-[1,8]naphthyridine as colourless solid; HPLC-MS: 1.50 min, [M+H] 516.

$^1$H NMR (500 MHz, DMSO) δ=9.28 (s, 1H), 9.23 (s, 1H), 8.80 (m, 2H), 8.49 (s, 1H), 8.39 (d, J=8.1, 1H), 8.19 (d, J=4.0, 1H), 8.13 (s, 1H), 7.72 (dd, J=8.2, 4.0, 1H), 7.68 (m, 1H), 7.51 (t, J=9.7, 1H), 4.59 (t, J=5.9, 2H), 3.55 (m, 4H), 2.81 (t, J=5.8, 2H), 2.45 (m, 4H).

The following compounds were synthesized analogously:
2-(2-Fluoro-phenyl)-4-{5-[1-(1-methyl-piperidin-4-yl)-1H-[1,2,3]triazol-4-yl]-pyridin-3-yl}-[1,8]naphthyridine (no. 55); HPLC-MS: 1.36 min, [M+H] 466

2-(5-Chloro-2-fluoro-phenyl)-4-{5-[1-(1-methyl-piperidin-4-yl)-1H-[1,2,3]triazol-4-yl]-pyridin-3-yl}-[1,8]naphthyridine (no. 57); HPLC-MS: 1.47 min, [M+H] 500

EXAMPLE 20

Synthesis of 2-(5-Chloro-2-fluoro-phenyl)-4-(6'-piperazin-1-yl-[3,3']bipyridinyl-5-yl)-[1,8]naphthyridine (no. 32) and 2-(5-chloro-2-fluoro-phenyl)-4-[6'-(4-methyl-piperazin-1-yl)-[3,3']bipyridinyl-5-yl]-[1,8]naphthyridine (no. 36)

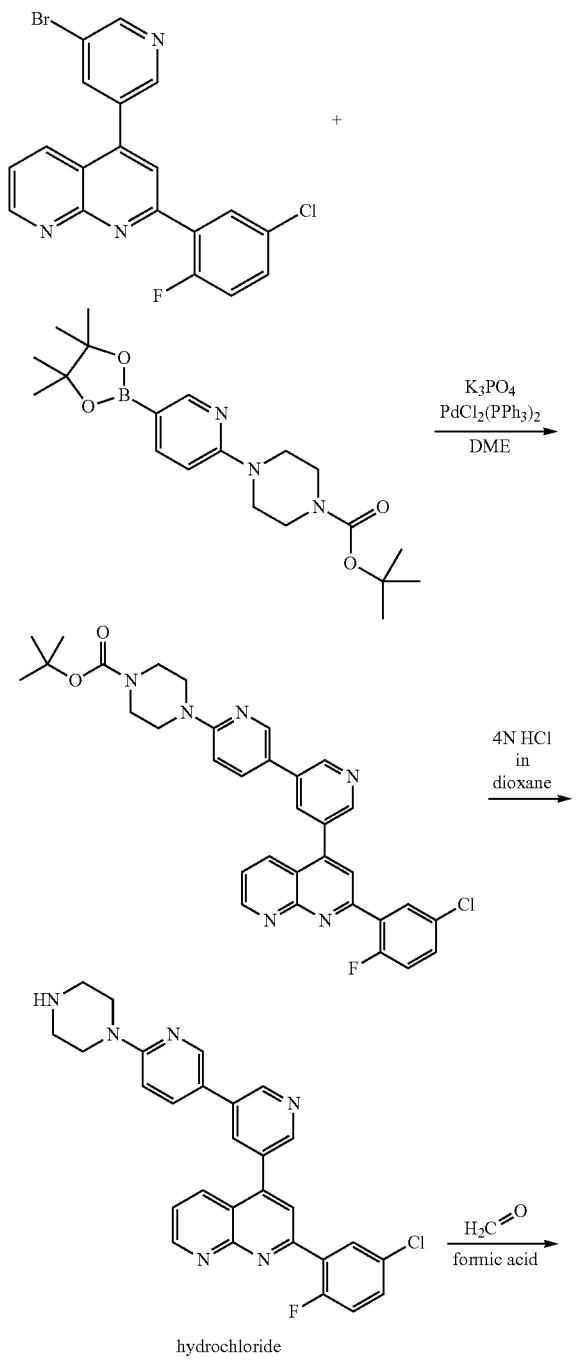

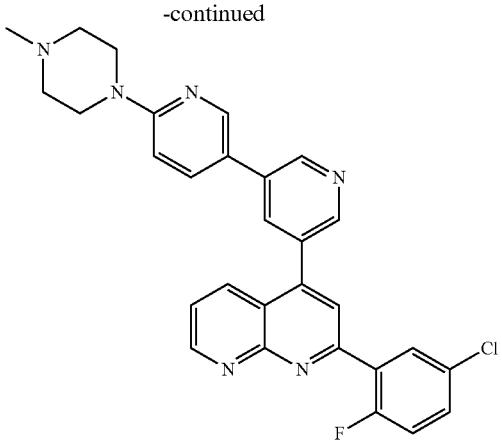

A slurry of 500 mg (1.21 mmol) 4-(5-bromo-pyridin-3-yl)-2-(5-chloro-2-fluoro-phenyl)-[1,8]naphthyridine, 516 mg (1.33 mmol) 4-[5-(4,4,5,5-tetramethyl-[1,3,2]dioxaborolan-2-yl)-pyridin-2-yl]-piperazine-1-carboxylic acid tert-butyl ester and 512 g (14.1 mmol) tri-potassium-phosphate-trihydrate in 30 ml 1,2-dimethoxyethane was heated to 80° C. under nitrogen. Then 85 mg (0.12 mmol) bis-(triphenylphosphine)-palladium(II)-chloride and 16 µl triethylamine were added. The reaction mixture was stirred for 5 hours at 80° C. The reaction mixture was partitioned between water and dichloromethane. The organic phase was dried over sodium sulfate and evaporated. The residue is chromatographed on a silica gel column with ethylacetate/methanol as eluent yielding 4-{5'-[2-(5-Chloro-2-fluoro-phenyl)-[1,8]naphthyridin-4-yl]-[3,3']bipyridinyl-6-yl}-piperazine-1-carboxylic acid tert-butyl ester as yellow oil; HPLC-MS: 2.69 min, [M+H] 597.

A solution of 438 mg (0.734 mmol) 4-{5'-[2-(5-Chloro-2-fluoro-phenyl)-[1,8]naphthyridin-4-yl]-[3,3']bipyridinyl-6-yl}-piperazine-1-carboxylic acid tert-butyl ester in 5 ml dioxane was treated with 6 ml of a 4 N solution of hydrochlorid acid in dioxane. The mixture was stirred for 20 minutes at room temperature. The resulting precipitate was filtered off, washed with dioxane and dried under vacuum yielding 2-(5-chloro-2-fluoro-phenyl)-4-(6'-piperazin-1-yl-[3,3']bipyridinyl-5-yl)-[1,8]naphthyridine hydrochloride as light yellow solid; HPLC-MS: 1.66 min, [M+H] 497.

A solution of 180 mg (0.34 mmol) 2-(5-chloro-2-fluoro-phenyl)-4-(6'-piperazin-1-yl-[3,3']bipyridinyl-5-yl)-[1,8]naphthyridine hydrochloride in 1.5 ml formic acid was treated with 80 µl (1.01 mmol) 35% aqueous formaldehyde solution and heated to 80° C. The reaction mixture was stirred at this temperature for 2 hours. The volume of the reaction mixture was reduced under vacuum and the residue made strongly alkaline with 2 N NaOH. The resulting precipitate was filtered off, washed with water and dried yielding 2-(5-chloro-2-fluoro-phenyl)-4-[6'-(4-methyl-piperazin-1-yl)-[3,3']bipyridinyl-5-yl]-[1,8]naphthyridine as gray-green solid; HPLC-MS: 1.55 min, [M+H] 511.

$^1$H NMR (500 MHz, DMSO) δ=9.21 (d, J=2.3, 1H), 9.08 (d, J=1.9, 1H), 8.75 (d, J=1.2, 1H), 8.64 (d, J=2.3, 1H), 8.43 (m, 1H), 8.34 (s, 1H), 8.17 (m, 2H), 8.05 (dd, J=8.9, 2.5, 1H), 7.71 (dd, J=8.4, 4.1, 1H), 7.67 (m, 1H), 7.51 (m, 1H), 6.97 (d, J=9.0, 1H), 3.59 (s, 4H), 2.45 (s, 4H), 2.25 (s, 3H).

The following compounds can be prepared similarly:
2-(5-Chloro-2-fluoro-phenyl)-4-[5-(4-piperazin-1-yl-phenyl)-pyridin-3-yl]-[1,8]naphthyridine (no. 33)

2-(5-Chloro-2-fluoro-phenyl)-4-{5-[4-(4-methyl-piperazin-1-yl)-phenyl]-pyridin-3-yl}-[1,8]naphthyridine (no. 38)

4-[3,4']Bipyridinyl-5-yl-2-(5-chloro-2-fluoro-phenyl)-[1,8]naphthyridine

4-[3,3']Bipyridinyl-5-yl-2-(5-chloro-2-fluoro-phenyl)-[1,8]naphthyridine

4-[2,3']Bipyridinyl-5-yl-2-(5-chloro-2-fluoro-phenyl)-[1,8]naphthyridine 2-(5-Chloro-2-fluoro-phenyl)-4-[6'-(4-methyl-piperazin-1-yl)-[3,3']bipyridinyl-5-yl]-[1,8]naphthyridine (no. 32); HPLC-MS: 1.66 min, [M+H] 497

2-(5-Chloro-2-fluoro-phenyl)-4-{5-[4-(4-methyl-piperazin-1-yl)-phenyl]-pyridin-3-yl}-[1,8]naphthyridine (no. 92); HPLC-MS: 1.56 min, [M+H] 510

2-(5-Chloro-2-fluoro-phenyl)-4-[6'-(4-methyl-piperazin-1-yl)-[3,3']bipyridinyl-5-yl]-[1,8]naphthyridine (no. 93); HPLC-MS: 1.55 min, [M+H] 511

2-(5-Chloro-2-fluoro-phenyl)-4-[5-(4-piperazin-1-yl-phenyl)-pyridin-3-yl]-[1,8]naphthyridine (no. 94); HPLC-MS: 1.62 min, [M+H] 498

2-(5-Chloro-2-fluoro-phenyl)-4-(6'-piperazin-1-yl-[3,3']bipyridinyl-5-yl)-[1,8]naphthyridine (no. 95); HPLC-MS: 1.66 min, [M+H] 499

EXAMPLE 21

Synthesis of 2-(5-chloro-2-fluoro-phenyl)-4-{5-[1-(2-piperazin-1-yl-ethyl)-1H-pyrazol-4-yl]-pyridin-3-yl}-[1,8]naphthyridine and 2-(5-chloro-2-fluoro-phenyl)-4-(5-{1-[2-(4-methyl-piperazin-1-yl)-ethyl]-1H-pyrazol-4-yl}-pyridin-3-yl)-[1,8]naphthyridine

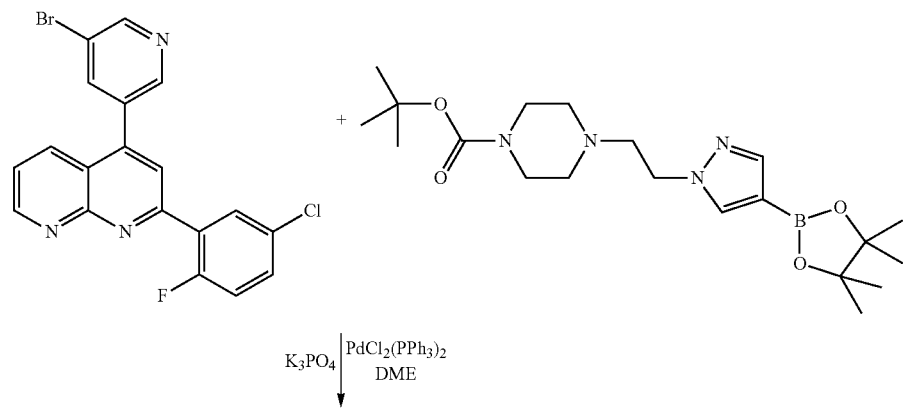

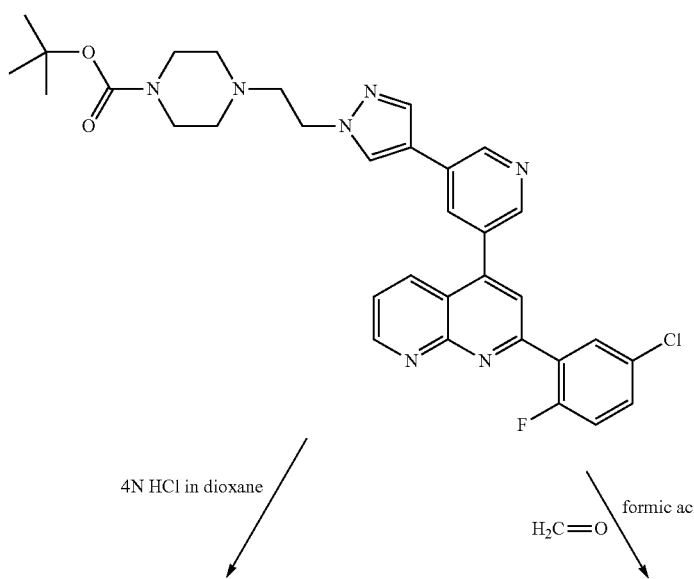

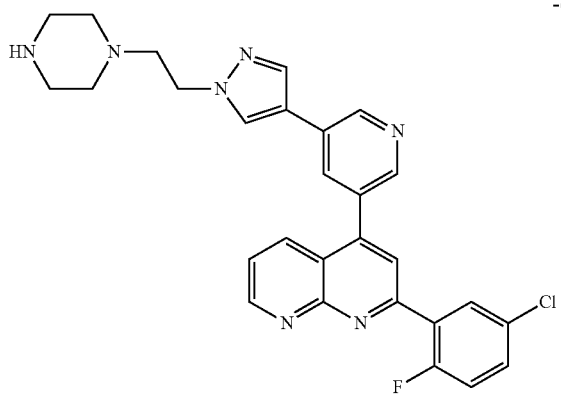

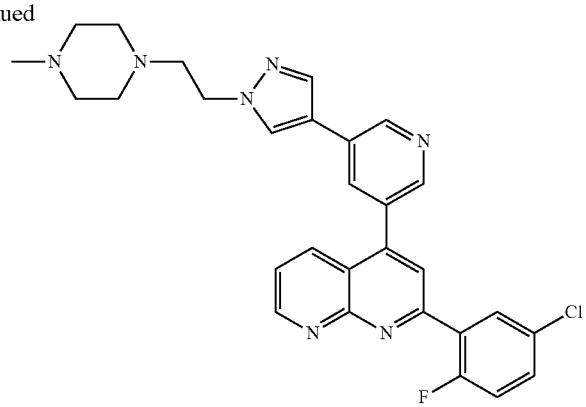

The first reaction step was carried out as in example 14, the reaction with 4 N HCl in dioxane as in example 8 step 3, the reaction with formaldehyde/formic acid as in example 13.

EXAMPLE 22

2-(5-Chloro-2-fluoro-phenyl)-4-(2-phenyl-pyridin-4-yl)-[1,8]naphthyridine (no. 20)

150 mg boronic acid from example 4, 120 mg 4-Bromo-2-phenylpyridine, 313 mg sodium carbonate and 57 mg tetrakistriphenylphosphine palladium(0) were suspended in 20 ml dioxan, flushed with nitrogen and heated to 90 C. After addition of 2 ml water heating to 90° C. was continued. Standard work-up after 3 hrs was performed by evaporation, extraction with ethylacetate from water, drying with sodiumsulfate, filtration and precipitation with ether yielded 116 mg of yellowish crude product, which was purified by HPLC on a C18 reversed phase column with an acetonitril gradient in water to give 70 mg of 2-(5-Chloro-2-fluoro-phenyl)-4-(5-phenyl-pyridin-3-yl)-[1,8]naphthyridine with correct mass found by LC MS: M+H+ 412 at $R_t$~2.55 min

EXAMPLE 23

Synthesis of 2-(5-Chloro-2-fluoro-phenyl)-4-(5-phenyl-pyridin-3-yl)-[1,8]naphthyridine (no. 4) M 411.87

150 mg 4-chloronaphthyridine from example 1, 184 mg 5-phenyl-3-pyridyl boronic acid, 326 mg sodium carbonate and 60 mg tetrakistriphenylphosphine palladium(0) were dissolved with 15 ml dioxan, flushed with nitrogen, and heated to 90° C. After addition of 2 ml water, heating continued at 90° C. for 90 minutes to give a dark turbid solution. Work-up as in example 20 yielded after precipitation with ether 141 mg product with correct LC mass: M+H+ 412 and $R_t$~2.53 min.

EXAMPLE 24

Synthesis of 2-(5-Chloro-2-fluoro-phenyl)-4-isoquinolin-4-yl-[1,8]naphthyridine (no. 2) M 385.83

426 mg 4-chloro naphthyridine from example 1, 682 mg 4-isoquinoline boronic acid pinacole ester, 945 mg sodium carbonate were dissolved with 30 ml dioxan and 3 ml water, flushed with nitrogen, and 172 mg tetrakistriphenylphosphine palladium(0) were added. After 105 min reflux workup as in example 20 yielded a brownish oil, which was crystallized with ether to give 436 mg of product with correct LC-MS: M+H+ 386 and $R_t$~2.22 min.

EXAMPLE 25

Synthesis of 4-Isoquinolin-4-yl-2-(6-methyl-pyridin-2-yl)-[1,8]naphthyridine (no. 3) M 348.41

190 mg 4-chloro naphthyridine from example 3, 341 mg 4-isoquinoline boronic acid pinacole ester, 473 mg sodium carbonate were dissolved with 20 ml dioxan and 5 ml water, flushed with nitrogen, and 86 mg tetrakistriphenylphosphine palladium(0) were added. After 90 min reflux, workup as in example 20 yielded a grey-brownish oil, which was crystallized with ether to give 176 mg correct product as a brownish powder with correct LC_MS: M+H+ 349 and $R_t$~1.76 min.

EXAMPLE 26

Synthesis of 2-(5-Chloro-2-fluoro-phenyl)-4-isoquinolin-4-yl-quinoline (no. 1) M 384.84

500 mg 4-bromoquinoline from example 27, 682 mg 4-isoquinoline boronic acid pinacol ester, 945 mg sodium carbonate were dissolved with 30 ml dioxan and 3 ml water, flushed with nitrogen, and 172 mg tetrakistriphenylphosphine palladium(0) were added. After 75 min reflux, workup as in example 20 yielded a partially crystalline oil, which was dissolved in dichloromethane, and purified by flash chromatography on 40 g silica in a 20 minutes gradient of ethylacetate in petrolether at 40 ml/min and UV monitoring at 254 nm to give 340 mg correct product as a white solid material with correct LC_MS: M+H+ 385 and $R_t$~2.94 min

EXAMPLE 27

Synthesis of 4-bromo-2-(5-chloro-2-fluoro-phenyl)-quinoline

Commercial 2-aminoacetophenone was acylated with commercial 5-chloro-2-fluoro-benzoylchloride to give the corresponding 4-hydroxy-2-phenyl-quinoline (aka its tautomer 2-(5-chloro-2-fluoro-phenyl)-1H-quinolin-4-one), which was brominated with phosphoroxytribromide in N-methylpyrrolidone to give the product 4-bromo-2-(5-chloro-2-fluoro-phenyl)-quinoline with correct LC-MS: M+H+ 338 and $R_t$~2.50 min.

EXAMPLE 27A

Synthesis of 2-(5-chloro-2-fluoro-phenyl)-4-{6-[1-(2-pyrrolidin-1-yl-ethyl)-1H-pyrazol-4-yl]-pyrazin-2-yl}-[1,8]naphthyridine (no. 43)

A slurry of 115 mg (0.31 mmol) 2-(5-chloro-2-fluoro-phenyl)-4-(6-chloro-pyrazin-2-yl)-[1,8]naphthyridine, 99.3 mg (0.34 mmol) 1-(2-pyrrolidin-1-yl-ethyl)-4-(4,4,5,5-tetramethyl-[1,3,2]dioxaborolan-2-yl)-1H-pyrazole and 165 mg (0.62 mmol) tri-potassium-phosphate-trihydrate in 1 ml 1,2-dimethoxyethane was heated to 80° C. under nitrogen. Then 4.3 mg (0.006 mmol) bis-(triphenylphosphine)-palladium(II)-chloride and a drop of triethylamine were added. The reaction mixture was stirred for 18 hours at 80° C. The reaction mixture was cooled to room temperature and water was added. The resulting precipitate was filtered off, washed with water and chromatographed on a silica gel column with dichloromethane/methanol as eluent to yield 2-(5-chloro-2-fluoro-phenyl)-4-{6-[1-(2-pyrrolidin-1-yl-ethyl)-1H-pyrazol-4-yl]-pyrazin-2-yl}-[1,8]naphthyridine as grey crystals; HPLC-MS: 1.52 min, [M+H] 500.

The following compounds were synthesized analogously:

2-(2-Fluoro-phenyl)-4-[6-(6-piperazin-1-yl-pyridin-3-yl)-pyrazin-2-yl]-[1,8]naphthyridine (no. 81); HPLC-MS: 1.56 min, [M+H] 465

2-(2-Fluoro-phenyl)-4-{6-[6-(4-methyl-piperazin-1-yl)-pyridin-3-yl]-pyrazin-2-yl}-[1,8]naphthyridine (no. 82); HPLC-MS: 1.50 min, [M+H] 479

2-(4-{6-[2-(2-Fluoro-phenyl)-[1,8]naphthyridin-4-yl]-pyrazin-2-yl}-pyrazol-1-yl)-ethanol (no. 83); HPLC-MS: 1.78 min, [M+H] 414

2-(2-Fluoro-phenyl)-4-{6-[1-(1-methyl-piperidin-4-yl)-1H-pyrazol-4-yl]-pyrazin-2-yl}-[1,8]naphthyridine (no. 85); HPLC-MS: 1.51 min, [M+H] 467

EXAMPLE 28

Synthesis of 2-(5-chloro-2-fluoro-phenyl)-4-(5-{1-[1-(2-methoxy-ethyl)-piperidin-4-yl]-1H-pyrazol-4-yl}-pyridin-3-yl)-[1,8]naphthyridine (no. 44); HPLC/MS: 1.65, [M+H] 543

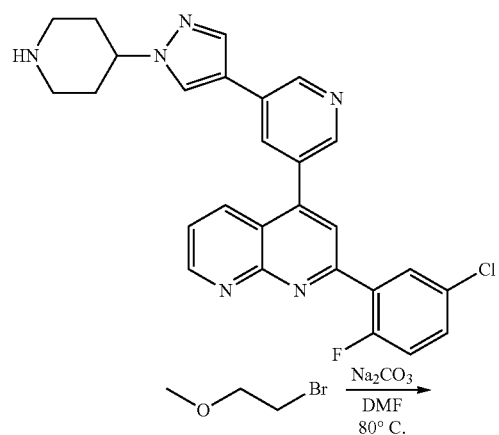

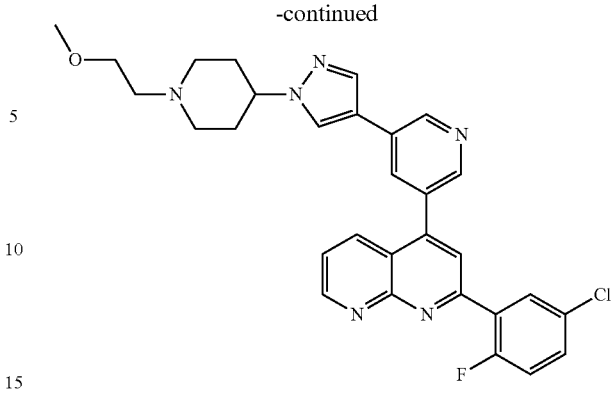

The following compounds were synthesized analogously:

2-[4-(4-{5-[2-(5-Chloro-2-fluoro-phenyl)-[1,8]naphthyridin-4-yl]-pyridin-3-yl}-pyrazol-1-yl)-piperidin-1-yl]-ethanol (no. 45); HPLC/MS: 1.60, [M+H] 529

2-(5-Chloro-2-fluoro-phenyl)-4-(5-{1-(1-ethyl-piperidin-4-yl)-1H-pyrazol-4-yl]-pyridin-3-yl}-[1,8]naphthyridine (no. 46); HPLC/MS: 2.00, [M+H] 513

2-(2,5-Difluoro-phenyl)-4-(5-{1-[1-(2-methoxy-ethyl)-piperidin-4-yl]-1H-pyrazol-4-yl}-pyridin-3-yl)-[1,8]naphthyridine (no. 50); HPLC/MS: 1.61, [M+H] 527

2-(2-Fluoro-phenyl)-4-(5-{1-[1-(2-methoxy-ethyl)-piperidin-4-yl]-1H-pyrazol-4-yl}-pyridin-3-yl)-[1,8]naphthyridine (no. 52); HPLC/MS: 1.55, [M+H] 509

2-[4-(4-{5-[2-(2-Fluoro-phenyl)-[1,8]naphthyridin-4-yl]-pyridin-3-yl}-pyrazol-1-yl)-piperidin-1-yl]-ethanol (no. 53); HPLC/MS: 1.47, [M+H] 495

EXAMPLE 29

Synthesis of 2-(5-chloro-2-fluoro-phenyl)-4-{5-[5-(4-methyl-piperazin-1-yl)-[1,2,4]oxadiazol-3-yl]-pyridin-3-yl}-[1,8]naphthyridine (no. 56); HPLC/MS: 1.55, [M+H] 502

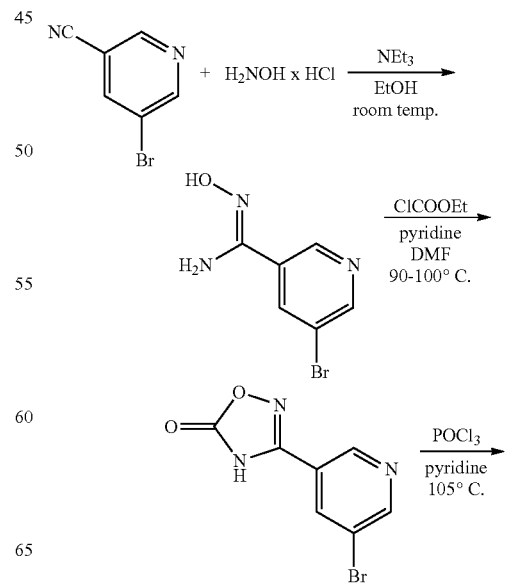

205

-continued

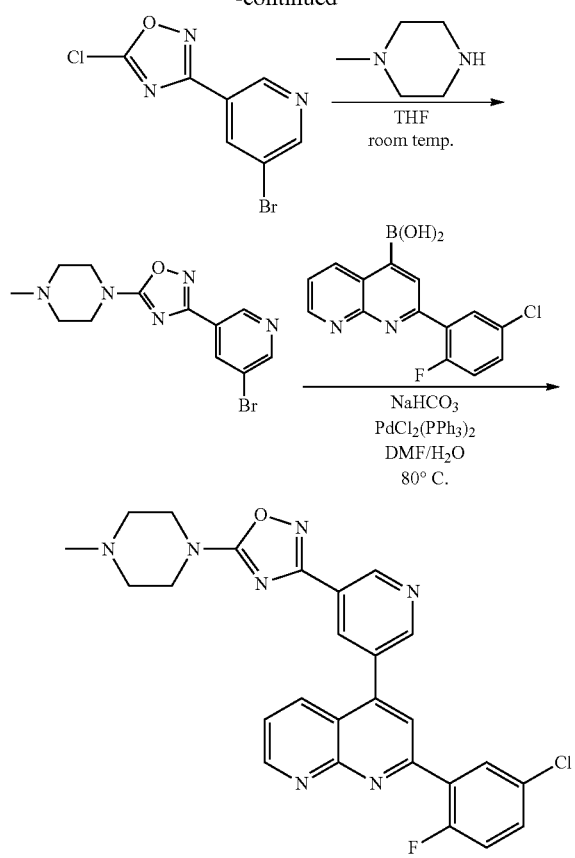

The following compound was synthesized analogously:
2-(2-Fluoro-phenyl)-4-{5-[5-(4-methyl-piperazin-1-yl)-[1,2,4]oxadiazol-3-yl]-pyridin-3-yl}-[1,8]naphthyridine (no. 54); HPLC/MS: 1.43, [M+H] 468

EXAMPLE 30

Synthesis of 2-(2-fluoro-phenyl)-4-{5-[5-(1-methyl-piperidin-4-yl)-[1,2,4]oxadiazol-3-yl]-pyridin-3-yl}-[1,8]naphthyridine (no. 60); HPLC/MS: 1.46, [M+H] 467

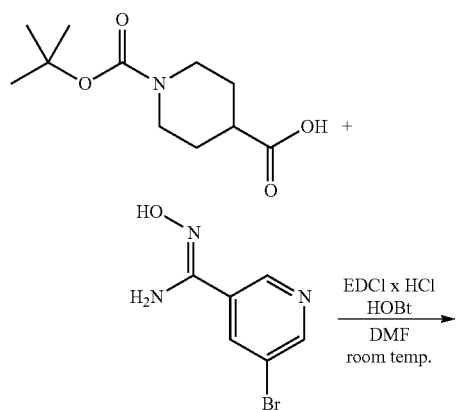

206

-continued

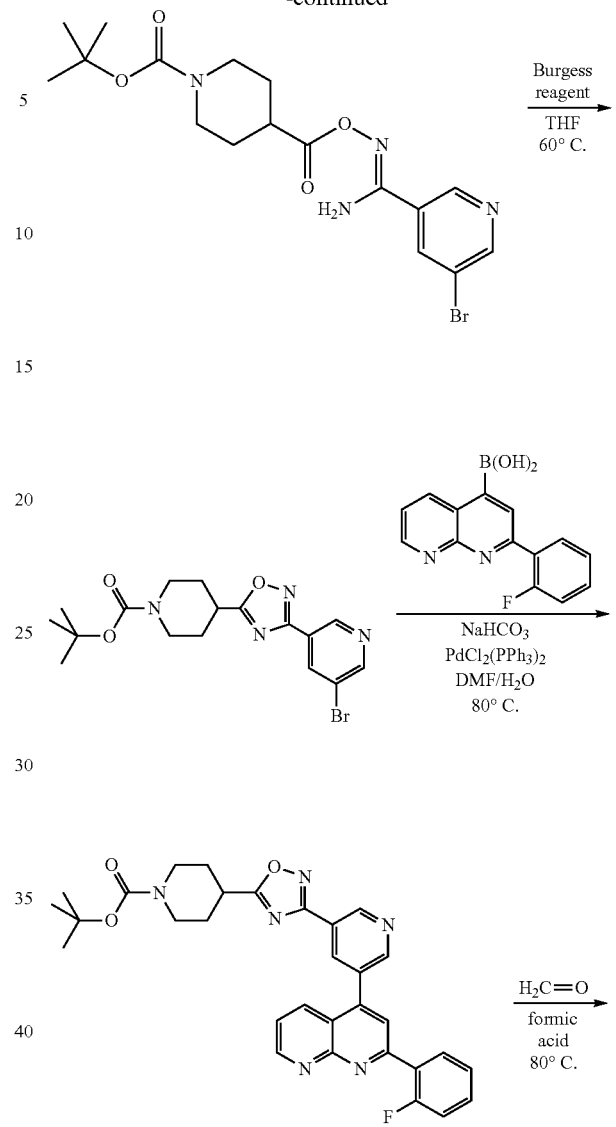

The following compound was synthesized analogously:
2-(5-Chloro-2-fluoro-phenyl)-4-{5-[5-(1-methyl-piperidin-4-yl)-[1,2,4]oxadiazol-3-yl]-pyridin-3-yl}-[1,8]naphthyridine (no. 61); HPLC/MS: 1.56, [M+H] 501

EXAMPLE 31
Synthesis of 2-(2-fluoro-phenyl)-4-{5-[4-(4-methyl-piperazin-1-yl)-pyrimidin-2-yl]-pyridin-3-yl}-[1,8]naphthyridine (no. 70) and 2-(2-fluoro-phenyl)-4-[5-(4-piperazin-1-yl-pyrimidin-2-yl)-pyridin-3-yl]-[1,8]naphthyridine (no. 71); HPLC/MS: 1.52, [M+H] 464
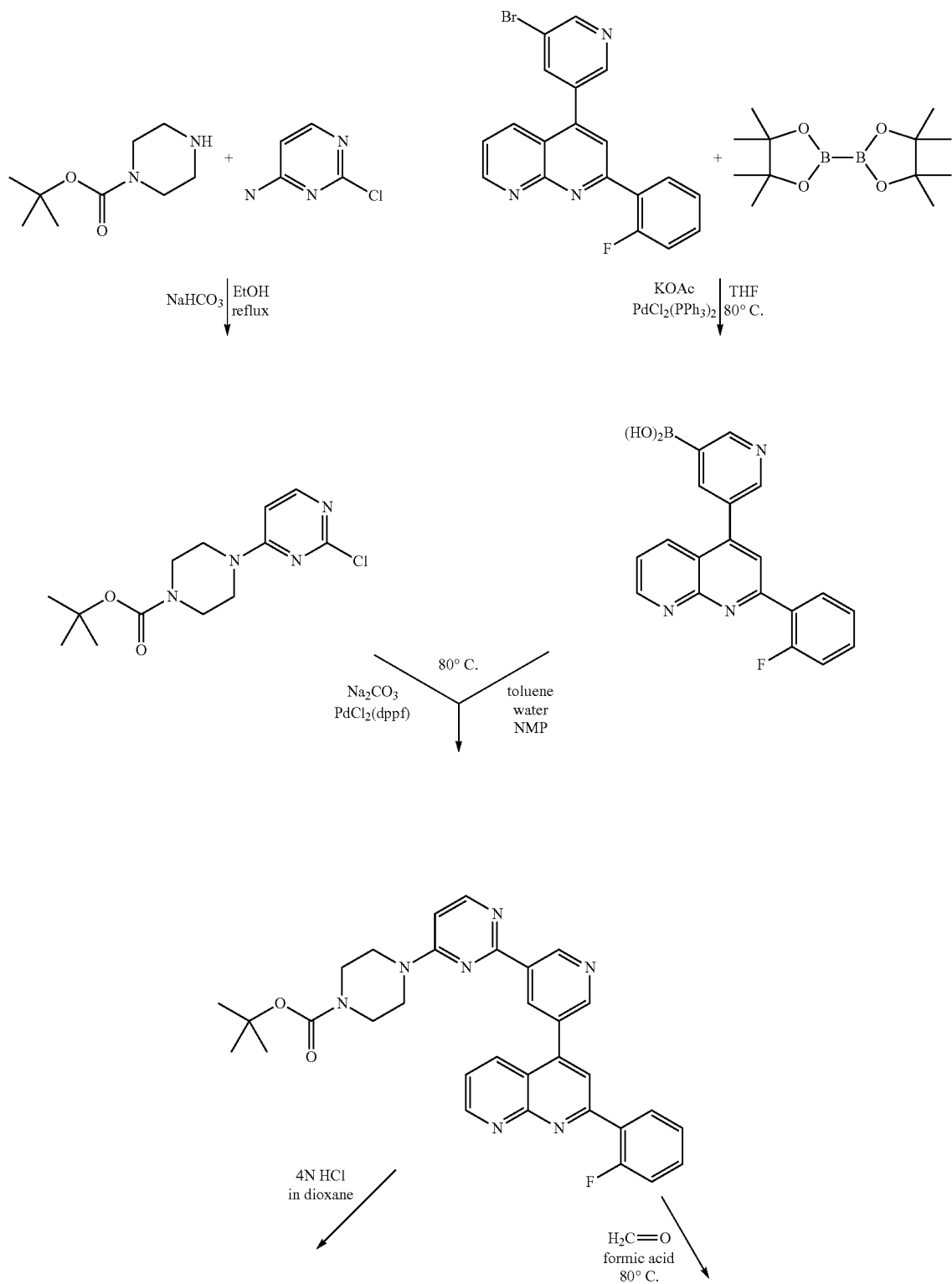

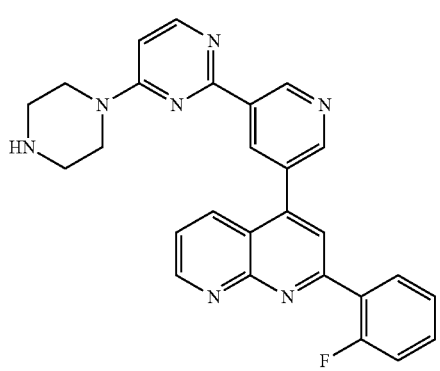

209

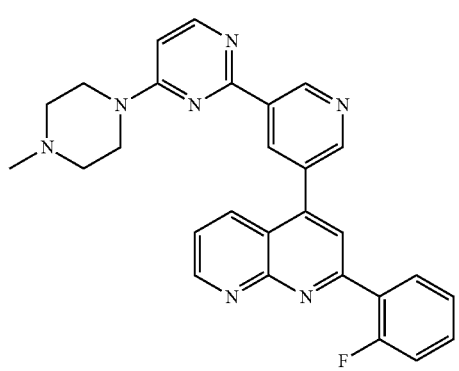

210

-continued

The following compounds were synthesized analogously:
2-(2-Fluoro-phenyl)-4-{5-[4-(4-methyl-piperazin-1-yl)-pyrimidin-2-yl]-pyridin-3-yl}-[1,8]naphthyridine (no. 70); HPLC/MS: 1.47, [M+H] 478
2-(2-Fluoro-phenyl)-4-[5-(1H-pyrazolo[3,4-b]pyridin-5-yl)-pyridin-3-yl]-[1,8]naphthyridine (no. 80); HPLC/MS: 1.87, [M+H] 420

EXAMPLE 32

Synthesis of 4-[2-(2-fluoro-phenyl)-[1,8]naphthyridin-4-yl]-[2,7]naphthyridin-1-ylamine (no. 72); HPLC/MS: 1.40, [M+H] 368

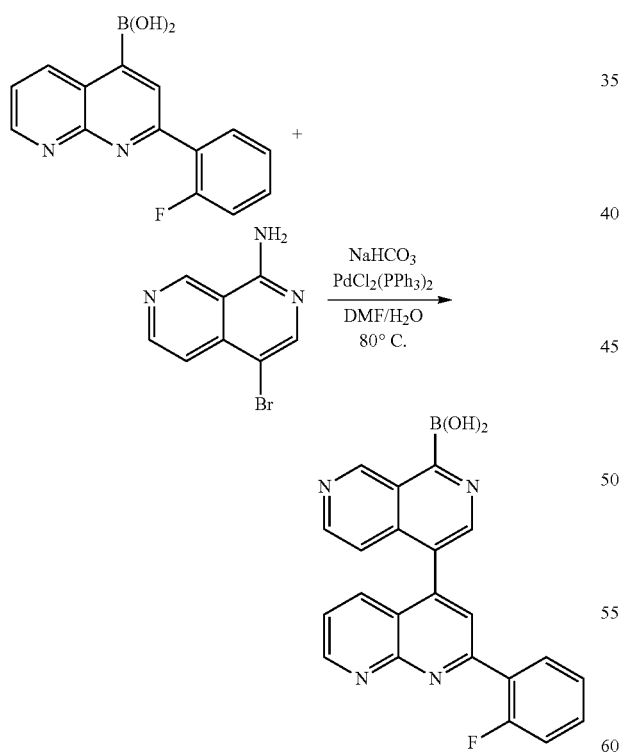

The following compounds were synthesized analogously:
4-[2-(2,5-Difluoro-phenyl)-[1,8]naphthyridin-4-yl]-[2,7]naphthyridin-1-ylamine (no. 73); HPLC/MS: 1.47, [M+H] 386
2-(2-Fluoro-phenyl)-4-[2,7]naphthyridin-4-yl-[1,8]naphthyridine (no. 75)

EXAMPLE 33

Synthesis of N-{4-[2-(2-fluoro-phenyl)-[1,8]naphthyridin-4-yl]-[2,7]naphthyridin-1-yl}-acetamide (no. 74); HPLC/MS: 1.64, [M+H] 369

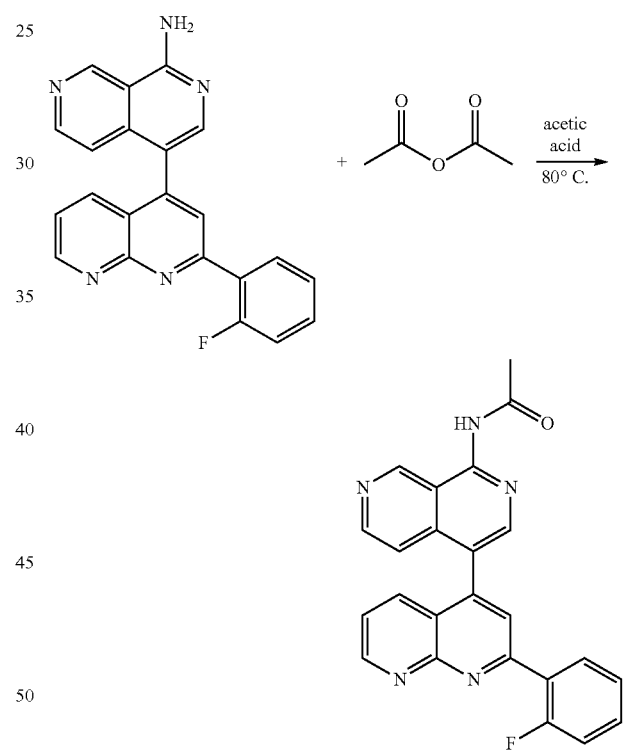

EXAMPLE 34

Synthesis of 5-[2-(2-fluoro-phenyl)-[1,8]naphthyridin-4-yl]-[2,7]naphthyridin-1-ylamine (no. 76)

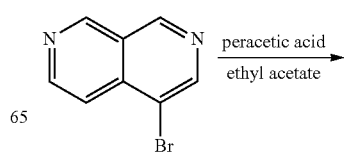

211

-continued

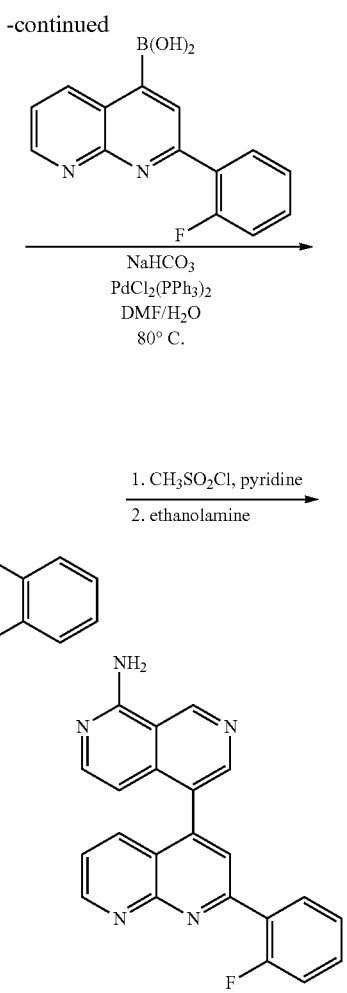

EXAMPLE 35

Cellular Assay for Testing TGF-beta Receptor I Kinase Inhibitors

As an example, the ability of the inhibitors to eliminate TGF-beta-mediated growth inhibition was tested. Cells of the lung epithelial cell line Mv1Lu were sown in a defined cell density in a 96-well microtiter plate and cultivated overnight under standard conditions. Next day, the medium was replaced by medium which comprises 0.5% of FCS and 1 ng/ml of TGF-beta, and the test substances were added in defined concentrations, generally in the form of dilution series with 5 fold steps. The concentration of the solvent DMSO was constant at 0.5%. After a further two days, Crystal Violet staining of the cells was carried out. After extraction of the Crystal Violet from the fixed cells, the absorption was measured spectrophotometrically at 550 nm. It could be used as a quantitative measure of the adherent cells present and thus of the cell proliferation during the culture.

EXAMPLE 35A

Inhibition of Smad2/3 Phosphorylation in Mv1Lu Cells by TGF-bta Receptor I Kinase Inhibitors This assay was used to determine the inhibitory potency of compounds on TGF-beta-induced phosphorylation of Smad2 (Ser465/467) and Smad3 (Ser423/425). Mv1-Lu cells (lung epithelial cell line from mink Mustela vison; ATCC number: CCL-64) were seeded in DMEM (Invitrogen) supplemented with 10% fetal bovine serum (Pan Biotech) at a defined cell density in 24-well or 96-well plates (24-well plate: $1.5 \times 10^5$ cells per well; 96-well plate: $4 \times 10^4$ cells per well). Cell cultures were incubated in DMEM at 37° C. and 10% $CO_2$. On the next day, the medium was replaced and cells were serum-starved for 16-20 hours. The following day, serial dilutions of compounds were added to the wells, pre-incubated for 1.5 hrs before recombinant TGF-beta 1 ligand (final concentration 5 ng/ml; R&D systems) was added. After one hour of ligand stimulation, lysates were prepared and analyzed using an enzyme-linked immunosorbent assay kit (PathScan Phospho-Smad2 Kit, Cell Signaling Technologies). The ELISA detects phosphorylated Smad2 as well as phosphorylated Smad3 with the phospho-specific antibody. TGF-beta stimulated cells and unstimulated cells served as positive and negative controls (100% and background control). The concentration of the vehicle DMSO was kept constant at 0.2% (v/v) in all wells. Dose-response relationships were fitted using curve fitting algorithms of the RS1 statistics software package (Brooks Automation Inc. RS/1—Statistical Tools Handbook. Release 6.2) to determine the concentration at which half-maximal inhibition ($IC_{50}$) of Smad2/3 phosphorylation was achieved. The results are given in Table 1 and 2.

EXAMPLE 36

In-vitro (Enzyme) Assay for Determination of the Efficacy of Inhibitors of the Inhibition of TGF-beta-Mediated Effects The kinase assay was carried out as 384-well flashplate assay. 31.2 nM of GST-ALK5, 439 nM of GST-SMAD2 and 3 mM of ATP (with 0.3 μCi of $^{33}$P-ATP/well) were incubated in a total volume of 35 μl (20 mM of HEPES, 10 mM of $MgCl_2$, 5 mM of $MnCl_2$, 1 mM of DTT, 0.1 of BSA, pH 7.4) without or with test substance (5-10 concentrations) at 30° C. for 45 min. The reaction was stopped using 25 μl of 200 mM EDTA solution, filtered with suction at room temperature after 30 min, and the wells were washed with 3 times 100 μl of 0.9% NaCl solution. Radioactivity was measured in the TopCount. The $IC_{50}$ values were calculated using RS1. The results are given in Table 1.

EXAMPLE 37

Pharmaceutical Preparations (A) Injection Vials: A solution of 100 g of an active ingredient according to the invention and 5 g of disodium hydrogen phosphate in 3 l of bidistilled water was adjusted to pH 6.5 using 2 N hydrochloric acid, sterile filtered, transferred into injection vials, lyophilized under sterile conditions and sealed under sterile conditions. Each injection vial contained 5 mg of active ingredient.

(B) Suppositories: A mixture of 20 g of an active ingredient according to the invention was melted with 100 g of soya lecithin and 1400 g of cocoa butter, poured into moulds and allowed to cool. Each suppository contained 20 mg of active ingredient.

(C) Solution: A solution was prepared from 1 g of an active ingredient according to the invention, 9.38 g of $NaH_2PO_4 \cdot 2H_2O$, 28.48 g of $Na_2HPO_4 \cdot 12H_2O$ and 0.1 g of benzalkonium chloride in 940 ml of bidistilled water. The pH was adjusted to 6.8, and the solution was made up to 1 l and sterilized by irradiation. This solution could be used in the form of eye drops.

(D) Ointment: 500 mg of an active ingredient according to the invention were mixed with 99.5 g of Vaseline under aseptic conditions.

(E) Tablets: A mixture of 1 kg of an active ingredient according to the invention, 4 kg of lactose, 1.2 kg of potato starch, 0.2 kg of talc and 0.1 kg of magnesium stearate was pressed to give tablets in a conventional manner in such a way that each tablet contained 10 mg of active ingredient.

(F) Coated Tablets: Tablets were pressed analogously to Example E and subsequently coated in a conventional manner with a coating of sucrose, potato starch, talc, tragacanth and dye.

(G) Capsules: 2 kg of an active ingredient according to the invention were introduced into hard gelatin capsules in a conventional manner in such a way that each capsule contained 20 mg of the active ingredient.

(H) Ampoules: A solution of 1 kg of an active ingredient according to the invention in 60 l of bidistilled water was sterile filtered, transferred into ampoules, lyophilized under sterile conditions and sealed under sterile conditions. Each ampoule contained 10 mg of active ingredient.

(I) Inhalation Spray: 14 g of an active ingredient according to the invention were dissolved in 10 l of isotonic NaCl solution, and the solution was transferred into commercially available spray containers with a pump mechanism. The solution could be sprayed into the mouth or nose. One spray shot (about 0.1 ml) corresponded to a dose of about 0.14 mg.

The invention claimed is:

1. Compounds of formula (I)

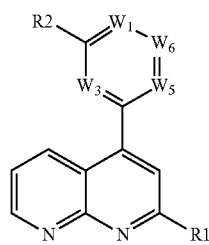

wherein $W_1$, $W_3$ denote CR3;
$W_5$, denotes N;
$W_6$ denotes CR4;
R1 denotes a monocyclic carboaryl having 5-8 C atoms, Het$^1$ or a monocyclic heteroaryl having 2-7 C atoms and 1-4 N, O and/or S atoms, each of which can be substituted by at least one substituent selected from the group of Y, Hal, CN, OY;
R2 denotes Ar, Het$^1$ or Het$^2$, each of which can be substituted by R5;
R3, R4 denotes independently from one another H, NYY, —NY—COY, A, OY or COOA;
R2, R3 together also denote Alk under the proviso that R2 and at most one R2-adjacent R3 are together;
R5 denotes Hal, A, —(CYY)$_n$—OY, —(CYY)$_n$—NYY, (CYY)$_n$-Het$^3$, SY, NO$_2$, CN, COOY, —CO—NYY, —NY—COA, —NY—SO$_2$A, —SO$_2$—NYY, S(O)$_m$A, —CO-Het$^3$, —O(CYY)$_n$—NYY, —O(CYY)$_n$-Het$^3$, —NH—COOA, —NH—CO—NYY, —NH—COO— (CYY)$_n$—NYY, —NH—COO—(CYY)$_n$-Het$^3$, —NH—CO—NH—(CYY)$_n$—NYY, —NH—CO— NH(CYY)$_n$-Het$^3$, —OCO—NH—(CYY)$_n$—NYY, —OCO—NH—(CYY)$_n$-Het$^3$, CHO, COA, =S, =NY, =O, Alk-OH, —CO—NY—(CYY)$_n$—NYY, —CO—NY-Het$^3$ or —SO$_2$-Het$^3$;
Y denotes H or A;
A denotes unbranched or branched alkyl having 1-10 C atoms,
in which 1-7 H atoms can be replaced independently from one another by Hal and/or in which one or two adjacent CH$_2$ groups can be replaced independently of one another by a O, S, SO, SO$_2$, a —CY=CY— group and/or a —C≡C— group;
Alk denotes unbranched alkylene, alkenyl or alkynyl having 2-5 C atoms, in which 1-2 H atoms can be replaced independently from one another by R5 and/or in which 1-4 C atoms can be replaced independently from one another by N, O and/or S;
Ar denotes a saturated, unsaturated or aromatic, mono- or bicyclic carbocycle having 6-10 C atoms;
Het$^1$ denotes a saturated or unsaturated, mono, bi- or tricyclic heterocycle having 2-19 C atoms and 1-5 N, O and/or S atoms;
Het$^2$ denotes a mono, bi- or tricyclic heteroaryl having 2-19 C atoms and 1-5 N, O and/or S atoms;
Het$^3$ denotes a saturated, unsaturated or aromatic, mono-, bi- or tricyclic heterocycle having 2-19 C atoms and 1-5 N, O and/or S atoms, which can be substituted by at least one substituent selected from the group of Hal, A, —(CYY)$_n$—OY, —(CYY)$_n$—NYY, SY, NO$_2$, CN, COOY, —CO—NYY, —NY—COA, —NY—SO$_2$A, —SO$_2$—NYY, S(O)$_m$A, —NH—COOA, —NH—CO—NYY, CHO, COA, =S, =NY, =O;
Hal denotes F, Cl, Br or I;
m denotes 0, 1 or 2; and
n denotes 0, 1, 2, 3 or 4;
and/or physiologically acceptable salts thereof.

2. Compounds according to claim 1, wherein
R1 denotes phenyl or a monocyclic heteroaryl having 3-5 C-atoms and 1-3 N
atoms, each of which can be mono-, di- or trisubstituted by at least one substituent selected from the group of A, Hal, CN and OA.

3. Compounds according to claim 1, wherein
R5 denotes Hal, A, —(CYY)$_n$—OY, —(CYY)$_n$—NYY, (CYY)$_n$-Het$^3$, —NY—COA, —CO—NY—(CYY)$_n$—NYY, —O(CYY)$_n$—Het$^3$, =O, —SO$_2$—NYY, —O(CYY)$_n$—CO—NYY, —O(CYY)$_n$—NYY, —(CYY)$_n$—NYY or COA.

4. Compounds according to claim 1, wherein
Alk denotes unbranched alkenyl having 3-4 C atoms, which can be monosubstituted by R5 and/or in which 1-2 C atoms can be replaced independently from one another by N, O and/or S.

5. Compounds according to claim 1, wherein
Het$^3$ denotes a saturated monocyclic heterocycle having 2-7 C atoms and 1-4 N, O and/or S atoms, which can be mono, di- or trisubstituted by at least one substituent selected from the group of Hal, A, —(CYY)$_n$—OY, —(CYY)$_n$—NYY.

6. Compounds according to claim 1 wherein
$W_1$, $W_3$ denote CR3;
$W_5$ denotes N;
$W_6$ denotes CR4;
R1 denotes phenyl or a monocyclic heteroaryl having 3-5 C-atoms and 1-3 N atoms, each of which can be mono-, di- or trisubstituted by at least one substituent selected from the group of A, Hal, CN and OA;

R2, R3 together denote unbranched alkenyl having 3-4 C atoms, which can be monosubstituted by R5 and/or in which 1-2 C atoms can be replaced independently from one another by N, O and/or S, under the proviso that R2 and at most one R2-adjacent R3 are together;

R5 denotes Hal, A, —(CYY)$_n$—OY, —(CYY)$_n$—NYY, (CYY)$_n$-Het$^3$, —NY—COA, —CO—NY—(CYY)$_n$—NYY, —O(CYY)$_n$-Het$^3$, =O, —SO$_2$—NYY, —O(CYY)$_n$—CO—NYY, —O(CYY)$_n$—NYY, —(CYY)$_n$—NYY or COA;

Y denotes H or A;

A denotes 1-4 C atoms, in which 1-5 atoms may be replaced by F and/or Cl;

Het$^3$ denotes a saturated monocyclic heterocycle having 3-6 C atoms and 1-2 N and/or O atoms, which can be mono- or disubstituted by at least one substituent selected from the group of Hal, A, —(CYY)$_n$—OY, —(CYY)$_n$—NYY;

Hal denotes F, Cl, Br or I; and n denotes 0, 1, 2, 3 or 4;

and/or physiologically acceptable salts thereof.

7. Process for manufacturing a compound of formula (I)

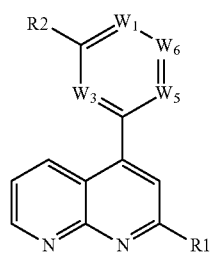

(I)

wherein R1, R2, W$_1$, W$_3$, W$_5$ and W$_6$ have the meaning as defined in claim 1, comprising the steps of:

reacting a compound of formula (III)

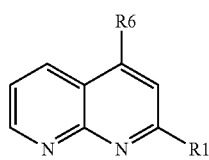

(III)

wherein

R6 denotes Hal, OH or B(OH)$_2$, and

R1 and Hal have the meaning as defined in claim 1, with a compound of formula (IV)

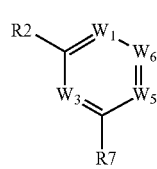

(IV)

wherein

R7 denotes Hal, OH, boronic acid or a ester of boronic acid, and

R2, W$_1$, W$_3$, W$_5$ W$_6$ and Hal have the meaning as defined in claim 1, to yield the compound of formula (I)

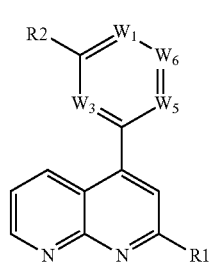

(I)

wherein R1, R2, W$_1$, W$_3$, W$_5$ and W$_6$ have the meaning as defined in claim 1.

8. Intermediate compounds of the formulae (V)

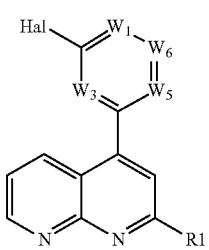

(V)

wherein

R1 denotes phenyl or a monocyclic 4-8 membered heteroaryl including 1-3 N atoms, each of which is mono-, di- or trisubstituted by at least one substituent selected from the group of A, Hal, CN and OA; and W$_1$, W$_3$, W$_5$, W$_6$ and Hal have the meaning as defined in claim 1; and/or physiologically acceptable salts thereof.

9. A pharmaceutical composition comprising as active ingredient an effective amount of at least one compound according to claim 1 and/or physiologically acceptable salts thereof together with pharmaceutically tolerable adjuvants.

10. The pharmaceutical composition according to claim 9, wherein the active ingredient is combined with at least another active ingredient selected from the group consisting of: (1) estrogen receptor modulators, (2) androgen receptor modulators, (3) retinoid receptor modulators, (4) cytotoxic agents, (5) antiproliferative agents, (6) prenyl-protein transferase inhibitors, (7) HMG-CoA reductase inhibitors, (8) HIV protease inhibitors, (9) reverse transcriptase inhibitors and (10) further angiogenesis inhibitors.

11. Process for manufacturing a compound of formula (I)

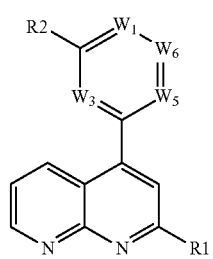

(I)

wherein R1, R2, $W_1$, $W_3$, $W_5$ and $W_6$ have the meaning as defined in claim 1, comprising the steps of:
reacting a compound of formula (V)

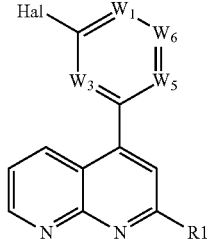

(V)

wherein R1, Hal $W_1$, $W_3$, $W_5$ and $W_6$ have the meaning as defined in claim 1,
with a compound of formula (VI) or a ester thereof

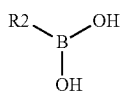

(VI)

wherein R2 has the meaning as defined in claim 1, to yield the compound of formula (I)

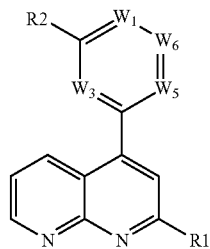

(I)

wherein R1, R2, $W_1$, $W_3$, $W_5$ and $W_6$ have the meaning as defined in claim 1.

12. The method of claim 7 further comprising converting the basic form of formula (I) into a salt thereof.

13. The method of claim 7 further comprising converting the acidic form of formula (I) into a salt thereof.

14. The method of claim 11 further comprising converting the basic form of formula (I) into a salt thereof.

15. The method of claim 11 further comprising converting the acidic form of formula (I) into a salt thereof."

\* \* \* \* \*